(12) United States Patent
Satomaa et al.

(10) Patent No.: US 8,759,005 B2
(45) Date of Patent: Jun. 24, 2014

(54) TISSUE CARBOHYDRATE COMPOSITIONS AND ANALYSIS THEREOF

(75) Inventors: Tero Satomaa, Helsinki (FI); Jari Natunen, Vantaa (FI); Annamari Heiskanen, Helsinki (FI); Maria Blomqvist, Itäsalmi (FI); Anne Olonen, Lahti (FI); Juhani Saarinen, Helsinki (FI)

(73) Assignee: Glykos Finland Oy, Helsinki (FI)

( * ) Notice: Subject to any disclaimer, the term of this patent is extended or adjusted under 35 U.S.C. 154(b) by 1112 days.

(21) Appl. No.: 11/988,563

(22) PCT Filed: Jul. 11, 2006

(86) PCT No.: PCT/FI2006/050335
§ 371 (c)(1),
(2), (4) Date: Apr. 28, 2008

(87) PCT Pub. No.: WO2007/012695
PCT Pub. Date: Feb. 1, 2007

(65) Prior Publication Data
US 2009/0104603 A1    Apr. 23, 2009

(30) Foreign Application Priority Data

Jul. 11, 2005 (FI) .................................. 20055404
Nov. 8, 2005 (FI) .................................. 20051133

(51) Int. Cl.
*G01N 33/53* (2006.01)
(52) U.S. Cl.
USPC ............................................. 435/7.1; 435/4
(58) Field of Classification Search
CPC ..................................................... G01N 33/53
USPC .............................................. 435/4, 7.1, 366
See application file for complete search history.

(56) References Cited

U.S. PATENT DOCUMENTS

| 8,110,366 | B2 * | 2/2012 | Laine et al. ..................... 435/7.1 |
| 2004/0197328 | A1 * | 10/2004 | Young et al. ............... 424/141.1 |
| 2005/0014718 | A1 * | 1/2005 | Natunen et al. ................. 514/54 |
| 2010/0003699 | A1 * | 1/2010 | Satomaa et al. .............. 435/7.2 |

FOREIGN PATENT DOCUMENTS

| WO | WO03/016915 | * | 2/2003 |
| WO | WO-2004/019040 A1 | | 3/2004 |

OTHER PUBLICATIONS

Matsuura et al. Structural Characterization of Novel Complex Oligosaccharides Accumulated in the Caprine Beta-Mannosidosis Kidney; The Journal of Biological Chemistry, vol. 260, No. 28 (1985 (15239-15245.*
Dillman (Annals of Internal Medicine, 1989 111:592-603).*
Udo et al (Clinical Chemistry, Jan. 2004, 50:58-66).*
Chapman et al., The Journal of Biological Chemistry, vol. 254 (1979), pp. 816-823.
Choi et al., Glycobiology, vol. 13, (2003), pp. 539-548.
Ogier-Denis et al., The Journal of Biological Chemistry, 1988, pp. 263 (13), pp. 6031-6037.

* cited by examiner

*Primary Examiner* — Mark Halvorson
*Assistant Examiner* — Yan Xiao
(74) *Attorney, Agent, or Firm* — Birch, Stewart, Kolasch & Birch, LLP

(57) ABSTRACT

The present invention reveals novel methods for producing novel carbohydrate compositions, glycomes, from animal tissues. The tissue substrate materials can be total tissue samples and fractionated tissue parts, or artificial models of tissues such as cultivated cell lines. The invention is further directed to the compositions and compositions produced by the methods according to the invention. The invention further represent methods for analysis of the glycomes, especially mass spectrometric methods.

36 Claims, 21 Drawing Sheets

A.

B.

C.

D.

TISSUE CARBOHYDRATE COMPOSITIONS AND ANALYSIS THEREOF

FIELD OF INVENTION

The present invention reveals novel methods for producing novel carbohydrate compositions, glycomes, from animal tissues. The tissue substrate materials can be total tissue samples and fractionated tissue parts, or artificial models of tissues such as cultivated cell lines. The invention is further directed to the compositions and compositions produced by the methods according to the invention. The invention further represent methods for analysis of the glycomes, especially mass spectrometric methods.

BACKGROUND

Multiple methods to produce and analyze oligosaccharides from isolated glycoproteins are known. The present invention is directed to specific methods to release and purify total oligosaccharide pools quantitatively from tissues. The invention is specifically directed to methods using very low amounts of tissues. It is realized that purification of an oligosaccharide mixture from complex tissue samples to level of purity useful for analysis is more complex task than isolation of the oligosaccharides from purified proteins. It is further realized that the purification methods are novel and useful for the effective analysis of protein derived glycans.

SUMMARY OF THE INVENTION

Figure 1:
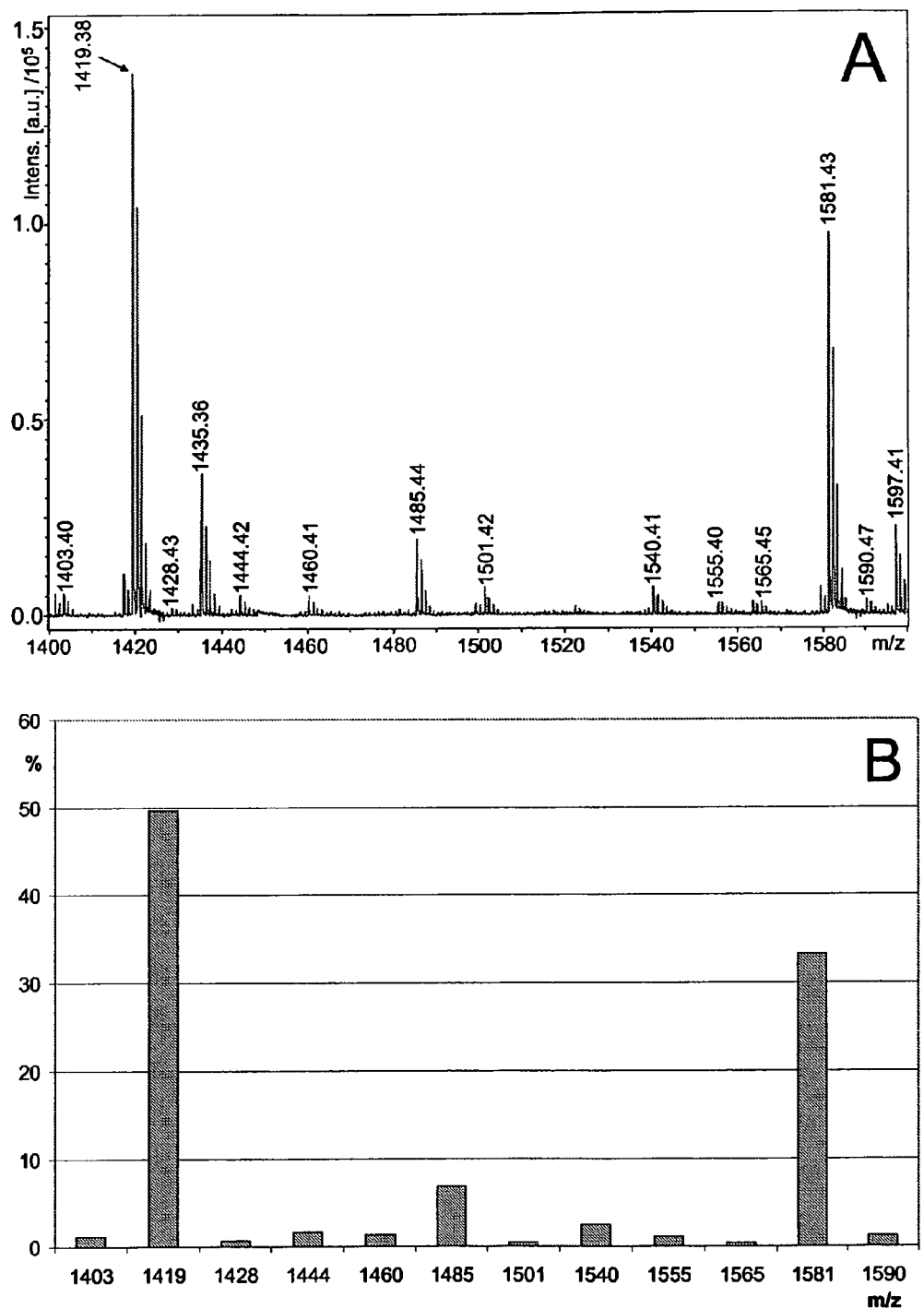
FIG. 1. Example of glycan signal analysis of MALDI-TOF mass spectrometric data. A. Mass spectrometric raw data showing a window of neutral N-glycan mass spectrum in positive ion mode, B. Glycan profile generated from the data in A.

The present invention reveals novel methods for producing novel carbohydrate compositions, glycomes from animal tissues, preferably from vertebrates, more preferably human and mammalian tissues. The tissue substrate materials can be total tissue samples and fractionated tissue parts, such as serums, secretions and isolated differentiated cells from the tissues, or artificial models of tissues such as cultivated cell lines. In a preferred embodiment the invention is directed to special methods for the analysis of the surfaces of tissues. The invention is further directed to the compositions and compositions produced by the methods according to the invention. The invention further represent preferred methods for analysis of the glycomes, especially mass spectrometric methods.

The invention represents effective methods for purification of oligosaccharide fractions from tissues, especially in very low scale. The prior art has shown analysis of separate glycome components from tissues, but not total glycomes. It is further realized that the methods according to the invention are useful for analysis of glycans from isolated proteins or peptides. The invention represents effective methods for the practical analysis of glycans from isolated proteins especially from very small amounts of samples.

The invention is further directed to novel quantitative analysis methods for glycomes. The glycome analysis produces large amounts of data. The invention reveals methods for the analysis of such data quantitatively and comparison of the data between different samples. The invention is especially directed to quantitative two-dimensional representation of the data.

The present invention is specifically directed to glycomes of tissues according to the invention comprising glycan material with monosaccharide composition for each of glycan mass components according to the Formula Mn:

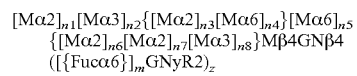

wherein p, n1, n2, n3, n4, n5, n6, n7, n8, and m, and z are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0;

y is anomeric linkage structure α and/or β or linkage from derivatized anomeric carbon, and $R_2$ is reducing end hydroxyl, chemical reducing end derivative or natural asparagine N-glycoside derivative such as asparagine N-glycosides including asparagines N-glycoside aminoacid and/or peptides derived from protein;

[ ] and ( ) indicates determinant either being present or absent depending on the value of n1, n2, n3, n4, n5, n6, n7, n8, and m; and { } indicates a branch in the structure, with the provisio that is 0 indication soluble mannose-GlcNAc1-glycome or there is 5, more preferably 4 or less mannose residues or m is 1 and there is 6 or less mannose units.

Typical glycomes comprise of subgroups of glycans, including N-glycans, O-glycans, glycolipid glycans, and neutral and acidic subglycomes.

The preferred analysis method includes:
1) Preparing a tissue sample containing glycans for the analysis
2) Releasing total glycans ort total glycan groups from a tissue sample, or extracting free glycans from a tissue sample
3) Optionally modifying glycans
4) Purification of the glycan fraction/fractions from biological material of the sample
5) Optionally modifying glycans
6) Analysis of the composition of the released glycans preferably by mass spectrometry
7a) Optionally presenting the data about released glycans quantitatively and
7b) Comparing the quantitative data set with another data set from another tissue sample or
8) Comparing data about the released glycans quantitatively or qualitatively with data produced from another tissue sample The invention is directed to diagnosis of clinical state of tissue samples, based on analysis of glycans present in the samples. The invention is especially directed to diagnosing cancer and the clinical state of cancer.

The invention is further directed to structural analysis of glycan mixtures present in tissue samples.

DESCRIPTION OF THE INVENTION

Tissue Derived Glycomes
Glycomes—Novel Glycan Mixtures from Tissue Samples

The present invention reveals novel methods for producing novel carbohydrate compositions, glycomes from animal tissues, preferably from vertebrates, more preferably human and mammalian tissues. The tissue substrate materials can be total tissue samples and
fractionated tissue parts, such as serums, secretions and isolated differentiated cells from the tissues, or
artificial models of tissues such as cultivated cell lines.

The invention revealed that the glycan structures on cell surfaces vary between the various tissues and same tissues under changing conditions.

The glycan structures on cell surfaces in general have been known to have numerous biological roles. Thus the knowledge about exact glycan mixtures from cell or tissue surfaces is important for knowledge about the status of cells. The invention revealed that multiple conditions affect the cells and cause changes in their glycomes.

Molecular Weight Distribution and Structure Groups of the Glycomes
Preferred Monosaccharide Compositions of the Glycomes
General Compositions The inventors were able to release or isolate various glycan fractions from tissue materials, which are useful for the characterization of the cellular material. The glycans or major part thereof are released preferably from glycoproteins or glycolipids of tissue samples. The invention is specifically directed to such glycan fractions.

The glycan fractions of tissue samples comprise typically multiple, at least about 10 "glycan mass components" typically corresponding at least ten glycans and in most cases clearly more than 10 glycan structures.

Glycan Mass Components and Corresponding Monosaccharide Compositions

The glycan mass components correspond to certain molecular weights observable by mass spectrometry and further correspond to specific monosaccharide composition or monosaccharide compositions. Each monosaccharide component is normally present in a glycan as glycosidically linked monosaccharide residue in the nonreducing end part of glycan and the reducing end monosaccharide may be in free alditol form or modified for example by reduction or conjugated to an reducing end modifying reagent well known in the art or to one, two or several amino acids in case of glycopeptides. Monosaccharide composition can be obtained from molecular mass in a mass spectrum (glycan mass component) after correcting potential effect of the ion forms observable by the specific mass spectrometry technologue such as protonation/deprotonation, $Na^+$, $K^+$, $Li^+$, or other adduct combinations, or isotope pattern derived effects. The monosaccharide compositions are calculated by fitting mixtures of individual monosaccharide (residue) masses and modification groups to corrected molecular mass of glycan mass component. Typically the molecular mass of fitting composition and the experimental mass correspond to each other very closely with similar first and even second decimals with optimal calibration.

The fitting may be further checked by measuring the experimental mass difference from the smaller and/or larger glycan mass component next in the putative biosynthetic series of a glycan type and comparing the difference with the exact molecular mass of corresponding monosaccharide unit (residue), typically the mass differences of fitting components in a good quality mass spectrum and with correct marking of peaks in decimals, preferably in second or third decimal of the mass number depending on the resolution of the specific mass spectrometric method. For optimal mass accuracy, an internal calibration may be used, where two or more known component's mass peaks are used to re-calculate masses for each components in the spectrum. Such calibration components are preferably selected among the most abundant glycan signals present in the glycan profiles, in the case of human or other animal cell derived glycan profiles most preferably selected among the most abundant glycan signals present in Figures described in the present invention.

The monosaccharide composition includes monosaccharide component names and number, typically as subscript, indicating how many of the individual mass components is present in the monosaccharide composition; and names of assigned modifying groups and numbers indicating their abundance.

It is further realized that the masses of glycan mass component may be obtained as exact monoisotopic mass of usually smallest isotope of the glycan mass component or as an average mass of the isotope distribution of the glycan mass component. Exact mass is calculated form exact masses of individual mass components and average from masses average masses of individual mass components. Person skilled in art can recognize from the peak shapes (i.e. by the resolution obtained) in the mass spectrum whether to use monoisotopic or average masses to interpret the spectra. It is further realized that average and exact masses can be converted to each other when isotope abundances of molecules are known, typically natural abundance without enrichment of isotopes can be assumed, unless the material is deliberately labelled with radioactive or stable isotope's.

It is further realized that specific rounded mass numbers can be used as names for glycan mass components. The present invention uses preferably mass numbers rounded down from the exact mass of the monosaccharide composition (and usually observable or observed mass) to closest integer as names of glycan mass components.

The masses of glycan mass components are obtained by calculating molecular mass of individual monosaccharide components (Hex, HexNAc, dhex, sialic acids) from the known atom compositions (for example hexose (Rex) corresponds to $C_6H_{12}O_6$) and subtracting for water in case of monosaccharide residue, followed by calculating the sum of the monosaccharide components (and possible modifications such as $SO_3$ or $PO_3H$). It is further realized that molecular masses of glycans may be calculated from atomic compositions or any other suitable mass units corresponding molecular masses of these. The molecular masses and calculation thereof are known in the art and masses of monosaccharide components/residues are available in tables with multiple decimals from various sources.

It is further realized that many of the individual monosaccharide compositions described in the present invention further correspond to several isomeric individual glycans. In addition, there exist also monosaccharide compositions that have nearly equal masses, for example dHex2 and NeuAc monosaccharide residues that have nearly equal masses, and other examples can be presented by a person skilled in the art. It is realized that the ability to differentiate compositions with nearly equal masses depends on instrumentation, and the present method is especially directed to a possibility to select also such compositions in place of proposed compositions.

The preferred glycans in glycomes comprise at least two of following monosaccharide component residues selected from group: Hexoses (Rex) which are Gal, Glc and Man; N-acetylhexosamines (HexNAc) which are GlcNAc and GalNAc; pentose, which is Xyl; Hexuronic acids which are GlcA and IdoA; deoxyhexoses (dHex), which is fucose and sialic acids which are NeuAc and/NeuGc; and further modification groups such as acetate (Ac), sulphate and phosphate forming esters with the glycans. The monosaccharide residues are further grouped as major backbone monosaccharides including GlcNAc, HaxA, Man and Gal; and specific terminal modifying monosaccharide units Glc, GalNAc, Xyl and sialic acids.

Detection of Glycan Modifications

The present invention is directed to analyzing glycan components from biological samples, preferably as mass spectrometric signals. Specific glycan modifications can be detected among the detected signals by determined indicative signals as exemplified below. Modifications can also be detected by more specific methods such as chemical or physical methods, for example mass spectrometric fragmentation or glycosidase detection as disclosed in the present invention. In a preferred form of the present method, glycan signals are assigned to monosaccharide compositions based on the detected m/z ratios of the glycan signals, and the specific glycan modifications can be detected among the detected monosaccharide compositions.

In a further aspect of the present invention, relative molar abundances of glycan components are assigned based on their relative signal intensities detected in mass spectrometry as described in the Examples, which allows for quantification of glycan components with specific modifications in relation to other glycan components. The present method is also directed to detecting changes in relative amounts of specific modifications in cells at different time points to detect changes in cell glycan compositions.

Glycome Glycan Fraction Further Comprising Monosaccharides

The invention is specifically directed to glycan compositions, which further comprise at least one monosaccharide component in free form, preferably a preferred monosaccharide component described above. The monosaccharide comprising compositions are in a preferred embodiment derived from a cell material or released glycomes, which has been in contact with monosaccharide releasing chemicals or enzymes, preferably with exoglycosidase enzymes or chemicals such as oxidating reagents and/or acid, more preferably with a glycosidase enzyme. The invention is further directed to compositions comprising a specific preferred monosaccharide according to the invention, an exoglycosidase enzyme capable releasing all or part of the specific monosaccharide and an glycan composition according to the invention from which at least part of the terminal specific monosaccharide has been released.

Limit of Detection for Glycome Components

It is further realized that by increasing the sensitivity of detection the number of glycan mass components can be increased. The analysis according to the invention can be in most cases performed from major or significant components in the glycome mixture. The present invention is preferably directed to detection of glycan mass components from a high quality glycan preparation with optimised experimental condition, when the glycan mass components have abundance at least higher than 0.01% of total amount of glycan mass components, more preferably of glycan mass components of abundance at least higher than 0.05%, and most preferably at least higher than 0.10% are detected. The invention is further directed practical quality glycome compositions and analytic process directed to it, when glycan mass components of at least about 0.5%, of total amount of glycan mass components, more preferably of glycan mass components of abundance at least higher than 1.0%, even more preferably at least higher than 2.0%, most preferably at least higher than 4.0% (presenting lower range practical quality glycome), are detected. The invention is further directed to glycomes comprising preferred number of glycan mass components of at least the abundance of observable in high quality glycomes, and in another embodiment glycomes comprising preferred number of glycan mass components of at least the abundance of observable in practical quality glycomes.

Subglycomes Obtainable by Purification or Specific Release Method

It further realized that fractionation or differential specific release methods of glycans from glycoconjugates can be applied to produce subglycomes containing part of glycome.

The subglycomes produced by fractionation of glycomes are called "fractionated subglycomes".

The glycomes produced by specific release methods are "linkage-subglycomes". The invention is further directed to combinations of linkage-subglycomes and fractionated subglycomes to produce "fractionated linkage-subglycomes", for example preferred fractionated linkage-subglycomes includes neutral O-glycans, neutral N-glycans, acidic O-glycans, and acidic N-glycans, which were found very practical in characterising target material according to the invention.

The fractionation can be used to enrich components of low abundance. It is realized that enrichment would enhance the detection of rare components. The fractionation methods may be used for larger amounts of cell material. In a preferred embodiment the glycome is fractionated based on the molecular weight, charge or binding to carbohydrate binding agents.

These methods have been found useful for specific analysis of specific subglycomes and enrichment more rare components. The present invention is in a preferred embodiment directed to charge based separation of neutral and acidic glycans. This method gives for analysis method, preferably mass spectroscopy material of reduced complexity and it is useful for analysis as neutral molecules in positive mode mass spectrometry and negative mode mass spectrometry for acidic glycans.

Differential release methods may be applied to get separately linkage specific subglycomes such as O-glycan, N-glycan, glycolipid or proteoglycan comprising fractions or combinations thereof. Chemical and enzymatic methods are known for release of specific fractions, furthermore there are methods for simultaneous release of O-glycans and N-glycans.

Novel Complete Compositions

It is realized that at least part of the glycomes have novelty as novel compositions of very large amount of components. The glycomes comprising very broad range substances are referred as complete glycomes.

Preferably the composition is a complete composition comprising essentially all degrees of polymerisation in general from at least about disaccharides, more preferably from trisaccharides to at least about 25-mers in a high resolution case and at least to about 20-mers or at least about 15-mer in case of medium and practical quality preparations.

It is realized that especially the lower limit, but also upper limit of a subglycome depend on the type of subglycome and/or method used for its production. Different complete ranges may be produced in scope of general glycomes by fractionation, especially based on size of the molecules.

Novel Compositions with New Combinations of Subglycomes and Preferred Glycan Groups It is realized that several glycan types are present as novel glycome compositions produced from the tissue samples. The invention is specifically directed to novel mixture composition comprising different subglycomes and preferred glycan groups Novel Quantitative Glycome Compositions It is realised that the glycome compositions as described in examples represent quantitatively new data about glycomes from the preferred tissue sample types. The proportions of various components cannot be derived from background data and are very useful for the analysis methods according to the invention. The invention is specifically directed to glycome compositions according to the examples when the glycan mass components are present in essentially similar relative amounts.

Preferred Composition Formulas

The present invention is specifically directed to glycomes of tissue samples according to the invention comprising glycan material with monosaccharide composition for each of glycan mass components according to the Formula I:

$$NeuAc_mNeuGc_nHex_oHexNAc_p\\dHex_qHexA_rPen_sAc_tModX_x, \quad (I)$$

where m, n, o, p, q, r, s, t, and x are independent integers with values ≥0 and less than about 100,
with the proviso that
for each glycan mass components at least two of the backbone monosaccharide variables o, p, or r is greater than 0, and ModX represents a modification (or N different modifications Mod1, Mod2, ..., ModN), present in the composition in an amount of x (or in independent amounts of x1, x2, ..., xN), Preferably examples of such modifications (Mod) including for example $SO_3$ or $PO_3H$ indicating esters of sulfate and phosphate, respectively
and the glycan composition is preferably derived from isolated human tissue samples or preferred subpopulations thereof according to the invention.

It is realized that usually glycomes contain glycan material for which the variables are less much less than 100, but large figures may be obtained for polymeric material comprising glycomes with repeating polymer structures, for example ones comprising glycosaminoglycan type materials. It is further realized that abundance of the glycan mass components with variables more than 10 or 15 is in general very low and observation of the glycome components may require purification and enrichment of larger glycome components from large amounts of samples.

Broad Mass Range Glycomes

In a preferred embodiment the invention is directed to broad mass range glycomes comprising polymeric materials and rare individual components as indicated above. Observation of large molecular weight components may require enrichment of large molecular weight molecules comprising fraction. The broad general compositions according to the Formula I are as described above,
with the proviso that
m, n, o, p, q, r, s, t, and x are independent integers with preferable values between 0 and 50, with the proviso that for each glycan mass components at least two of o, p, or r is at least 1, and the sum of the monosaccharide variables; m, n, o, p, q, r, and s, indicating the degree of polymerization or oligomerization, for each glycan mass component is less than about 100 and the glycome comprises at least about 20 different glycans of at least disaccharides.

Practical Mass Range Glycomes

In a preferred embodiment the invention is directed to practical mass range and high quality glycomes comprising lower molecular weight ranges of polymeric material. The lower molecular weight materials at least in part and for preferred uses are observable by mass spectrometry without enrichment.

In a more preferred general composition according to the Formula I as described above,
m, n, o, p, q, r, s, t, and x are independent integers with preferable values between 0 and about 20, more preferably between 0 and about 15, even more preferably between 0 and about 10,
with the proviso that at least two of o, p, or r is at least 1, and the sum of the monosaccharide variables; m, n, o, p, q, r, and s, indicating the degree of polymerization or oligomerization, for each glycan mass component is less than about 50 and more preferably less than about 30,
and the glycome comprises at least about 50 different glycans of at least trisaccharides.

In a preferred embodiment the invention is directed to practical mass range high quality glycomes which may comprise some lower molecular weight ranges of polymeric material. The lower molecular weight materials at least in part and for preferred uses are observable by mass spectrometry without enrichment.

In a more preferred general composition according to the Formula I as described above,
m, n, o, p, q, r, s, t, and x are independent integers with preferable values between 0 and about 10, more preferably between 0 and about 9, even more preferably, between 0 and about 8,
with the proviso that at least two of o, p, or r is at least 1, and the sum of the monosaccharide variables; m, n, o, p, q, r, and s, indicating the degree of polymerization or oligomerization, for each glycan mass component is less than about 30 and more preferably less than about 25,
and the glycome comprises at least about 50 different glycans of at least trisaccharides.

The practical mass range glycomes may typically comprise tens of components, for example in positive ion mode MALDI-TOF mass spectrometry for neutral subglycomes it is usually possible to observe even more than 50 molecular mass components, even more than 100 mass component corresponding to much larger number of potentially isomeric glycans. The number of components detected depends on sample size and detection method.

Preferred Subglycomes

The present invention is specifically directed to subglycomes of tissue sample glycomes according to the invention comprising glycan material with monosaccharide compositions for each of glycan mass components according to the Formula I and as defined for broad and practical mass range glycomes. Each subglycome has additional characteristics based on glycan core structures of linkage-glycomes or fractionation method used for the fractionated glycomes. The preferred linkage glycomes includes:
N-glycans, O-glycans, glycolipid glycans, neutral and acidic subglycomes, N-Glycan Subglycome Protein N-glycosidase releases N-glycans comprising typically two N-acetylglycosamine units in the core, optionally a core linked fucose unit and typically then 2-3 hexoses (core mannoses), after which the structures may further comprise hexoses being mannose or in complex—type N-glycans further N-acetylglycosamines and optionally hexoses and sialic acids.

N-glycan subglycomes released by protein N-glycosidase comprise N-glycans containing N-glycan core structure and are releasable by protein N-glycosidase from cells.

The N-glycan core structure is Manβ4GlcNAcβ(Fucα6)$_n$4GlcNAc, wherein n is 0 or 1 and the N-glycan structures can be elongated from the Manβ4 with additional mannosyl residues. The protein N-glycosidase cleaves the reducing end GlcNAc from Asn in proteins. N-glycan subglycomes released by endo-type N-glycosidases cleaving between GlcNAc units contain Manβ4GlcNAcβ-core, and the N-glycan structures can be elongated from the Manβ4 with additional mannosyl residues.

In case the Subglycome and analysis representing it as Glycan profile is formed from N-glycans liberated by N-glycosidase enzyme, the preferred additional constraints for Formula I are:
p>0, more preferably 1≤p≤100, typically p is between 2 and about 20, but polymeric structures containing glycomes may comprise larger amounts of HexNAc and
it is realized that in typical core of N-glycans indicating presence of at least partially complex type structure when p≥3 it follows that o≥1.

Glycolipid Subglycome

In case the Subglycome and analysis representing it as Glycan profile is formed from lipid-linked glycans liberated by endoglycoceramidase enzyme, the preferred additional constraints for Formula I are:
o>0, more preferably 1≤o≤100, and
when p≥1 it follows that o≥2.

Typically glycolipids comprise two hexoses (a lactosyl residue) at the core. The degree of oligomerization in a usual practical glycome from glycolipds is under about 20 and more preferably under 10. Very large structures comprising glycolipids, polyglycosylceramides, may need enrichment for effective detection.

Neutral and Acidic Subglycomes

Most preferred fractionated Subglycomes includes 1) subglycome of neutral glycans and 2) subglycome of acidic glycans. The major acidic monosaccharide unit is in most cases a sialic acid, the acidic fraction may further comprise natural negatively charged structure/structures such as sulphate(s) and/phosphate(s).

In case the Subglycome and analysis representing it as Glycan profile is formed from sialylated glycans, the preferred additional constraints for Formula I are:

(m+n)>0, more preferably 1≤(m+n)≤100.

Large amounts of sialic acid in a glycan mass component would indicate presence of polysailic acid type structures. Practical and high resolutions acidic glycomes usually have m+n values for individual major glycan mass components with preferred abundance between 1 and 10, more preferably and of the between 1-5 and most preferably between 14 for a usual glycomes according to the invention. For neutral glycans, (m+n)=0, and they do not contain negatively charged groups as above.

Preferred Structure Groups Observable in Glycome Profiles

The present invention is specifically directed to the glycomes of tissue samples according to the invention comprising as major components at least one of structure groups selected from the groups described below.

Glycan Groups

According to the present invention, the Glycan signals are optionally organized into Glycan groups and Glycan group profiles based on analysis and classification of the assigned monosaccharide and modification compositions and the relative amounts of monosaccharide and modification units in the compositions, according to the following classification rules:

1° The glycan structures are described by the formulae:

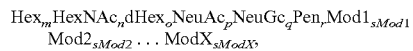

Hex$_m$HexNAc$_n$dHex$_o$NeuAc$_p$NeuGc$_q$Pen$_r$Mod1$_{sMod1}$
Mod2$_{sMod2}$ ... ModX$_{sModX}$, wherein m, n, o, p, q, individual sMod, and X, are each independent variables, and Mod is a functional group covalently linked to the glycan structure.

2° Glycan structures in general are classified as follows:
a. Structures (p,q=0) are classified as "non-sialylated",
b. Structures p,q>0) are classified as "sialylated",
c. Structures (q>0) are classified as "NeuGc-containing",
d. Relation [2(p+q):(m+n)] describes the general sialylation degree of a glycan structure,
e. In the case of mammalian glycans, structures (o=0) are classified as "non-fucosylated",
f. In the case of mammalian glycans, structures (o>0) are classified as "fucosylated",
g. Structures (Mod=Ac and sAc>0) are classified as 'acetylated',
h. Structures (Mod=SO$_3$ and sSO$_3$>0) are classified as 'sulfated', and
i. Structures (Mod=PO$_3$H and sPO$_3$H>0) are classified as 'phosphorylated'.

3° N-glycan glycan structures, generated e.g. by the action of peptide-N-glycosidases, are classified as follows:
a. Structures (n=2 and m>0 and p,q=0) are classified as "mannose-terminated N-glycans",
b. Structures (n=2 and m>5 and o,p,q=0) are classified as "high-mannose N-glycans",
c. Structures (n=2 and m>5 and o>0 and p,q=0) are classified as "fucosylated high-mannose N-glycans", d. Structures (n=2 and 4≥m≥1 and p,q=0) are classified as "low-mannose N-glycans", e. Structures (n=2 and 4≥m≥1 and o>0 and p,q=0) are classified as "fucosylated low-mannose N-glycans", f. Structures (n=3 and m≥2) are classified as "hybrid-type or monoantennary N-glycans", g. Structures (n≥4 and m≥3) are classified as "complex-type N-glycans", h. Structures (n>m≥2) are classified as "N-glycans containing non-reducing terminal N-acetylhexosamine", i. Structures (n=m≥5) are classified as "N-glycans potentially containing bisecting N-acetylglucosamine", j. In the case of mammalian N-glycans, structures (o≥2) are classified as "N-glycans containing α2-, α3-, or α-4-linked fucose", k. Relation [2 (p+q):(m+n−5)] describes the "overall sialylation degree" of a sialylated N-glycan structure, and l. Specifically, sum (p+q) describes the "sialylation degree" of a sialylated hybrid-type or monoantennary N-glycan structure.

4° Mucin-type O-glycan structures, generated e.g. by alkaline O-elimination, are classified as follows:

a. Structures (n=m), with (N=n=m), are classified as "Type N O-glycans", b. More specifically, structures (n=m=1) are classified as "Type 1 O-glycans", c. More specifically, structures (n=m=2) are classified as "Type 2 O-glycans", d. More specifically, structures (n=m=3) are classified as "Type 3 O-glycans", e. Relation [2 (p+q):(m+n)] describes the overall sialylation degree of a sialylated N-glycan structure, and f. Specifically, relation [(p+q):N] describes the sialylation degree of a sialylated Type N O-glycan structure.

Lipid-linked can also be classified into structural groups based on their monosaccharide compositions, as adopted from the classifications above according to the invention.

For example, glycan signal corresponding to a tissue sample N-glycan structure:

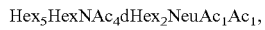

$Hex_5HexNAc_4dHex_2NeuAc_1Ac_1$, is classified as belonging to the following Glycan Groups:
sialylated (general sialylation degree: 2/9),
fucosylated,
acetylated,
complex-type N-glycans (overall sialylation degree: 0.5),
N-glycans containing α2-, α3-, or α-4-linked fucose.

Glycomes Comprising Novel Glycan Types

The present invention revealed novel unexpected components among in the glycomes studied. The present invention is especially directed to glycomes comprising such unusual materials Preferred Glycome Types Derivatized Glycomes It is further realized that the glycans may be derivatized chemically during the process of release and isolation. Preferred modifications include modifications of the reducing end and or modifications directed especially to the hydroxyls- and/or N-atoms of the molecules. The reducing end modifications include modifications of reducing end of glycans involving known derivatization reactions, preferably reduction, glycosylamine, glycosylamide, oxime (aminooxy-) and reductive amination modifications. Most preferred modifications include modification of the reducing end. The derivatization of hydroxyl- and/or amine groups, such as produced by methylation or acetylation methods including permethylation and peracetylation has been found especially detrimental to the quantitative relation between natural glycome and the released glycome.

Non-Derivatized Released Glycomes

In a preferred embodiment the invention is directed to non-derivatized released glycomes. The benefit of the non-derivatized glycomes is that less processing needed for the production. The non-derivatized released glycomes correspond more exactly to the natural glycomes from which these are released. The present invention is further directed to quantitative purification according to the invention for the non-derivatized releases glycomes and analysis thereof.

The present invention is especially directed to released glycomes when the released glycome is not a permodified glycome such as permethylated glycome or peracetyated glycome. The released glycome is more preferably reducing end derivatized glycome or a non derivatized glycome, most preferably non-derivatized glycome.

Novel Cell Surface Glycomes and Released Glycomes of the Target Material

The present invention is further directed to novel total compositions of glycans or oligosaccharides referred as glycomes and in a more specific embodiment as released glycomes observed from or produced from the target material according to the invention. The released glycome indicates the total released glycans or total specific glycan subfractions released from the target material according to the invention. The present invention is specifically directed to released glycomes meaning glycans released from the target material according to the invention and to the methods according to the invention directed to the glycomes.

The present invention preferably directed to the glycomes released as truncated and/or non-truncated glycans and/or derivatized according to the invention.

The invention is especially directed to N-linked and/or O-linked and/or Lipid linked released glycomes from the target material according to the invention. The invention is more preferably directed to released glycomes comprising glycan structures according to the invention, preferably glycan structures as defined in formula I. The invention is more preferably directed to N-linked released glycomes comprising glycan structures according to the invention, preferably glycan structures as defined in formula I.

Non-Derivatized Released Cell Surface Glycomes and Production

In a preferred embodiment the invention is directed to non-derivatized released cell surface glycomes. The non-derivatized released cell surface glycomes correspond more exactly to the fractions of glycomes that are localized on the cell surfaces, and thus available for biological interactions. These cell surface localized glycans are of especial importance due to their availability for biological interactions as well as targets for reagents (e.g. antibodies, lectins etc. . . . ) targeting the cells or tissues of interest. The invention is further directed to release of the cell surface glycomes, preferably from intact cells by hydrolytic enzymes such as proteolytic enzymes, including proteinases and proteases, and/or glycan releasing enzymes, including endo-glycosidases or protein N-glycosidases. Preferably the surface glycoproteins are cleaved by proteinase such as trypsin and then glycans are analysed as glycopeptides or preferably released further by glycan releasing enzyme.

Analysis of the Glycomes

Analysis of the glycan mixtures by physical means, preferably by mass spectrometry The present invention is directed to analysis of glycan mixtures present in tissue samples.

Quantitative and Qualitative Analysis of Glycan Profile Data

The invention is directed to novel methods for qualitative analysis of glycome data. The inventors noticed that there are specific components in glycomes according to the invention, the presence or absence of which are connected or associated with specific cell type or cell status. It is realized that qualitative comparison about the presence of absence of such signals are useful for glycome analysis. It is further realized that signals either present or absent that are derived from a general glycome analysis may be selected to more directed assay measuring only the qualitatively changing component or components optionally with a more common component or components useful for verification of data about the presence or absence of the qualitative signal.

The present invention is further specifically directed to quantitative analysis of glycan data from tissue samples. The inventors noted that quantitative comparisons of the relative abundances of the glycome components reveal substantial differences about the glycomes useful for the analysis according to the invention.

Essential Steps of the Glycome Analysis

The process contains essential key steps which should be included in every process according to the present invention.

The essential key steps of the analysis are:
1. Release of total glycans or total glycan groups from a tissue sample
2. Purification of the glycan fraction/fractions from biological material of the sample, preferably by a small scale column array or an array of solid-phase extraction steps
3. Analysis of the composition of the released glycans, preferably by mass spectrometry In most cases it is useful to compare the data with control sample data. The control sample may be for example from a healthy tissue or cell type and the sample from same tissue altered by cancer or another disease. It is preferable to compare samples from same individual organism, preferably from the same human individual.

Specific Types of the Glycome Analysis

Comparative Analysis

The steps of a comparative analysis are:
1. Release of total glycans or total glycan groups from tissue sample
2. Purification of the glycan fraction/fractions from biological material of the sample, preferably by a small scale column array or an array of solid-phase extraction steps
3. Analysis of the composition of the released glycans, preferably by mass spectrometry
4. Comparing data about the released glycans quantitatively or qualitatively with data produced from another tissue sample It may be useful to analyse the glycan structural motifs present in the sample, as well as their relative abundances. The ability to elucidate structural motifs results from the quantitative nature of the present analysis procedure, comparison of the data to data from previously analyzed samples, and knowledge of glycan biosynthesis.

Analysis Including Characterization of Structural Motives

The glycome analysis may include characterization of structural motives of released glycans. The structural motif analysis may be performed in combination with structural analysis. Preferred methods to reveal specific structural motifs include
a) direct analysis of specific structural modifications of the treatment of glycans preferably by exo- or endoglycosidases and/or chemical modification or
b) indirect analysis by analysis of correlating factors for the structural motives for such as mRNA-expression levels of glycosyltransferases or enzymes producing sugar donor molecules for glycosyltransferases.

The direct analyses are preferred as they are in general more effective and usually more quantitative methods, which can be combined to glycome analysis.

In a preferred embodiment the invention is directed to combination of analysis of structural motifs and glycome analysis.

The Steps of a Structural Motif Analysis are:
1. Release of total glycans or total glycan groups from a tissue sample
2. Purification of the glycan fraction/fractions from biological material of the sample, preferably by a small scale column array or an array of solid-phase extraction steps
3. Analysis of the composition of the released glycans, preferably by mass spectrometry
4. Analysis of structural motifs present in of the glycan mixture, and optionally their relative abundancies
5. Optionally, comparing data about the glycan structural motifs with data produced from another tissue sample The steps 3 and 4 may be combined or performed in order first 4 and then 3.

Preferred Detailed Glycome Analysis Including Quantitative Data Analysis

Detailed Preferred Glycome Analysis According to the Invention

More detailed preferred analysis method include following analysis steps:
1. Preparing a tissue sample containing glycans for the analysis
2. Release total glycans or total glycan groups from a tissue sample
3. Optionally modifying glycans or part of the glycans.
4. Purification of the glycan fraction/fractions from biological material and reagents of the sample by a small scale column array
5. Optionally modifying glycans and optionally purifying modified glycans
6. Analysis of the composition of the released glycans preferably by mass spectrometry using at least one mass spectrometric analysis method
7. a) Optionally presenting the data about released glycans quantitatively and
7. b) Comparing the quantitative data set with another data set from another tissue sample and/or alternatively to 7a) and 7b)
8. Comparing data about the released glycans quantitatively or qualitatively with data produced from another tissue sample The present methods further allow the possibility to use part of the non-modified material or material modified in step 3 or 5 for additional modification step or step and optionally purified after modification step or steps, optionally combining modified samples, and analysis of additionally modified samples, and comparing results from differentially modified samples.

As mentioned above. It is realized that many of the individual monosaccharide compositions in a given glycome further corresponds to several isomeric individual glycans. The present methods allow for generation of modified glycomes. This is of particular use when modifications are used to reveal such information about glycomes of interest that is not directly available from a glycan profile alone (or glycome profiles to compare). Modifications can include selective removal of particular monosaccharides bound to the glycome by a defined glycosidic bond, by degradation by specific exoglycosidases or selective chemical degradation steps such as e.g. periodic acid oxidation. Modifications can also be introduced by using selective glycosyltransferase reactions to label the free acceptor structures in glycomes and thereby introduction of a specific mass label to such structures that can act as acceptors for the given enzyme. In preferred embodiment several of such modifications steps are combined and used to glycomes to be compared to gain further insights of glycomes and to facilitate their comparison.

Quantitative Presentation of Glycome Analysis

The present invention is specifically directed to quantitative presentation of glycome data.

Two-Dimensional Presentation by Quantitation and Component Indicators

The quantitative presentation means presenting quantitative signals of components of the glycome, preferably all major components of the glycome, as a two dimensional presentation including preferably a single quantitative indicator presented together with component identifier.

The preferred two dimensional presentations includes tables and graphs presenting the two dimensional data. The preferred tables list quantitative indicators in connection with, preferably beside or under or above the component identifiers, most preferably beside the identifier because in this format the data comprising usually large number of component identifier—quantitation indicator pairs.

Quantitation Indicator

The quantitation indicator is a value indicating the relative abundance of the single glycome component with regard to other components of total glycome or subglycome. The quantitation indicator can be directly derived from quantitative experimental data, or experimental data corrected to be quantitative.

Normalized Quantitation Indicator

The quantitation indicator is preferably a normalized quantitation indicator. The normalized quantitation indicator is defined as the experimental value of a single experimental quantitation indicator divided by total sum of quantitation indicators multiplied by a constant quantitation factor.

Preferred quantitation factors includes integer numbers from 1-1000 0000 000, more preferably integer numbers 1, 10 or 100, and more preferably 1 or 100, most preferably 100. The quantitation number one is preferred as commonly understandable portion from 1 concept and the most preferred quantitation factor 100 corresponds to common concept of percent values.

The quantitation indicators in tables are preferably rounded to correspond to practical accuracy of the measurements from which the values are derived from. Preferred rounding includes 2-5 meaningful accuracy numbers, more preferably 2-4 numbers and most preferably 2-3 numbers.

Component Indicators

The preferred component indicators may be experimentally derived component indicators. Preferred components indicators in the context of mass spectrometric analysis includes mass numbers of the glycome components, monosaccharide or other chemical compositions of the components and abbreviation corresponding to thereof, names of the molecules preferably selected from the group: descriptive names and abbreviations; chemical names, abbreviations and codes; and molecular formulas including graphic representations of the formulas.

It is further realized that molecular mass based component indicators may include multiple isomeric structures. The invention is in a preferred embodiment directed to practical analysis using molecular mass based component indicators. In more specific embodiment the invention is further directed to chemical or enzymatic modification methods or indirect methods according to the invention in order to resolve all or part of the isomeric components corresponding to a molecular mass based component indicators.

Glycan Signals

The present invention is directed to a method of accurately defining the molecular masses of glycans present in a sample, and assigning monosaccharide compositions to the detected glycan signals.

The Glycan signals according to the present invention are glycan components characterized by:

1° mass-to-charge ratio (m/z) of the detected glycan ion,
2° molecular mass of the detected glycan component, and/or
3° monosaccharide composition proposed for the glycan component.

Glycan Profiles

The present invention is further directed to a method of describing mass spectrometric raw data of Glycan signals as two-dimensional tables of:

1° monosaccharide composition, and
2° relative abundance, which form the Glycan profiles according to the invention. Monosaccharide compositions are as described above. For obtaining relative abundance values for each Glycan signal, the raw data is recorded in such manner that the relative signal intensities of the glycan signals represent their relative molar proportions in the sample. Methods for relative quantitation in MALDI-TOF mass spectrometry of glycans are known in the art (Naven & Harvey, 19xx; Papac et al., 1996) and are described in the present invention. However, the relative signal intensities of each Glycan signal are preferably corrected by taking into account the potential artifacts caused by e.g. isotopic overlapping, alkali metal adduct overlapping, and other disturbances in the raw data, as described below.

By forming these Glycan profiles and using them instead of the raw data, analysis of the biological data carried by the Glycan profiles is improved, including for example the following operations:

1° identification of glycan signals present in the glycan profile,
2° comparison of glycan profiles obtained from different samples,
3° comparison of relative intensities of glycan signals within the glycan profile, and
4° organizing the glycan signals present in the glycan profile into subgroups or subprofiles.

Analysis of Associated Signals to Produce Single Quantitative Signal (Quantitation Indicator)

Analysis of Associated Signals: Isotope Correction

Glycan signals and their associated signals may have overlapping isotope patterns. Overlapping of isotope patterns is corrected by calculating the experimental isotope patterns and subtracting overlapping isotope signals from the processed data.

Analysis of Associated Signals: Adduct Ion Correction in Positive Ion Mode

Glycan signals may be associated with signals arising from multiple adduct ions in positive ion mode, e.g. different alkali metal adduct ions. Different Glycan signals may give rise to adduct ions with similar m/z ratios: as an example, the adduct ions [Hex+Na]$^+$ and [dHex+K]$^+$ have m/z ratios of 203.05 and 203.03, respectively. Overlapping of adduct ions is corrected by calculating the experimental alkali metal adduct ion ratios in the sample and using them to correct the relative intensities of those Glycan signals that have overlapping adduct ions in the experimental data. Preferably, the major adduct ion type is used for comparison of relative signal intensities of the Glycan signals, and the minor adduct ion types are removed from the processed data. The calculated proportions of minor adduct ion types are subtracted from the processed data.

Analysis of Associated Signals: Adduct Ion Correction in Negative Ion Mode

Also in negative ion mode mass spectrometry, Glycan signals may be associated with signals arising from multiple adduct ions. Typically, this occurs with Glycan signals that correspond to multiple acidic group containing glycan structures. As an example, the adduct ions [NeuAc$_2$—H+Na]$^-$ at m/z 621.2 and [NeuAc—H+K]$^-$ at m/z 637.1, are associated with the Glycan signal [NeuAc$_2$—H]$^-$ at m/z 599.2. These adduct ion signals are added to the Glycan signal and thereafter removed from the processed data. In cases where different Glycan signals and adduct ion signals overlap, this is corrected by calculating the experimental alkali metal adduct ion ratios in the sample and using them to correct the relative intensities of those Glycan signals that have overlapping adduct ions in the experimental data.

Analysis of Associated Signals: Removal of Elimination Products

Glycan signals may be associated with signals, e.g. elimination of water (loss of $H_2O$), or lack of methyl ether or ester groups (effective loss of $CH_2$), resulting in experimental m/z values 18 or 14 mass units smaller than the Glycan signal respectively. These signals are not treated as individual Glycan signals, but are instead treated as associated signals and removed from the processed data.

Classification of Glycan Signals into Glycan Groups

According to the present invention, the Glycan signals are optionally organized into Glycan groups and Glycan group profiles based on analysis and classification of the assigned monosaccharide and modification compositions and the relative amounts of monosaccharide and modification units in the compositions, according to the classification rules described above:

Generation of Glycan Group Profiles.

To generate Glycan group profiles, the proportions of individual Glycan signals belonging to each Glycan group are summed. The proportion of each Glycan group of the total Glycan signals equals its prevalence in the Glycan profile. The Glycan group profiles of two or more samples can be compared. The Glycan group profiles can be further analyzed by arranging Glycan groups into subprofiles, and analyzing the relative proportions of different Glycan groups in the subprofiles. Similarly formed subprofiles of two or more samples can be compared.

Specific Technical Aspects of Tissue Glycome Analysis

Preferred Sample Sizes

The present invention is especially useful when low sample amounts are available. Practical cellular or tissue material may be available for example for diagnostic only in very small amounts.

Sample Sizes for Preferred Pico-Scale Preparation Methods

The inventors found surprisingly that glycan fraction could be produced and analysed effectively from samples containing low amount of material, for example 100 000-1 000 000 cells or a cubic millimeter (microliter) of the cells.

The combination of very challenging biological samples and very low amounts of samples forms another challenge for the present analytic method. The yield of the purification process must be very high. The estimated yields of the glycan fractions of the analytical processes according to the present invention varies between about 50% and 99%. Combined with effective removal of the contaminating various biological materials even more effectively over the wide preferred mass ranges according to the present invention show the ultimate performance of the method according to the present invention.

Isolation of Glycans and Glycan Fractions

The present invention is directed to a method of preparing an essentially unmodified glycan sample for analysis from the glycans present in a given sample.

A preferred glycan preparation process consists of the following steps:

1° isolating a glycan-containing fraction from the sample,
2° . . . Optionally purification the fraction to useful purity for glycome analysis The preferred isolation method is: chosen according to the desired glycan fraction to be analyzed. The isolation method may be either one or a combination of the following methods, or other fractionation methods that yield fractions of the original sample:

1° extraction with water or other hydrophilic solvent, yielding water-soluble glycans or glycoconjugates such as free oligosaccharides or glycopeptides, 2° extraction with hydrophobic solvent, yielding hydrophilic glycoconjugates such as glycolipids, 3° N-glycosidase treatment, especially *Flavobacterium meningosepticum* N-glycosidase F treatment, yielding N-glycans, 4° alkaline treatment, such as mild (e.g. 0.1 M) sodium hydroxide or concentrated ammonia treatment, either with or without a reductive agent such as borohybride, in the former case in the presence of a protecting agent such as carbonate, yielding O-elimination products such as O-glycans and/or other elimination products such as N-glycans, 5° endoglycosidase treatment, such as endo-β-galactosidase treatment, especially *Escherichia freundii* endo-β-galactosidase treatment, yielding fragments from poly-N-acetyllactosamine glycan chains, or similar products according to the enzyme specificity, and/or 6° protease treatment, such as broad-range or specific protease treatment, especially trypsin treatment, yielding proteolytic fragments such as glycopeptides.

The released glycans are optionally divided into sialylated and non-sialylated subfractions and analyzed separately. According to the present invention, this is preferred for improved detection of neutral glycan components, especially when they are rare in the sample to be analyzed, and/or the amount or quality of the sample is low. Preferably, this glycan fractionation is accomplished by graphite chromatography.

According to the present invention, sialylated glycans are optionally modified in such manner that they are isolated together with the non-sialylated glycan fraction in the non-sialylated glycan specific isolation procedure described above, resulting in improved detection simultaneously to both non-sialylated and sialylated glycan components. Preferably, the modification is done before the non-sialylated glycan specific isolation procedure. Preferred modification processes include neuraminidase treatment and derivatization of the sialic acid carboxyl group, while preferred derivatization processes include amidation and esterification of the carboxyl group.

Glycan Release Methods

The preferred glycan release methods include, but are not limited to, the following methods:

Free glycans—extraction of free glycans with for example water or suitable water-solvent mixtures.

Protein-linked glycans including O- and N-linked glycans—alkaline elimination of protein-linked glycans, optionally with subsequent reduction of the liberated glycans.

Mucin-type and other Ser/Thr O-linked glycans—alkaline β-elimination of glycans, optionally with subsequent reduction of the liberated glycans.

N-glycans—enzymatic liberation, optionally with N-glycosidase enzymes including for example N-glycosidase F from *C. meningosepticum*, Endoglycosidase H from *Streptomyces*, or N-glycosidase A from almonds.

Lipid-linked glycans including glycosphingolipids—enzymatic liberation with endoglycoceramidase enzyme; chemical liberation; ozonolytic liberation.

Glycosaminoglycans—treatment with endo-glycosidase cleaving glycosaminoglycans such as chondroinases, chondroitin lyases, hyalurondases, heparanases, heparatinases, or keratanases/endo-beta-galactosidases; or use of O-glycan release methods for O-glycosidic Glycosaminoglycans; or N-glycan release methods for N-glycosidic glycosaminoglycans or use of enzymes cleaving specific glycosaminoglycan core structures; or specific chemical nitrous acid cleavage methods especially for amine/N-sulphate comprising glycosaminoglycans Glycan fragments—specific exo- or endoglycosidase enzymes including for example keratanase, endo-β-galactosidase, hyaluronidase, sialidase, or other exo- and endoglycosidase enzyme; chemical cleavage methods; physical methods Effective Purification Process The invention describes special purification methods for glycan mixtures from tissue samples. Previous glycan sample purification methods have required large amounts of material and involved often numerous chromatographic steps and even purification of specific proteins. It is known that protein glycosylation varies protein specifically and single protein specific data can thus not indicate the total tissue level glycosylation. Purification of single protein is a totally different task than purifying the glycan fraction according to the present invention.

When the purification starts from a tissue or cells, the old processes of prior art involve often laborious homogenisation steps affecting the quality of the material produced. The present purification directly from a biological sample such as cell or tissue material, involves only a few steps and allows quick purification directly from the biological material to analysis preferably by mass spectrometry.

Purification from Cellular Materials of Cells and/or Tissues

The cellular material contains various membranes, small metabolites, various ionic materials, lipids, peptides, proteins etc. All of the materials can prevent glycan analysis by mass spectrometry if these cannot be separated from the glycan fraction. Moreover, for example peptide or lipid materials may give rise to mass spectrometric signals within the preferred mass range within which glycans are analysed. Many mass spectrometric methods, including preferred MALDI-mass spectrometry for free glycan fractions, are more sensitive for peptides than glycans. With the MALDI method peptides in the sample may be analysed with approximately 1000-fold higher sensitivity in comparison to methods for glycans. Therefore the method according to the present invention should be able to remove for example potential peptide contaminations from free glycan fractions most effectively. The method should remove essential peptide contaminations from the whole preferred mass range to be analysed.

Purification Suitable for Mass Spectrometry, Especially MALDI-TOF Mass Spectrometry The inventors discovered that the simple purification methods would separate released glycans from all possible cell materials so that 1) The sample is technically suitable for mass spectrometric analysis.

This includes two major properties, a) the samples is soluble for preparation of mass spectrometry sample and b) does not have negative interactions with chemicals involved in the mass spectrometric method, preferably the sample dries or crystallizes properly with matrix chemical used in MALDI-TOF mass spectrometry When using MALDI-technologies, the sample does not dry or crystallize properly if the sample contains harmful impurity material in a significant amount.

2) The purity allows production of mass spectrum of suitable quality.

a) The sample has so low level impurities that it gives mass spectrometric signals. Especially when using MALDI-TOF mass spectrometry, signals can be suppressed by background so that multiple components/peaks cannot be obtained.

b) the sample is purified so that there is no major impurity signals in the preferred mass ranges to be measured.

Preferably the present invention is directed to analysis of unusually small sample amounts. This provides a clear benefit over prior art, when there is small amount amount of sample available from a small region of diseased tissue or diagnostic sample such as tissue slice produced for microscopy or biopsy sample. Methods to achieve such purity (purity being a requirement for the sensitivity needed for such small sample amounts) from tissue or cell samples (or any other complex biological matices e.g. serum, saliva) has not been described in the prior art.

In a preferred embodiment the method includes use of non-derived glycans and avoiding general derived glycans. There are methods of producing glycan profiles including modification of all hydroxyl groups in the sample such as permethylation. Such processes require large sample amounts and produces chemical artifacts such as undermethylated molecules lowering the effectivity of the method. These artefact peaks cover all minor signals in the spectra, and they can be misinterpreted as glycan structures. It is of importance to note that in glycome analyses the important profile to profile differences often reside in the minor signals. In a specific embodiment the present invention is directed to site specific modification of the glycans with effective chemical or enzyme reaction, preferably a quantitative reaction.

Preferred Analytical Technologies for Glycome Analysis

Mass Spectrometric Analysis of Glycomes

The present invention is specifically directed to quantitative mass spectrometric methods for the analysis of glycomes. Most preferred mass spectrometric methods are MALDI-TOF mass spectrometry methods.

MALDI-TOF Analysis

The inventors were able to optimise MALDI-TOF mass spectrometry for glycome analysis.

The preferred mass spectrometric analysis process is MALDI-TOF mass spectrometry, where the relative signal intensities of the unmodified glycan signals represent their relative molar proportions in the sample, allowing relative quantification of both neutral (Naven & Harvey, 19xx) and sialylated (Papac et al., 1996) glycan signals. Preferred experimental conditions according to the present invention are described under Experimental procedures of Examples listed below.

Preferred mass ranges for MALDI-TOF Analysis and Released Non-Modified Glycomes

For MALDI-TOF mass spectrometry of unmodified glycans in positive ion mode, optimal mass spectrometric data recording range according to the present invention is over m/z 200, more preferentially between m/z 200-10000, or even more preferably between m/z 200-4000 for improved data quality. In the most preferred form according to the present invention, the data is recorded between m/z 700-4000 for accurate relative quantification of glycan signals.

For MALDI-TOF mass spectrometry of unmodified glycans in negative ion mode, optimal mass spectrometric data recording range according to the present invention is over m/z 300, more preferentially between m/z 300-10000, or even more preferably between m/z 300-4000 for improved data quality. In the most preferred forms according to the present invention, the data is recorded between m/z 700-4000 or most preferably between m/z 800-4000 for accurate relative quantification of glycan signals.

Practical mz-Ranges

The practical ranges comprising most of the important signals, as observed by the present invention may be more limited than these. Preferred practical ranges includes lower limit of about m/z 400, more preferably about m/z 500, and even more preferably about m/z 600, and most preferably m/z about 700 and upper limits of about m/z 4000, more preferably m/z about 3500 (especially for negative ion mode), even more preferably m/z about 3000 (especially for negative ion mode), and in particular at least about 2500 (negative or positive ion mode) and for positive ion mode to about m/z 2000 (for positive ion mode analysis). The preferred range depends on the sizes of the sample glycans, samples with high branching or polysaccharide content or high sialylation levels are preferably analysed in ranges containing higher upper limits as described for negative ion mode. The limits are preferably combined to form ranges of maximum and minimum sizes or lowest lower limit with lowest higher limit, and the other limits analogously in order of increasing size Preferred Analysis Modes for MALDI-TOF for Effective Glycome Analysis The inventors were able to show effective quantitative analysis in both negative and positive mode mass spectrometry.

Sample Handling

The inventors developed optimised sample handling process for preparation of the samples for MALDI-TOF mass spectrometry.

Glycan Purification

The glycan purification method according to the present invention consists of at least one of purification options, preferably in specific combinations described below, including the following purification options:
1) Precipitation-extraction;
2) Ion-exchange;
3) Hydrophobic interaction;
4) Hydrophilic interaction; and
5) Affinity to graphitized carbon.

1) Precipitation-extraction may include precipitation of glycans or precipitation of contaminants away from the glycans. Preferred precipitation methods include:
1. Glycan material precipitation, for example acetone precipitation of glycoproteins, oligosaccharides, glycopeptides, and glycans in aqueous acetone, preferentially ice-cold over 80% (v/v) aqueous acetone; optionally combined with extraction of glycans from the precipitate, and/or extraction of contaminating materials from the precipitate;
2. Protein precipitation, for example by organic solvents or trichloroacetic acid, optionally combined with extraction of glycans from the precipitate, and/or extraction of contaminating materials from the precipitate;
3. Precipitation of contaminating materials, for example precipitation with trichloroacetic acid or organic solvents such as aqueous methanol, preferentially about ⅔ aqueous methanol for selective precipitation of proteins and other non-soluble materials while leaving glycans in solution;

2) Ion-exchange may include ion-exchange purification or enrichment of glycans or removal of contaminants away from the glycans. Preferred ion-exchange methods include:
1. Cation exchange, preferably for removal of contaminants such as salts, polypeptides, or other cationizable molecules from the glycans; and
2. Anion exchange, preferably either for enrichment of acidic glycans such as sialylated glycans or removal of charged contaminants from neutral glycans, and also preferably for separation of acidic and neutral glycans into different fractions.

3) Hydrophilic interaction may include purification or enrichment of glycans due to their hydrophilicity or specific adsorption to hydrophilic materials, or removal of contaminants such as salts away from the glycans. Preferred hydrophilic interaction methods include:
1. Hydrophilic interaction chromatography, preferably for purification or enrichment of glycans and/or glycopeptides;
2. Adsorption of glycans to cellulose in hydrophobic solvents for their purification or enrichment, preferably to microcrystalline cellulose, and even more preferably using an n-butanol:methanol:water or similar solvent system for adsorption and washing the adsorbed glycans, in most preferred system n-butanol:methanol:water in relative volumes of 10:1:2, and water or water:ethanol or similar solvent system for elution of purified glycans from cellulose.

4) Affinity to graphitized carbon may include purification or enrichment of glycans due to their affinity or specific adsorption to graphitized carbon, or removal of contaminants away from the glycans. Preferred graphitized carbon affinity methods include porous graphitized carbon chromatography.

Preferred purification methods according to the invention include combinations of one or more purification options. Examples of the most preferred combinations include the following combinations:
1) For neutral underivatized glycan purification: 1. cation exchange of contaminants, 2. hydrophobic adsorption of contaminants, and 3. graphitized carbon affinity purification of glycans.
1) For sialylated underivatized glycan purification: 1. cation exchange of contaminants, 2. hydrophobic adsorption of contaminants, 3. adsorption of glycans to cellulose, and 4. graphitized carbon affinity purification of glycans.

NMR-Analysis of Glycomes

The present invention is directed to analysis of released glycomes by spectrometric method useful for characterization of the glycomes. The invention is directed to NMR spectroscopic analysis of the mixtures of released glycans. The inventors showed that it is possible to produce a released glycome from tissue samples in large scale enough and useful purity for NMR-analysis of the glycome.

In a preferred embodiment the NMR-analysis of the tissue glycome is one dimensional proton NMR-analysis showing structural reporter groups of the major components in the glycome. The present invention is further directed to combination of the mass spectrometric and NMR analysis of small scale tissue samples.

Analysis of Changes Related to Animal Individuals, Animal Species and Animal Status The inventors further realized major glycome differences between samples from the same species. The invention is specifically directed to analysis of individual differences between animals. The invention is further directed to the use of the information in breeding of animals, especially production animals.

The inventors further realized major glycome differences between samples from animals related to the status of the animal. The invention is especially directed to the analysis of biological status related changes of animal.

The inventors further noticed major species specific differences in the total released glycomes analysed. It is realized that species specific glycome differences are useful for analysis of effects of glycosylations when animal materials from different species are in contact with each other.

In a preferred embodiment the glycosylation is analysed when one animal is consumed as food or feed of another and the analysis is directed to potential allergic or immunogenic effects in the animal consuming the other animal. Preferably the invention is directed to the use of analysis of animal derived human feeds and feeds derived from other animals.

In another embodiment the invention is directed to analysis the invention is directed to situations when one animal species is exposed to material from another animal in air, especially in context of allergy inducing air mediated animal contacts.

Preferred Target Species, Especially Animals for Tissue Analysis

The invention revealed that glycome oligosaccharide mixtures can be produced effectively from eukaryotic species especially animal tissues.

Plant and insect differentiated cells are separately preferred eukaryotic materials.

Preferred animals include vertebrate animals, more preferably mammals, more preferably domestic or farm animals or human, analysis of human samples is most preferred. The preference of animals is based on similarity of sample compositions and availability animal materials and presence of individual, species and status related changes.

Most preferred domestic or farm animals includes pets such as cat, dog, pet rodents (such as mouse, hamster, rat) and production/farm animals such as animals selected from the group: pig, ruminats (especially ones producing milk such as cow, buffalo); avian production animals (such as hen (chicken), turkey, duck), and horse.

The invention is especially directed to analysis of specific tissues of animal in context of breeding of animals especially production animals, horse and cats or dogs. The invention is especially directed to analysis of specific tissues of animal in context of breeding of especially production animals, and major pets under extensive breeding preferably cats or dogs.

The invention is further directed to analysis of species specific differences between the preferred domestic or farm animals in two preferred contexts either in context when the animal is context of food contact with human or in context of air contact with human. The preferred animal in food contact are major production/farm animals, which are also preferred in air contact with animals as well as major pets cats and dogs.

The invention is further directed to analysis of domestic and farm animals in context of the status of the animal. It is realized that it is useful to analyze of status of the cells, when the health or physiological status of the animal is needed to revealed.

The invention is in a preferred embodiment directed to analysis of human type primates such as monkeys especially apes (examples include chimpanzee, pygmy chimpanzee, gorilla, orangutan) and human, the preference is based on close similarity of primates and human on genetic and cell biological level, providing similarity for samples to be analysed and scientifically important evolution based glycosylation changes between similar species.

The invention is further directed to analysis of animals useful for development of pharmaceutical and therapeutic materials. The preferred animals include rodents (such as mouse, hamster, rat) and human type primates. It is further preferred to analyze these animals in context of air mediated contact with human or other animals.

The invention is further directed to animals involved in sports, especially horses and dogs. It is realized that development of animals in sports involves especially analysis of individual and animal status related changes. It is further preferred to analyze these animals in context of air mediated contact with human or other animals.

Targets of Analysis—Tissue Materials

The present invention refers as "tissue materials" all preferred target tissue related material including for example tissues, secretions and cultivated differentiated cells Preferred Tissue Type The present invention is preferably directed to specific tissue types for the analysis according to the invention. The tissue type are found to be very suitable and feasible for the analysis according to the invention. The analysis is especially directed to analysis of 1) tissues of gastrointestinal track, preferably mouth, larynx, stomach, large and small intestine
2) internal organs such as ovarian tissue, liver, lungs, or kidney
3) tissues of circulatory system, especially blood
4) cultivated cell line models of the differentiated tissues Preferred Tissue Parts The present invention is preferably directed to specific parts of tissue for the analysis according to the invention. The inventors realized that it is possible perform glycomics analysis of specific parts of tissues and reveal differences useful for studies of diseases and disease induced changes and other changes or presence of receptor structures on specific subtissues. Preferred subtissues includes 1) tissues surfaces, especially epithelia of gastrointestinal tract and cell surfaces and
2) components of circulatory system, preferably serum/plasma, and blood cells, especially red cells and white blood cells Preferred Tissue Derivatives to be Analysed Including Liquid Secretions The invention is further directed to material produced by tissues.

Preferably the invention is directed to the analysis of secretions of tissues, preferably liquid secretions of tissues, preferably milk, saliva or urine. It is realized that liquid secretions form a specific group of tissue derived materials found especially useful for the glycome analysis methods according to the invention.

Milk is especially preferred as a food material consumed by animals and human and analysis with regard to each of individual specific, animal status specific and species specific differences.

The invention is under separate preferred embodiment directed to the analysis of specific conjugated glycomes such as protein or lipid derived glycomes, from the secretions and in another preferred embodiment free soluble glycomes of the secretions.

Soluble Glycome Materials: Tissue and/or Secretion Materials, Especially with High Protein Content The invention is in a preferred embodiment directed to specific methods developed for the analysis of soluble glycome material from tissues and secretions. This group includes background for purification different from solid tissue and cell derived materials. The group includes tissue solutions such as blood serum/plasma and liquid secretions such as milk, saliva and urine.

The invention is further directed to the soluble glycome materials with high protein content including preferably milk and serum/plasma. The materials are especially directed as specific target of technologies directed to analysis of high protein content solutions, in separate preferred embodiments the technologies are directed to analysis human serum or bovine milk.

Milk Glycomes

The present invention is specifically directed to glycome analysis of milks form human and other animals, preferably from ruminant animals such as bovine, buffalo, sheep, goat, and camel, the most common milk production animals bovine and buffalo are preferred. Most preferably the common bovine milk is analysed.

Preferred Ruminant Milk Glycomes

The invention is specifically directed to analysis of colostrums and regular milks of ruminant milks. The invention represent novel total glycomics analysis methods for both secreted and conjugated glycomes. The invention is further directed to glycome analysis according to the invention to food production fractions and specific milk products of ruminant milks.

Bovine Milk Glycomes

The invention is especially directed to novel total glycomics analysis methods for both secreted and conjugated glycomes from bovine milks. The invention specifically represents novel glycomes released from proteins of bovine milks.

The invention is further directed to glycomes released from proteins from regular milk and in a separate embodiment to glycomes released from proteins of bovine colostrums. The invention is further directed to glycome analysis according to the invention to food production fractions and specific milk products of bovine milk such whey, low fat milk, or buttermilk.

Subcomponents of Glycomes, Especially from Secreted Proteins such as Milks

The invention is further directed to methods for selecting specific components of glycomes and searching enriched fractions such as specific protein fraction comprising the specific glycome components.

As a specific example and embodiment of a purified glycome component the invention is directed to protein, referred as mannose protein, containing enriched with mannose glycans such as high-mannose or low mannose glycans isolated from bovine milk. The invention is especially directed to bovine lactoferrin carrying almost exclusively mannose glycans. It was further revealed that the lactoferrin is expressed only in certain milk batches.

The present invention is further directed to analysis of milks to reveal specific animals and conditions for effective production of mannose proteins, especially mannose lactoferrin. The invention is further directed to single step chromatographic purification of the mannose lactoferrin.

Tissue Surface Glycomes

In a preferred embodiment the invention is directed to special methods for the analysis of the surfaces of tissues.

The preferred tissue surfaces includes
1) epithelia of the preferred gastrointestinal tract tissues and
2) surfaces of cells according to cells on surface of tissues or separable homogeneously from tissue, such as blood cells and
3) surfaces of cultivated cells which may be used as models for differentiated tissues.

Non-Derivatized Released Target Material Surface Glycomes and Production

In a preferred embodiment the invention is directed to non-derivatized released cell surface glycomes. The non-derivatized released cell surface glycomes correspond more exactly to the fractions of glycomes that are localized on the cell surfaces, and thus available for biological interactions. These cell surface localized glycans are of especial importance due to their availability for biological interactions as well as targets for reagents (e.g. antibodies, lectins etc. . . . ) targeting the cells or tissues of interest. The invention is further directed to release of the cell surface glycomes, preferably from intact cells by hydrolytic enzymes such as proteolytic enzymes, including proteinases and proteases, and/or glycan releasing enzymes, including endo-glycosidases or protein N-glycosidases. Preferably the surface glycoproteins are cleaved by proteinase such as trypsin and then glycans are analysed as glycopeptides or preferably released further by glycan releasing enzyme.

Cell Models of Differentiated Tissues

The invention is further directed to cultured cells corresponding to differentiated cells. Such cells may be used as models for differentiated cells. The differentiated cells include differentiated cell models of cancer.

Stably growing differentiated cultured cell lines are also used in production mammalian proteins and for other biotechnical production for example in cell therapies.

It is realized that the differentiated cells would need to be controlled with regard to cells status and individual cell line specific differences. It is realized that cell status would need to be checked with regard to numerous factors related to cell status. It is further realized that there is differences between individual cell lines when these are derived from different animal individuals.

In case the differentiated cells would be used in context of contact with other animals from different species than from which the cell line is derived there is need for controlling species specific differences.

It is especially realized that it would be useful to check status of differentiated cells used in production of biotechnical products, such as recombinant therapeutic proteins such as antibodies, growth factors and recombinant receptors including recombinant TNF-alpha receptors. The invention is especially directed to the analysis of differentiated cell lines producing recombinant proteins.

The Glycome Compositions

The invention is further directed to the compositions and compositions produced by the methods according to the invention. The invention further represent preferred methods for analysis of the glycomes, especially mass spectrometric methods.

The invention is specifically directed to released glycomes derived conjugated glycans from preferred tissue materials and cell models of differentiated tissues.

Purification Method

The invention represents effective methods for purification of oligosaccharide fractions from tissues, especially in very low scale. The prior art has shown analysis of separate glycome components from tissues, but not total glycomes. It is further realized that the methods according to the invention are useful for analysis of glycans from isolated proteins or peptides.

Analysis of Glycomes

The invention is further directed to novel quantitative analysis methods for glycomes. The glycome analysis produces large amounts of data. The invention reveals methods for the analysis of such data quantitatively and comparison of the data between different samples. The invention is especially directed to quantitative two-dimensional representation of the data.

Integrated Glycome Analysis

The invention is further directed to integrated glycomics or glycome analysis process including
1) Optional release of glycans from tissues
2) isolation/purification of glycans from sample,
3) analysis of the glycome
4) quantitative presentation of the data The first step is optional as the method is further directed to analysis of known and novel secretion derivable soluble glycomes.

Application of the Methods for Analysis of Proteins

The invention represents effective methods for the practical analysis of glycans from isolate proteins especially from very small amounts of samples. The invention is especially directed to the application of the methods for the analysis of proteins using the purification method, analysis methods and/or integrated glycome analysis.

Product by Process

The present invention is specifically directed to the glycan fraction produced according to the present invention from the pico scale tissue material sample according to the present invention. The preferred glycan fraction is essentially devoid of signals of contaminating molecules within the preferred mass range when analysed by MALDI mass spectrometry according to the present invention.

Preferred Uses of Glycomes and Analysis Thereof with Regard to Status of Cells

In the present invention the word cell refer to cells of tissue material according to the invention, especially cultivated differentiated cells Product by Process The present invention is specifically directed to the glycan fraction produced according to the present invention from the pico scale tissue material sample according to the present invention. The preferred glycan fraction is essentially devoid of signals of contaminating molecules within the preferred mass range when analysed by MALDI mass spectrometry according to the present invention.

The glycome products from tissue samples according to present invention are produced preferably directly from complete tissue material cells or membrane fractions thereof, more preferably directly from intact cells as effectively shown in examples. In another preferred embodiment the glycome fractions are cell surface glycomes and produced directly from surfaces of complete tissue material cells, preferably intact or essentially intact cells of tissue materials or surfaces of intact tissues according to the invention. In another embodiment the glycome products according to the invention are produced directly from membrane fraction Preferred Uses of Glycomes and Analysis Thereof with Regard to Status of Cells Search of Novel of Novel Carbohydrate Marker Structures It is further realized that the analysis of glycome is useful for search of most effectively altering glycan structures in the tissue materials for analysis by other methods.

The glycome component identified by glycome analysis according to the invention can be further analysed/verified by known methods such as chemical and/or glycosidase enzymatic degradation(s) and further mass spectrometric analysis and by fragmentation mass spectrometry, the glycan component can be produced in larger scale by know chromatographic methods and structure can be verified by NMR— spectroscopy.

The other methods would preferably include binding assay using specific labelled carbohydrate binding agents including especially carbohydrate binding proteins (lectins, antibodies, enzymes and engineered proteins with carbohydrate binding activity) and other chemicals such as peptides or aptamers aimed for carbohydrate binding. It is realized that the novel marker structure can be used for analysis of cells, cell status and possible effects of contaminats to cell with similar indicative value as specific signals of the glycan mass components in glycome analysis by mass spectrometry according to the invention.

The invention is especially directed to search of novel carbohydrate marker structures from cell/tissue surfaces, preferably by using cell surface profiling methods. The cell surface carbohydrate marker structures would be further preferred for the analysis and/or sorting of cells.

Control of Cell Status and Potential Contaminations by Glycosylation Analysis

Control of Cell Status

Contamination/Harmful Effect Due to Nature of Raw Material for Producing a Cell Population Species specific, tissue specific, and individual specific differences in glycan structures are known. The difference between the origin of the cell material and the potential recipient of transplanted material may cause for example immunologic or allergic problems due to glycosylation differences. It is further noticed that culture of cells may cause changes in glycosylation. When considering human derived cell materials according to the present invention, individual specific differences in glycosylation are a potent source of harmful effects.

Control of Raw Material Cell Population

The present invention is directed to control of glycosylation of cell populations to be used in therapy.

The present invention is specifically directed to control of glycosylation of cell materials, preferably when
1) there is difference between the origin of the cell material and the potential recipient of transplanted material. In a preferred embodiment there are potential inter-individual specific differences between the donor of cell material and the recipient of the cell material. In a preferred embodiment the invention is directed to animal or human, more preferably human specific, individual person specific glycosylation differences. The individual specific differences are preferably present in tissue materials. The invention is preferably not directed to observation of known individual specific differences such as blood group antigens changes on erythrocytes.
2) There is possibility in variation due to disease specific variation in the materials. The present invention is specifically directed to search of glycosylation differences in the tissue materials according to the present invention associated with infectious disease, inflammatory disease, or malignant disease. Part of the inventors have analysed numerous types of early human cells and observed similar glycosylation types in certain cancers and tumors.
3) There is a possibility of specific inter-individual biological differences in the animals, preferably humans, from which the cell are derived for example in relation to species, strain, population, isolated population, or race specific differences in the cell materials.

Time Dependent Changes During Cultivation of Cells

Furthermore during long term cultivation of cells spontaneous mutations may be caused in cultivated cell materials. It is noted that mutations in cultivated cell lines often cause harmful defects on glycosylation level.

It is further noticed that cultivation of cells may cause changes in glycosylation. It is realized that minor changes in any parameter of cell cultivation including quality and concentrations of various biological, organic and inorganic molecules, any physical condition such as temperature, cell density, or level of mixing may cause difference in cell materials and glycosylation. The present invention is directed to monitoring glycosylation changes according to the present invention in order to observe change of cell status caused by any cell culture parameter affecting the cells.

The present invention is in a preferred embodiment directed to analysis of glycosylation changes when the density of cells is altered. The inventors noticed that this has a major impact of the glycosylation during cell culture.

In case there is heterogeneity in cell material this may cause observable changes or harmful effects in glycosylation.

Furthermore, the changes in carbohydrate structures, even non-harmful or functionally unknown, can be used to obtain information about the exact genetic status of the cells.

The present invention is specifically directed to the analysis of changes of glycosylation, preferably changes of sialylation according to the present invention in order to observe changes of cell status during cell cultivation.

Contaminations or Alterations in Cells Due to Process Conditions

Conditions and Reagents Inducing Harmful Glycosylation or Harmful Glycosylation Related Effects to Cells During Cell Handling The inventors further revealed conditions and reagents inducing harmful glycans to be expressed by cells with same associated problems as the contaminating glycans. The inventors found out that several reagents used in a regular cell purification process caused changes cells being purified.

It is realized, that the materials during cell handling may affect the glycosylation of cell materials. This may be based on the adhesion, adsorption, or metabolic accumulation of the structure in cells under processing.

In a preferred embodiment the cell handling reagents are tested with regard to the presence glycan component being antigenic or harmful structure such as cell surface NeuGc, Neu-O-Ac or mannose structure.

The inventors note effects of various effector molecules in cell culture on the glycans expressed by the cells if absorption or metabolic transfer of the carbohydrate structures have not been performed. The effectors typically mediate a signal to cell for example through binding a cell surface receptor.

The effector molecules include various cytokines, growth factors, and their signalling molecules and co-receptors. The effector molecules may be also carbohydrates or carbohydrate binding proteins such as lectins.

Controlled Cell Isolation/Purification and Culture Conditions to Avoid Contaminations with Harmful Glycans or Other Alteration in Glycome Level Stress Caused by Cell Handling It is realized that cell handling including isolation/purification, and handling in context of cell storage and cell culture processes are not natural conditions for cells and cause physical and chemical stress for cells. The present invention allows control of potential changes caused by the stress. The control may be combined by regular methods may be combined with regular checking of cell viability or the intactness of cell structures by other means.

Examples of Physical and/or Chemical Stress in Cell Handling Step

Washing and centrifuging cells cause physical stress which may break or harm cell membrane structures. Cell purifications and separations or analysis under non-physiological flow conditions also expose cells to certain non-physiological stress. Cell storage processes and cell preservation and handling at lower temperatures affects the membrane structure. All handling steps involving change of composition of media or other solution, especially washing solutions around the cells affect the cells for example by altered water and salt balance or by altering concentrations of other molecules effecting biochemical and physiological control of cells.

Observation and Control of Glycome Changes by Stress in Cell Handling Processes

The inventors revealed that the method according to the invention is useful for observing changes in cell membranes which usually effectively alter at least part of the glycome observed according to the invention. It is realized that this related to exact organization and intact structures cell membranes and specific glycan structures being part of the organization.

The present invention is specifically directed to observation of total glycome and/or cell surface glycomes, these methods are further aimed for the use in the analysis of intactness of cells especially in context of stressful condition for the cells, especially when the cells are exposed to physical and/or chemical stress. It is realized that each new cell handling step and/or new condition for a cell handling step is useful to be controlled by the methods according to the invention. It is further realized that the analysis of glycome is useful for search of most effectively altering glycan structures for analysis by other methods such as binding by specific carbohydrate binding agents including especially carbohydrate binding proteins (lectins, antibodies, enzymes and engineered proteins with carbohydrate binding activity).

Controlled Cell Preparation (Isolation or Purification) with Regard to Reagents

The inventors analysed process steps of common cell preparation methods. Multiple sources of potential contamination by animal materials were discovered.

The present invention is specifically directed to carbohydrate analysis methods to control of cell preparation processes. The present invention is specifically directed to the process of controlling the potential contaminations with animal type glycans, preferably N-glycolylneuraminic acid at various steps of the process.

The invention is further directed to specific glycan controlled reagents to be used in cell isolation The glycan-controlled reagents may be controlled on three levels:

1. Reagents controlled not to contain observable levels of harmful glycan structure, preferably N-glycolylneuraminic acid or structures related to it 2. Reagents controlled not to contain observable levels of glycan structures similar to the ones in the cell preparation 3. Reagent controlled not to contain observable levels of any glycan structures.

The control levels 2 and 3 are useful especially when cell status is controlled by glycan analysis and/or profiling methods. In case reagents in cell preparation would contain the indicated glycan structures this would make the control more difficult or prevent it. It is further noticed that glycan structures may represent biological activity modifying the cell status.

Cell Preparation Methods Including Glycan-Controlled Reagents

The present invention is further directed to specific cell purification methods including glycan-controlled reagents.

Storage Induced Changes Causing Harmful Glycosylations or Change in the Status of Cells It was realized that storage of the cell materials may cause harmful changes in glycosylation or changes in cell status observable by glycosylation analysis according to the present invention.

Changes Observable in Context of Low Temperature Storage or Handling of Cells

The inventors discovered that keeping the cells in lower temperatures alters the status of cells and this is observable by analysing the chemical structures of cells, preferably the glycosylation of the cells. The lower temperatures usually vary between 0-36 degrees of Celsius including for example incubator temperature below about 36 degrees of Celsius more preferably below 35 degrees of Celsius, various room temperatures, cold room and fridge temperatures typically between 2-10 degrees of Celsius, and temperatures from incubation on ice close to 0 degrees of Celsius typically between 0-4 degrees of Celsius. The lowered temperatures are typically needed for processing of cells or temporary storage of the preferred cells.

The present invention is specifically directed to analysis of the status of cells kept in low temperatures in comparison to natural body temperatures. In a preferred embodiment the control is performed after certain time has passed from process in lower temperature in order to confirm the recovery of the cells from the lower temperature. In another preferred embodiment the present invention is directed to development of lower temperature methods by controlling the chemical structures of cells, preferably by controlling glycosylation according to the present invention.

Changes Observable in Context of Cryopreservation

The inventors discovered that cryopreservation alters the status of cells and this observable analysing the chemical structures of cells, preferably the glycosylation of the cells. The present invention is specifically directed to analysis of the status of cryopreserved cells. In a preferred embodiment the control is performed after certain time has passed from preservation in order to confirm the recovery of the cells from the cryopreservation. In another preferred embodiment the present invention is directed to development of cryopreservation methods by controlling the chemical structures of cells, preferably by controlling glycosylation according to the present invention.

Contaminations with Harmful Glycans Such as Antigenic Animal Type Glycans

Several glycans structures contaminating cell products may weaken the biological activity of the product.

The harmful glycans can affect the viability during handling of cells, or viability and/or desired bioactivity and/or safety in therapeutic use of cells.

The harmful glycan structures may reduce the in vitro or in vivo viability of the cells by causing or increasing binding of destructive lectins or antibodies to the cells. Such protein material may be included e.g. in protein preparations used in cell handling materials. Carbohydrate targeting lectins are also present on human tissues and cells, especially in blood and endothelial surfaces. Carbohydrate binding antibodies in human blood can activate complement and cause other immune responses in vivo. Furthermore immune defense lectins in blood or leukocytes may direct immune defense against unusual glycan structures.

Additionally harmful glycans may cause harmful aggregation of cells in vivo or in vitro. The glycans may cause unwanted changes in developmental status of cells by aggregation and/or changes in cell surface lectin mediated biological regulation.

Additional problems include allergenic nature of harmful glycans and misdirected targeting of cells by endothelia/cellular carbohydrate receptors in vivo.

Contaminations from Reagents

The present invention is specifically directed to control of the reagents used to prevent contamination by harmful glycan structures. The harmful glycan structures may originate from reagents used during cell handling processes such as cell preservation, cell preparation, and cell culture.

Preferred reagents to be controlled according to the present invention include cell blocking reagents, such as antibody receptor blocking reagents, washing solutions during cell processing, material blocking reagents, such as blocking reagents for materials like for example magnetic beads. Preferably the materials are controlled:

1. so that these would not contain a contaminating structure, or more specifically preferred glycan structure according to the invention
2. so that the materials contain very low amounts or do not contain any potentially harmful structures according to the invention.

Structural Features Derived from the Glycome Compositions
Novel Glycomes from Tissues The present invention revealed that it is possible to profile tissues by released glycomes from tissues. The invention revealed novel glycan groups which haven't been observed in any similar composition derived from biological materials. The novel glycan groups include 1. Degraded mannose glycans including
   a. novel low mannose glycan group,
   b. novel Soluble mannose oligomer comprising glycome comprising single reducing terminal GlcNAc-unit, soluble mannose-GlcNAc1-glycome
2. non-sialylated acidic (sulphated and/or fosforylated) glycans and
3. N-glycans containing terminal glucose structures The invention invention is directed to glycome compositions, derived from tissue material according to the invention, wherein the glycome composition contain at least one of the preferred novel glycan groups in combination with other glycan groups; such as neutral glycans including high mannose glycan, GlcNAcβ2Man-glycans, complex type-glycans, hybrid type glycans acidic glycans; according to the invention obtainable from tissue materials according to the invention.

Most preferred novel glycan group degraded mannose glycan. The most preferred mannose glycans includes Mannose type glycans containing less than 6 mannose units including low mannose glycans, fucosylated low mannose (up to 4-5 mannose residues) or fucosylated high mannose structures (4-5 mannose residues), and soluble mannose-GlcNAc1-glycome Most preferred Mannose type glycan including, high- and low mannose type structures are according to the Formula Mn:

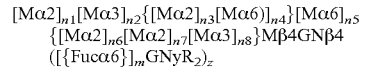

wherein p, n1, n2, n3, n4, n5, n6, n7, n8, and m, and z are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0;

y is anomeric linkage structure α and/or β or linkage from derivatized anomeric carbon, and $R_2$ is reducing end hydroxyl, chemical reducing end derivative or natural asparagine N-glycoside derivative such as asparagine N-glycosides including asparagines N-glycoside aminoacid and/or peptides derived from protein;

[ ] and ( ) indicates determinant either being present or absent depending on the value of n1, n2, n3, n4, n5, n6, n7, n8, and m; and { } indicates a branch in the structure, with the provisio that is 0 indicating soluble mannose-GlcNAc1-glycome or there is 5, more preferably 4 or less mannose residues or m is 1 and there is 6 or less mannose units.

Marker Structures and Glycomes

The invention revealed individual glycan structures and structure groups, which are novel markers for the cell materials according to the invention. The present invention is directed to the use of the marker structures and their combinations for analysis, for labelling and for cell separation, as modification targets and for other methods according to invention.

The present invention revealed large groups of glycans, which can be derived from cells according to the invention. The present invention is especially directed to release of various protein or lipid linked oligosaccharide and/or polysaccharide chains as free glycan, glycan reducing end derivative or glycopeptide fractions referred as glycomes from the cell material according to the invention. The glycans can be released separately from differently linked glycan groups on proteins and or glycolipids or in combined process producing several isolated glycome fractions and/or combined glycome fractions, which comprise glycans released at least from two different glycomes. The relative amounts of various components/component groups observable in glycan profiling as peaks in mass spectra and in quantitative presentations of glycan based profiling information, especially in analysis of mass spectrometric and/or NMR-data were revealed to be characteristic for individual cell types. The glycomes was further revealed to contain glycan subgroups or subglycomes which are very useful for characterization of the cell materials according to the invention.

Glycome Types Based on Linkage Structures

The invention revealed four major glycome types based on the linkage structures. Two protein linked glycomes are N-linked glycomes and O-linked glycomes. The majority of the glycosaminoglycan (gag) glycomes (gagomes) are also linked to certain proteins by specific core and linkage structures. The glycolipid glycome is linked to lipids, usually sphingolipids.

Core Structures of Glycomes and Terminal Glycome Specific and Common Structures

The invention has revealed specific glycan core structures for the specific subglycomes studied. The various structures in specific glycomes were observed to contain common reducing end core structures such as N-glycan and O-glycan, Glycosaminoglycan and glycolipid cores. The cores are elongated with varying glycan chains usually comprising groups of glycans with different chain length. The presence of a core structures is often observably as a characteristic monosaccharide composition as monosaccharide composition of the core structure causing different relation of monosaccharide residues in specific glycan signals of glycomes when profiled by mass spectrometry according to the invention. The present invention further revealed specific non-reducing end terminal structures of specific marker glycans. Part of the non-reducing end terminal structures are characteristic for several glycomes, for example N-acetyllactosamine type terminal structures, including fucosylated and sialylated variants were revealed from complex N-glycans, O-glycan and Glycolipid glycomes. Part of the structures are specific for glycomes such terminal Man-structures in Low-mannose and High-mannose N-glycans.

Combined Analysis of Different Glycomes

The invention revealed similar structures on protein and lipid linked glycomes in the cell materials according to the invention. It was revealed that combined analysis of the different glycomes is useful characterization of specific cell materials according to the invention. The invention specifically revealed similar lactosamine type structures in glycolipid and glycoprotein linked glycomes.

The invention further revealed glycosaminoglycan glycome and glycome profile useful for the analysis of the cell status and certain synergistic characteristics glycosaminoglycan glycomes and other protein linked glycomes such as non-sialic acid containing acidic structures in N-liked glycomes. The biological roles of glycosaminoglycans and glycolipids in regulation of cell biology and their biosynthetic difference and distance revealed by glycome analysis make these a useful combination for analysis of cell status. It is further realized that combination of all all glycomes including O-glycan and N-glycan glycomes, glycolipid glycome and glycosaminoglycan glycome are useful for analysis of cells according to the invention. The invention further revealed common chemical structural features in the all glycomes according invention supporting the effective combined production, purification and analysis of glycomes according to the invention.

In a preferred embodiment the invention is directed to combined analysis of following glycome combinations, more preferably the glycomes are analysed from same sample to obtain exact information about the status of the cell material:

1. Two protein linked glycomes: N-glycan and O-glycan glycomes
2. Glycolipid glycomes with protein linked glycomes, especially preferred glycolipid glycomes and N-glycan glycomes
3. Protein linked glycome or glycomes with glycosaminoglycan glycome, in preferred embodiment a glycosaminoglycan glycome and N-glycan glycome.
4. Lipid linked glycome or glycomes with glycosaminoglycan glycome
5. Protein linked O-glycan and N-glycan glycomes, glycolipid glycome and glycosaminoglycan glycome.

The invention further revealed effective methods for the analysis of different glycomes. It was revealed that several methods developed for sample preparation are useful for both lipid and protein linked glycomes, in a preferred embodiment proteolytic treatment is used for both production of protein linked glycome and a lipid linked glycome, especially for production of cell surface glycomes. For production of Total cell glycomes according to the invention the extraction of glycolipids is preferably used for degradation of cells and protein fraction obtained from the lipid extraction is used for protein linked glycome analysis. The invention is further directed to the chemical release of glycans, preferably for simultaneous release of both O-linked and N-linked glycans. Glycolipid and other glycomes, especially N-linked glycome, can be effectively released enzymatically, the invention is directed to sequential release of glycans by enzymes, preferably including step of inactivating enzymes between the treatments and using glycan controlled enzymes to avoid contamination or controlling contamination of glycans originating from enzymes.

Common Structural Features of all Glycomes and Preferred Common Subfeatures

The present invention reveals useful glycan markers for tissue materials and combinations thereof and glycome compositions comprising specific amounts of key glycan structures. The invention is furthermore directed to specific terminal and core structures and to the combinations thereof.

The preferred glycome glycan structure(s) and/or glycomes from cells according to the invention comprise structure(s) according to the formula C0:

$$R_1Hex\beta z\{R_3\}_{n1}Hex(NAc)_{n2}XyR_2,$$

Wherein X is glycosidically linked disaccharide epitope $\beta4(Fuc\alpha6)_nGN$, wherein n is 0 or 1, or X is nothing and Hex is Gal or Man or GlcA, HexNAc is GlcNAc or GalNAc, y is anomeric linkage structure α and/or β or linkage from derivatized anomeric carbon, z is linkage position 3 or 4, with the provision that when z is 4 then HexNAc is GlcNAc and then Hex is Man or Hex is Gal or Hex is GlcA, and when z is 3 then Hex is GlcA or Gal and HexNAc is GlcNAc or GalNAc;

n 1 is 0 or 1 indicating presence or absence of R3;

n2 is 0 or 1, indicating the presence or absence of NAc, with the proviso that n2 can be 0 only when Hexβz is Galβ4, and n2 is preferably 0, n2 structures are preferably derived from glycolipids;

$R_1$ indicates 1-4, preferably 1-3, natural type carbohydrate substituents linked to the core structures or nothing;

$R_2$ is reducing end hydroxyl, chemical reducing end derivative or natural asparagine N-glycoside derivative such as asparagine N-glycosides including asparagine N-glycoside aminoacids and/or peptides derived from protein, or natural serine or threonine linked O-glycoside derivative such as serine or threonine linked O-glycosides including asparagine N-glycoside aminoacids and/or peptides derived from protein, or when n2 is 1 R2 is nothing or a ceramide structure or a derivative of a ceramide structure, such as lysolipid and amide derivatives thereof;

R3 is nothing or a branching structure representing a GlcNAcβ6 or an oligosaccharide with GlcNAcβ6 at its reducing end linked to GalNAc (when HexNAc is GalNAc); or when Hex is Gal and HexNAc is GlcNAc, and when z is 3 then R3 is Fucα4 or nothing, and when z is 4 R3 is Fucα3 or nothing.

The preferred disaccharide epitopes in the glycan structures and glycomes according to the invention include structures Galβ4GlcNAc, Manβ4GlcNAc, GlcAβ4GlcNAc, Galβ3GlcNAc, Galβ3GalNAc, GlcAβ3GlcNAc, GlcAβ3GalNAc, and Galβ4Glc, which may be further derivatized from reducing end carbon atom and non-reducing monosaccharide residues and is in a separate embodiment branched from the reducing end residue. Preferred branched epitopes include Galβ4(Fucα3)GlcNAc, Galβ3(Fucα4)GlcNAc, and Galβ3(GlcNAcβ6)GalNAc, which may be further derivatized from reducing end carbon atom and non-reducing monosaccharide residues.

Preferred Epitopes for Methods According to the Invention

N-acetyllactosamine Galβ3/4GlcNAc Terminal Epitopes

The two N-acetyllactosamine epitopes Galβ4GlcNAc and/or Galβ3GlcNAc represent preferred terminal epitopes present on tissue materials or backbone structures of the preferred terminal epitopes for example further comprising sialic acid or fucose derivatisations according to the invention. In a preferred embodiment the invention is directed to fucosylated and/or non-substituted glycan non-reducing end forms of the terminal epitopes, more preferably to fucosylated and non-substituted forms. The invention is especially directed to non-reducing end terminal (non-substituted) natural Galβ4GlcNAc and/or Galβ3GlcNAc-structures from human tissue material glycomes. The invention is in a specific embodiment directed to non-reducing end terminal fucosylated natural Galβ4GlcNAc and/or Galβ3GlcNAc-structures from human tissue material glycomes.

Preferred fucosylated N-acetyllactosamines

The preferred fucosylated epitopes are according to the Formula TF:

$$(Fuc\alpha2)_{n1}Gal\beta3/4(Fuc\alpha4/3)_{n2}GlcNAc\beta-R$$

Wherein n1 is 0 or 1 indicating presence or absence of Fucα2;

n2 is 0 or 1, indicating the presence or absence of Fucα4/3 (branch), and

R is the reducing end core structure of N-glycan, O-glycan and/or glycolipid.

The preferred structures thus include type 1 lactosamines (Galβ3GlcNAc based):

Galβ3(Fucα4)GlcNAc (Lewis a), Fucα2Galβ3GlcNAc H-type 1, structure and,

Fucα2Galβ3(Fucα4)GlcNAc (Lewis b) and type 2 lactosamines (Galβ4GlcNAc based):

Galβ4(Fucα3)GlcNAc (Lewis x), Fucα2Galβ4GlcNAc H-type 2, structure and,

Fucα2Galβ4(Fucα3)GlcNAc (Lewis y).

The type 2 lactosamines (fucosylated and/or terminal non-substituted) form an especially preferred group in context of tissue materials. Type 1 lactosamines (Galβ3GlcNAc—structures) are especially preferred in context of tissue materials. Lactosamines Galβ3/4GlcNAc and Glycolipid Structures Comprising Lactose Structures (Galβ4Glc)

The lactosamines form a preferred structure group with lactose-based glycolipids. The structures share similar features as products of β3/4Gal-transferases. The β3/4 galactose based structures were observed to produce characteristic features of protein linked and glycolipid glycomes.

The invention revealed that furthermore Galβ3/4GlcNAc-structures are a key feature of glycolipids of human cells. Such glycolipids comprise two preferred structural epitopes according to the invention. The most preferred glycolipid types include thus lactosylceramide based glycosphingolipids and especially lacto-(Galβ3GlcNAc), such as lactotetraosylceramide Galβ3GlcNAcβ3Galβ4GlcβCer, preferred structures further including its non-reducing terminal structures selected from the group: Galβ3(Fucα4)GlcNAc (Lewis a), Fucα2Galβ3GlcNAc (H-type 1), structure and, Fucα2Galβ3(Fucα4)GlcNAc (Lewis b) or sialylated structure SAα3Galβ3GlcNAc or SAα3Galβ3(Fucα4)GlcNAc, wherein SA is a sialic acid, preferably Neu5Ac preferably replacing Galβ3GlcNAc of lactotetraosylceramide and its fucosylated and/or elongated variants such as preferably according to the Formula:

$$(Sac\alpha3)_{n5}(Fuc\alpha2)_{n1}Gal\beta3(Fuc\alpha4)_{n3}GlcNAc\beta3$$
$$[Gal\beta3/4(Fuc\alpha4/3)_{n2}GlcNAc\beta3]_{n4}Gal\beta4Glc\beta Cer$$

wherein n1 is 0 or 1, indicating presence or absence of Fucα2;

n2 is 0 or 1, indicating the presence or absence of Fucα4/3 (branch), n3 is 0 or 1, indicating the presence or absence of Fucα4 (branch)

n4 is 0 or 1, indicating the presence or absence of (fucosylated) N-acetyllactosamine elongation;

n5 is 0 or 1, indicating the presence or absence of Sacα3 elongation;

Sac is terminal structure, preferably sialic acid, with α3-linkage, with the proviso that when Sac is present, n5 is 1, then n1 is 0 and neolacto (Galβ4GlcNAc)-comprising glycolipids such as neolactotetraosylceramide Galβ4GlcNAcβ3Galβ4GlcβCer, preferred structures further including its non-reducing terminal Galβ4(Fucα3)GlcNAc (Lewis x), Fucα2Galβ4GlcNAc H-type 2, structure and, Fucα2Galβ4(Fucα3)GlcNAc (Lewis y) and its fucosylated and/or elongated variants such as preferably

$(Sac\alpha 3/6)_{n5}(Fuc\alpha 2)_{n1}Gal\beta 4(Fuc\alpha 3)_{n3}GlcNAc\beta 3$
$[Gal\beta 4(Fuc\alpha 3)_{n2}GlcNAc\beta 3]_{n4}Gal\beta 4Glc\beta Cer$ n1 is 0 or 1 indicating presence or absence of Fucα2;
n2 is 0 or 1, indicating the presence or absence of Fucα3 (branch),
n3 is 0 or 1, indicating the presence or absence of Fucα3 (branch)
n4 is 0 or 1, indicating the presence or absence of (fucosylated) N-acetyllactosamine elongation,
n5 is 0 or 1, indicating the presence or absence of Sacα3/6 elongation;
Sac is terminal structure, preferably sialic acid (SA) with α3-linkage, or sialic acid with α6-linkage, with the proviso that when Sac is present, n5 is 1, then n1 is 0, and when sialic acid is bound by α6-linkage preferably also n3 is 0.

Preferred human cell glycosphingolipid glycan profiles, compositions, and marker structures The inventors were able to describe human cell glycolipid glycomes by mass spectrometric profiling of liberated free glycans, revealing about 80 glycan signals from different cell types.

The proposed monosaccharide compositions of the neutral glycans were composed of 2-7 Hex, 0-5 HexNAc, and 0-4 dhex. The proposed monosaccharide compositions of the acidic glycan signals were composed of 0-2 NeuAc, 2-9 Hex, 0-6 HexNAc, 0-3 dhex, and/or 0-1 sulphate or phosphate esters. The present invention is especially directed to analysis and targeting of such human cell glycan profiles and/or structures for the uses described in the present invention with respect to human cells. The present invention is further specifically directed to glycosphingolipid glycan signals specific to human cell types.

Terminal glycan epitopes that were demonstrated in the present experiments in human cell glycosphingolipid glycans are useful in recognizing cells or specifically binding to the cells via glycans, and other uses according to the present invention, including terminal epitopes: Gal, Galβ4Glc (Lac), Galβ4GlcNAc (LacNAc type 2), Galβ3, Non-reducing terminal HexNAc, Fuc, α1,2-Fuc, α1,3-Fuc, Fucα2Gal, Fucα2Galβ4GlcNAc (H type 2), Fucα2Galβ4Glc (2'-fucosyllactose), Fucα3GlcNAc, Galβ4(Fucα3)GlcNAc (Lex), Fucα3Glc, Galβ4(Fucα3)Glc (3-fucosyllactose), Neu5Ac, Neu5Acα2,3, and Neu5Acα2,6. The present invention is further directed to the total terminal epitope profiles within the total human cell glycosphingolipid glycomes and/or glycomes.

The present invention revealed characteristic variations (increased or decreased expression in comparison to similar control cell or a contaminating cell or like) of both structure types in various tissue and cell materials according to the invention. The structures were revealed with characteristic and varying expression in three different glycome types: N-glycans, O-glycans, and glycolipids. The invention revealed that the glycan structures are a characteristic feature of tissue materials and are useful for various analysis methods according to the invention. Amounts of these and relative amounts of the epitopes and/or derivatives varies between tissue materials or between cells exposed to different conditions during growing, storage, or induction with effector molecules such as cytokines and/or hormones.

The preferred glycome glycan structure(s) and/or glycomes from cells according to the invention comprise structure(s) according to
the formula C1:

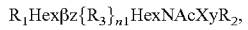

$R_1Hex\beta z\{R_3\}_{n1}HexNAcXyR_2$,

Wherein X is glycosidically linked disaccharide epitope β4(Fucα6)$_n$GN, wherein n is 0 or 1, or X is nothing and
Hex is Gal or Man or GlcA,
HexNAc is GlcNAc or GalNAc,
y is anomeric linkage structure α and/or β or linkage from derivatized anomeric carbon,
z is linkage position 3 or 4, with the provision that when z is 4 then HexNAc is GlcNAc and then Hex is Man or Hex is Gal or Hex is GlcA, and
when z is 3 then Hex is GlcA or Gal and HexNAc is GlcNAc or GalNAc,
$R_1$ indicates 1-4, preferably 1-3, natural type carbohydrate substituents linked to the core structures,
$R_2$ is reducing end hydroxyl, chemical reducing end derivative or natural asparagine N-glycoside derivative such as asparagine N-glycosides including asparagines N-glycoside aminoacids and/or peptides derived from protein, or natural serine or threonine linked O-glycoside derivative such as serine or threonine linked O-glycosides including asparagines N-glycoside aminoacids and/or peptides derived from protein.

R3 is nothing or a branching structure representing a GlcNAcβ6 or an oligosaccharide with GlcNAcβ6 at its reducing end linked to GalNAc (when HexNAc is GalNAc) or when Hex is Gal and HexNAc is GlcNAc the then when z is 3 R3 is Fucα4 or nothing and when z is 4 R3 is Fucα3 or nothing.

The preferred disaccharide epitopes in the glycan structures and glycomes according to the invention include structures Galβ3GlcNAc, Manβ4GlcNAc, GlcAβ4GlcNAc, Galβ3GlcNAc, Galβ3GalNAc, GlcAβ3GlcNAc and GlcAβ3GalNAc, which may be further derivatized from reducing end carbon atom and non-reducing monosaccharide residues and is separate embodiment branched from the reducing end residue. Preferred branched epitopes include Galβ4(Fucα3)GlcNAc, Galβ3(Fucα4)GlcNAc, Galβ3 (GlcNAcβ6)GalNAc, which may be further derivatized from reducing end carbon atom and non-reducing monosaccharide residues.

The preferred disaccharide epitopes of glycoprotein or glycolipid structures present on glycans of human cells according to the invention comprise structures based on the formula C2:

$R_1Hex\beta 4GlcNAcXyR_2$,

Wherein Hex is Gal OR Man and when Hex is Man then X is glycosidically linked disaccharide epitope β4(Fucα6)$_n$GN, wherein n is 0 or 1, or X is nothing and
when Hex is Gal then X is β3GalNAc of O-glycan core or β2/4/6Manα3/6 terminal of N-glycan core (as in formula NC3)
y is anomeric linkage structure α and/or β or linkage from derivatized anomeric carbon,
$R_1$ indicates 1-4, preferably 1-3, natural type carbohydrate substituents linked to the core structures,
when Hex is Gal preferred R1 groups include structures SAα3/6, SAα3/6Galβ4GlcNAcβ3/6, when Hex is Man preferred R1 groups include Manα3, Manα6, branched structure Manα3{Manα6} and elongated variants thereof as described for low mannose, high-mannose and complex type N-glycans below, $R_2$ is reducing end hydroxyl, chemical reducing end derivative or natural asparagine N-glycoside derivative such as asparagine N-glycosides including asparagines N-glycoside aminoacids and/or peptides derived from protein, or natural serine or threonine linked O-glycoside derivative such as serine or threonine linked O-glycosides including asparagines N-glycoside aminoacids and/or peptides derived from protein.

Structures of N-Linked Glycomes
Common Core Structure of N-Linked Glycomes

The inventors revealed that the N-glycans released by specific N-glycan release methods from the cells according to the invention, and preferred cells according to the invention, comprise mostly a specific type of N-glycan core structure.

The preferred N-glycan structure of each cell type is characterised and recognized by treating cells with a N-glycan releasing enzyme releasing practically all N-glycans with core type according to the invention. The N-glycan releasing enzyme is preferably protein N-glycosidase enzyme, preferably by protein N-glycosidase releasing effectively the N-glycomes according to the invention, more preferably protein N-glycosidase with similar specificity as protein N-glycosidase F, and in a specifically preferred embodiment the enzyme is protein N-glycosidase F from *F. meningosepticum*. Alternative chemical N-glycan release method was used for controlling the effective release of the N-glycomes by the N-glycan releasing enzyme.

The inventors used the NMR glycome analysis according to the invention for further characterization of released N-glycomes from small cell samples available. NMR spectroscopy revealed the N-glycan core signals of the preferred N-glycan core type of the cells according to the invention.

The Minimum Formula

The present invention is directed to glycomes derived from cells and comprising a common N-glycosidic core structures. The invention is specifically directed to minimum formulas covering both $GN_1$-glycomes and $GN_2$-glycomes with difference in reducing end structures.

The minimum core structure includes glycans from which reducing end GlcNAc or Fucα6GlcNAc has been released. These are referred as $GN_1$-glycomes and the components thereof as $GN_1$-glycans. The present invention is specifically directed to natural N-glycomes from cells comprising $GN_1$-glycans. In a preferred embodiment the invention is directed to purified or isolated practically pure natural $GN_1$-glycome from human cells. The release of the reducing end GlcNAc-unit completely or partially may be included in the production of the N-glycome or N-glycans from cells for analysis. The invention is specifically directed to soluble high/low mannose glycome of $GN_1$-type.

The glycomes including the reducing end GlcNAc or Fucα6GlcNAc are referred as $GN_2$-glycomes and the components thereof as $GN_2$-glycans. The present invention is also specifically directed to natural N-glycomes from cells and tissues comprising $GN_2$-glycans. In a preferred embodiment the invention is directed to purified or isolated practically pure natural $GN_2$-glycome from cells.

The preferred N-glycan core structure(s) and/or N-glycomes from cells according to the invention comprise structure(s) according to the formula NC1:

Wherein X is glycosidically linked disaccharide epitope β4(Fucα6)$_n$GN, wherein n is 0 or 1, or X is nothing and y is anomeric linkage structure α and/or β or linkage from derivatized anomeric carbon, and $R_1$ indicates 1-3, preferably 1-3, natural type carbohydrate substituents linked to the core structures, $R_2$ is reducing end hydroxyl, chemical reducing end derivative or natural asparagine N-glycoside derivative such as asparagine N-glycosides including asparagines N-glycoside aminoacids and/or peptides derived from protein.

It is realized that when the invention is directed to a glycome, the formula indicates mixture of several or typically more than ten or even higher number of different structures according to the Formulas describing the glycomes according to the invention.

The possible carbohydrate substituents $R_1$ comprise at least one mannose (Man) residue, and optionally one or several GlcNAc, Gal, Fuc, SA and/GalNAc residues, with possible sulphate and or phosphate modifications.

When the glycome is released by N-glycosidase the free N-glycome saccharides comprise in a preferred embodiment reducing end hydroxyl with anomeric linkage A having structure α and/or β, preferably both α and β. In another embodiment the glycome is derivatized by a molecular structure which can be reacted with the free reducing end of a released glycome, such as amine, aminooxy or hydrazine or thiol structures. The derivatizing groups comprise typically 3 to 30 atoms in aliphatic or aromatic structures or can form terminal group spacers and link the glycomes to carriers such as solid phases or microparticles, polymeric carries such as oligosaccharides and/or polysaccharide, peptides, dendrimer, proteins, organic polymers such as plastics, polyethyleneglycol and derivatives, polyamines such as polylysines.

When the glycome comprises asparagine N-glycosides, A is preferably beta and R is linked asparagine or asparagine peptide. The peptide part may comprise multiple different aminoacid residues and typically multiple forms of peptide with different sequences derived from natural proteins carrying the N-glycans in cell materials according to the invention. It is realized that for example proteolytic release of glycans may produce mixture of glycopeptides. Preferably the peptide parts of the glycopeptides comprises mainly a low number of amino acid residues, preferably two to ten residues, more preferably two to seven amino acid residues and even more preferably two to five aminoacid residues and most preferably two to four amino acid residues when "mainly" indicates preferably at least 60% of the peptide part, more preferably at least 75% and most preferably at least 90% of the peptide part comprising the peptide of desired low number of aminoacid residues.

The Preferred $GN_2$—N-glycan Core Structure(s)

The preferred $GN_2$—N-glycan core structure(s) and/or N-glycomes from cells according to the invention comprise structure(s) according to the formula NC2:

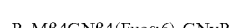

wherein n is 0 or 1 and
wherein y is anomeric linkage structure α and/or β or linkage from derivatized anomeric carbon and $R_1$ indicates 1-4, preferably 1-3, natural type carbohydrate substituents linked to the core structures, $R_2$ is reducing end hydroxyl, chemical reducing end derivative or natural asparagine N-glycoside derivative such as asparagine N-glycosides including asparagines N-glycoside aminoacid and/or peptides derived from protein.

The preferred compositions thus include one or several of the following structures NC2a: Mα3{Mα6}Mβ4GNβ4{Fucα}$_{n1}$GNyR$_2$
NC2b: Mα6Mβ4GNβ4{Fucα6}$_{n1}$GNyR$_2$
NC2c: Mα3Mβ4GNβ4{Fucα6}$_{n1}$GNyR$_2$ More preferably compositions comprise at least 3 of the structures or most preferably both structures according to the formula NC2a and at least both fucosylated and non-fucosylated with core structure(s) NC2b and/or NC2c.

The Preferred GN$_1$—N-Glycan Core Structure(s)

The preferred GN$_1$—N-glycan core structure(s) and/or N-glycomes from cells according to the invention comprise structure(s) according to
the formula NC3:

$$R_1M\beta 4GNyR_2,$$

wherein y is anomeric linkage structure α and/or β or linkage from derivatized anomeric carbon and R$_1$ indicates 1-4, preferably 1-3, natural type carbohydrate substituents linked to the core structures, R$_2$ is reducing end hydroxyl, chemical reducing end derivative or natural asparagine N-glycoside derivative such as asparagine N-glycosides including asparagine N-glycoside aminoacids and/or peptides derived from protein.

Multi-Mannose GN$_1$—N-Glycan Core Structure(s)

The invention is specifically directed glycans and/or glycomes derived from preferred cells according to the present invention when the natural glycome or glycan comprises Multi-mannose GN$_1$—N-glycan core structure(s) structure(s) according to
the formula NC4:

$$[R_1M\alpha 3]_{n3}\{R_3M\alpha 6\}_{n2}M\beta 4GNXyR_2,$$

R$_1$ and R$_3$ indicate nothing or one or two, natural type carbohydrate substituents linked to the core structures, when the substituents are α-linked mannose monosaccharide and/or oligosaccharides and the other variables are as described above.

Furthermore common elongated GN$_2$—N-glycan core structures are preferred types of glycomes according to the invention The preferred N-glycan core structures further include differently elongated GN$_2$—N-glycan core structures according to the
formula NC5:

$$[R_1M\alpha 3]_{n3}\{R_3M\alpha 6\}_{n2}M\beta 4GN\beta 4\{Fuc\alpha 6\}_{n1}GNyR_2,$$

wherein n1, n2 and n3 are either 0 or 1 and
wherein y is anomeric linkage structure α and/or β or linkage from derivatized anomeric carbon and
R$_1$ and R$_3$ indicate nothing or 1-4, preferably 1-3, most preferably one or two, natural type carbohydrate substituents linked to the core structures,
R$_2$ is reducing end hydroxyl, chemical reducing end derivative or natural asparagine N-glycoside derivative such as asparagine N-glycosides including asparagine N-glycoside aminoacids and/or peptides derived from protein,
GN is GlcNAc, M is mannosyl-, [ ] indicate groups either present or absent in a linear sequence.
{ } indicates branching which may be also present or absent. with the provision that at least n2 or n3 is 1. Preferably the invention is directed to compositions comprising with all possible values of n2 and n3 and all saccharide types when R1 and/or are R3 are oligosaccharide sequences or nothing.

Preferred N-Glycan Types in Glycomes Comprising N-Glycans

The present invention is preferably directed to N-glycan glycomes comprising one or several of the preferred N-glycan core types according to the invention. The present invention is specifically directed to specific N-glycan core types when the compositions comprise N-glycan or N-glycans from one or several of the groups Low mannose glycans, High mannose glycans, Hybrid glycans, and Complex glycans, in a preferred embodiment the glycome comprise substantial amounts of glycans from at least three groups, more preferably from all four groups.

Major Subtypes of N-Glycans in N-Linked Glycomes

The invention revealed certain structural groups present in N-linked glycomes. The grouping is based on structural features of glycan groups obtained by classification based on the monosaccharide compositions and structural analysis of the structural groups. The glycans were analysed by NMR, specific binding reagents including lectins and antibodies and specific glycosidases releasing monosaccharide residues from glycans. The glycomes are preferably analysed as neutral and acidic glycomes The Major Neutral Glycan Types The neutral glycomes mean glycomes comprising no acidic monosaccharide residues such as sialic acids (especially NeuNAc and NeuGc), HexA (especially GlCA, glucuronic acid) and acid modification groups such as phosphate and/or sulphate esters. There are four major types of neutral N-linked glycomes which all share the common N-glycan core structure: High-mannose N-glycans, low-mannose N-glycans, hybrid type and complex type N-glycans. These have characteristic monosaccharide compositions and specific substructures. The complex and hybrid type glycans may include certain glycans comprising monoantennary glycans.

The groups of complex and hybrid type glycans can be further analysed with regard to the presence of one or more fucose residues. Glycans containing at least one fucose units are classified as fucosylated. Glycans containing at least two fucose residues are considered as glycans with complex fucosylation indicating that other fucose linkages, in addition to the α1,6-linkage in the N-glycan core, are present in the structure. Such linkages include α1,2-, α1,3-, and α1,4-linkage.

Furthermore the complex type N-glycans may be classified based on the relations of HexNAc (typically GlcNAc or GalNAc) and Hex residues (typically Man, Gal). Terminal HexNAc glycans comprise at least three HexNAc units and at least two Hexose units so that the number of Hex Nac residues is at least larger or equal to the number of hexose units, with the provision that for non branched, monoantennary glycans the number of HexNAcs is larger than number of hexoses.

This consideration is based on presence of two GlcNAc units in the core of N-glycan and need of at least two Mannose units to for a single complex type N-glycan branch and three mannose to form a trimannosyl core structure for most complex type structures. A specific group of HexNAc N-Glycans contains the same number of HexNAcs and Hex units, when the number is at least 5.

Preferred Mannose Type Structures

The invention is further directed to glycans comprising terminal Mannose such as Mα6-residue or both Mα6- and Mα3-residues, respectively, can additionally substitute other Mα2/3/6 units to form a Mannose-type structures including hybrid, low-Man and High-Man structures according to the invention.

Preferred high- and low mannose type structures with GN2-core structure are according to the Formula M2:

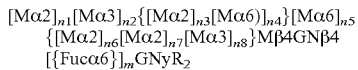

wherein p, n1, n2, n3, n4, n5, n6, n7, n8, and m are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; When n8 is 0, also n6 and n7 are 0;

y is anomeric linkage structure at and/or P or linkage from derivatized anomeric carbon, and $R_2$ is reducing end hydroxyl, chemical reducing end derivative or natural asparagine N-glycoside derivative such as asparagine N-glycosides including asparagines N-glycoside aminoacid and/or peptides derived from protein;

[ ] indicates determinant either being present or absent depending on the value of n1, n2, n3, n4, n5, n6, n7, n8, and m; and { } indicates a branch in the structure.

Preferred $yR_2$-structures include $[\beta\text{-N-Asn}]_p$, wherein p is either 0 or 1.

Preferred Mannose Type Glycomes Comprising GN1-Core Structures

As described above a preferred variant of N-glycomes comprising only single GlcNAc-residue in the core. Such structures are especially preferred as glycomes produced by endo-N-acetylglucosaminidase enzymes and Soluble glycomes. Preferred Mannose type glycomes include structures according to the Formula M2

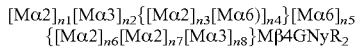

Fucosylated high-mannose N-glycans according to the invention have molecular compositions $Man_{5-9}GlcNAc_2Fuc_1$. For the fucosylated high-mannose glycans according to the formula, the sum of n1, n2, n3, n4, n5, n6, n7, and n8 is an integer from 4 to 8 and m is 0.

The low-mannose structures have molecular compositions $Man_{1-4}GlcNAc_2Fuc_{0-1}$. They consist of two subgroups based on the number of Fuc residues: 1) nonfucosylated low-mannose structures have molecular compositions $Man_{1-4}GlcNAc_2$ and 2) fucosylated low-mannose structures have molecular compositions $Man_{1-4}GlcNAc_2Fuc_1$. For the low mannose glycans the sum of n1, n2, n3, n4, n5, n6, n7, and n8 is less than or equal to (m+3); and preferably n1, n3, n6, and n7 are 0 when m is 0.

Low Mannose Glycans

The invention revealed a very unusual group glycans in N-glycomes of invention defined here as low mannose N-glycans. These are not clearly linked to regular biosynthesis of N-glycans, but may represent unusual biosynthetic midproducts or degradation products. The low mannose glycans are especially characteristics changing during the changes of cell status, the differentiation and other changes according to the invention, for examples changes associated with differentiation status of cells and their differentiated products and control cell materials.

The invention is especially directed to recognizing low amounts of low-mannose type glycans in cell types, such as with low degree of differentiation.

The invention revealed large differences between the low mannose glycan expression in the cell and tissue glycomes and material from tissue secretions such as human serum.

The invention is especially directed to the use of specific low mannose glycan comprising glycomes for analysis of tissues and cells, preferably cultivated cells.

The invention further revealed specific mannose directed recognition methods useful for recognizing the preferred glycomes according to the invention. The invention is especially directed to combination of glycome analysis and recognition by specific binding agents, most preferred binding agent include enzymes and these derivatives. The invention further revealed that specific low mannose glycans of the low mannose part of the glycomes can be recognized by degradation by specific α-mannosidase ($Man_{2-4}GlcNAc_2Fuc_{0-1}$) or β-mannosidase ($Man_1GlcNAc_2Fuc_{0-1}$) enzymes and optionally further recognition of small low mannose structures, even more preferably low mannose structures comprising terminal Man 4-structures according to the invention.

The low mannose N-glycans, and preferred subgroups and individual structures thereof, are especially preferred as markers of the novel glycome compositions of the cells according to the invention useful for characterization of the cell types.

The low-mannose type glycans includes a specific group of α3- and/or α6-linked mannose type structures according to the invention including a preferred terminal and core structure types according to the invention.

The inventions further revealed that low mannose N-glycans comprise a unique individual structural markers useful for characterization of the cells according to the invention by specific binding agents according to the invention or by combinations of specific binding agents according to the invention.

Neutral low-mannose type N-glycans comprise one to four or five terminal Man-residues, preferentially Manα structures; for example $Man\alpha_{0-3}Man\beta 4GlcNAc\beta 4GlcNAc(\beta\text{-N-Asn})$ or $Man\alpha_{0-4}Man\beta 4GlcNAc\beta 4(Fuc\alpha 6)GlcNAc(\beta\text{-N-Asn})$.

Low-mannose N-glycans are smaller and more rare than the common high-mannose N-glycans ($Man_{5-9}GlcNAc_2$). The low-mannose N-glycans detected in cell samples fall into two subgroups: 1) non-fucosylated, with composition $Man_nGlcNAc_2$, where $1 \leq n \leq 4$, and 2) core-fucosylated, with composition $Man_nGlcNAc_2Fuc_1$, where $1 \leq n \leq 5$. The largest of the detected low-mannose structure structures is $Man_5GlcNAc_2Fuc_1$ (m/z 1403 for the sodium adduct ion), which due to biosynthetic reasons most likely includes the structure below (in the figure the glycan is free oligosaccharide and β-anomer; in glycoproteins in tissues the glycan is N-glycan and β-anomer):

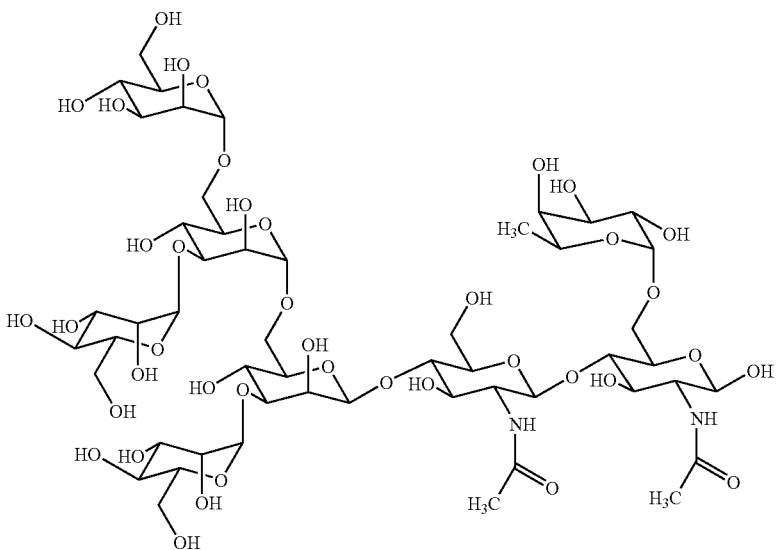 [SMILES: CC(=O)NC1C(O)OC(COC2OC(C)C(O)C(O)C2O)C(OC2OC(CO)C(OC3OC(COC4OC(COC5OC(CO)C(O)C(O)C5O)C(O)C(OC5OC(CO)C(O)C(O)C5O)C4O)C(O)C(OC4OC(CO)C(O)C(O)C4O)C3O)C(O)C2NC(C)=O)C1O]

Preferred General Molecular Structural Features of Low Man Glycans

According to the present invention, low-mannose structures are preferentially identified by mass spectrometry, preferentially based on characteristic $Hex_{1-4}HexNAc_2dHex_{0-1}$ monosaccharide composition. The low-mannose structures are further preferentially identified by sensitivity to exoglycosidase digestion, preferentially α-mannosidase ($Hex_{2-4}HexNAc_2dHexc_{0-1}$) or β-mannosidase ($Hex_1HexNAc_2dHex_{0-1}$) enzymes, and/or to endoglycosidase digestion, preferentially N-glycosidase F detachment from glycoproteins, Endoglycosidase H detachment from glycoproteins (only $Hex_{1-4}HexNAc_2$ liberated as $Hex_{1-4}HexNAc_1$), and/or Endoglycosidase F2 digestion (only $Hex_{1-4}HexNAc_2dHex_1$ digested to $Hex_{1-4}HexNAc_1$). The low-mannose structures are further preferentially identified in NMR spectroscopy based on characteristic resonances of the Manβ4GlcNAcβ4GlcNAc N-glycan core structure and Manα residues attached to the Manβ4 residue.

Several preferred low Man glycans described above can be presented in a single Formula:

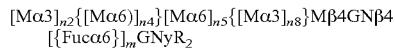

wherein p, n2, n4, n5, n8, and m are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0; the sum of n1, n2, n3, n4, n5, n6, n7, and n8 is less than or equal to (m+3); [ ] indicates determinant either being present or absent depending on the value of n2, n4, n5, n8, and m; and { } indicates a branch in the structure;
y and R2 are as indicated above.

Preferred non-fucosylated low-mannose glycans are according to the formula:

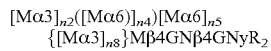

wherein p, n2, n4, n5, n8, and m are either independently 0 or 1,
with the provisio that when n5 is 0, also n2 and n4 are 0, and preferably either n2 or n4 is 0,
[ ] indicates determinant either being present or absent depending on the value of, n2, n4, n5, n8,
{ } and ( ) indicates a branch in the structure,
y and R2 are as indicated above.

Preferred Individual Structures of Non-Fucosylated Low-Mannose Glycans
Special Small Structures Small non-fucosylated low-mannose structures are especially unusual among known N-linked glycans and characteristic glycans group useful for separation of cells according to the present invention. These include:

Mβ4GNβ4GNyR$_2$
Mα6Mβ4GNβ4GNyR$_2$
Mα3Mβ4GNβ4GNyR$_2$ and
Mα6{Mα3}Mβ4GNβ4GNyR$_2$.

Mβ4GNβ4GNyR$_2$ trisaccharide epitope is a preferred common structure alone and together with its mono-mannose derivatives Mα6Mβ4GNβ4GNyR$_2$ and/or Mα3Mβ4GNβ4GNyR$_2$, because these are characteristic structures commonly present in glycomes according to the invention. The invention is specifically directed to the glycomes comprising one or several of the small non-fucosylated low-mannose structures. The tetrasaccharides are in a specific embodiment preferred for specific recognition directed to α-linked, preferably α3/6-linked Mannoses as preferred terminal recognition element.

Special Large Structures

The invention further revealed large non-fucosylated low-mannose structures that are unusual among known N-linked glycans and have special characteristic expression features among the preferred cells according to the invention. The preferred large structures include

more specifically
Mα6Mα6{Mα3}Mβ4GNβ4GNyR$_2$
Mα3Mα6{Mα3}Mβ4GNβ4GNyR$_2$ and
Mα3(Mα6)Mα6{Mα3}Mβ4GNβ4GNyR$_2$.

The hexasaccharide epitopes are preferred in a specific embodiment as rare and characteristic structures in preferred cell types and as structures with preferred terminal epitopes. The heptasaccharide is also preferred as structure comprising a preferred unusual terminal epitope Mα3(Mα6)Mα useful for analysis of cells according to the invention.

Preferred fucosylated low-mannose glycans are derived according to the formula:

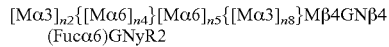

wherein p, n2, n4, n5, n8, and m are either independently 0 or 1, with the provisio that when n5 is 0, also n2 and n4 are 0, [ ] indicates determinant either being present or absent depending on the value of n1, n2, n3, n4, ( ) indicates a branch in the structure;
and wherein n1, n2, n3, n4 and m are either independently 0 or 1,
with the provisio that when n3 is 0, also n1 and n2 are 0,
[ ] indicates determinant either being present or absent depending on the value of n1, n2, n3, n4 and m,
{ } and ( ) indicate a branch in the structure.

Preferred Individual Structures of Fucosylated Low-Mannose Glycans

Small fucosylated low-mannose structures are especially unusual among known N-linked glycans and form a characteristic glycan group useful for separation of cells according to the present invention. These include:
Mβ4GNβ4(Fucα6)GNyR$_2$
Mα6 Mβ4GNβ4(Fucα6)GNyR$_2$
Mα3Mβ4GNβ4(Fucα6)GNyR$_2$ and
Mα61Mα3)Mβ4GNβ4(Fucα6)GNyR$_2$.
Mβ4GNβ4(Fucα6)GNyR$_2$ tetrasaccharide epitope is a preferred common structure alone and together with its monomannose derivatives Mα6Mβ4GNβ4(Fucα6)GNyR$_2$ and/or Mα3Mβ4GNβ4(Fucα6)GNyR$_2$, because these are commonly present characteristics structures in glycomes according to the invention. The invention is specifically directed to the glycomes comprising one or several of the small non-fucosylated low-mannose structures. The tetrasaccharides are in a specific embodiment preferred for specific recognition directed to α-linked, preferably α3/6-linked Mannoses as preferred terminal recognition element.

Special Large Structures

The invention further revealed large fucosylated low-mannose structures are unusual among known N-linked glycans and have special characteristic expression features among the preferred cells according to the invention. The preferred large structure includes

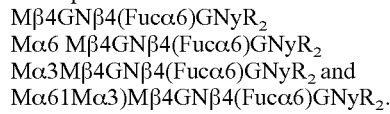

more specifically
Mα6Mα6{Mα3}Mβ4GNβ4(Fucα6)GNyR$_2$
Mα3Mα6{Mα3}Mβ4GNβ4(Fucα6)GNyR$_2$ and
Mα3(Mα6)Mα6{Mα3}Mβ4GNβ4(Fucα6)GNyR$_2$.
The heptasaccharide epitopes are preferred in a specific embodiment as rare and characteristic structures in preferred cell types and as structures with preferred terminal epitopes. The octasaccharide is also preferred as structure comprising a preferred unusual terminal epitope Mα3(Mα6)Mα useful for analysis of cells according to the invention.

Preferred Non-Reducing End Terminal Mannose-Epitopes

The inventors revealed that mannose-structures can be labeled and/or otherwise specifically recognized on cell surfaces or cell derived fractions/materials of specific cell types. The present invention is directed to the recognition of specific mannose epitopes on cell surfaces by reagents binding to specific mannose structures from cell surfaces.

The preferred reagents for recognition of any structures according to the invention include specific antibodies and other carbohydrate recognizing binding molecules. It is known that antibodies can be produced for the specific structures by various immunization and/or library technologies such as phage display methods representing variable domains of antibodies. Similarly with antibody library technologies, including aptamer technologies and including phage display for peptides, exist for synthesis of library molecules such as polyamide molecules including peptides, especially cyclic peptides, or nucleotide type molecules such as aptamer molecules.

The invention is specifically directed to specific recognition high-mannose and low-mannose structures according to the invention. The invention is specifically directed to recognition of non-reducing end terminal Manα-epitopes, preferably at least disaccharide epitopes, according to the formula:

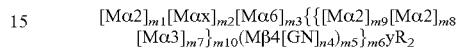

wherein m1, m2, m3, m4, m5, m6, m7, m8, m9 and m10 are independently either 0 or 1; with the proviso that when m3 is 0, then m1 is 0 and, when m7 is 0 then either m1-5 are 0 and m8 and m9 are 1 forming Mα2Mα2—disaccharide or both m8 and m9 are 0
y is anomeric linkage structure α and/or β or linkage from derivatized anomeric carbon, and
R$_2$ is reducing end hydroxyl, chemical reducing end derivative
and x is linkage position 3 or 6 or both 3 and 6 forming branched structure,
{ } indicates a branch in the structure.

The invention is further directed to terminal Mα2-containing glycans containing at least one Mα2-group and preferably Mα2-group on each, branch so that m1 and at least one of m8 or m9 is 1. The invention is further directed to terminal Mα3 and/or Mα6-epitopes without terminal Mα2-groups, when all m1, m8 and m9 are 1.

The invention is further directed in a preferred embodiment to the terminal epitopes linked to a Mβ-residue and for application directed to larger epitopes. The invention is especially directed to Mβ4GN-comprising reducing end terminal epitopes.

The preferred terminal epitopes comprise typically 2-5 monosaccharide residues in a linear chain. According to the invention short epitopes comprising at least 2 monosaccharide residues can be recognized under suitable background conditions and the invention is specifically directed to epitopes comprising 2 to 4 monosaccharide units and more preferably 2-3 monosaccharide units, even more preferred epitopes include linear disaccharide units and/or branched trisaccharide non-reducing residue with natural anomeric linkage structures at reducing end. The shorter epitopes may be preferred for specific applications due to practical reasons including effective production of control molecules for potential binding reagents aimed for recognition of the structures.

The shorter epitopes such as Mα2M-may is often more abundant on target cell surface as it is present on multiple arms of several common structures according to the invention.

Preferred Disaccharide Epitopes Includes

Manα2Man, Manα3Man, Manα6Man, and more preferred anomeric forms Manα2Manα, Manα3Manβ, Manα6Manβ, Manα3Manα and Manα6Manα.

Preferred branched trisaccharides includes Manα3(Manα6)Man, Manα3(Manα6)Manβ, and Manα3(Manα6)Manα.

The invention is specifically directed to the specific recognition of non-reducing terminal Manα2-structures especially in context of high-mannose structures.

The invention is specifically directed to following linear terminal mannose epitopes:
a) preferred terminal Manα2-epitopes including following oligosaccharide sequences:
Manα2Man,
Manα2Manα,
Manα2Manα2Man, Manα2Manα3Man,
Manα2Manα6Man,
Manα2Manα2Manα, Manα2Manα3Manβ,
Manα2Manα6Manα,
Manα2Manα2Manα3Man, Manα2Manα3Manα6Man,
Manα2Manα6Manα6Man
Manα2Manα2Manα3Manβ, Manα2Manα3Manα6Manβ,
Manα2Manα6Manα6Manβ;

The invention is further directed to recognition of and methods directed to non-reducing end terminal Manα3- and/or Manα6-comprising target structures, which are characteristic features of specifically important low-mannose glycans according to the invention. The preferred structural groups includes linear epitopes according to b) and branched epitopes according to the c3) especially depending on the status of the target material.
b) preferred terminal Manα3- and/or Manα6-epitopes including following oligosaccharide sequences:
Manα3Man, Manα6Man, Manα3Manβ, Manα6Manβ,
Manα3Manα, Manα6Manα, Manα3Manα6Man,
Manα6Manα6Man, Manα3Manα6Manβ,
Manα6Manα6Manβ and to following
c) branched terminal mannose epitopes, are preferred as characteristic structures of especially high mannose structures (c1 and c2) and low-mannose structures (c3), The preferred branched epitopes include:
c1) branched terminal Manα2-epitopes
Manα2Manα3(Manα2Manα6)Man, Manα2Manα3 (Manα2Manα6)Manα,
Manα2Manα3(Manα2Manα6)Manα6Man, Manα2Manα3 (Manα2Manα6)Manα6Manβ,
Manα2Manα3(Manα2Manα6)Manα6(Manα2Manα3) Man,
Manα2Manα3(Manα2Manα6)Manα6 (Manα2Manα2Manα3)Man,
Manα2Manα3 (Manα2Manα6)Manα6(Manα2Manα3) Manβ
Manα2Manα3(Manα2Manα6)Manα6 (ManαManα2Manα3)Manβ
c2) branched terminal Manα2- and Manα3 or Manα6-epitopes
according to formula when m1 and/or m8 and/m9 is 1 and the molecule comprise at least one nonreducing end terminal Manα3 or Manα6-epitope
c3) branched terminal Manα3 or Manα6-epitopes
Manα3(Manα6)Man, Manα3(Manα6)Manβ, Manα3 (Manα6)Manα,
Manα3(Manα6)Manα6Man, Manα3(Manα6)Manα6Manβ,
Manα3(Manα6)Manα6(Manα3)Man, Manα3(Manα6) Manα6(Manα3)Manβ

The present invention is further directed to increase of selectivity and sensitivity in recognition of
Target glycans by combining recognition methods for terminal Manα2 and Manα3 and/or Manα6-comprising structures. Such methods would be especially useful in context of cell material according to the invention comprising both high-mannose and low-mannose glycans.

Complex Type N-Glycans

According to the present invention, complex-type structures are preferentially identified by mass spectrometry, preferentially based on characteristic monosaccharide compositions, wherein HexNAc≥4 and Hex≥3. In a more preferred embodiment of the present invention, 4≤HexNAc≤20 and 3≤Hex≤21, and in an even more preferred embodiment of the present invention, 4≤HexNAc≤10 and 3≤Hex≤11. The complex-type structures are further preferentially identified by sensitivity to endoglycosidase digestion, preferentially N-glycosidase F detachment from glycoproteins. The complex-type structures are further preferentially identified in NMR spectroscopy based on characteristic resonances of the Manα3(Manα6)Manβ4GlcNAcβ4GlcNAc N-glycan core structure and GlcNAc residues attached to the Manα3 and/or Manα6 residues.

Beside Mannose-type glycans the preferred N-linked glycomes include GlcNAcβ2-type glycans including Complex type glycans comprising only GlcNAcβ2-branches and Hybrid type glycan comprising both Mannose-type branch and GlcNAcβ2-branch.

GlcNAcβ2-Type Glycans

The invention revealed GlcNAcβ2Man structures in the glycomes according to the invention. Preferably GlcNAcβ2Man-structures comprise one or several of GlcNAcβ2Manα-structures, more preferably GlcNAcβ2Manα3 or GlcNAcβ2Manα6-structure.

The Complex type glycans of the invention comprise preferably two GlcNAcβ2Manα structures, which are preferably GlcNAcβ2Manα3 and GlcNAcβ2Manα6-. The Hybrid type glycans comprise preferably GlcNAcβ2Manα3-structure.

The present invention is directed to at least one of natural oligosaccharide sequence structures and structures truncated from the reducing end of the N-glycan according to the Formula GNβ2

$$[R_1GN\beta2]_{n1}[M\alpha3]_{n2}\{[R_3]_{n3}$$
$$[GN\beta2]_{n4}M\alpha6\}_{n5}M\beta4GNXyR_2,$$

with optionally one or two or three additional branches according to formula $[R_xGN\beta z]_{nx}$ linked to Mα6-, Mα3-, or Mβ4 and $R_x$ may be different in each branch
wherein n1, n2, n3, n4, n5 and nx, are either 0 or 1, independently,
with the proviso that when n2 is 0 then n1 is 0 and when n3 is 1 or/and n4 is 1 then n5 is also 1, and at least n1 or n4 is 1, or n3 is 1,
when n4 is 0 and n3 is 1 then $R_3$ is a mannose type substituent or nothing and
wherein X is glycosidically linked disaccharide epitope β4(Fucα6)$_n$GN, wherein n is 0 or 1, or X is nothing and y is anomeric linkage structure α and/or β or linkage from derivatized anomeric carbon, and
$R_1$, $R_x$ and $R_3$ indicate independently one, two or three, natural substituents linked to the core structure,
$R_2$ is reducing end hydroxyl, chemical reducing end derivative or natural asparagine N-glycoside derivative such as asparagine N-glycosides including asparagines N-glycoside aminoacids and/or peptides derived from protein.
[ ] indicate groups either present or absent in a linear sequence. { } indicates branching which may be also present or absent.

Elongation of GlcNAcβ2-Type Structures, Complex/Hybrid Type Structures

The substituents $R_1$, $R_x$ and $R_3$ may form elongated structures. In the elongated structures $R_1$, and $R_x$ represent substituents of GlcNAc (GN) and $R_3$ is either substituent of GlcNAc or when n4 is 0 and n3 is 1 then $R_3$ is a mannose type substituent linked to mannosea6-branch forming a Hybrid type structure. The substituents of GN are monosaccharide Gal, GalNAc, or Fuc or and acidic residue such as sialic acid or sulfate or fosfate ester.

GlcNAc or GN may be elongated to N-acetyllactosaminyl also marked as GalβGN or di-N-acetyllactosdiaminyl GalNAcβGlcNAc preferably GalNAcβ4GlcNAc. LNβ2M can be further elongated and/or branched with one or several other monosaccharide residues such as by galactose, fucose, SA or LN-unit(s) which may be further substituted by SAα-structures, and/or Mα6 residue and/or Mα3 residues can be further substituted one or two β6-, and/or β4-linked additional branches according to the formula,
and/or either of Mα6 residue or Mα3 residue may be absent and/or Mα6-residue can be additionally substitutes other Manα units to form a hybrid type structures
and/or Manβ4 can be further substituted by GNβ4,
and/or SA may include natural substituents of sialic acid and/or it may be substituted by other SA-residues preferably by α8- or α9-linkages.

The SAα-groups are linked to either 3- or 6-position of neighboring Gal residue or on 6-position of GlcNAc, preferably 3- or 6-position of neighboring Gal residue. In separately preferred embodiments the invention is directed structures comprising solely 3-linked SA or 6-linked SA, or mixtures thereof.

Hybrid Type Structures

According to the present invention, hybrid-type or monoantennary structures are preferentially identified by mass spectrometry, preferentially based on characteristic monosaccharide compositions, wherein HexNAc=3 and Hex≥2. In a more preferred embodiment of the present invention 2≤Hex≤11, and in an even more preferred embodiment of the present invention 2≤Hex≤9. The hybrid-type structures are further preferentially identified by sensitivity to exoglycosidase digestion, preferentially α-mannosidase digestion when the structures contain non-reducing terminal α-mannose residues and Hex≥3, or even more preferably when Hex≥4, and to endoglycosidase digestion, preferentially N-glycosidase F detachment from glycoproteins. The hybrid-type structures are further preferentially identified in NMR spectroscopy based on characteristic resonances of the Manα3(Manα6)Manβ4GlcNAcβ4GlcNAc N-glycan core structure, a GlcNAcβ residue attached to a Manα residue in the N-glycan core, and the presence of characteristic resonances of non-reducing terminal α-mannose residue or residues.

The monoantennary structures are further preferentially identified by insensitivity to α-mannosidase digestion and by sensitivity to endoglycosidase digestion, preferentially N-glycosidase F detachment from glycoproteins. The monoantennary structures are further preferentially identified in NMR spectroscopy based on characteristic resonances of the Manα3Manβ4GlcNAcβ4GlcNAc N-glycan core structure, a GlcNAcβ residue attached to a Manα residue in the N-glycan core, and the absence of characteristic resonances of further non-reducing terminal α-mannose residues apart from those arising from a terminal α-mannose residue present in a ManαManβ sequence of the N-glycan core.

The present invention is directed to at least one of natural oligosaccharide sequence structures and structures truncated from the reducing end of the N-glycan according to the Formula HY1

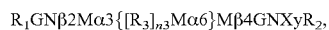

wherein n3, is either 0 or 1, independently, and
wherein X is glycosidically linked disaccharide epitope β4(Fucα6)$_n$GN, wherein n is 0 or 1, or X is nothing and y is anomeric linkage structure α and/or β or linkage from derivatized anomeric carbon, and $R_1$ indicate nothing or substituent or substituents linked to GlcNAc, $R_3$ indicates nothing or Mannose-substituent(s) linked to mannose residue, so that each of $R_1$, and $R_3$ may correspond to one, two or three, more preferably one or two, and most preferably at least one natural substituents linked to the core structure,
$R_2$ is reducing end hydroxyl, chemical reducing end derivative or natural asparagine N-glycoside derivative such as asparagine N-glycosides including asparagines N-glycoside aminoacids and/or peptides derived from protein.
[ ] indicate groups either present or absent in a linear sequence. { } indicates branching which may be also present or absent.

Preferred Hybrid Type Structures

The preferred hybrid type structures include one or two additional mannose residues on the preferred core structure.

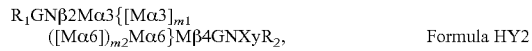
Formula HY2 wherein n3, is either 0 or 1, and m1 and m2 are either 0 or 1, independently,
{ } and ( ) indicates branching which may be also present or absent,
other variables are as described in Formula HY1.

Furthermore the invention is directed to structures comprising additional lactosamine type structures on GNβ2-branch. The preferred lactosamine type elongation structures includes N-acetyllactosamines and derivatives, galactose, GalNAc, GlcNAc, sialic acid and fucose.

Preferred structures according to the formula HY2 include:
Structures containing non-reducing end terminal GlcNAc
As a specific preferred group of glycans
GNβ2Mα3{Mα3Mα6}Mβ4GNXyR$_2$,
GNβ2Mα3{Mα6Mα6}Mβ4GNXyR$_2$,
GNβ2Mα3{Mα3(Mα6)Mα6}Mβ4GNXyR$_2$,
and/or elongated variants thereof
R$_1$GNβ2Mα3{Mα3Mα6}Mβ4GNXyR$_2$,
R$_1$GNβ2Mα3{Mα6}Mβ4GNXyR$_2$,
R$_1$GNβ2Mα3{Mα3(Mα6)Mα6}Mβ4GNXyR$_2$,

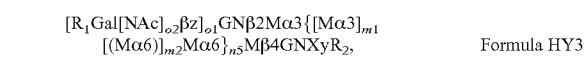
Formula HY3 wherein n1, n2, n3, n5, m1, m2, o1 and o2 are either 0 or 1, independently,
z is linkage position to GN being 3 or 4, ? in a preferred embodiment 4,
R$_1$, indicates on or two a N-acetyllactosamine type elongation groups or nothing,
{ } and ( ) indicates branching which may be also present or absent,
other variables are as described in Formula HY1.

Preferred structures according to the formula HY3 include especially
structures containing non-reducing end terminal Galβ, preferably Galβ3/4 forming a terminal N-acetyllactosamine structure. These are preferred as a special group of Hybrid type structures, preferred as a group of specific value in characterization of balance of Complex N-glycan glycome and High mannose glycome:
GalβzGNβ2Mα3{Mα3Mα6}Mβ4GNXyR$_2$,
GalβzGNβ2Mα3{Mα6Mα6}Mβ4GNXyR$_2$,
GalβzGNβ2Mα3{Mα3(Mα6)Mα6}Mβ4GNXyR$_2$,
and/or elongated variants thereof preferred for carrying additional characteristic terminal structures useful for characterization of glycan materials
R$_1$GalβzGNβ2Mα3{Mα3Mα6}Mβ4GNXyR$_2$,
R$_1$GalβzGNβ2Mα3{Mα6Mα6}Mβ4GNXyR$_2$, $R_1Gal\beta zGN\beta 2M\alpha 3\{M\alpha 3(M\alpha 6)M\alpha 6\})M\beta 4GNXyR_2$. Preferred elongated materials include structures wherein $R_1$ is a sialic acid, more preferably NeuNAc or NeuGc.

Complex N-Glycan Structures

The present invention is directed to at least one of natural oligosaccharide sequence structures and structures truncated from the reducing end of the N-glycan according to the Formula CO1

$$[R_1GN\beta 2]_{n1}[M\alpha 3]_{n2}\{[R_3GN\beta 2]_{n4}M\alpha 6\}_{n5}M\beta 4GNXyR_2$$

with optionally one or two or three additional branches according to formula $[R_xGN\beta z]_{nx}$ linked to $M\alpha 6$-, $M\alpha 3$-, or $M\beta 4$ and $R_x$ may be different in each branch
wherein n1, n2, n4, n5 and nx, are either 0 or 1, independently, with the proviso that when n2 is 0 then n1 is 0 and when n4 is 1 then n5 is also 1, and at least n1 is 1 or n4 is 1, and at least either of n1 and n4 is 1 and
wherein X is glycosidically linked disaccharide epitope $\beta 4(Fuc\alpha 6)_n GN$, wherein n is 0 or 1, or X is nothing and
y is anomeric linkage structure $\alpha$ and/or $\beta$ or linkage from derivatized anomeric carbon, and $R_1$, $R_x$, and $R_3$ indicate independently one, two or three, natural substituents linked to the core structure,
$R_2$ is reducing end hydroxyl, chemical reducing end derivative or natural asparagine N-glycoside derivative such as asparagine N-glycosides including asparagines N-glycoside aminoacids and/or peptides derived from protein.
[ ] indicate groups either present or absent in a linear sequence. { } indicates branching which may be also present or absent.

Preferred Complex Type Structures
Incomplete monoantennary N-Glycans

The present invention revealed incomplete Complex monoantennary N-glycans, which are unusual and useful for characterization of glycomes according to the invention. The most of the in complete monoantennary structures indicate potential degradation of biantennary N-glycan structures and are thus preferred as indicators of cellular status. The incomplete Complex type monoantennary glycans comprise only one GNβ2-structure.

The invention is specifically directed to structures are according to the Formula CO1 above when only n1 is 1 or n4 is one and mixtures of such structures.

The preferred mixtures comprise at least one monoantennary complex type glycans
A) with single branches from a likely degradative biosynthetic process:
$R_1GN\beta 2M\alpha 3\beta 4GNXyR_2$
$R_3GN\beta 2M\alpha 6M\beta 4GNXyR_2$ and
B) with two branches comprising mannose branches
  B1) $R_1GN\beta 2M\alpha 3\{M\alpha 6\}_{n5}M\beta 4GNXyR_2$
  B2) $M\alpha 3\{R_3GN\beta 2M\alpha 6\}_{n5}M\beta 4GNXyR_2$
The structure B2 is preferred with A structures as product of degradative biosynthesis, it is especially preferred in context of lower degradation of Manα3-structures. The structure B1 is useful for indication of either degradative biosynthesis or delay of biosynthetic process Biantennary and Multiantennary Structures The inventor revealed a major group of biantennary and multiantennary N-glycans from cells according to the invention, the preferred biantennary and multiantennary structures comprise two GNβ2 structures.

These are preferred as an additional characteristics group of glycomes according to the invention and are represented according to the Formula CO2:

$$R_1GN\beta 2M\alpha 3\{R_3GN\beta 2M\alpha 6\}M\beta 4GNXyR_2$$

with optionally one or two or three additional branches according to formula $[R_xGN\beta z]_{nx}$ linked to $M\alpha 6$-, $M\alpha 3$-, or $M\beta 4$ and $R_x$ may be different in each branch
wherein nx is either 0 or 1,
and other variables are according to the Formula CO1.

Preferred Biantennary Structure

A biantennary structure comprising two terminal GNβ-epitopes is preferred as a potential indicator of degradative biosynthesis and/or delay of biosynthetic process. The more preferred structures are according to the Formula CO2 when $R_1$ and $R_3$ are nothing.

Elongated Structures

The invention revealed specific elongated complex type glycans comprising Gal and/or GalNAc-structures and elongated variants thereof. Such structures are especially preferred as informative structures because the terminal epitopes include multiple informative modifications of lactosamine type, which characterize cell types according to the invention. The present invention is directed to at least one of natural oligosaccharide sequence structure or group of structures and corresponding structure(s) truncated from the reducing end of the N-glycan according to
the Formula CO3

$$[R_1Gal[NAc]_{o2}\beta z2]_{o1}GN\beta 2M\alpha 3\{[R_1Gal[NAc]_{o4}\beta z2]_{o3}GN\beta 2M\alpha 6\}M\beta 4GNXyR_2,$$

with optionally one or two or three additional branches according to formula $[R_xGN\beta z1]_{nx}$ linked to $M\alpha 6$-, $M\alpha 3$-, or $M\beta 4$ and $R_x$ may be different in each branch
wherein nx, o1, o2, o3, and o4 are either 0 or 1, independently, with the provisio that at least o1 or o3 is 1, in a preferred embodiment both are 1
z2 is linkage position to GN being 3 or 4, in a preferred embodiment 4,
z1 is linkage position of the additional branches.
$R_1$, Rx and $R_3$ indicate one or two a N-acetyllactosamine type elongation groups or nothing,
{ } and ( ) indicates branching which may be also present or absent,
other variables are as described in Formula CO1.

Galactosylated Structures

The inventors characterized especially directed to digalactosylated structure
$Gal\beta zGN\beta 2M\alpha 3\{Gal\beta zGN\beta 2M\alpha 6\}M\beta 4GNXyR2$,
and monogalactosylated structures
$Gal\beta zGN\beta 2M\alpha 3\{GN\beta 2M\alpha 6\}M\beta 4GNXyR_2$,
$GN\beta 2M\alpha 3\{Gal\beta zGN\beta 2M\alpha 6\}M\beta 4GNXyR_2$,
and/or elongated variants thereof preferred for carrying additional characteristic terminal structures useful for characterization of glycan materials
$R_1Gal\beta zGN\beta 2M\alpha 3\{R_3Gal\beta zGN\beta 2M\alpha 6\}M\beta 4GNXyR_2$
$R_1Gal\beta zGN\beta 2M\alpha 3\{GN\beta 2M\alpha 6\}M\beta 4GNXyR_2$, and
$GN\beta 2M\alpha 3\{R_3Gal\beta zGN\beta 2M\alpha 6\}M\beta 4GNXyR_2$.
Preferred elongated materials include structures wherein $R_1$ is a sialic acid, more preferably NeuNAc or NeuGc.

LacdiNAc-Structure Comprising N-Glycans

The present invention revealed for the first time LacdiNAc, GalNacbGlcNAc structures from the cell according to the invention. Preferred N-glycan lacdiNAc structures are included in structures according to the Formula CO1, when at least one the variable o2 and o4 is 1.

The Major Acidic Glycan Types

The acidic glycomes mean glycomes comprising at least one acidic monosaccharide residue such as sialic acids (especially NeuNAc and NeuGc) forming sialylated glycome, HexA (especially GlcA, glucuronic acid) and/or acid modification groups such as phosphate and/or sulphate esters.

According to the present invention, presence of phosphate and/or sulphate ester (SP) groups in acidic glycan structures is preferentially indicated by characteristic monosaccharide compositions containing one or more SP groups. The preferred compositions containing SP groups include those formed by adding one or more SP groups into non-SP group containing glycan compositions, while the most preferential compositions containing SP groups according to the present invention are selected from the compositions described in the acidic N-glycan fraction glycan group tables. The presence of phosphate and/or sulphate ester groups in acidic glycan structures is preferentially further indicated by the characteristic fragments observed in fragmentation mass spectrometry corresponding to loss of one or more SP groups, the insensitivity of the glycans carrying SP groups to sialidase digestion. The presence of phosphate and/or sulphate ester groups in acidic glycan structures is preferentially also indicated in positive ion mode mass spectrometry by the tendency of such glycans to form salts such as sodium salts as described in the Examples of the present invention. Sulphate and phosphate ester groups are further preferentially identified based on their sensitivity to specific sulphatase and phosphatase enzyme treatments, respectively, and/or specific complexes they form with cationic probes in analytical techniques such as mass spectrometry.

Complex N-Glycan Glycomes, Sialylated

The present invention is directed to at least one of natural oligosaccharide sequence structures and structures truncated from the reducing end of the N-glycan according to the Formula

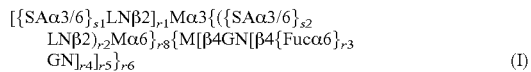
(I)

with optionally one or two or three additional branches according to formula

{SAα3/6}$_{s3}$LNβ, (IIb)

wherein r1, r2, r3, r4, r5, r6, r7 and r8 are either 0 or 1, independently,
wherein s1, s2 and s3 are either 0 or 1, independently,
with the proviso that at least r1 is 1 or r2 is 1, and at least one of s1, s2 or s3 is 1.
LN is N-acetyllactosaminyl also marked as GalβGN or di-N-acetyllactosdiaminyl GalNAcβGlcNAc preferably GalNAcβ4GlcNAc, GN is GlcNAc, M is mannosyl-, with the proviso LNβ2M or GNβ2M can be further elongated and/or branched with one or several other monosaccharide residues such as by galactose, fucose, SA or LN-unit(s) which may be further substituted by SAα-structures,
and/or one LNβ can be truncated to GNβ
and/or Mα6 residue and/or Mα3 residues can be further substituted one or two β6-, and/or β4-linked additional branches according to the formula,
and/or either of Mα6 residue or Mα3 residue may be absent and/or Mα6-residue can be additionally substitutes other Manα units to form a hybrid type structures
and/or Manβ4 can be further substituted by GNβ4,
and/or SA may include natural substituents of sialic acid and/or it may be substituted by other SA-residues preferably by α8- or α9-linkages.
( ), { }, [ ] and [ ] indicate groups either present or absent in a linear sequence. { } indicates branching which may be also present or absent.

The SAα-groups are linked to either 3- or 6-position of neighboring Gal residue or on 6-position of GlcNAc, preferably 3- or 6-position of neighboring Gal residue. In separately preferred embodiments the invention is directed structures comprising solely 3-linked SA or 6-linked SA, or mixtures thereof. In a preferred embodiment the invention is directed to glycans wherein r6 is 1 and r5 is 0, corresponding to N-glycans lacking the reducing end GlcNAc structure.

The LN unit with its various substituents can in a preferred general embodiment represented by the formula:

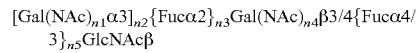

wherein n1, n2, n3, n4, and n5 are independently either 1 or 0, with the provisio that
the substituents defined by n2 and n3 are alternative to presence of SA at the non-reducing end terminal
the reducing end GlcNAc-unit can be further β3- and/or β6-linked to another similar LN-structure forming a poly-N-acetyllactosamine structure
with the provision that for this LN-unit n2, n3 and n4 are 0, the Gal(Ac)β and GlcNAcβ units can be ester linked a sulphate ester group,
( ), and [ ] indicate groups either present or absent in a linear sequence; { } indicates branching which may be also present or absent.

LN unit is preferably Galβ4GN and/or Galβ3GN. The inventors revealed that early human cells can express both types of N-acetyllactosamine, the invention is especially directed to mixtures of both structures. Furthermore the invention is directed to special relatively rear type 1 N-acetyllactosamines, Galβ3GN, without any non-reducing end/site modification, also called lewis c-structures, and substituted derivatives thereof, as novel markers of early human cells.

Uses of Glycan Structure Grouping and Analysis

In the present invention, glycan signals with preferential monosaccharide compositions can be grouped into structure groups based on classification rules described in the present invention. The present invention includes parallel and overlapping classification systems that are used for the classification of the glycan structure groups.

Glycan signals isolated from the N-glycan fractions from the tissue material types studied in the present invention are grouped into glycan structure groups based on their preferential monosaccharide compositions according to the invention, in Table 6 for neutral glycan fractions and Table 7 for acidic glycan fractions. Taken together, the analyses revealed that all the structure groups according to the invention are present in the studied tissue material types. In another aspect of the present invention, the glycan structure grouping is used to compare different tissue materials and characterize their specific glycosylation features. According to the present invention the discovered and analyzed differences between the glycan signals within the glycan signal groups between different tissue material samples are used for comparison and characterization.

The quantitative glycan profiling combined with glycan structural classification is used according to the present invention to characterize and identify glycosylation features occurring in tissue materials, glycosylation features specific for certain tissue materials as well as differences between different tissue materials. According to the present invention, the classification is used to characterize and compare glycosylation features of different tissues, of normal and diseased tissues, preferentially cancerous tissues, and solid tissues such as lung tissue and fluid tissues such as blood and/or serum. In another aspect of the present invention, the glycan structure grouping is used to compare different tissue materials and characterize their specific glycosylation features. According to the present invention differences between relative proportions of glycan signal structure groups are used to compare different tissue material samples.

In a further aspect of the present invention, analysis of the glycan structure groups, preferentially including terminal HexNAc and/or low-mannose and optionally other groups separately or in combination, is used to differentiate between different tissue materials or different stages of tissue materials, preferentially to identify human disease and more preferentially human cancer. In a further preferred form the present method is used to differentiate between benign and malignant tumors. According to the present invention analysis of human serum glycan groups or combinations thereof according to the present invention can be used to identify the presence of other tissue materials in blood or serum samples, more preferably to identify disease and preferably malignant cancer.

Integrated Glycome Analysis Technology

The invention is directed to analysis of present cell materials based on single or several glycans (glycome profile) of cell materials according to the invention. The analysis of multiple glycans is preferably performed by physical analysis methods such as mass spectrometry and/or NMR.

The invention is specifically directed to integrated analysis process for glycomes, such as total glycomes and cell surface glycomes. The integrated process represent various novel aspects in each part of the process. The methods are especially directed to analysis of low amounts of cells. The integrated analysis process includes A) preferred preparation of substrate cell materials for analysis, including one or several of the methods: use of a chemical buffer solution, use of detergents, chemical reagents and/or enzymes.

B) release of glycome(s), including various subglycome type based on glycan core, charge and other structural features, use of controlled reagents in the process C) purification of glycomes and various subglycomes from complex mixtures D) preferred glycome analysis, including profiling methods such as mass spectrometry and/or NMR spectroscopy E) data processing and analysis, especially comparative methods between different sample types and quantitative analysis of the glycome data A. Preparation of Cell Materials Cell substrate material and its preparation for total and cell surface glycome analysis. The integrated glycome analysis includes preferably a cell preparation step to increase the availability of cell surface glycans. The cell preparation step preferably degrades either total cell materials or cell surface to yield a glycome for more effective glycan release. The degradation step preferably includes methods of physical degradation and/or chemical degradation. In a preferred embodiment at least one physical and one chemical degradation methods are combined, more preferably at least one physical method is combined with at least two chemical methods, even more preferably with at least three chemical methods.

The physical degration include degration by energy including thermal and/or mechanical energy directed to the cells to degrade cell structures such as heating, freezing, sonication, and pressure. The chemical degradation include use of chemicals and specific concentrations of chemicals for distruption distruption of cells preferably detergents including ionic and neutral detergents, chaotropic salts, denaturing chemicals such as urea, and non-physiological salt concentrations for distruption of the cells.

The glycome analysis according to the invention is divided to two methods including Total cell glycomes, and Cell surface glycomes. The production of Total cell glycomes involves degradation of cells by physical and/or chemical degradation methods, preferably at least by chemical methods, more preferably by physical and chemical methods. The Cell surface glycomes is preferably released from cell surface preserving cell membranes intact or as intact as possible, such methods involve preferably at least one chemical method, preferably enzymatic method. The cell surface glycomes may be alternatively released from isolated cell membranes, this method involves typically chemical and/or physical methods similarity as production of total cell glycomes, preferably at least use of detergents.

a. Total Cell Glycomes

The present invention revealed special methods for effective purification of released glycans from total cell derived materials so that free oligosaccharides can be obtained. In a preferred embodiment a total glycome is produced from a cell sample, which is degraded to form more available for release of glycans. A preferred degraded form of cells is detergent lysed cells optionally involving physical distruption of cell materials.

Preferred detergents and reaction conditions include, $\alpha 1$) ionic detergents, preferably SDS type anionic detergent comprising an anionic group such as sulfate and an alkyl chain of 8-16 carbon atoms, more preferably the anionic detergent comprise 10-14 carbon atoms and it is most preferably sodium dodecyl sulfate (SDS), and/or $\alpha 2$) non-ionic detergents such as alkylglycosides comprising a hexose and 4-12 carbon alkyl chain more preferably the alkyl chain comprises a hexoses being galactose, glucose, and/or mannose, more preferably glucose and/or mannose and the alkyl comprises 6-10 carbon atoms, preferably the non-ionic detergent is octylglucoside It is realized that various detergent combinations may be produced and optimized. The combined use of an ionic, preferably anionic, and non-ionic detergents according to the invention is especially preferred.

Preferred Cell Preparation Methods for Production of Total cell Glycome

The preferred methods of cell degration for Total cell glycomes include physical degration including at least heat treatment heat and chemical degration by a detergent method or by a non-detergent method preferably enzymatic degradation, preferably heat treatment. Preferably two physical degradation methods are included.

A Preferred Non-Detergent Method Includes

A non-detergent method is preferred for avoiding detergent in later purification. The preferred non-detergent method involves physical degradation of cells preferably pressure and or by heat and a chemical degradation by protease. A preferred non-detergent method includes:

i) cell degradation by physical methods, for example by pressure methods such as by French press.

The treatment is preferably performed quickly in cold temperatures, preferably at 0-2 degrees of Celsius, and more preferably at about 0 or 1 degree of celsius and/or in the presence of glycosidase inhibitors.

ii) The degraded cells are further treated with chemical degradation, preferably by effective general protease, more preferably trypsin is used for the treatment. Preferred trypsin preparation according to the invention does not cause glycan contamination to the sample/does not contain glycans releasable under the reaction conditions.

iii) optionally the physical degradation and chemical degradation are repeated.

iv) At the end of protease treatment the sample is boiled for further denaturing the sample and the protease. The boiling is performed at temperature denaturing/degrading further the sample and the protease activity (conditions thus depend on the protease used) preferably about 100 degrees Celsius for time enough for denaturing protease activity preferably about 10-20 minutes for trypsin, more preferably about 15 minutes.

Preferred Detergent Method for Production of Total Glycomes

The invention is in another preferred embodiment directed to detergent based method for lysing cells. The invention includes effective methods for removal of detergents in later purification steps. The detergent methods are especially preferred for denaturing proteins, which may bind or degrade glycans, and for degrading cell membranes to increase the accessibility of intracellular glycans.

For the detergent method the cell sample is preferably a cell pellet produced at cold temperature by centrifuging cells but avoiding distruption of the cells, optionally stored frozen and melted on ice. Optionally glycosidase inhibitors are used during the process.

The method includes following steps:
i) production of cell pellet preferably by centrifugation,
ii) lysis by detergent on ice, the detergent is preferably an anionic detergent according to the invention, more preferably SDS. The concentration of the detergent is preferably between about 0.1% and 5%, more preferably between 0.5%-3%, even more preferably between 0.5-1.5% and most preferably about 1% and the detergent is SDS (or between 0.9-1.1%). the solution is preferably produced in ultrapure water,
iii) mixing by effective degradation of cells, preferably mixing by a Vortex-mixer as physical degradation step,
iv) boiling on water bath, preferably for 3-10 min, most preferably about 5 min (4-6 min) as second physical degradation step, it is realized that even longer boiling may be performed for example up to 30 min or 15 min, but it is not optimal because of evaporation sample
v) adding one volume of non-ionic detergent, preferably alkyl-glycoside detergent according to the invention, most preferably n-octyl-β-D-glucoside, the preferred amount of the detergent is about 5-15% as water solution, preferably about 10% of octyl-glucoside. The non-ionic detergent is especially preferred in case an enzyme sensitive to SDS, such as a N-glycosidase, is to be used in the next reaction step. and
vi) incubation at room temperature for about 5 min to about 14 hours, more preferably less than half an hour, and most preferably about 15 min.

Preferred Amount of Detergents in the Detergent Method

Preferably the anionic detergent and cationic detergent solutions are used in equal volumes. Preferably the solutions are about 1% SDS and about 10% octyl-glucoside. The preferred amounts of the solutions are preferably from 0.1 µl to about 2 µl, more preferably 0.15 µl to about 1.5 µl per and most preferably from 0.16 µl to 1 µl per 100 000 cells of each solution. Lower amounts of the detergents are preferred if possible for reduction of the amount of detergent in later purification, highest amounts in relation to the cell amounts are used for practical reasons with lowest volumes. It is further realized that corresponding weight amounts of the detergents may be used in volumes of about 10% to about 1000%, or from about 20% to about 500% and even more effectively in volumes from 30% to about 300% and most preferably in volumes of range from 50% to about 150% of that described. It is realized that critical micellar concentration based effects may reduce the effect of detergents at lowest concentrations.

In a preferred embodiment a practical methods using tip columns as described in the invention uses about 1-3 µl of each detergent solution, more preferably 1.5-2.5 µL and most preferably about 2 µl of the preferred detergent solutions or corresponding detergent amounts are used for about 200 000 or less cells (preferably between 2000 and about 250 000 cells, more preferably from 50 000 to about 250 000 cells and most preferably from 100 000 to about 200 000 cells). Another practical method uses about 2-10 µl of each detergent solution, more preferably 4-8 µL and most preferably about 5 µl (preferably between 4 and 6 µl and more preferably between 4.5 and 5.5 µl) of detergent solutions or corresponding amount of the detergents for lysis of cell of a cell amount from about 200 000-3 million cells (preferred more exact ranges include 200 000-3.5 million, 200 000 to 3 million and 200 000 to 2.5 million cells), preferably a fixed amount (specific amount of microliters preferably with the accuracy of at least 0.1 microliter) in a preferred range such as of 5.0 µl is used for the wider range of cells 200 000-3 million. It was invented that is possible to handle similarity wider range of materials. It is further realized that the method can be optimized so that exact amount of detergent, preferably within the ranges described, is used for exact amount of cells, such method is preferably an automized when there is possible variation in amounts of sample cells.

b. Cell Surface Glycomes

In another preferred embodiment the invention is directed to release of glycans from intact cells and analysis of released cell surface glycomes. The present invention is directed to specific buffer and enzymatic cell pre-modification conditions that would allow the efficient use of enzymes for release and optionally modification and release of glycans.

B. The Glycan Release Methods

The invention is directed to various enzymatic and chemical methods to release glycomes. The release step is not needed for soluble glycomes according to the invention. The invention further revealed soluble glycome components which can be isolated from the cells using methods according to the invention.

C. Purification of glycans from cell derived materials The purification of glycome materials form cell derived molecules is a difficult task. It is especially difficult to purify glycomes to obtain picomol or low nanomol samples for glycome profiling by mass spectrometry or NMR-spectrometry. The invention is especially directed to production of material allowing quantitative analysis over a wide mass range. The invention is specifically directed to the purification of non-derivatized or reducing end derivatized glycomes according to the invention and glycomes containing specific structural characteristics according to the invention. The structural characteristics were evaluated by the preferred methods according to the invention to produce reproducible and quantitative purified glycomes.

Glycan Purification Process Steps

The glycan purification method according to the present invention consists of at least one of purification options, preferably in specific combinations described below, including one or several of following the following purification process steps in varying order:
6) Precipitation-extraction;
7) Ion-exchange;
8) Hydrophobic interaction;
9) Hydrophilic interaction; and
10) Affinity to carbon materials especially graphitized carbon.

Prepurification and Purification Process Steps

In general the purification steps may be divided to two major categories:

Prepurification steps to remove major contaminations and purification steps usually directed to specific binding and optionally fractionation of glycomes a) Prepurification to Remove Non-Carbohydrate Impurities The need for prepurification depends on the type and amounts of the samples and the amounts of impurities present. Certain samples it is possible to omit all or part of the prepurification steps. The prepurification steps are aimed for removal of major non-carbohydrate impurities by separating the impurity and the glycome fraction(s) to be purified to different phases by precipitation/extraction or binding to chromatography matrix and the separating the impurities from the glycome fraction(s).

The prepurification steps include one, two or three of following major steps:
Precipitation-extraction, Ion-exchange, Hydrophobic interaction.

The precipitation and/or extraction is based on the high hydrophilic nature of glycome compositions and components, which is useful for separation from different cellular components and chemicals. The prepurification ion exchange chromatography is directed to removal of classes molecules with different charge than the preferred glycome or glycome fraction to be studied. This includes removal of salt ions and aminoacids, and peptides etc. The glycome may comprise only negative charges or in more rare case also only positive charges and the same charge is selected for the chromatography matrix for removal of the impurities for the same charge without binding the glycome at prepurification.

In a preferred embodiment the invention is directed to removal of cationic impurities from glycomes glycomes containing neutral and/or negatively charged glycans. The invention is further directed to use both anion and cation exchange for removal of charged impurities from non-charged glycomes. The preferred ion exchange and cation exchange materials includes polystyrene resins such as Dowex resins.

The hydrophilic chromatography is preferably aimed for removal of hydrophobic materials such as lipids detergents and hydrophobic protein materials. The preferred hydrophobic chromatography materials includes.

It is realized that different combinations of the prepurification are useful depending on the cell preparation and sample type. Preferred combinations of the prepurification steps include:
Precipitation-extraction and Ion-exchange; Precipitation-extraction and Hydrophobic interaction; and Ion-exchange and Hydrophobic interaction. The two prepurification steps are preferably performed in the given order.

Purification Steps Including Binding and Optionally Fractionation of Glycomes

The purification steps utilize two major concepts for binding to carbohydrates and combinations thereof: a) Hydrophilic interactions and b) Ion exchange a) Hydrophilic Interactions The present invention is specifically directed to use of matrices with repeating polar groups with affinity for carbohydrates for purification of glycome materials according to the invention in processes according of the invention. The hydrophilic interaction material may include additional ion exchange properties.

The preferred hydrophilic interaction materials includes carbohydrate materials such as carbohydrate polymers in presence of non-polar organic solvents. A especially preferred hydrophilic interaction chromatography matrix is cellulose.

A specific hydrophilic interaction material includes graphitized carbon. The graphitized carbon separates non-charged carbohydrate materials based mainly on the size on the glycan. There is also possible ion exchange effects. In a preferred embodiment the invention is directed to graphitized carbon chromatography of prepurified samples after desalting and removal of detergents.

The invention is specifically directed to purification of non-derivatized glycomes and neutral glycomes by cellulose chromatography. The invention is further directed to purification of non-derivatized glycomes and neutral glycomes by graphitized carbon chromatography. In a preferred embodiment the purification according to the invention includes both cellulose and graphitized carbon chromatography.

b) Ion Exchange

The glycome may comprise only negative charges or in more rare case also only positive charges. At purification stage the ion exchange material is selected to contain opposite charge than the glycome or glycome fraction for binding the glycome. The invention is especially directed to the use of anion exchange materials for binding of negatively charged. Preferred ion exchange materials includes ion exchange and especially anion exchange materials includes polystyrene resins such as Dowex-resins, preferably quaternary amine resins anion exchange or sulfonic acid cation exchange resins It was further revealed that even graphitized carbon can be used for binding of negatively charged glycomes and the materials can be eluted from the carbon separately from the neutral glycomes or glycome fractions according to the invention.

The invention is specifically directed to purification of anionic glycomes by anion exchange chromatography.

The invention is specifically directed to purification of anionic glycomes by anion exchange chromatography.

The invention is further directed to purification of anionic glycomes by cellulose chromatography. The preferred anionic glycomes comprise sialic acid and/or sulfo/fosfo esters, more preferably both sialic acid and sulfo/fosfo esters. A preferred class of sulfo/fosfoester glycomes are complex type N-glycans comprising sulfate esters.

Prepurification and Purification Steps in Detail

1) Precipitation-extraction may include precipitation of glycans or precipitation of contaminants away from the glycans. Preferred precipitation methods include:
   1. Glycan material precipitation, for example acetone precipitation of glycoproteins, oligosaccharides, glycopeptides, and glycans in aqueous acetone, preferentially ice-cold over 80% (v/v) aqueous acetone; optionally combined with extraction of glycans from the precipitate, and/or extraction of contaminating materials from the precipitate;
   2. Protein precipitation, for example by organic solvents or trichloroacetic acid, optionally combined with extraction of glycans from the precipitate, and/or extraction of contaminating materials from the precipitate;
   3. Precipitation of contaminating materials, for example precipitation with trichloroacetic acid or organic solvents such as aqueous methanol, preferentially about ⅔ aqueous methanol for selective precipitation of proteins and other non-soluble materials while leaving glycans in solution;

2) Ion-exchange may include ion-exchange purification or enrichment of glycans or removal of contaminants away from the glycans. Preferred ion-exchange methods include:
   1. Cation exchange, preferably for removal of contaminants such as salts, polypeptides, or other cationizable molecules from the glycans; and
   2. Anion exchange, preferably either for enrichment of acidic glycans such as sialylated glycans or removal of charged contaminants from neutral glycans, and also preferably for separation of acidic and neutral glycans into different fractions.

3) Hydrophilic interaction may include purification or enrichment of glycans due to their hydrophilicity or specific adsorption to hydrophilic materials, or removal of contaminants such as salts away from the glycans. Preferred hydrophilic interaction methods include:

1. Hydrophilic interaction chromatography with specific organic or inorganic polar interaction materials, preferably for purification or enrichment of glycans and/or glycopeptides;
2. Preferably adsorption of glycans to carbohydrate materials, preferably to cellulose in hydrophobic solvents for their purification or enrichment, preferably to microcrystalline cellulose, and elution by polar solvents such as water and or alcohol which is preferably ethanol or methanol. The solvent system for absorption comprise preferably
   i) a hydrophobic alcohol comprising about three to five carbon atoms, including propanols, butanols, and pentanols, more preferably being n-butanol;
   ii) a hydrophilic alcohol such as methanol or ethanol, more preferably methanol, or a hydrophilic weak organic acid, preferably acetic acid and;
   iii) water. The hydrophobic alcohol being the major constituent of the mixture with multifold excess to other components. The absorption composition is preferably using an n-butanol:methanol:water or similar solvent system for adsorption and washing the adsorbed glycans, in most preferred system n-butanol:methanol:water in relative volumes of 10:1:2. The preferred polar solvents for elution of the glycomes are water or water:ethanol or similar solvent system for elution of purified glycans from cellulose. Fractionation is possible by using first less polar elution solvent to elute a fraction of glycome compositions and the eluting rest by more polar solvent such as water
3. Affinity to carbon may include purification or enrichment of glycans due to their affinity or specific adsorption to specific carbon materials preferably graphitized carbon, or removal of contaminants away from the glycans. Preferred graphitized carbon affinity methods includes porous graphitized carbon chromatography.

Preferred purification methods according to the invention include combinations of one or more prepurification and/or purification steps. The preferred method include preferably at least two and more preferably at least three prepurification steps according to the invention. The preferred method include preferably at least one and more preferably at least two purification steps according to the invention. It is further realized that one prepurification step may be performed after a purification step or one purification step may be performed after a prepurification step. The method is preferably adjusted based on the amount of sample and impurities present in samples. Examples of the preferred combinations include the following combinations:

For neutral underivatized glycan purification:
A. 1. precipitation and/or extraction 2. cation exchange of contaminants, 3. hydrophobic adsorption of contaminants, and 4. hydrophilic purification, preferably by carbon, preferably graphitized carbon, and/or carbohydrate affinity purification of glycans.
B. 1. precipitation and/or extraction, 2. hydrophobic adsorption of contaminants 3. cation exchange of contaminants, 4. hydrophilic purification by carbon, preferably graphitized carbon, and/or carbohydrate affinity purification of glycans The preferred method variants further includes preferred variants when
1. both carbon and carbohydrate chromatography is performed in step 4,
2. only carbon chromatography is performed in step 4
3. only carbohydrate chromatography is performed in step 4
4. order steps three and four is exchanged
5. both precipitation and extraction are performed in prepurification step 2) For sialylated/acidic underivatized glycan purification: The same methods are preferred but preferably both carbon and carbohydrate chromatography is performed in step 4. The carbohydrate affinity chromatography is especially preferred for acidic and/sialylated glycans. In a preferred embodiment for additional purification one or two last chromatography methods are repeated.

D. Analysis of the Glycomes

The present invention is specifically directed to detection various component in glycomes by specific methods for recognition of such components. The methods includes binding of the glycome components by specific binding agents according to the invention such as antibodies and/or enzymes, these methods preferably include labeling or immobilization of the glycomes. For effective analysis of the glycome a large panel of the binding agents are needed.

The invention is specifically directed to physicochemical profiling methods for exact analysis of glycomes. The preferred methods includes mass spectrometry and NMR-spectroscopy, which give simultaneously information of numerous components of the glycomes. In a preferred embodiment the mass spectrometry and NMR-spectroscopy methods are used in a combination.

E. Quantitative and Qualitative Analysis of Glycome Data

The invention revealed methods to create reproducible and quantitative profiles of glycomes over large mass ranges and degrees of polymerization of glycans. The invention further reveals novel methods for quantitative analysis of the glycomics data produced by mass spectrometry. The invention is specifically directed to the analysis of non-derivatized or reducing end derivatized glycomes according to the invention and the glycomes containing specific structural characteristics according of the invention.

The invention revealed effective means of comparison of glycome profiles from different cell types or cells with difference in cell status or cell types. The invention is especially directed to the quantitative comparison of relative amount of individual glycan signal or groups of glycan signals described by the invention.

The invention is especially directed to
i) calculating average value and variance values of signal or signals, which have obtained from several experiments/samples and which correspond to an individual glycan or glycan group according to the invention for a first cell sample and for a second cell sample
ii) comparing these with values derived for the corresponding signal(s)
iii) optionally calculating statistic value for testing the probability of similarity of difference of the values obtained for the cell types or
estimating the similarity or difference based on the difference of the average and optionally also based on the variance values.
iv) preferably repeating the comparison one or more signals or signal groups, and further preferably performing combined statistical analysis to estimate the similarity and/or differences between the data set or estimating the difference or similarity
v) preferably use of the data for estimating the differences between the first and second cell samples indicating difference in cell status and/or cell type The invention is further directed to combining information of several quantitative comparisons of between corresponding signals by method of
i) calculating differences between quantitative values of corresponding most different glycan signals or glycan group signals, changing negative values to corresponding positive values, optionally multiplying selected signals by selected factors to adjust the weight of the signals in the calculation
ii) adding the positive difference values to a sum value
iii) comparing the sum values as indicators of cell status or type.

It was further revealed that there is characteric signals that are present in certain cell types according to the invention but absent or practically absent in other cell types. The invention is therefore directed to the qualitative comparison of relative amount of individual glycan signal or groups of glycan signals described by the invention and observing signals present or absent/practically absent in a cell type. The invention is further directed to selection of a cut off value used for selecting absent or practically absent signals from a mass spectrometric data, for example the preferred cut off value may be selected in range of 0-3% of relative amount, preferably the cut off value is less than 2%, or less than 1% or less than 0.5%. In a preferred embodiment the cut off value is adjusted or defined based on quality of the mass spectrum obtained, preferably based on the signal intensities and/or based on the number of signals observable.

The invention is further directed to automized qualitative and/or quantitative comparisons of data from corresponding signals from different samples by computer and computer programs processing glycome data produced according to the invention. The invention is further directed to raw data based analysis and neural network based learning system analysis as methods for revealing differences between the glycome data according to the invention.

Identification and Classification of Differences in Glycan Datasets

The present invention is specifically directed to analyzing glycan datasets and glycan profiles for comparison and characterization of different tissue materials. In one embodiment of the invention, glycan signals or signal groups associated with given tissue material are selected from the whole glycan datasets or profiles and indifferent glycan signals are removed. The resulting selected signal groups have reduced background and less observation points, but the glycan signals most important to the resolving power are included in the selection. Such selected signal groups and their patterns in different sample types serve as a signature for the identification of the cell type and/or glycan types or biosynthetic groups that are typical to it. By evaluating multiple samples from the same tissue material, glycan signals that have individual i.e. cell line specific variation can be excluded from the selection. Moreover, glycan signals can be identified that do not differ between tissue materials, including major glycans that can be considered as housekeeping glycans.

To systematically analyze the data and to find the major glycan signals associated with given tissue material according to the invention, difference-indicating variables can be calculated for the comparison of glycan signals in the glycan datasets. Preferential variables between two samples include variables for absolute and relative difference of given glycan signal between the datasets from two tissue materials. Most preferential variables according to the invention are:
1. absolute difference $A=(S2-S1)$, and
2. relative difference $R=A/S1$,
wherein S1 and S2 are relative abundances of a given glycan signal in cell types 1 and 2, respectively.

It is realized that other mathematical solutions exist to express the idea of absolute and relative difference between glycan datasets, and the above equations do not limit the scope of the present invention. According to the present invention, after A and R are calculated for the glycan profile datasets of the two tissue materials, the glycan signals are thereafter sorted according to the values of A and R to identify the most significant differing glycan signals. High value of A or R indicates association with tissue material 2, and vice versa. In the list of glycan data sorted independently by R and A, the tissue material specific glycans occur at the top and the bottom of the lists. More preferentially, if a given signal has high values of both A and R, it is more significant.

Preferred Representation of the Dataset When Comparing Two Tissue Materials

The present invention is specifically directed to the comparative presentation of the quantitative glycome dataset as multidimensional graphs comparing the parallel data or as other three dimensional presentations or for example as two dimensional matrix showing the quantities with a quantitative code, preferably by a quantitative color code.

Methods for Low Sample Amounts

The present invention is specifically directed to methods for analysis of low amounts of samples.

The invention further revealed that it is possible to use the methods according to the invention for analysis of low sample amounts. It is realized that the cell materials are scarce and difficult to obtain from natural sources. The effective analysis methods would spare important cell materials. Under certain circumstances such as in context of cell culture the materials may be available from large scale. The required sample scale depends on the relative abundancy of the characteristic components of glycome in comparison to total amount of carbohydrates. It is further realized that the amount of glycans to be measured depend on the size and glycan content of the cell type to be measured and analysis including multiple enzymatic digestions of the samples would likely require more material. The present invention revealed especially effective methods for free released glycans.

The picoscale samples comprise preferably at least about 1000 cells, more preferably at least about 50 000 cells, even more more preferably at least 100 000 cells, and most preferably at least about 500 000 cells. The invention is further directed to analysis of about 1 000 000 cells. The preferred picoscale samples contain from at least about 1000 cells to about 10 000 000 cells according to the invention. The useful range of amounts of cells is between 50 000 and 5 000 000, even more preferred range of cells is between 100 000 and 3 000 000 cells. A preferred practical range for free oligosaccharide glycomes is between about 500 000 and about 2 000 000 cells. It is realized that cell counting may have variation of less than 20%, more preferably 10% and most preferably 5%, depending on cell counting methods and cell sample, these variations may be used instead of term about. It is further understood that the methods according to the present invention can be upscaled to much larger amounts of material and the pico/nanoscale analysis is a specific application of the technology.

The invention is specifically directed to use of microcolumn technologies according to the invention for the analysis of the preferred picoscale and low amount samples according to the invention, The invention is specifically directed to purification to level, which would allow production of high quality mass spectrum covering the broad size range of glycans of glycome compositions according to the invention.

Glycan Preparation and Purification for Glycome Analysis of Cell Materials According to the Invention, Especially for Mass Spectrometric Methods Use of Microfluidistic Methods Including Microcolumn Chromatography The present invention is especially directed to use microfluidistic methods involving low sample volumes in handling of the glycomes in low volume cell preparation, low volume glycan release and various chromatographic steps. The invention is further directed to integrated cell preparation, glycan release, and purification and analysis steps to reduce loss of material and material based contaminations. It is further realized that special cleaning of materials is required for optimal results.

Low Volume Reaction in Cell Preparation and Glycan Release

The invention is directed to reactions of volume of 1-100 microliters, preferably about 2-50 microliters and even more preferably 3-20 microliters, most preferably 4-10 microliter. The most preferred reaction volumes includes 5-8 microliters+/−1 microliters. The minimum volumes are preferred to get optimally concentrated sample for purification. The amount of material depend on number of experiment in analysis and larger amounts may be produced preferably when multiple structural analysis experiments are needed.

It is realized that numerous low volume chromatographic technologies may be applied, such low volume column and for example disc based microfluidistic systems.

The inventors found that the most effective methods are microcolumns. Small column can be produced with desired volume. Preferred volumes of microcolumns are from about 2 Microliters to about 500 microliters, more preferably for routine sample sizes from about 5 microliter to about 100 microliters depending on the matrix and size of the sample. Preferred microcolumn volumes for graphitised carbon, cellulose chromatography and other tip-columns are from 2 to 20 µl, more preferably from 3 to 15 µl, even more preferably from 4 to 10 µl, For the microcolumn technologies in general the samples are from about 10 000 to about million cells. The methods are useful for production of picomol amounts of total glycome mixtures from cells according to the invention.

In a preferred embodiment microcolumns are produced in regular disposable usually plastic pipette tips used for example in regular "Finnpipette"-type air-piston pipettes. The pipette-tip microcolumn contain the preferred chromatographic matrix. In a preferred embodiment the microcolumn contains two chromatographic matrixes such as an anion and cation exchange matrix or a hydrophilic and hydrophobic chromatography matrix.

The pipette tips may be chosen to be a commercial tip contain a filter. In a preferred embodiment the microcolumn is produced by narrowing a thin tip from lower half so that the preferred matrix is retained in the tip. The narrowed tip is useful as the volume of filter can be omitted from washing steps The invention is especially directed to plastic pipette tips containing the cellulose matrix, and in an other embodiment to the pipette tip microcolumns when the matrix is graphitised carbon matrix. The invention is further directed to the preferred tip columns when the columns are narrowed tips, more preferably with column volumes of 1 microliter to 100 microliters.

The invention is further directed to the use of the tip columns containing any of the preferred chromatographic matrixes according to the invention for the purification of glycomes according to the invention, more preferably matrixes for ion exchange, especially polystyrene anion exchangers and cation exchangers according to the invention; hydrophilic chromatographic matrixes according to the invention, especially carbohydrate matrixes and most cellulose matrixes.

The Binding Methods for Recognition of Structures from Cell Surfaces

Recognition of Structures from Glycome Materials and on Cell Surfaces by Binding Methods The present invention revealed that beside the physicochemical analysis by NMR and/or mass spectrometry several methods are useful for the analysis of the structures. The invention is especially directed to two methods:

i) Recognition by enzymes involving binding and alteration of structures.

This method alters specific glycan structures by enzymes capable of altering the glycan structures. The preferred enzymes includes a) glycosidase-type enzymes capable of releasing monosaccharide units from glycans b) glycosyltransferring enzymes, including transglycosylating enzymes and glycosyltransferases c) glycan modifying enzymes including sulfate and or fosfate modifying enzymes ii) Recognition by molecules binding glycans referred as the binders These molecules bind glycans and include property allowing observation of the binding such as a label linked to the binder. The preferred binders include a) Proteins such as antibodies, lectins and enzymes b) Peptides such as binding domains and sites of proteins, and synthetic library derived analogs such as phage display peptides c) Other polymers or organic scaffold molecules mimicking the peptide materials The peptides and proteins are preferably recombinant proteins or corresponding carbohydrate recognition domains derived thereof, when the proteins are selected from the group monoclonal antibody, glycosidase, glycosyl transferring enzyme, plant lectin, animal lectin or a peptide mimetic thereof, and wherein the binder includes a detectable label structure.

Preferred Binder Molecules

The present invention revealed various types of binder molecules useful for characterization of cells according to the invention and more specifically the preferred cell groups and cell types according to the invention. The preferred binder molecules are classified based on the binding specificity with regard to specific structures or structural features on carbohydrates of cell surface. The preferred binders recognize specifically more than single monosaccharide residue.

It is realized that most of the current binder molecules such as all or most of the plant lectins are not optimal in their specificity and usually recognize roughly one or several monosaccharides with various linkages. Furthermore the specificities of the lectins are usually not well characterized with several glycans of human types.

The preferred high specificity binders recognize

A) at least one monosaccharide residue and a specific bond structure between those to another monosaccharides next monosaccharide residue referred as MS1B1-binder, B) more preferably recognizing at least part of the second monosaccharide residue referred as MS2B1-binder, C) even more preferably recognizing second bond structure and or at least part of third mono saccharide residue, referred as MS3B2-binder, preferably the MS3B2 recognizes a specific complete trisaccharide structure.

D) most preferably the binding structure recognizes at least partially a tetrasaccharide with three bond structures, referred as MS4B3-binder, preferably the binder recognizes complete tetrasaccharide sequences.

The preferred binders includes natural human and or animal, or other proteins developed for specific recognition of glycans. The preferred high specificity binder proteins are specific antibodies preferably monoclonal antibodies; lectins, preferably mammalian or animal lectins; or specific glycosyltransferring enzymes more preferably glycosidase type enzymes, glycosyltransferases or transglycosylating enzymes.

Target Structures for Specific Binders and Examples of the Binding Molecules

Combination of Terminal Structures in Combination with Specific Glycan Core Structures It is realized that part of the structural elements are specifically associated with specific glycan core structure. The recognition of terminal structures linked to specific core structures are especially preferred, such high specificity reagents have capacity of recognition almost complete individual glycans to the level of physicochemical characterization according to the invention. For example many specific mannose structures according to the invention are in general quite characteristic for N-glycan glycomes according to the invention. The present invention is especially directed to recognition terminal epitopes.

Common Terminal Structures on Several Glycan Core Structures

The present invention revealed that there are certain common structural features on several glycan types and that it is possible to recognize certain common epitopes on different glycan structures by specific reagents when specificity of the reagent is limited to the terminal without specificity for the core structure. The invention especially revealed characteristic terminal features for specific cell-types according to the invention. The invention realized that the common epitopes increase the effect of the recognition. The common terminal structures are especially useful for recognition in the context with possible other cell types or material, which do not contain the common terminal structure in substantial amount.

Specific Preferred Structural Groups

The present invention is directed to recognition of oligosaccharide sequences comprising specific terminal monosaccharide types, optionally further including a specific core structure. The preferred oligosaccharide sequences classified based on the terminal monosaccharide structures.

1. Structures with Terminal Mannose Monosaccharide

Preferred mannose-type target structures have been specifically classified by the invention. These include various types of high and low-mannose structures and hybrid type structures according to the invention.

Low or Uncharacterised Specificity Binders

Preferred for recognition of terminal mannose structures includes mannose-monosaccharide binding plant lectins.

Preferred High Specific High Specificity Binders Include i) Specific mannose residue releasing enzymes such as linkage specific mannosidases, more preferably an α-mannosidase or β-mannosidase.

Preferred α-mannosidases includes linkage specific α-mannosidases such as α-Mannosidases cleaving preferably non-reducing end terminal α2-linked mannose residues specifically or more effectively than other linkages, more preferably cleaving specifically Manα2-structures; or α6-linked mannose residues specifically or more effectively than other linkages, more preferably cleaving specifically Manα6-structures;

Preferred β-mannosidases includes β-mannosidases capable of cleaving β4-linked mannose from non-reducing end terminal of N-glycan core Manβ4GlcNAc-structure without cleaving other C-linked monosaccharides in the glycomes.

ii) Specific binding proteins recognizing preferred mannose structures according to the invention. The preferred reagents include antibodies and binding domains of antibodies (Fab-fragments and like), and other engineered carbohydrate binding proteins. The invention is directed to antibodies recognizing MS2B1 and more preferably MS3B2-structures 2. Structures with Terminal Gal-Monosaccharide Preferred galactose-type target structures have been specifically classified by the invention. These include various types of N-acetyllactosamine structures according to the invention.

Low or Uncharacterised Specificity Binders for Terminal Gal

Preferred for recognition of terminal galactose structures includes plant lectins such as ricin lectin (*ricinus communis* agglutinin RCA), and peanut lectin(/agglutinin PNA).

Preferred High Specific High Specificity Binders Include i) Specific galactose residue releasing enzymes such as linkage specific galactosidases, more preferably α-galactosidase or β-galactosidase.

Preferred α-galactosidases include linkage galactosidases capable of cleaving Galα3Gal-structures revealed from specific cell preparations Preferred β-galactosidases includes β-galactosidases capable of cleaving β4-linked galactose from non-reducing end terminal Galβ4GlcNAc-structure without cleaving other β-linked monosaccharides in the glycomes and β3-linked galactose from non-reducing end terminal Galβ3GlcNAc-structure without cleaving other β-linked monosaccharides in the glycomes ii) Specific binding proteins recognizing preferred galactose structures according to the invention. The preferred reagents include antibodies and binding domains of antibodies (Fab-fragments and like), and other engineered carbohydrate binding proteins and animal lectins such as galectins.

3. Structures with Terminal GalNAc-Monosaccharide

Preferred GalNAc-type target structures have been specifically revealed by the invention. These include especially LacdiNAc, GalNAcβGlcNAc-type structures according to the invention.

Low or Uncharacterised Specificity Binders for Terminal GalNAc

Several plant lectins has been reported for recognition of terminal GalNAc. It is realized that some GalNAc-recognizing lectins may be selected for low specificity recognition of the preferred LacdiNAc-structures.

Preferred High Specific High Specificity Binders Include i) The invention revealed that β-linked GalNAc can be recognized by specific β-N-acetylhexosaminidase enzyme in combination with β-N-acetylhexosaminidase enzyme. This combination indicates the terminal monosaccharide and at least part of the linkage structure.

Preferred β-N-acetylhexosaminidase, includes enzyme capable of cleaving β-linked GalNAc from non-reducing end terminal GalNAcβ4/3-structures without cleaving α-linked HexNAc in the glycomes; preferred N-acetylglucosaminidases include enzyme capable of cleaving β-linked GlcNAc but not GalNAc.

ii) Specific binding proteins recognizing preferred GalNAcβ4, more preferably

GalNAcβ4GlcNAc, structures according to the invention. The preferred reagents include antibodies and binding domains of antibodies (Fab-fragments and like), and other engineered carbohydrate binding proteins, and a special plant lectin WFA (*Wisteria floribunda* agglutinin).

4. Structures with Terminal GlcNAc-Monosaccharide

Preferred GlcNAc-type target structures have been specifically revealed by the invention. These include especially GlcNAcβ-type structures according to the invention.

Low or Uncharacterised Specificity Binders for Terminal GlcNAc

Several plant lectins has been reported for recognition of terminal GlcNAc. It is realized that some GlcNAc-recognizing lectins may be selected for low specificity recognition of the preferred GlcNAc-structures.

Preferred High Specific High Specificity Binders Include
i) The invention revealed that β-linked GlcNAc can be recognized by specific β-N-acetylglucosaminidase enzyme.

Preferred β-N-acetylglucosaminidase includes enzyme capable of cleaving C-linked GlcNAc from non-reducing end terminal GlcNAcβ2/3/6-structures without cleaving β-linked GalNAc or α-linked HexNAc in the glycomes;

ii) Specific binding proteins recognizing preferred GlcNAcβ2/3/6, more preferably GlcNAcβ2Manα, structures according to the invention. The preferred reagents include antibodies and binding domains of antibodies (Fab-fragments and like), and other engineered carbohydrate binding proteins.

5. Structures with Terminal Fucose-Monosaccharide

Preferred fucose-type target structures have been specifically classified by the invention. These include various types of N-acetyllactosamine structures according to the invention.

Low or Uncharacterised Specificity Binders for Terminal Fuc

Preferred for recognition of terminal fucose structures includes fucose monosaccharide binding plant lectins. Lectins of *Ulex europeaus* and *Lotus tetragonolobus* has been reported to recognize for example terminal Fucoses with some specificity binding for α2-linked structures, and branching α3-fucose, respectively.

Preferred High Specific High Specificity Binders Include
i) Specific fucose residue releasing enzymes such as linkage fucosidases, more preferably α-fucosidase.

Preferred α-fucosidases include linkage fucosidases capable of cleaving Fucα2Gal-, and Galβ4/3(Fucα3/4) GlcNAc-structures revealed from specific cell preparations.

ii) Specific binding proteins recognizing preferred fucose structures according to the invention. The preferred reagents include antibodies and binding domains of antibodies (Fab-fragments and like), and other engineered carbohydrate binding proteins and animal lectins such as selectins recognizing especially Lewis type structures such as Lewis x, Galβ4 (Fucα3)GlcNAc, and sialyl-Lewis x, SAα3Galβ4(Fucα3) GlcNAc.

The preferred antibodies includes antibodies recognizing specifically Lewis type structures such as Lewis x, and sialyl-Lewis x. More preferably the Lewis x-antibody is not classic SSEA-1 antibody, but the antibody recognizes specific protein linked Lewisxstructures such as Galβ4(Fucα3) GlcNAcβ2Manα-linked to N-glycan core.

6. Structures with terminal Sialic Acid-Monosaccharide

Preferred sialic acid-type target structures have been specifically classified by the invention.

Low or Uncharacterised Specificity Binders for Terminal Fuc

Preferred for recognition of terminal sialic acid structures includes sialic acid monosaccharide binding plant lectins.

Preferred High Specific High Specificity Binders Include
i) Specific sialic acid residue releasing enzymes such as linkage sialidases, more preferably α-sialidases.

Preferred α-sialidases include linkage sialidases capable of cleaving SAα3Gal- and SAα6Gal-structures revealed from specific cell preparations by the invention.

Preferred lectins, with linkage specificity include the lectins, that are specific for SAα3Gal-structures, preferably being *Maackia amurensis* lectin and/or lectins specific for SAα6Gal-structures, preferably being *Sambucus nigra* agglutinin.

ii) Specific binding proteins recognizing preferred sialic acid oligosaccharide sequence structures according to the invention. The preferred reagents include antibodies and binding domains of antibodies (Fab-fragments and like), and other engineered carbohydrate binding proteins and animal lectins such as selectins recognizing especially Lewis type structures such as sialyl-Lewis x, SAα3Galβ4(Fucα3)GlcNAc or sialic acid recognizing Siglec-proteins.

The preferred antibodies includes antibodies recognizing specifically sialyl-N-acetyllactosamines, and sialyl-Lewis x.

Preferred antibodies for NeuGc-structures includes antibodies recognizes a structure NeuGcα3Galβ4Glc(NAc)$_{0\ or\ 1}$ and/or GalNAcβ4[NeuGcα3]Galβ4Glc(NAc)$_{0\ or\ 1}$, wherein [ ] indicates branch in the structure and ( )$_{0\ or\ 1}$ a structure being either present or absent. In a preferred embodiment the invention is directed recognition of the N-glycolyl-Neuraminic acid structures by antibody, preferably by a monoclonal antibody or human/humanized monoclonal antibody. A preferred antibody contains the variable domains of P3-antibody.

Binder-Label Conjugates

The present invention is specifically directed to the binding of the structures according to the present invention, when the binder is conjugated with "a label structure". The label structure means a molecule observable in a assay such as for example a fluorescent molecule, a radioactive molecule, a detectable enzyme such as horse radish peroxidase or biotin/streptavidin/avidin. When the labelled binding molecule is contacted with the cells according to the invention, the cells can be monitored, observed and/or sorted based on the presence of the label on the cell surface. Monitoring and observation may occur by regular methods for observing labels such as fluorescence measuring devices, microscopes, scintillation counters and other devices for measuring radioactivity.

Use of Binder and Labelled Binder-Conjugates for Cell Sorting

The invention is specifically directed to use of the binders and their labelled conjugates for sorting or selecting cells from biological materials or samples including cell materials comprising other cell types. The preferred cell types includes cultivated cells and associated cells such as feeder cells. The labels can be used for sorting cell types according to invention from other similar cells. In another embodiment the cells are sorted from different cell types such as blood cells or in context of cultured cells preferably feeder cells, for example in context of complex cell cultures corresponding feeder cells such as human or mouse feeder cells. A preferred cell sorting method is FACS sorting. Another sorting methods utilized immobilized binder structures and removal of unbound cells for separation of bound and unbound cells.

Use of Immobilized Binder Structures

In a preferred embodiment the binder structure is conjugated to a solid phase. The cells are contacted with the solid phase, and part of the material is bound to surface. This method may be used to separation of cells and analysis of cell surface structures, or study cell biological changes of cells due to immobilization. In the analytics involving method the cells are preferably tagged with or labelled with a reagent for the detection of the cells bound to the solid phase through a binder structure on the solid phase. The methods preferably further include one or more steps of washing to remove unbound cells.

Preferred solid phases include cell suitable plastic materials used in contacting cells such as cell cultivation bottles, petri dishes and microtiter wells; fermentor surface materials Specific Recognition Between Preferred Tissue Materials and Contaminating Materials The invention is further directed to methods of recognizing different tissue materials, preferably human tissues and more preferably human excretions or serum. It is further realized, that the present reagents can be used for purification of tissue materials by any fractionation method using the specific binding reagents.

Preferred fractionation methods includes fluorescence activated cell sorting (FACS), affinity chromatography methods, and bead methods such as magnetic bead methods.

The invention is further directed to positive selection methods including specific binding to the tissue material but not to contaminating tissue materials. The invention is further directed to target selection methods including specific binding to the contaminating tissue material but not to the target tissue materials. In yet another embodiment of recognition of tissue materials the tissue material is recognized together with a homogenous reference sample, preferably when separation of other materials is needed. It is realized that a reagent for positive selection can be selected so that it binds tissue materials as in the present invention and not to the contaminating tissue materials and a reagent for negative selection by selecting opposite specificity. In case of tissue material type according to the invention is to be selected amongst novel tissue materials not studied in the present invention, the binding molecules according to the invention maybe used when verified to have suitable specificity with regard to the novel tissue material (binding or not binding). The invention is specifically directed to analysis of such binding specificity for development of a new binding or selection method according to the invention.

The preferred specificities according to the invention include recognition of:
 i) mannose type structures, especially alpha-Man structures like lectin PAA
 ii) sialylated structures similarity as by MAA-lectin
 iii) Gal/GalNAc binding specificity, preferably Gal1-3/GalNAc1-3 binding specificity, more preferably Galβ1-3/GalNAcβ1-3 binding specificity similar to PNA Preferred Cell Population to be Produced by Glycomodification According to the Present Invention The present invention is directed to specific cell populations comprising in vitro enzymatically altered glycosylations according to the present invention. It is realized that special structures revealed on cell surfaces have specific targeting, and immune recognition properties with regard to cells carrying the structures. It is realized that sialylated and fucosylated terminal structures such as sialyl-lewis x structures target cells to selectins involved in bone marrow homing of cells and invention is directed to methods to produce such structures on cells surfaces. It is further realized that mannose and galactose terminal structures revealed by the invention target cells to liver and/or to immune recognition, which in most cases are harmful for effective cell therapy, unless liver is not targeted by the cells. NeuGc is target for immune recognition and has harmful effects for survival of cells expressing the glycans.

The invention revealed glycosidase methods for removal of the structures from cell surface while keeping the cells intact. The invention is especially directed to sialyltransferase methods for modification of terminal galactoses. The invention further revealed novel method to remove mannose residues from intact cells by alpha-mannosidase.

The invention is further directed to metabolic regulation of glycosylation to alter the glycosylation for reduction of potentially harmful structures.

The present invention is directed to specific cell populations comprising in vitro enzymatically altered sialylation according to the present invention. The preferred cell population includes cells with decreased amount of sialic acids on the cell surfaces, preferably decreased from the preferred structures according to the present invention. The altered cell population contains in a preferred embodiment decreased amounts of α3-linked sialic acids. The present invention is preferably directed to the cell populations when the cell populations are produced by the processes according to the present invention.

Cell Populations with Altered Sialylated Structures

The invention is further directed to novel cell populations produced from the preferred cell populations according to the invention when the cell population comprises altered sialylation as described by the invention. The invention is specifically directed to cell populations comprising decreased sialylation as described by the invention. The invention is specifically directed to cell populations comprising increased sialylation of specific glycan structures as described by the invention. Furthermore invention is specifically directed to cell populations of specifically altered α3- and or α6-sialylation as described by the invention. These cells are useful for studies of biological functions of the cell populations and role of sialylated, linkage specifically sialylated and non-sialylated structures in the biological activity of the cells.

Preferred Cell Populations with Decreased Sialylation

The preferred cell population includes cells with decreased amount of sialic acids on the cell surfaces, preferably decreased from the preferred structures according to the present invention. The altered cell population contains in a preferred embodiment decreased amounts of α3-linked sialic or α6-linked sialic acid. In a preferred embodiment the cell populations comprise practically only α3-sialic acid, and in another embodiment only α6-linked sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably cultivated human or animal cell populations according to the invention.

Preferred Cell Populations with Increased Sialylation

The preferred cell population includes cells with increased amount of sialic acids on the cell surfaces, preferably decreased from the preferred structures according to the present invention. The altered cell population contains in preferred embodiments increased amounts of α3-linked sialic or α6-linked sialic acid. In a preferred embodiment the cell populations comprise practically only α3-sialic acid, and in another embodiment only α6-linked sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably cultivated cells or tissue derived cell populations according to the invention.

Preferred Cell Populations with Altered Sialylation

The preferred cell population includes cells with altered linkage structures of sialic acids on the cell surfaces, preferably decreased from the preferred structures according to the present invention. The altered cell population contains in a preferred embodiments altered amount of α3-linked sialic and/or α6-linked sialic acid. The invention is specifically directed to cell populations having a sialylation level similar to the original cells but the linkages of structures are altered to α3-linkages and in another embodiment the linkages of structures are altered to α6-structures. In a preferred embodiment the cell populations comprise practically only α3-sialic acid, and in another embodiment only α6-linked sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably cultivated cells or tissue derived cell populations according to the invention.

Cell Populations Comprising Preferred Cell Populations with Preferred Sialic Acid Types The preferred cell population includes cells with altered types of sialic acids on the cell surfaces, preferably on the preferred structures according to the present invention. The altered cell population contains in a preferred embodiment altered amounts of NeuAc and/or NeuGc sialic acid. The invention is specifically directed to cell populations having sialylation levels similar to original cells but the sialic acid structures altered to NeuAc and in another embodiment the sialic acid type structures altered to NeuGc. In a preferred embodiment the cell populations comprise practically only NeuAc, and in another embodiment only NeuGc sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably cultivated or tissue derived cell populations according to the invention.

Methods to Alter (Remove or Reduce or Change) Glycosylation of Cells

Analysis and Degradative Removal of the Harmful Glycan Structure

The present invention is further directed to degradative removal of specific harmful glycan structures from cell, preferably from desired cell populations according to the invention.

The removal of the glycans or parts thereof occur preferably by enzymes such as glycosidase enzymes.

In some cases the removal of carbohydrate structure may reveal another harmful structure. In another preferred embodiment the present invention is directed to replacement of the removed structure by less harmful or better tolerated structure more optimal for the desired use.

Desialylation Methods

Preferred Special Target Cell Type

Effective and specific desialylation methods for the specific cell populations were developed. The invention is specifically directed to desialylation methods for modification of human tissue and cell culture cells. The present invention is further directed to desialylation modifications of any human cell or tissue cell subpopulation according to the invention. Sialylation modifications of cultivated cells have not been studied previously in detail.

The present invention is specifically directed to methods for desialylation of the preferred structures according to the present invention from the surfaces of preferred cells. The present invention is further directed to preferred methods for the quantitative verification of the desialylation by the preferred analysis methods according to the present invention. The present invention is further directed to linkage specific desialylation and analysis of the linkage specific sialylation on the preferred carbohydrate structures using analytical methods according to the present invention.

The invention is preferably directed to linkage specific α3-desialylation of the preferred structures according to the invention without interfering with the other sialylated structures according to the present invention. The invention is further directed to simultaneous desialylation α3- and α6-sialylated structures according to the present invention.

Furthermore the present invention is directed to desialylation when both NeuAc and NeuGc are quantitatively removed from cell surface, preferably from the preferred structures according to the present invention. The present invention is specifically directed to the removal of NeuGc from preferred cell populations, most preferably cultivated or tissue derived populations and from the preferred structures according to the present invention. The invention is further directed to preferred methods according to the present invention for verification of removal of NeuGc, preferably quantitative verification and more preferably verification performed by mass spectrometry.

Modification of Cell Surfaces of the Preferred Cells by Glycosyltransferases

The inventors revealed that it is possible to produce controlled cell surface glycosylation modifications on the preferred cells according to the invention. The present invention is specifically directed to glycosyltransferase catalysed modifications of N-linked glycans on the surfaces of cells, preferably blood cells, more preferably leukocytes or cultivated cells or more preferably the preferred cell or tissue materials according to the present invention.

The present invention is directed to cell modifications by sialyltransferases and fucosyltransferases. Two most preferred transfer reactions according to the invention are α3-modification reactions such as α3-sialylation and α3-fucosylations. When combined these reactions can be used to produce important cell adhesion structures which are sialylated and fucosylated N-acetyllactosamines such as sialyl-Lewis x (sLex).

Sialylation

Possible α6-sialylation has been implied in bone marrow cells and in peripheral blood CD34+ cells released from bone marrow to circulation by growth factor administration, cultivated or other cell types have not been investigated. Furthermore, the previous study utilized an artificial sialic acid modification method, which may affect the specificity of the sialyltransferase enzyme and, in addition, the actual result of the enzyme reaction is not known as the reaction products were not analysed by the investigators. The reactions are likely to have been very much limited by the specificity of the α6-sialyltransferase used and cannot be considered prior art in respect to the present invention.

The inventors of the present invention further revealed effective modification of the preferred cells according to the present inventions by sialylation, in a preferred embodiment by α3-sialylation.

The prior art data cited above does not indicate the specific modifications according to the present invention to cultivated cells, preferably cultivated or tissue derived cells. The present invention is specifically directed to sialyltransferase reactions towards these cell types. The invention is directed to sialyltransferase catalyzed transfer of a natural sialic acid, preferably NeuAc, NeuGc or Neu-O-Ac, from CMP-sialic acid to target cells.

Sialyltransferase catalyzed reaction according to Formula:

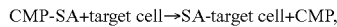

CMP-SA+target cell→SA-target cell+CMP,

Wherein SA is a sialic acid, preferably a natural sialic acid, preferably NeuAc, NeuGc or Neu-O-Ac and
the reaction is catalysed by a sialyltransferase enzyme preferably by an
α3-sialyltransferase and
the target cell is a cultured cell or tissue derived cell.

Preferably the sialic acid is transferred to at least one N-glycan structure on the cell surface, preferably to form a preferred sialylated structure according to the invention Fucosyltransferase Reactions In the prior art fucosyltransferase reactions towards unspecified cell surface structures has been studied The prior art indicates that human cord blood cell populations may be be α3-fucosylated by human fucosyltransferase VI and such modified cell populations may be directed to bone marrow due to interactions with selecting.

Directing Cells and Selectin Ligands

The present invention describes reactions effectively modifying blood cells or cultivated cells in vitro by fucosyltransferases, especially in order to produce sialylated and fucosylated N-acetyllactosamines on cell surfaces, preferably sLex and related structures. The present invention is further directed to the use of the increased sialylated and/or fucosylated structures on the cell surfaces for targeting the cells, in a preferred embodiment for selectin directed targeting of the cells.

The invention is further directed to α3- and/or α4-fucosylation of cultured cells, tissue cells.

Fucosylation of Human Peripheral Blood Mononuclear Cell Populations

In a specific embodiment the present invention is directed to α3-fucosylation of the total mononuclear cell populations from human peripheral blood. Preferably the modification is directed to at least to one protein linked glycan, more preferably to a N-linked glycan. The prior art reactions reported about cord blood did not describe reactions in such cell populations and the effect of possible reaction cannot be known. The invention is further directed to combined increased α3-sialylation and fucosylation, preferably α3-sialylation of human peripheral blood leukocytes. It is realized that the structures on the peripheral blood leukocytes can be used for targeting the peripheral blood leukocytes, preferably to selecting expressing sites such as selectin expressing malignant tissues.

Methods for Combined Increased α3-sialylation and α3-fucosylation

The invention is specifically directed to selection of a cell population from the preferred cell population according to the present invention, when the cell population demonstrate increased amount of α3-sialylation when compared with the baseline cell populations.

Use of Selected Cultured α3-sialic Acid Expressing Cell Populations

The inventors revealed that specific subpopulations of native cells express increased amounts of α3-linked sialic acid Furthermore it was found that cultured cells according to the invention have a high tendency to express α3-sialic acid instead to α6-linked sialic acids. The present invention is preferably directed to cultured cell lines, tissue cells expressing increased amounts of α3-linked sialic acid Fucosylation of α3-sialylated Cells The present invention is preferably directed to fucosylation after α3-sialylation of cells, preferably the preferred cells according to the invention. The invention describes for the first time combined reaction by two glycosyltransferases for the production of specific terminal epitopes comprising two different monosaccharide types on cell surfaces.

Fucosylation of Desialylated and α3-sialylated Cells

The present invention is preferably directed to fucosylation after desialylation and α3-sialylation of cells, preferably the preferred cells according to the invention. The invention describes for the first time combined reaction by two glycosyltransferases and a glycosidase for the production of specific terminal epitopes comprised of two different monosaccharide types on cell surfaces.

Sialylation Methods

Preferred Special Target Cell Type

Cultivated Cells and Tissues

Effective specific sialylation methods for the specific cell populations were developed. The invention is specifically directed to sialylation methods for modification of human cultivated cells and subpopulations thereof as cell lines and human tissues.

Production of Preferred Sialylated Structures

Present invention is specifically directed to methods for sialylation to produce preferred structures according to the present invention from the surfaces of preferred cells. The present invention is specifically directed to production preferred NeuGc- and NeuAc-structures. The invention is directed to production of potentially in vivo harmful structures on cells surfaces, e.g. for control materials with regard to cell labelling. The invention is further directed to production of specific preferred terminal structure types, preferably α3- and α6-sialylated structures, and specifically NeuAc- and NeuGc-structures for studies of biological activities of the cells.

The present invention is further directed to preferred methods for the quantitative verification of the sialylation by the preferred analysis methods according to the present invention. The present invention is further directed to linkage specific sialylation and analysis of the linkage specific sialylation on the preferred carbohydrate structures using analytical methods according to the present invention.

The invention is preferably directed to linkage specific α3-sialylation of the preferred structures according to the invention without interfering with the other sialylated structures according to the present invention. The invention is preferably directed to linkage specific α6-sialylation of the preferred structures according to the invention without interfering with the other sialylated structures according to the present invention.

The invention is further directed to simultaneous sialylation α3- and α6-sialylated structures according to the present invention. The invention is further directed for the production of preferred relation of α3- and α6-sialylated structures, preferably in single reaction with two sialyl-transferases.

Furthermore the present invention is directed to sialylation when either NeuAc or NeuGc are quantitatively synthesized to the cell surface, preferably on the preferred structures according to the present invention. Furthermore the invention is directed to sialylation when both NeuAc and NeuGc are, preferably quantitatively, transferred to acceptor sites on the cell surface.

The present invention is specifically directed to the removal of NeuGc from preferred cell populations, most preferably cultivated cell populations and from the preferred structures according to the present invention, and resialylation with NeuAc.

The invention is further directed to preferred methods according to the present invention for verification of removal of NeuGc, and resialylation with NeuAc, preferably quantitative verification and more preferably verification performed by mass spectrometry with regard to the preferred structures.

Controlled Cell Modification

The present invention is further directed to cell modification according to the invention, preferably desialylation or sialylation of the cells according to the invention, when the sialidase reagent is a controlled reagent with regard of presence of carbohydrate material.

Purification of Cells with Regard to Modification Enzyme

The preferred processes according to the invention comprise of the step of removal of the enzymes from the cell preparations, preferably the sialyl modification enzymes according to the invention. Most preferably the enzymes are removed from a cell population aimed for therapeutic use. The enzyme proteins are usually antigenic, especially when these are from non-mammalian origin. If the material is not of human origin its glycosylation likely increases the antigenicity of the material. This is particularly the case when the glycosylation has major differences with human glycosylation, preferred examples of largely different glycosylations includes: procaryotic glycosylation, plant type glycosylation, yeast or fungal glycosylation, mammalian/animal glycosylation with Galα3Galβ4GlcNAc-structures, animal glycosylations with NeuGc structures. The glycosylation of a recombinant enzyme depends on the glycosylation in the production cell line, these produce partially non-physiological glycan structures. The enzymes are preferably removed from any cell populations aimed for culture or storage or therapeutic use. The presence of enzymes which have affinity with regard to cell surface may otherwise alter the cells as detectable by carbohydrate binding reagents or mass spectrometric or other analysis according to the invention and cause adverse immunological responses.

Under separate embodiment the cell population is cultured or stored in the presence of the modification enzyme to maintain the change in the cell surface structure, when the cell surf-ace structures are recovering from storage especially at temperatures closer physiological or culture temperatures of the cells. Preferably the cells are then purified from trace amounts of the modification enzyme before use.

The invention is furthermore directed to methods of removal of the modification reagents from cell preparations, preferably the modification reagents are desialylation or resialylation reagents. It is realized that soluble enzymes can be washed from the modified cell populations. Preferably the cell material to be washed is immobilized on a matrix or centrifuged to remove the enzyme, more preferably immobilized on a magnetic bead matrix.

However, extraneous washing causes at least partial destruction of cells and their decreased viability. Furthermore, the enzymes have affinity with regard to the cell surface. Therefore the invention is specifically directed to methods for affinity removal of the enzymes. The preferred method includes a step of contacting the modified cells with an affinity matrix binding the enzyme after modification of the cells.

Under specific embodiment the invention is directed to methods of tagging the enzyme to be removed from the cell population. The tagging step is performed before contacting the enzyme with the cells. The tagging group is designed to bind preferably covalently to the enzyme surface, without reduction or without major reduction of the enzyme activity. The invention is further directed to the removal of the tagged enzyme by binding the tag to a matrix, which can be separated from the cells. Preferably the matrix comprises at least one matrix material selected from the group: polymers, beads, magnetic beads, or solid phase surface Enzymes Acceptable for Humans for Modification of Reagents or Cells Under specific embodiment the invention is directed to the use for modification of the cells according to the invention, or in a separate embodiment reagents for processes according to the invention, of a human acceptable enzyme, preferably a glycosidase according to the invention or in preferred embodiment sialidase or sialyltransferase, which is acceptable at least in certain amounts to human beings without causing harmful allergic or immune reactions. It is realized that the human acceptable enzymes may not be needed to be removed from reaction mixtures or less washing steps are needed for desirable level of the removal. The human acceptable enzyme is in preferred embodiment a human glycosyltransferase or glycosidase. The present invention is separately directed to human acceptable enzyme which is a sialyltransferase. The present invention is separately directed to human acceptable enzyme which is a sialidase, the invention is more preferably directed to human sialidase which can remove specific type of sialic acid from cells.

In a preferred embodiment the human acceptable enzyme is purified from human material, preferably from human serum, urine or milk. In another preferred embodiment the enzyme is recombinant enzyme corresponding to natural human enzyme. More preferably the enzyme corresponds to human natural enzyme corresponds to natural cell surface or a secreted from of the enzyme, more preferably serum or urine or human milk form of the enzyme. Even more preferably the present invention is directed to human acceptable enzyme which corresponds to a secreted form of a human sialyltransferase or sialidase, more preferably secreted serum/blood form of the human enzyme. In a preferred embodiment the human acceptable enzyme, more preferably recombinant human acceptable enzyme, is a controlled reagent with regard to potential harmful glycan structures, preferably NeuGc-structures according to the invention. The recombinant proteins may contain harmful glycosylation structures and inventors revealed that these kinds of structures are also present on recombinant glycosyltransferases, even on secreted (truncated) recombinant glycosyltransferases.

mRNA Corresponding to Glycosylation Enzymes

The present invention is further directed to correlation of specific messenger mRNA molecules with the preferred glycan structures according to the present invention. It is realized that glycosylation can be controlled in multiple levels and one of them is transcription. The presence of glycosylated structures may in some case correlate with mRNAs involved in the synthesis of the structures.

The present invention is especially directed to analysis of mRNA-species having correlation with expressed fucosylated glycan structures and "terminal HexNAc" containing structures preferred according to the present invention. The preferred mRNA-species includes mRNA corresponding to fucosyltransferases and N-acetylglucosaminyltransferases.

Observation of Glycan Binding Structures, Lectins, Corresponding mRNA-Markers

The invention further revealed changes in mRNA-expression of glycosylation recognizing lectins such as galectins. The cells were further revealed to contain lactosamine receptors for lectins. The invention is especially directed to analysis of expression levels of human lectins and lactosamine galectin receptors, preferably analysis of galectins and selectins more preferably galectins for analysis of status of cells according to the present invention.

The invention specifically revealed novel NeuGc(N-glycolylneuraminic acid)-binding lectin activity from human cells. The lectin lectin recognizes polyvalent NeuGc but does not bind effectively to polyvalent NeuNAc. The present invention is especially directed to labelling cells according to the invention by carbohydrate conjugates binding cells according to the invention, preferably labelled conjugates of NeuGc. The invention is further directed to sorting and selecting cells, and cell derived materials and purifying proteins from cells, using labelled carbohydrate conjugates, preferably, conjugates of NeuGc.

NMR-Analysis of Glycomes

The present invention is directed to analysis of released glycomes by spectrometric method useful for characterization of the glycomes from tissue specimens or cells. The invention is directed to NMR spectroscopic analysis of the mixtures of released glycans.

The invention is especially directed to methods of producing NMR from specific subglycomes, preferably N-linked glycome, O-linked glycome, glycosaminoglycan glycome and/or glycolipid glycome. The NMR-profiling according to the invention is further directed to the analysis of the novel and rare structure groups revealed from cell glycomes according to the invention. The general information about complex cell glycome material directed NMR-methods are limited.

Preferably the NMR-analysis is performed from an isolated subglycome. The preferred isolated subglycomes include acidic glycomes and neutral glycomes.

NMR-Glycome Analysis of Larger Tissue Specimens or Larger Amounts of Cells

It is realized that numerous methods have been described for purification of oligosaccharide mixtures useful for NMR from various materials, including usually purified individual proteins. It is realized that present methods are useful for NMR-profiling even for larger tissue specimens or higher amounts of cells according to the invention, especially in combination with NMR-profiling according to the invention and/or when directed to the analysis specific and preferred structure groups according to the invention. The preferred purification methods are effective and form an optimised process for purification of glycomes from even larger amounts of cells and tissues than described for nanoscale methods below. The methods are preferred also for any larger amount of cells.

Purification Method for Low Amount Nanoscale NMR-profiling of Samples

Moreover, when purification methods for larger amounts of carbohydrate materials exists, but very low and complex carbohydrate materials with very complex impurities such as cell-derived materials have been less studied as low amounts, especially when purity useful for NMR-analysis is needed.

Preferred Sample Amounts Allowing Effective NMR Analysis of Cell Glycomes

The invention is directed to analysis of NMR-samples that can be produced from very low amounts of cells according to the invention. Preferred sample amounts of cells or corresponding amount of tissue material for a one-dimensional proton-NMR profiling are from about 2 million to 100 million cells, more preferably 10-50 million cells. It is further realized that good quality NMR data can be obtained from samples containing at least about 10-20 million cells.

The preferred analysis methods is directed to high resolution NMR observing oligosaccharide/saccharide conjugate mixture from an amount of at least 4 nmol, more preferably at least 1 nmol and the cell amount yielding the preferred amount of saccharide mixture. For nanoscale analysis according to the invention cell material is selected so that it would yield at least about 50 nmol of oligosaccharide mixture, more preferably at least about 5 nmol and most preferably at least about 1 nmol of oligosaccharide mixture. Preferred amounts of major components in glycomes to be observed effectively by the methods according to the invention include yield at least about 10 nmol of oligosaccharide component, more preferably at least about 1 nmol and most preferably at least about 0.2 nmol of oligosaccharide component.

The preferred cell amount for analysis of a subglycome from a cell type is preferably optimised by measuring the amounts of glycans produced from the cell amounts of preferred ranges.

It is realized that depending on the cell and subglycome type the required yield of glycans and the heterogeneity of the materials vary yielding different amounts of major components.

Preferred Purification Methods

For the production of sample for nanoscale NMR, the methods described for preparation of cell samples and release of oligosaccharides for mass spectrometric profiling according to the invention may be applied.

For the purification of sample for nanoscale NMR the methods described for purification mass spectrometry profiling samples according to the invention may be applied.

The preferred purification method for nanoscale NMR-profiling according to the invention include following general purification process steps:
1) Precipitation/extraction;
2) Hydrophobic interaction;
3) Affinity to carbon material, especially graphitized carbon.
4) Gel filtration chromatography The more preferred purification process includes precipitation/extraction aimed for removal of major non-carbohydrate impurities by separating the impurity and the glycome fraction(s) to be purified to different phases. Hydrophobic interaction step aims to purify the glycome components from more hydrophobic impurities as these are bound to hydrophobic chromatography matrix and the glycome components are not retained. Chromatography on graphitized carbon may include purification or enrichment of glycans due to their affinity or specific adsorption to graphitized carbon, or removal of contaminants from the glycans. The glycome components obtained by the aforementioned steps are then subjected to gel filtration chromatography, separating molecules according to their hydrodynamic volume, i.e. size in solution. The gel filtration chromatography step allows detection and quantitation of glycome components by absorption at low wavelengths (205-214 nm).

The most preferred purification process includes precipitation/extraction and hydrophobic interaction steps aimed for removal of major non-carbohydrate impurities and more hydrophobic impurities. Chromatography on graphitized carbon is used for removal of contaminants from the glycans, and to divide the glycome components to fractions of neutral glycome components and acidic glycome components. The neutral and acidic glycome component fractions are then subjected to gel filtration chromatography, which separates molecules according to their size. Preferably, a high-performance liquid chromatography (HPLC) type gel filtration column is used. The neutral glycome component fraction is preferably chromatographed in water and the acidic glycome component fraction is chromatographed in 50-200 mM aqueous ammonium bicarbonate solution. Fractions are collected and evaporated prior to further analyses. The gel filtration chromatography step allows detection and quantitation of glycome components by absorption at low wavelengths (205-214 nm). Quantitation is performed against external standards. The standards are preferably N-acetylglucosamine, N-acetylneuraminic acid, or oligosaccharides containing the same. Fractions showing absorbance are subjected to MALDI-TOF mass spectrometry. Preferably, the neutral glycome components are analyzed in the positive-ion mode and the acidic glycome components in the negative-ion mode in a delayed-extraction MALDI-TOF mass spectrometer.

Preferred Methods for Producing Enriched Glycome Fractions for NMR

The fractionation can be used to enrich components of low abundance. It is realized that enrichment would enhance the detection of rare components. The fractionation methods may be used for larger amounts of cell material. In a preferred embodiment the glycome is fractionated based on the molecular weight, charge or binding to carbohydrate binding agents such as lectins and/or other binding agents according to the invention.

These methods have been found useful for specific analysis of specific subglycomes and enrichment more rare components. The present invention is in a preferred embodiment directed to charge based separation of neutral and acidic glycans. This method gives for analysis method, preferably mass spectroscopy material of reduced complexity and it is useful for analysis as neutral molecules in positive mode mass spectrometry and negative mode mass spectrometry for acidic glycans.

It is realized that preferred amounts of enriched glycome oligosaccharide mixtures and major component comprising fractions can be produced from larger glycome preparations.

In a preferred embodiment the invention is directed to size based fractionation methods for effective analysis of preferred classes of glycans in glycomes. The invention is especially directed to analysis of lower abundance components with lower and higher molecular weight than the glycomes according to the invention. The preferred method for size based fractionation is gel filtration. The invention is especially directed to analysis of enriched group glycans of N-linked glycomes preferably including lower molecular weight fraction including low-mannose glycans, and one or several preferred low mannose glycan groups according to the invention.

Preferred NMR-Methods

In a preferred embodiment the NMR-analysis of the glycome is one-dimensional proton-NMR analysis showing structural reporter groups of the major components in the glycome. The invention is further directed to specific two- and multidimensional NMR experiments of the glycomes when enough sample is available. It is realized that two-dimensional NMR-experiments require about a ten-fold increase in sample amount compared to proton-NMR analyses.

Combination of NMR- and Mass Spectrometry for Glycome Analysis

The present invention is further directed to combination of the mass spectrometric and NMR glycome analyses. The preferred method include production of any mass spectrometric profile from any glycome according to the invention from a cell sample according to the invention, optionally characterizing the glycome by other methods like glycosidase digestion, fragmentation mass spectrometry, specific binding agents, and production of NMR-profile from the same sample glycome or glycomes to compare these profiles.

Specific Characteristic Marker Structures and Glycome Marker Components/Compositions The N-glycan analysis of total profiles of released N-glycans revealed beside the glycans above, which were verified to comprise 1) complex biantennary N-glycans, such as Galβ4GlcNAcβ2Manα3(Galβ4GlcNAcβ2Manα6) Manβ4GlcNAcβ4(Fucα6)$_{0-1}$GlcNAcβ-, wherein the reminal N-acetyllactosamines can be elongated from Gal with NeuNAcα3 and/or NeuNAcα6 and 2) terminal mannose containing N-glycans such as High-mannose glycans with formula Hex$_{5-9}$HexNAc$_2$ and degradation products thereof comprising low number of mannose residues (Low mannose glycans) Hex$_{1-4}$HexNAc$_2$.

The specific N-glycan core marker structure

The glycan share common core structure according to the Formula:

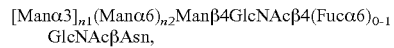
[Manα3]$_{n1}$(Manα6)$_{n2}$Manβ4GlcNAcβ4(Fucα6)$_{0-1}$ GlcNAcβAsn, wherein n1 and n2 are integers 0 or 1, independently indicating the presence or absence of the terminal Man-residue, and wherein the non-reducing end terminal Manα3/Manα6-residues can be elongated to the complex type, especially biantennary structures or to mannose type (high-Man and/or low Man) or to hybrid type structures as described in examples.

It was further analyzed that the N-glycan compositions contained only very minor amounts of glycans with additional HexNAx in comparison to monosaccharide compositions of the complex type glycan above, which could indicate presence of no or very low amounts of the N-glycan core linked GlcNAc-residues described by Stanley PM and Raju TS (JBC-(1998) 273 (23) 14090-8; JBC (1996) 271 (13) 7484-93) and/or bisecting GlcNAc. is realized that part of the terminal HexNAc-type structures appear to represent bisecting GlcNAc-type type glycans, and quite low or non-existent amounts of the GlcNAcα6-branching and also low amounts of GlcNAcβ2-branch of Manβ4 described by Stanley and colleagues. Here, essentially devoid of indicates less than 10% of all the protein linked N-glycans, more preferably the additional HexNAc units are present in less than 8% of the tissue material N-glycans by mass spectrometric analysis.

The invention thus describes the major core structure of N-glycans in human tissue materials verified by NMR-spectroscopy and by specific glycosidase digestions and was further quantitated to comprise a characteristic smaller structural group glycans comprising specific terminal HexNAc group and/or bisecting GlcNAc-type structures, which additionally modify part of the core structure. The invention further reveals that the core structure is a useful target structure for analysis of tissue materials.

The characteristic monosaccharide composition of the core structure will allow recognition of the major types of N-glycan structure groups present as additional modification of the core structure. Furthermore composition of the core structure is characteristic in mass spectrometric analysis of N-glycan and allow immediate recognition for example from Hex$_x$HexNAc$_1$-type (preferentially Man$_x$GlcNAc$_1$) glycans also present in total glycome composition.

Low-Molecular Weight Glycan Marker Structures and Tissue Material Glycome Components The invention describes novel low-molecular weight acidic glycan components within the acidic N-glycan and/or soluble glycan fractions with characteristic monosaccharide compositions SA$_x$Hex$_{1-2}$HexNAc$_{1-2}$, wherein x indicates that the corresponding glycans are preferentially sialylated with one or more sialic acid residues. The inventors realized that such glycans are novel and unusual with respect to N-glycan biosynthesis and described mammalian cell glycan components, as reveal also by the fact that they are classified as "other (N-)glycan types" in N-glycan classification scheme of the present invention. The invention is directed to analyzing, isolating, modifying, and/or binding to these novel glycan components according to the methods and uses of the present invention, and further to other uses of specific marker glycans as described here. As demonstrated in the Examples of the present invention, such glycan components were specific parts of total glycomes of certain tissue materials and preferentially to certain tissue material types, making their analysis and use beneficial with regard to tissue materials. The invention is further directed to tissue material glycomes and subglycomes containing these glycan components.

Preferred Glycomes

The present invention is specifically directed to tissue material glycomes, which are essentially pure glycan mixtures comprising various glycans as described in the invention preferably in proportions shown by the invention. The essentially pure glycan mixtures comprise the key glycan components in proportions which are characteristics to tissue material glycomes. The preferred glycomes are obtained from human tissue materials according to the invention.

The invention is further directed to glycomes as products of purification process and variations thereof according to the invention. The products purified from tissue materials by the simple, quantitative and effective methods according to the invention are essentially pure. The essentially pure means that the mixtures are essentially devoid of contaminations disturbing analysis by MALDI mass spectrometry, preferably by MALDI-TOF mass spectrometry. The mass spectra produced by the present methods from the essentially pure glycomes reveal that there is essentially no non-carbohydrate impurities with weight larger than trisaccharide and very low amount of lower molecular weight impurities so that crystallization of MALDI matric is possible and the glycan signals can be observed for broad glycomes with large variations of monosaccharide compositions and ranges of molecular weight as described by the invention. It is realized that the purification of the materials from low amounts of tissue materials comprising very broad range of cellular materials is very challenging task and the present invention has accomplished this.

Combination Compositions of the Preferred Glycome Mixtures with Matrix for Analysis Mass Spectrometric Matrix The invention further revealed that it is possible to combine the glycomes with matrix useful for a mass spectrometric analysis and to obtain combination mixture useful for spectrometric analysis. The preferred mass spectrometric matrix is matrix for MALDI (matrix assisted laser desorption ionization mass spectrometry) with mass spectrometric analysis (abbreviated as MALDI matrix), MALDI is preferably performed with TOF (time of flight) detection.

Preferred MALDI matrices include aromatic preferably benzene ring structure comprising molecules with following characteristic. The benzene ring structure molecules preferably comprises 1-4 substituents such as hydroxyl, carboxylic acid or ketone groups. Known MALDI matrixes have been reviewed in Harvey, Mass. Spec. Rev. 18, 349 (1999). The present invention is especially and separately directed to specific matrixes for analysis in negative ion mode of MALDI mass spectrometry, preferred for analysis of negatively charged (acidic, such as sialylated and/or sulfated and/or phosphorylated) subglycome, and in positive ion mode of MALDI mass spectrometry (preferred for analysis of neutral glycomes). It is realized that the matrices can be optimized for negative ion mode and positive ion mode.

The present invention is especially directed to glycome matrix composition optimized for the use in positive ion mode, and to the use of the MALDI-TOF matrix and matrix glycome composition, that is optimized for the use in the analysis in positive ion mode, for the analysis of glycome, preferably neutral glycome. The preferred matrices for positive ion mode are aromatic matrices, e.g. 2,5-dihydroxybenzoic acid, 2,5-dihydroxybenzoic acid/2-hydroxy-5-methoxybenzoic acid, 2,4,6-trihydroxyacetophenone or 6-aza-2-thiothymine, more preferably 2,5-dihydroxybenzoic acid. The present invention is especially directed to glycome matrix composition optimized for the use in negative ion mode, and to the use of the MALDI-TOF matrix and the matrix glycome compositions, that is optimized for the negative ion mode, for the analysis of glycome, preferably acidic glycome. The preferred matrices for negative ion mode are aromatic matrices, e.g. 2,4,6-trihydroxyacetophenone, 3-hydroxypicolinic acid, 2,5-dihydroxybenzoic acid, 2,5-dihydroxybenzoic acid/2-hydroxy-5-methoxybenzoic acid, or 6-aza-2-thiothymine, more preferably 2,4,6-trihydroxyacetophenone. The invention is further directed to analysis method and glycome-matrix composition for the analysis of glycome compositions, wherein the glycome composition comprises both negative and neutral glycome components. Preferred matrices for analysis of negative and neutral glycome components comprising glycome are aromatic matrices, e.g. 2,4,6-trihydroxyacetophenone, 3-hydroxypicolinic acid, 2,5-dihydroxybenzoic acid, 2,5-dihydroxybenzoic acid/2-hydroxy-5-methoxybenzoic acid, or 6-aza-2-thiothymine, more preferably 2,4,6-trihydroxyacetophenone.

The MALDI-matrix is a molecule capable of
1) Specifically and effectively co-crystallizing with glycome composition with the matrix, crystallizing meaning here forming a solid mixture composition allowing analysis of glycome involving two steps below
2) absorbing UV-light typically provided by a laser in MALDI-TOF instrument, preferred wavelength of the light is 337 nm as defined by the manuals of MALDI-TOF methods
3) transferring energy to the glycome composition so that these will ionize and be analyzable by the MALDI-TOF mass spectrometry. The present invention is especially directed to compositions of glycomes in complex with MALDI mass spectrometry matrix.

The present invention is specifically directed to methods of searching novel MALDI-matrixes with the above characteristic, preferably useful for analysis by the method below. The method for searching novel MALDI-matrixes using the method in the next paragraph.

The present invention is specifically directed to methods of analysis of glycomes by MALDI-TOF including the steps:
1) Specifically and effectively co-crystallizing the glycome composition with the MALDI-TOF-matrix, crystallizing meaning here forming a solid mixture composition allowing analysis of glycome involving two steps below 2) Providing UV light to crystalline sample by a laser in MALDI-TOF instrument allowing the ionization of sample
3) Analysis of the ions produced by the MALDI mass spectrometer, preferably by TOF analysis. The invention is further directed to the combination of glycome purification methods and/or quantitative and qualitative data analysis methods according to the invention.

Crystalline Compositions of Glycomes

The present invention is further directed to essentially pure glycome compositions in solid co-crystalline form with MALDI matrix. The invention is preferably a neutral and/or acidic glycome as complex with a matrix optimized for analysis of the specific glycome type, preferably analysis in negative ion mode with a matrix such as 2,4,6-trihydroxyacetophenone.

The invention is preferably a neutral (or non-acidic) glycome as complex with a matrix optimized for analysis in positive ion mode such as 2,5-dihydroxybenzoic acid.

The invention revealed that it is possible to analyze glycomes using very low amount of sample. The preferred crystalline glycome composition comprises between 0.1-100 pmol, more preferably 0.5-10 pmol, more preferably 0.5-5 pmol and more preferably about 0.5-3 pmol, more preferably about 0.5-2 pmol of sample co-crystallized with optimized amount of matrix preferably about 10-200 nmol, more preferably 30-150 nmol, and more preferably about 50-120 nmol and most preferably between 60-90 nmols of the matrix, preferably when the matrix is 2,5-dihydroxybenzoic acid. The matrix and analyte amounts are optimized for a round analysis spot with radius of about 1 mm and area of about 0.8 $mm^2$. It is realized that the amount of materials can be changed in proportion of the area of the spot, smaller amount for smaller spot. Examples of preferred amounts per area of spot are 0.1-100 pmol/0.8 $mm^2$ and 10-200 pmol/3 $mm^2$. Preferred molar excess of matrix is about 5000-1000000 fold, more preferably about 10000-500000 fold and more preferably about 15000 to 200 000 fold and most preferably about 20000 to 100000 fold excess when the matrix is 2,5-dihydroxybenzoic acid.

It is realized that the amount and relative amount of new matrix is optimized based on forming suitable crystals and depend on chemical structure of the matrix. The formation of crystals is observed by microscope and further tested by performing test analysis by MALDI mass spectrometry.

The invention is further directed to specific methods for crystallizing MALDI-matrix with glycome. Preferred method for crystallization in positive ion mode includes steps: (1) optionally, elimination of impurities, like salts and detergents, which interfere with the crystallization, (2) providing solution of glycome in $H_2O$ or other suitable solvent in the preferred concentration, (3) mixing the glycome with the matrix in solution or depositing the glycome in solution on a precrystallized matrix layer and (4) drying the solution preferably by a gentle stream of air.

Preferred method for crystallization in negative ion mode includes steps: (1) optionally, elimination of impurities, like salts and detergents, which interfere with the crystallization, (2) providing solution of glycome in $H_2O$ or other suitable solvent in the preferred concentration, (3) mixing the glycome with the matrix in solution or depositing the glycome in solution on a precrystallized matrix layer and (4) drying the solution preferably by vacuum.

Other Preferred Glycome Analysis Compostions
Binder Glycome Compositions

The invention is further directed to compositions of essentially pure glycome composition with specific glycan binding molecules such as lectins, glycosidases or glycosyltransferases and other glycosyl modifying enzymes such as sulfateses and/or phosphatases and antibodies. It is realized that these composition are especially useful for analysis of glycomes.

The present invention revealed that the complex glycome compositions can be effectively and even quantitatively modified by glycosidases even in very low amounts. It was revealed that the numerous glycan structures similar to target structures of the enzymes do not prevent the degradation by competitive inhibition, especially by the enzymes used. The invention is specifically directed to preferred amounts directed to MALDI analysis for use in composition with a glycosyl modifying enzyme, preferably present in low amounts. Preferred enzymes suitable for analysis include enzymes according to the Examples.

The invention is further directed to binding of specific component of glycome in solution with a specific binder. The preferred method further includes affinity chromatography step for purification of the bound component or analysis of the non-bound fraction and comparing it to the glycome solution without the binding substance. Preferred binders include lectins engineered to be lectins by removal of catalytic amino acids (methods published by Roger Laine, Anomeric, Inc., USA, and Prof. Jukka Finne, Turku, Finland), lectins and antibodies or antibody fragments or minimal binding domains of the proteins.

Additional Data Analysis and Related Methods

The present invention is especially directed to the use of glycome data for production of mathematical formulas, or algorithms, for specific recognition or identification of specific tissue materials. Data analysis methods are presented e.g. in Example 17.

The invention is especially directed to selecting specific "structural features" such as mass spectrometric signals (such as individual mass spectrometric signal corresponding to one or several monosaccharide compositions and/or glycan structures), or signal groups or subglycomes or signals corresponding to specific glycan classes, which are preferably according to the invention, preferably the signal groups (preferably defined as specific structure group by the invention), from quantitative glycome data, preferably from quantitative glycome data according to the invention, for the analysis of status of tissue materials. The invention is furthermore directed to the methods of analysis of the tissue materials by the methods involving the use of the specific signals or signal groups and a mathematical algorithm for analysis of the status of a tissue material.

Preferred algorithm includes use of proportion (such as %-proportion) of the specific signals from total signals as specific values (structural features) and creating a "glycan score", which is algorithm showing characteristics/status of a tissue material based on the specific proportional signal intensities (or quantitative presence of glycan structures measured by any quantitation method such as specific binding proteins or quantitative chromatographic or electrophoresis analysis such as HPLC analysis). Preferably signals which are, preferably most specifically, upregulated in specific tissue materials and signals which are, preferably most specifically, downregulated in the tissue material in comparison to control tissue materials are selected to for the glycan score. In a preferred embodiment value(s) of downregulated signals are subtracted from upregulated signals when glycan score is calculated. The method yields largest score values for a specific tissue material type or types selected to be differentiated from other tissue materials.

The invention is specifically directed to methods for searching characteristic structural features (values) from glycome profiling data, preferably quantitative or qualitative glycome profiling data. The preferred methods include methods for comparing the glycome data sets obtained from different samples, or from average data sets obtained from a group of similar samples such as parallel samples from same or similar tissue material preparations. Methods for searching characteristic features are briefly described in the section: identification and classification of differences in glycan datasets. The comparison of datasets of the glycome data according to the invention preferably includes calculation of relative and/or absolute differences of signals, preferably each signal between two data sets, and in another preferred embodiment between three or more datasets. The method preferably further includes step of selecting the differing signals, or part thereof, for calculating glycan score.

It is further realized that the analyzed glycome data has other uses preferred by the invention such as use of the selected characteristic signals and corresponding glycan material:

1) for targets for structural analysis of glycans (preferably chemically by glycosidases, fragmentation mass spectrometry and/or NMR spectroscopy as shown by the present invention and/or structural analysis based on the presence of other signals and knowledge of biosynthesis of glycans). The preferred use for targets includes estimation of chemical characteristics of potential corresponding glycans for complete or partial purification/separation of the specific glycan(s). The preferred chemical characteristics to be analysed preferably include one or several of following properties: a) acidity (e.g. by presence of acidic residues such as sialic acid and/or sulfate and/or phosphate) for charge based separation, b) molecular weight or hydrodynamic volume affecting chromatographic separation, e.g. estimation of the elution volume in gel filtration methods (the effect of acidic residue can be estimated from effects of similar structures and the "size" of HexNAc (GalNAc/GlcNAc) is in general twice the size of Hex (such as Gal, Man or Glc), c) estimation (e.g. based on composition and biosynthetic knowledge of glycans) of presence of epitopes for specific binding reagents for labelling identification in a mixture or for affinity purification, d) estimation of presence of target epitopes for specific glycosyl modifying enzymes including glycosidases and/or glycosyltransferases (types of binding reagents) or for specific chemical modification reagents (such as periodate for specific oxidation or acid for specific acid hydrolysis), for modification of glycans and recognition of the modification by potential chemical change such as incorporation of radioactive label or by change of mass spectrometric signal of the glycan for labelling identification in a mixture.

2) use of the signals or partially or fully analysed glycan structures corresponding to the signals for searching specific binding reagents for recognition of tissue materials which are preferably selected as described by the present invention (especially as described above) and in the methods for identification and classification of differences in glycan datasets and/or signals selected and/or tested by glycan score methods, are preferably selected for targets for structural analysis of glycans (preferably by glycosidases, fragmentation mass spectrometry and/or NMR spectroscopy as shown by the present invention) and/or for use of the signals or partially or fully analysed glycan structures corresponding to the signals for searching specific binding reagents for recognition of tissue materials.

The preferred method includes the step of comparing the values, and preferably presenting the score values in graphs such as ones shown in FIG. 36 (example 23), and preferably evaluating the statistic significance of the result by a statistic analysis methods such as a mathematical test for statistic significance. tissue material type refers here to tissue materials with specific status and/or identity, e.g. malignancy, with possible individual variability, e.g. between individual patients.

It is realized that to differentiate a tissue materials type from other(s) different characteristic signals may be selected than for another tissue material type. The invention however revealed that for tissue materials and especially for human cancer patients preferred characteristic signals include ones selected in the Examples as described above. It is realized that a glycan score can be also created with less characteristic signals or with only part of signals and still relevant results can be obtained. The invention is further directed to methods for optimisation of glycan score algorithms and methods for selecting signals for glycan scores.

In case the specific proportion (value) of a characteristic signal is low in comparison to other values a specific factor can be selected for increase the relative "weight" of the value in the glycan scores to be calculated for the cell populations.

The preferred statuses of tissue materials, to be analysed by mathematical methods such as algorithms using quantitative glycome profiling data according to the invention include differentiation status, individual characteristics and mutation, cell culture or storage conditions related status, effects of chemicals or biochemicals on cells, and other statuses described by the invention.

Preferred Structures of Glycan glycomes of Tissue Materials

The present invention is especially directed to following O-glycan marker structures of tissue materials:

Core 1 type O-glycan structures following the marker composition NeuAc$_2$Hex$_1$HexNAc$_1$, preferably including structures SAα3Galβ3GalNAc and/or SAα3Galβ3(SAα6)GalNAc; and Core 2 type O-glycan structures following the marker composition NeuAc$_{0-2}$Hex$_2$HexNAc$_2$dHex$_{0-1}$, more preferentially further including the glycan series NeuAc$_{0-2}$Hex$_{2+n}$HexNAc$_{2+n}$dHex$_{0-1}$, wherein n is either 1, 2, or 3 and more preferentially n is 1 or 2, and even more preferentially n is 1;

more specifically preferably including R$_1$Galβ4(R$_3$)GlcNAcβ6(R$_2$Galβ3)GalNAc, wherein R$_1$ and R$_2$ are independently either nothing or sialic acid residue, preferably α2,3-linked sialic acid residue, or an elongation with Hex$_n$HexNAc$_n$, wherein n is independently an integer at least 1, preferably between 1-3, most preferably between 1-2, and most preferably 1, and the elongation may terminate in sialic acid residue, preferably α2,3-linked sialic acid residue; and R$_3$ is independently either nothing or fucose residue, preferably α1,3-linked fucose residue. It is realized that these structures correlate with expression of β6GlcNAc06GlcNAc-transferases synthesizing core 2 structures.

Preferred Qualitative and Quantitative Complete N-Glycomes of Tissue Materials

High-Mannose Type and Glucosylated N-Glycans

The present invention is especially directed to glycan compositions (structures) and analysis of high-mannose type and glucosylated N-glycans according to the formula:

Hex$_{n3}$HexNAc$_{n4}$, wherein n3 is 5, 6, 7, 8, 9, 10, 11, or 12, and n4=2.

According to the present invention, within total N-glycomes of tissue materials the major high-mannose type and glucosylated N-glycan signals preferentially include the compositions with 5≤n3≤10: Hex5HexNAc2 (1257), Hex6HexNAc2 (1419), Hex7HexNAc2 (1581), Hex8HexNAc2 (1743), Hex9HexNAc2 (1905), and Hex10HexNAc2 (2067);
and more preferably with 5≤n3≤9:Hex5HexNAc2 (1257), Hex6HexNAc2 (1419), Hex7HexNAc2 (1581), Hex8HexNAc2 (1743), and Hex9HexNAc2 (1905).

Low-Mannose Type N-Glycans

The present invention is especially directed to glycan compositions (structures) and analysis of low-mannose type N-glycans according to the formula:

$Hex_{n3}HexNAc_{n4}dHex_{n5}$, wherein n3 is 1, 2, 3, or 4, n4=2, and n5 is 0 or 1.

According to the present invention, within total N-glycomes of tissue materials the major low-mannose type N-glycan signals preferably include the compositions with 2≤n3≤4: Hex2HexNAc2 (771), Hex3HexNAc2 (933), Hex4HexNAc2 (1095), Hex2HexNAc2dHex (917), Hex3HexNAc2dHex (1079), and Hex4HexNAc2dHex (1241); and more preferably when n5 is 0: Hex2HexNAc2 (771), Hex3HexNAc2 (933), and Hex4HexNAc2 (1095).

As demonstrated in the present invention by glycan structure analysis of tissue materials, preferably this glycan group in tissue materials includes the molecular structures:
(Manα)$_{1-3}$Manβ4GlcNAcβ4(Fucα6)$_{0-1}$GlcNAc within the glycan signals 771, 917, 933, 1079, 1095, and 1095, and the preferred low-Man structures includes structures common all tissue material types, tri-Man and tetra-Man structures according to the Examples,
(Manα)$_{0-1}$Manα6(Manα3)Manβ4GlcNAcβ4(Fucα6)$_{0-1}$GlcNAc, more preferably the tri-Man structures:
Manα6(Manα3)Manβ4GlcNAcβ4(Fucα6)$_{0-1}$GlcNAc
even more preferably the abundant molecular structure:
Manα6(Manα3)Manβ4GlcNAcβ4GlcNAc within the glycan signal 933.

Quantitative Analysis Directed to the Low-Man Components

Beside the qualitative variations the low-Man glycans have specific value in quantitative analysis of tissue materials. The present invention revealed that the low-Man glycans are especially useful for the analysis of status of the cells. For example the analysis in the Examples revealed that the amounts of the glycans vary between total tissue profiles and specific organelles, preferably lysosomes.

The group of low-Man glycans form a characteristic group among glycome compositions. The relative total amount of neutral glycans is notable in average human tissues. The glycan group was revealed also to be characteristic in cancerous tissues and tumorsa with total relative amount of neutral glycomes increased. The difference is more pronounced within lysosomal organelle-specific glycome, wherein low-Man structures accounted nearly 50% of the neutral protein-linked glycome. Glycome analysis of tissue materials is especially useful for methods for development of binder reagents for separation of different tissue materials.

The invention is directed to analysis of relative amounts of low-Man glycans, and to the specific quantitative glycome compositions, especially neutral glycan compositions, comprising about 0 to 50% of low-Man glycans, more preferably between about 1 to 50% of solid tissue glycomes, for the analysis of tissue materials according to the invention, and use of the composition for the analysis of tissue materials.

Fucosylated High-Mannose Type N-Glycans

The present invention is especially directed to glycan compositions (structures) and analysis of fucosylated high-mannose type N-glycans according to the formula:

$Hex_{n3}HexNAc_{n4}dHex_{n5}$, wherein n3 is 5, 6, 7, 8, or 9, n4=2, and n5=1.

According to the present invention, within total N-glycomes of tissue materials the major fucosylated high-mannose type N-glycan signal preferentially is the composition Hex5HexNAc2dHex (1403).

Soluble Glycans

The present invention is especially directed to glycan compositions (structures) and analysis of neutral soluble N-glycan type glycans according to the formula:

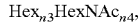

$Hex_{n3}HexNAc_{n4}$, wherein n3 is 1, 2, 3, 4, 5, 6, 7, 8, or 9, and n4=1.

Within total N-glycomes of tissue materials the major soluble N-glycan signals include the compositions with 4≤n3≤8, more preferably 4≤n3≤7: Hex4HexNAc (892), Hex5HexNAc (1054), Hex6HexNAc (1216), Hex7HexNAc (1378). In the most preferred embodiment of the present invention, the major glycan signal in this group within total neutral glycomes of tissue materials is Hex5HexNAc (1054).

Neutral Monoantennary or Hybrid-Type N-Glycans

The present invention is especially directed to glycan compositions (structures) and analysis of neutral monoantennary or hybrid-type N-glycans according to the formula:

$Hex_{n3}HexNAc_{n4}dHex_{n5}$, wherein n3 is an integer greater or equal to 2, n4=3, and n5 is an integer greater or equal to 0.

According to the present invention, within total N-glycomes of tissue materials the major neutral monoantennary or hybrid-type N-glycan signals preferentially include the compositions with 2≤n3≤8 and 0≤n5≤2, more preferentially compositions with 3≤n3≤6 and 0≤n5≤1, with the proviso that when n3=6 also n5=0: preferentially Hex4HexNAc3 (1298), Hex4HexNAc3dHex (1444), Hex5HexNAc3 (1460), and Hex6HexNAc3 (1622).

Neutral Complex-Type N-Glycans

The present invention is especially directed to glycan compositions (structures) and analysis of neutral complex-type N-glycans according to the formula:

$Hex_{n3}HexNAc_{n4}dHex_{n5}$, wherein n3 is an integer greater or equal to 3, n4 is an integer greater or equal to 4, and n5 is an integer greater or equal to 0.

Within the total N-glycomes of tissue materials the major neutral complex-type N-glycan signals preferentially include the compositions with 3≤n3≤8, 4≤n4≤7, and 0≤n5≤4, more preferentially the compositions with 3≤n3≤5 n4=4, and 0≤n5≤1, with the proviso that when n3 is 3 or 4, then n5=1: Hex3HexNAc4dHex (1485), Hex4HexNAc4dHex (1647), Hex5HexNAc4 (1663), Hex5HexNAc4dHex (1809); and even more preferentially also including the composition Hex3HexNAc5dHex (1688).

In another embodiment of the present invention, the N-glycan signal Hex3HexNAc4dHex (1485) contains non-reducing terminal GlcNAcβ, and more preferentially the total N-glycome includes the structure:
GlcNAcβ2Manα3(GlcNAcβ2Manα6)Manβ4GlcNAcβ4(Fucα6)GlcNAc (1485).

In yet another embodiment of the present invention, within the total N-glycome of tissue materials, the N-glycan signal Hex5HexNAc4dHex (1809), more preferentially also Hex5HexNAc4 (1663), contain non-reducing terminal β1,4-Gal. Even more preferentially the total N-glycome includes the structure:
Galβ4GlcNAcβ2Manα3(Galβ4GlcNAcβ2Manα6)Manβ4GlcNAcβ4GlcNAc (1663); and in a further preferred embodiment the total N-glycome includes the structure:
Galβ4GlcNAcβ2Manα3(Galβ4GlcNAcβ2Manα6)Manβ4GlcNAcβ4(Fucα6)GlcNAc (1809).

Neutral Fucosylated N-Glycans

The present invention is especially directed to glycan compositions (structures) and analysis of neutral fucosylated N-glycans according to the formula:

$Hex_{n3}HexNAc_{n4}dHex_{n5}$, wherein n5 is an integer greater than or equal to 1.

Within the total N-glycomes of tissue materials the major neutral fucosylated N-glycan signals preferentially include glycan compositions wherein $1 \leq n5 \leq 4$, more preferentially $1 \leq n5 \leq 3$, even more preferentially $1 \leq n5 \leq 2$, and further more preferentially compositions Hex3HexNAc2dHex (1079), more preferentially also Hex2HexNAc2dHex (917), and even more preferentially also Hex5HexNAc4dHex (1809).

The inventors further found that within the total N-glycomes of tissue materials a major fucosylation form is N-glycan core α1,6-fucosylation. In a preferred embodiment of the present invention, major fucosylated N-glycan signals contain GlcNAcβ4(Fucα6)GlcNAc reducing end sequence.

Neutral N-Glycans with Non-Reducing Terminal HexNAc

The present invention is especially directed to glycan compositions (structures) and analysis of neutral N-glycans with non-reducing terminal HexNAc according to the formula:

$Hex_{n3}HexNAc_{n4}dHex_{n5}$, wherein $n4 \geq n3$.

Preferably these glycan signals include Hex3HexNAc4dHex (1485) in all tissue materials.

Acidic Hybrid-Type or Monoantennary N-Glycans

The present invention is especially directed to glycan compositions (structures) and analysis of acidic hybrid-type or monoantennary N-glycans according to the formula:

$NeuAc_{n1}NeuGc_{n2}Hex_{n3}HexNAc_{n4}dHex_{n5}SP_{n6}$, wherein n1 and n2 are either independently 1, 2, or 3; n3 is an integer between 3-9; n4 is 3; n5 is an integer between 0-3; and n6 is an integer between 0-2; with the proviso that the sum n1+n2+n6 is at least 1.

Within the total N-glycomes of tissue materials the major acidic hybrid-type or monoantennary N-glycan signals preferentially include glycan compositions wherein $3 \leq n3 \leq 6$, more preferentially $3 \leq n5 \leq 5$, and further more preferentially composition NeuAcHex4HexNAc3dHex (1711).

Acidic Complex-Type N-Glycans

The present invention is especially directed to glycan compositions (structures) and analysis of acidic complex-type N-glycans according to the formula:

$NeuAc_{n1}NeuGc_{n2}Hex_{n3}HexNAc_{n4}dHex_{n5}SP_{n6}$, wherein n1 and n2 are either independently 1, 2, 3, or 4; n3 is an integer between 3-10; n4 is an integer between 4-9; n5 is an integer between 0-5; and n6 is an integer between 0-2; with the proviso that the sum n1+n2+n6 is at least 1.

Within the total N-glycomes of tissue materials the major acidic complex-type N-glycan signals preferentially include glycan compositions wherein $4 \leq n4 \leq 8$, more preferentially $4 \leq n4 \leq 6$, more preferentially $4 \leq n4 \leq 5$, and further more preferentially compositions NeuAcHex5HexNAc4 (1930), NeuAcHex5HexNAc4dHex (2076), NeuAc2Hex5HexNAc4 (2221), NeuAcHex5HexNAc4dHex2 (2222), and NeuAc2Hex5HexNAc4dHex (2367).

Modified Glycan Types

The inventors found that tissue material total N-glycomes; and soluble+N-glycomes further contain characteristic modified glycan signals, including sialylated fucosylated N-glycans, multifucosylated glycans, sialylated N-glycans with terminal HexNAc (the N>H and N=H subclasses), and sulphated or phosphorylated N-glycans, which are subclasses of the abovementioned glycan classes. According to the present invention, their quantitative proportions in different tissue materials have characteristic values as described in Tables 8 and 13.

Phosphorylated and Sulphated Glycans

Specifically, major phosphorylated glycans, typical to tissue materials, more preferentially to lysosornal organelle glycomes, include Hex5HexNAc2(HPO$_3$) (1313), Hex6HexNAc2(HPO$_3$) (1475), and Hex7HexNAc2(HPO$_3$) (1637).

Preferred Combinations of Glycan Types in Complete Glycomes

The preferred complete glycomes of tissue materials include low-mannose type, hybrid-type or monoantennary, hybrid, and complex-type N-glycans, which more preferentially contain fucosylated glycans, even more preferentially also sialylated glycans, and further more preferentially also sulphated and/or phosphorylated glycans; and most preferentially also including soluble glycans as described in the present invention.

In a preferred embodiment of the present invention the tissue material total N-glycome contains the three glycan types: 1) high-mannose type, 2) hybrid-type or monoantennary, and 3) complex-type N-glycans; and more preferably, in the case of solid tissues or cells also 4) low-mannose type N-glycans; and further more preferably, in the case of solid tissues or cells additionally 5) soluble glycans.

In a preferred embodiment of the preferred glycan type combinations within the tissue material complete glycomes, their relative abundances are as described in Tables 8 and 13.

Example 1

Glycan Isolation and Analysis

Examples of Glycan Isolation Methods

Glycan Isolation.

N-linked glycans are preferentially detached from cellular glycoproteins by *F. meningosepticum* N-glycosidase F digestion (Calbiochem, USA) essentially as described previously (Nyman et al., 1998), after which the released glycans are preferentially purified for analysis by solid-phase extraction methods, including ion exchange separation, and divided into sialylated and non-sialylated fractions. For O-glycan analysis, glycoproteins are preferentially subjected to reducing alkaline β-elimination essentially as described previously (Nyman et al., 1998), after which sialylated and neutral glycan alditol fractions are isolated as described above. Free glycans are preferentially isolated by extracting them from the sample with water.

Example of a Glycan Purification Method.

Isolated oligosaccharides can be purified from complex biological matrices as follows, for example for MALDI-TOF mass spectrometric analysis. Optionally, contaminations are removed by precipitating glycans with 80-90% (v/v) aqueous acetone at −20° C., after which the glycans are extracted from the precipitate with 60% (v/v) ice-cold methanol. After glycan isolation, the glycan preparate is passed in water through a strong cation-exchange resin, and then through $C_{18}$ silica resin. The glycan preparate can be further purified by subjecting it to chromatography on graphitized carbon material, such as porous graphitized carbon (Davies, 1992). To increase purification efficiency, the column can be washed with aqueous solutions. Neutral glycans can be washed from the column and separated from sialylated glycans by elution with aqueous organic solvent, such as 25% (v/v) acetonitrile. Sialylated glycans can be eluted from the column by elution with aqueous organic solvent with added acid, such as 0.05% (v/v) trifluoroacetic acid in 25% (v/v) acetonitrile, which elutes both neutral and sialylated glycans. A glycan preparation containing sialylated glycans can be further purified by subjecting it to chromatography on microcrystalline cellulose in n-butanol:ethanol:water (10:1:2, v/v) and eluted by aqueous solvent, preferentially 50% ethanol:water (v/v). Preferentially, glycans isolated from small sample amounts are purified on miniaturized chromatography columns and small elution and handling volumes. An efficient purification method comprises most of the abovementioned purification steps. In an efficient purification sequence, neutral glycan fractions from small samples are purified with methods including carbon chromatography and separate elution of the neutral glycan fraction, and glycan fractions containing sialylated glycans are purified with methods including both carbon chromatography and cellulose chromatography.

MALDI-TOF Mass Spectrometry.

MALDI-TOF mass spectrometry is performed with a Voyager-DE STR BioSpectrometry Workstation or a Bruker Ultraflex TOF/TOF instrument, essentially as described previously (Saarinen et al., 1999; Harvey et al., 1993). Relative molar abundancies of both neutral (Naven & Harvey, 1996) and sialylated (Papac et al., 1996) glycan components are assigned based on their relative signal intensities. The mass spectrometric fragmentation analysis is done with the Bruker Ultraflex TOF/TOF instrument according to manufacturer's instructions.

Results

Examples of Analysis Sensitivity.

Protein-linked and free glycans, including N- and O-glycans, are typically isolated from as little as about $5 \times 10^4$ cells in their natural biological matrix and analyzed by MALDI-TOF mass spectrometry.

Examples of Analysis Reproducibility and Accuracy.

The present glycan analysis methods have been validated for example by subjecting a single biological sample, containing human cells in their natural biological matrix, to analysis by five different laboratory personnel. The results were highly comparable, especially by the terms of detection of individual glycan signals and their relative signal intensities, indicating that the reliability of the present methods in accurately describing glycan profiles of biological samples including cells is excellent. Each glycan isolation and purification phase has been controlled by its reproducibility and found to be very reproducible. The mass spectrometric analysis method has been validated by synthetic oligosaccharide mixtures to reproduce their molar proportions in a manner suitable for analysis of complex glycan mixtures and especially for accurate comparison of glycan profiles from two or more samples. The analysis method has also been successfully transferred from one mass spectrometer to another and found to reproduce the analysis results from complex glycan profiles accurately by means of calibration of the analysis.

Examples of Biological Samples and Matrices for Successful Glycan Analysis.

The method has been successfully implied on analysis of e.g. blood cells, cell membranes, aldehyde-fixated cells, glycans isolated from glycolipids and glycoproteins, free cellular glycans, and free glycans present in biological matrices such as blood. The experience indicates that the method is especially useful for analysis of oligosaccharide and similar molecule mixtures and their optional and optimal purification into suitable form for analysis.

Example 2

Glycan Profiling

Generation of Glycan Profiles from Mass Spectrometric Data.

FIG. 1A shows a MALDI-TOF mass spectrum recorded in positive ion mode from a sample of neutral N-glycans. The profile includes multiple signals that interfere with the interpretation of the original sample's glycosylation, including non-glycan signals and multiple signals arising from single glycan signals. According to the present invention, the mass spectrometric data is transformed into a glycan profile (FIG. 1B), which represents better the original glycan profile of the sample. An exemplary procedure is briefly as follows, and it includes following steps: 1) The mass spectrometric signals are first assigned to proposed monosaccharide compositions e.g. according to Table 1. 2) The mass spectrometric signals of ions in the molecular weight are of glycan signals typically show isotopic patterns, which can be calculated based on natural abundancies of the isotopes of the elements in the Earth's crust. The relative signal intensities of mass spectrometric signals near each other can be overestimated or underestimated, if their isotopic patterns are not taken into account. According to the present method, the isotopic patterns are calculated for glycan signals near each other, and relative intensities of glycan signals corrected based on the calculations. 3) Glycan ions are predominantly present as [M+Na]+ ions in positive ion mode, but also as other adduct ions such as [M+K]+. The proportion of relative signal intensities of [M+Na]+ to [M+K]+ ions is deduced from several signals in the spectrum, and the proportion is used to remove the effect of [M+K]+ adduct ions from the spectrum. 4) Other contaminating mass spectrometric signals not arising from the original glycans in the sample can optionally be removed from the profile, such as known contaminants, products of elimination of water, or in a case of permethylated oligosaccharides, undermethylate glycan signals. 5) The resulting glycan signals in the profile are normalized, for example to 100%, for allowing comparison between samples.

Figure 2:
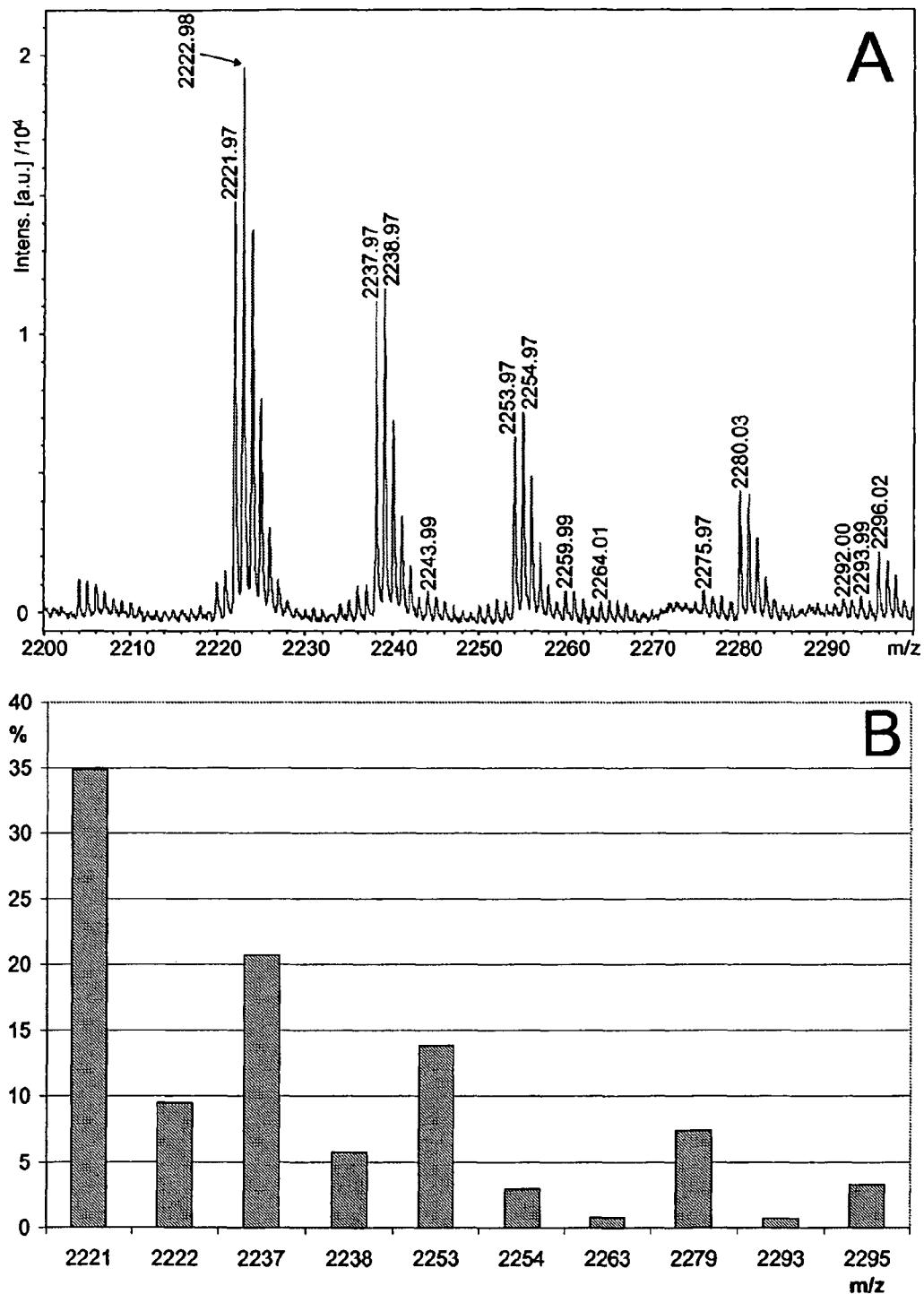
FIG. 2. Example of glycan signal analysis of MALDI-TOF mass spectrometric data. A. Mass spectrometric raw data showing a window of sialylated N-glycan mass spectrum in negative ion mode, B. Glycan profile generated from the data in A.

FIG. 2A shows a MALDI-TOF mass spectrum recorded in negative ion mode from a sample of neutral N-glycans. The profile includes multiple signals that interfere with the interpretation of the original sample's glycosylation, including non-glycan signals and multiple signals arising from single glycan signals. According to the present invention, the mass spectrometric data is transformed into a glycan profile (FIG. 2B), which represents better the original glycan profile of the sample. An exemplary procedure is briefly as follows, and it includes following steps: 1) The mass spectrometric signals are first assigned to proposed monosaccharide compositions e.g. according to Table 2. 2) The mass spectrometric signals of ions in the molecular weight are of glycan signals typically show isotopic patterns, which can be calculated based on natural abundancies of the isotopes of the elements in the Earth's crust. The relative signal intensities of mass spectrometric signals near each other can be overestimated or underestimated, if their isotopic patterns are not taken into account. According to the present method, the isotopic patterns are calculated for glycan signals near each other, and relative intensities of glycan signals corrected based on the calculations. 3) Glycan ions are predominantly present as [M−H]− ions in negative ion mode, but also as ions such as [M−2H+Na]− or [M−2H+K]−. The proportion of relative signal intensities of e.g. [M−H]− to [M−2H+Na]− and [M−2H+K]− ions is deduced from several signals in the spectrum, and the proportion is used to remove the effect of e.g. these adduct ions from the spectrum 4) Other contaminating mass spectrometric signals not arising from the original glycans in the sample can optionally be removed from the profile, such as known contaminants or products of elimination of water. 5) The resulting glycan signals in the profile are normalized, for example to 100%, for allowing comparison between samples.

Example 3

Glycoprotein-Linked Glycans of Human Serum

Experimentation and Results

Glycoprotein-linked glycans in human serum. Protein-linked glycans, corresponding to both N- and O-glycans, were isolated as described above from glycoproteins precipitated from serum of one donor, and analyzed by MALDI-TOF mass spectrometry. Major glycans that were detected included 1) in the neutral glycan fraction, biantennary neutral N-glycans (IgG type), and $Hex_{5-9}HexNAc_2$ N-glycans (high-mannose type), and 2) in the sialylated N-glycan fraction, biantennary and larger sialylated N-glycans (orosomucoid type). The obtained serum protein-linked glycomes serve as a control database against which changes in serum glycoprotein glycans can be detected. It was noted that the neutral N-glycan fraction isolated according to the present invention could be detected by the present method from significantly smaller sample amounts than total N-glycan glycomes or sialylated N-glycan glycomes. It is suggested that the neutral glycan fraction isolated from human serum glycoproteins allows very sensitive detection of changes in serum protein-linked glycan profiles.

Example 4

Profiling of Human Blood Cell Glycosylation

Experimentation and Results

Isolation and Analysis of Protein-Linked Glycans from Human Blood Cells.

Mononuclear cells and red blood cells are isolated from human blood for example by gradient centrifugation in solution containing sodium citrate (Vacutainer CPT, BD) and washed with phosphate buffered saline. Total cellular glycoproteins are precipitated and washed with organic solvents, such as aqueous solutions of acetone and ethanol. N-glycans and O-glycans are isolated from the precipitated glycoproteins, divided into sialylated and neutral glycan fractions, and analyzed by MALDI-TOF mass spectrometry as described above.

White Blood Cell N-Glycan Profiles.

The isolated neutral N-glycans included glycan signals corresponding to glycan groups according to the present invention: high-mannose type, low-mannose type, hybrid-type/monoantennary, and complex N-glycans, as well as monosaccharide compositions $Hex_{1-9}HexNAc_1$, the latter possibly being free glycans and not protein-linked glycans. The isolated sialylated N-glycans included glycan signals corresponding to glycan groups according to the present invention: hybrid-type, monoantennary, and complex-type N-glycans. The resulting profiles differed from both serum glycoprotein glycan profiles and human tissue protein-linked glycans.

Example 5

Profiling of Human Blood Cell Glycosylation After In Vitro Cell Culture

Examples of Cell Material Production

A lymphocyte subpopulation was isolated from human blood using Ficoll isolation (Amersham Pharmacia Biotech) and differentiation marker affinity purification. Cells were cultured for one week in a synthetic cell culture medium supplemented with 1% human serum Experimentation and Results N- and O-glycan profiling analysis. Glycans are isolated from cells, purified, and analyzed by MALDI-TOF mass spectrometry as described above. Typically, at least 25 and more preferentially 50 sialylated N-linked glycan signals, at least 10 and more preferentially over 15 neutral N-linked glycan signals, at least 5 sialylated O-glycan signals, and at least 2 neutral O-glycan signals can be detected and their relative abundancies determined according to the present method. Changes in glycan profiles and specific glycan structures upon in vitro cell culture can be detected by comparing the glycosylation data before and after in vitro culture. Examples of such analyses are presented below.

Glycan Profile Analysis.

Protein-linked glycans were isolated from a human lymphocyte subpopulation grown in cell culture conditions for one week. In glycan profiling analysis it was observed that the relative amounts of five major neutral N-glycans at m/z 1257, 1419, 1581, 1743, and 1905, corresponding to $[M+Na]^+$ ions of high-mannose type N-glycans $Hex_{5-9}HexNAc_2$, were significantly more abundant than the major sialylated N-glycans. This is in contrast to native human cells.

Sialic Acid Linkage Analysis.

The isolated sialylated N- and O-glycans were treated with recombinant S. pneumoniae α2,3-sialidase essentially as described previously (Saarinen et al., 1999). The vast majority of the sialylated N-glycans were susceptible to hydrolysis by the enzyme, indicating that nearly all sialic acids in the sialylated N-glycans were α2,3-linked. This is in contrast to native human cells. α2,3-linkage was also predominant in the O-glycans.

Fucosylation Analysis.

By sequential digestions with specific glycosidases performed essentially as described previously (Hemmerich et al., 1995), except that analysis of digestion results was performed by MALDI-TOF mass spectrometry according to the present invention, it was shown that fucose residues in O-glycans occurred in the sialyl-Lewis x epitope, Neu5Acα2-3Galβ1-4(Fucα1-3)GlcNAcβ. In contrast, fucose residues were shown by similar sequential digestions to reside mainly in the N-glycan core sequence. The latter result is in accordance with the initial glycan grouping according to the present invention, because sialylated N-glycans in the original sample did not include significant amounts of glycans with proposed monosaccharide compositions with more than one deoxyhexose residue, which was not indicative of other fucose linkages apart from α1,6-Fuc of the N-glycan core sequence.

Conclusions

The present results demonstrate that cell glycosylation profiles can change significantly upon in vitro cell culture even in a relatively short time. In particular, the present results indicate that cell cultivation can change the relative amounts of high-mannose N-glycans compared to other glycan types, N-glycan sialic acid linkages, and the overall glycosylation profile. It was also demonstrated that these glycosylation changes can be detected and characterized according to the present method. It was also shown that N- and O-glycan specific fucosylation can be characterized by the present method.

Example 6

Effect of Culture Conditions and Cell Line Age on Protein-Linked Glycosylation of SW 480 Cells Experimental Procedures
Cell Culture.

SW 480 cells (human colon adenocarcinoma cell line) were cultured in 5% $CO_2$ atmosphere in RPMI medium containing 10% fetal calf serum (FCS). Cells were split twice a week. The bigger the passage was, more rapidly the cells grew. For starvation cells were washed twice with RPMI containing 0.2% FCS and incubated in the same medium for 14 hours. Normally cells were approximately 70% confluent, except for sample "confluent" which was 100% confluent.

Membrane Protein Isolation.

Membrane protein isolation was performed at +0-+4° C. Cells were washed with phosphate buffered saline and collected by centrifugation. The cells were incubated in hypotonic buffer (25 mM Tris-HCl pH 8.5), broken by homogenisation, and brought back to isotonic buffer by the addition of NaCl to 150 mM. The homogenate was centrifuged at 40,000 g in order to recover the cell membranes. The crude membrane pellet was homogenized in detergent buffer containing 25 mM Tris-HCl pH 7.5, 150 mM NaCl, and 1% (w/v) β-octylglucoside. After incubation, the preparate was centrifuged at 100,000 g and the supernatant that contained the detergent extracted proteins was collected. Buffer salts and the detergent were removed by cold acetone precipitation as described previously (Verostek et al., 2000).

Results and Discussion

Glycan Profiling of Cultured Cells in Different Cell Culture Phases.

Figure 3:
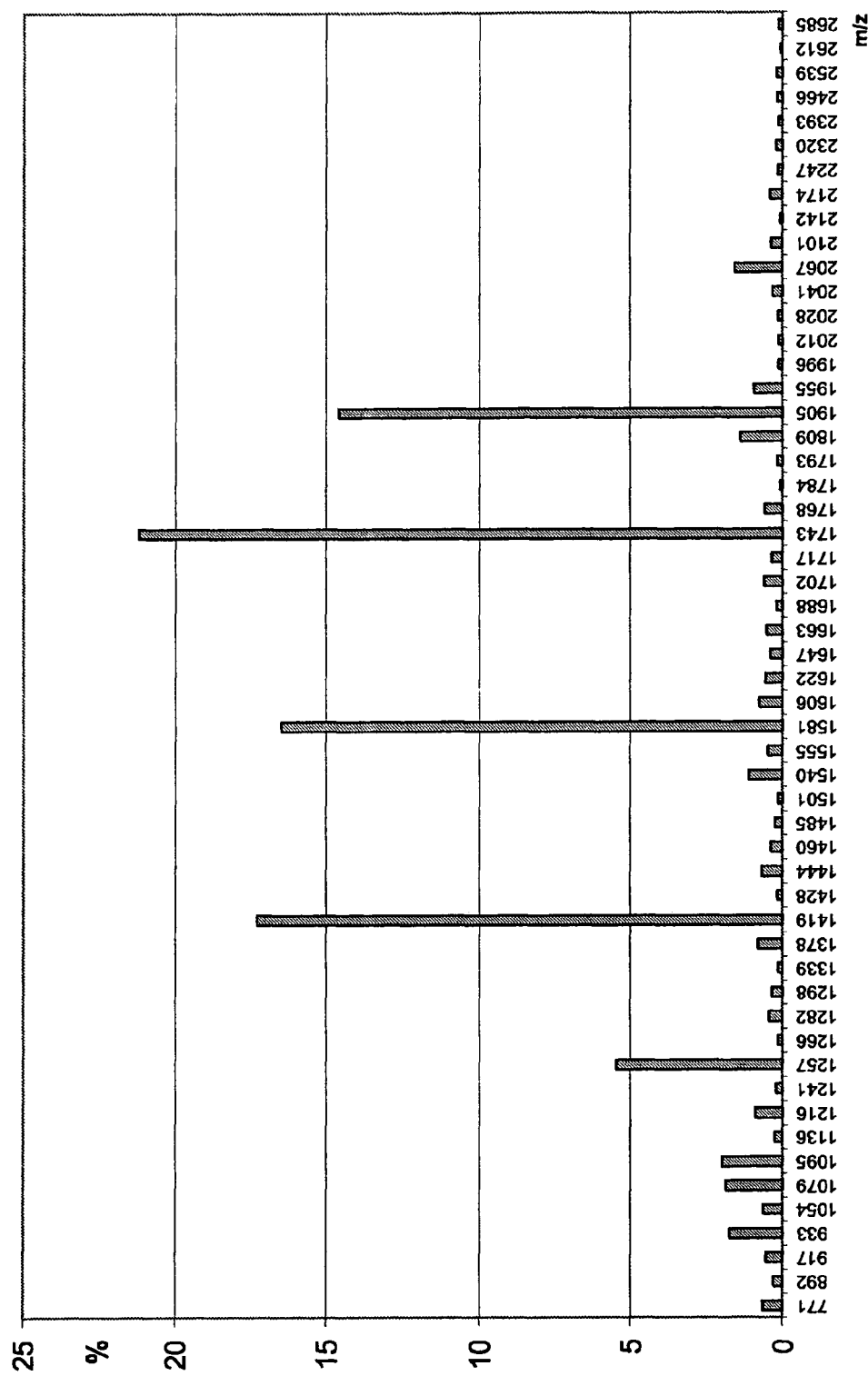
FIG. 3. SW 480 (human colon adenocarcinoma cell line) neutral N-glycans (passage n+4).
Figure 4:
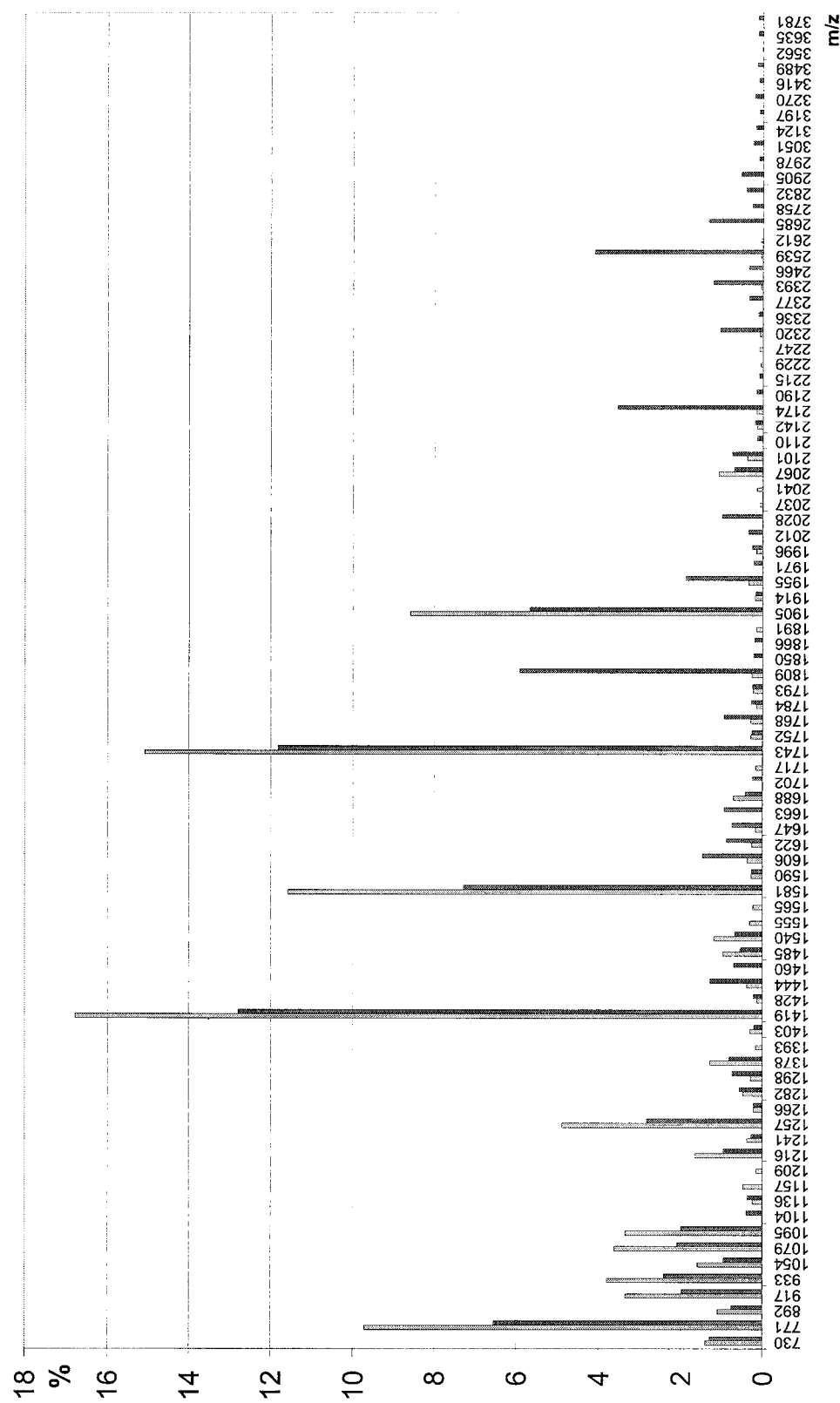
FIG. 4. Glycan profiles of neutral (light columns) and combined neutral and desialylated (sialylated) glycans (dark columns) of SW 480 cells (passage n+39).
Figure 5:
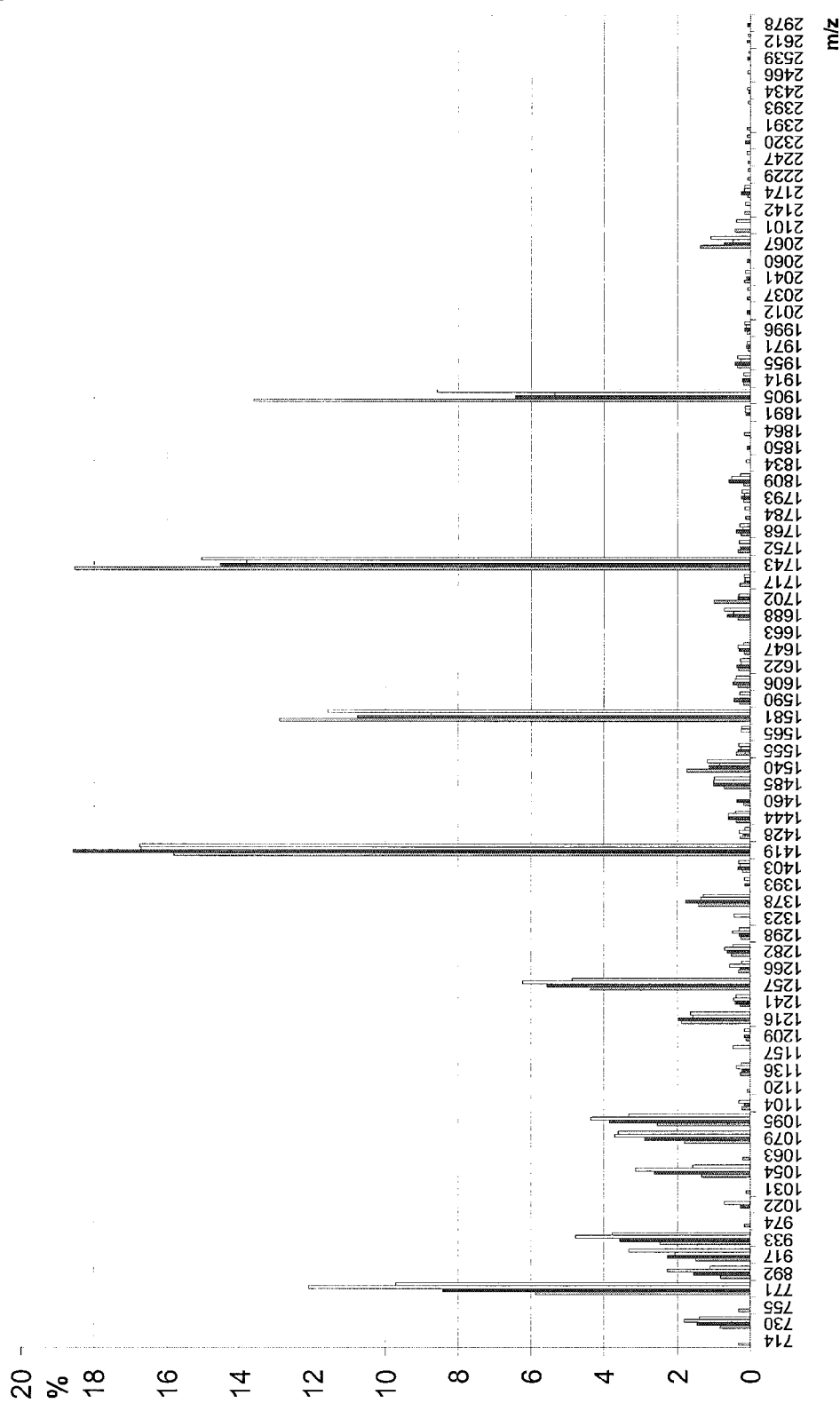
FIG. 5. Neutral protein-linked glycans of SW 480 cells. Differently shaded columns from left to right; Light columns: young cell line in growth phase (passage n+4); Dark columns: starvated (passage n+8); Blank columns: confluent (passage n+8); Light columns: old cell line in growth phase (passage n+39).
Figure 6:
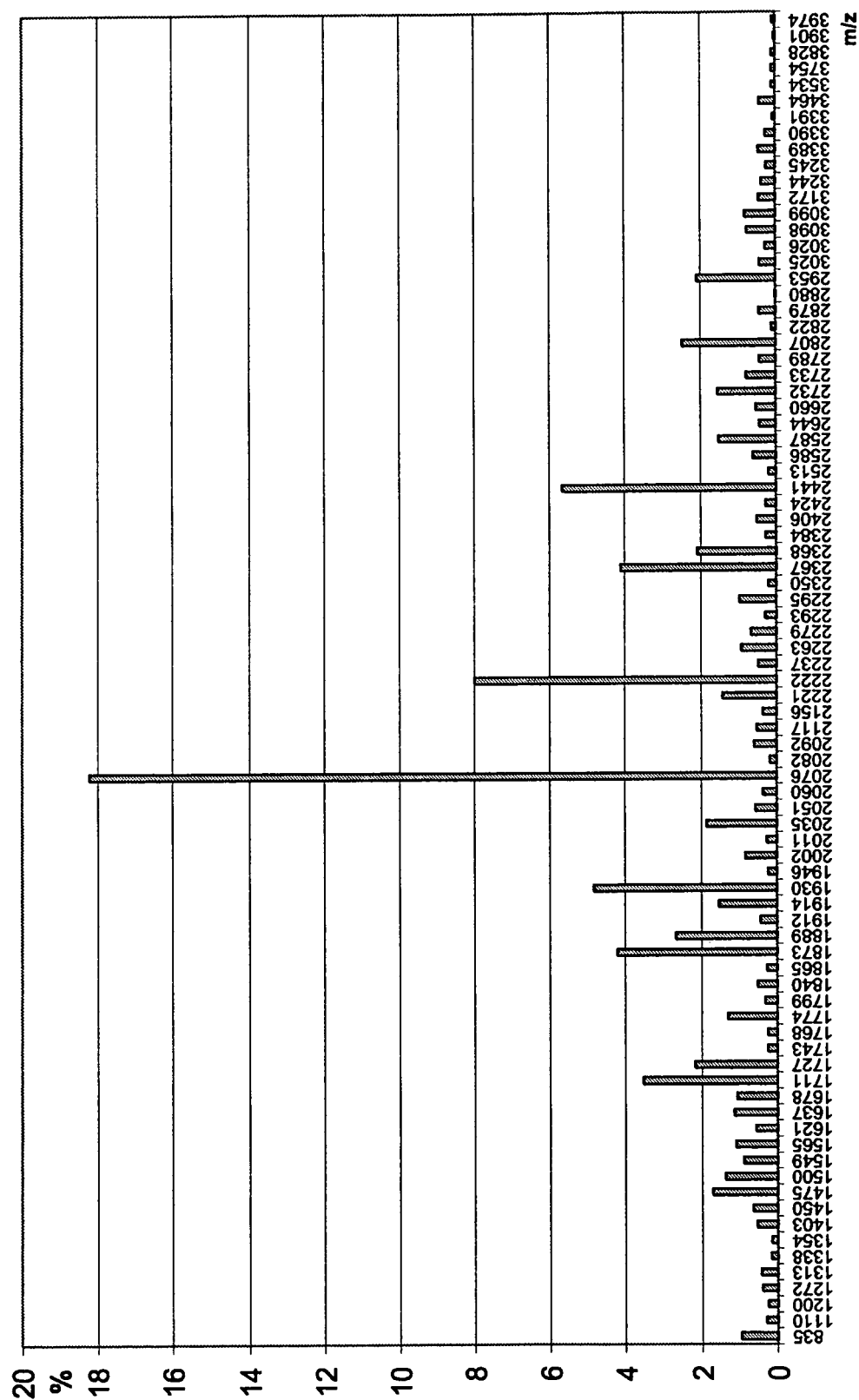
FIG. 6. Sialylated N-glycan fraction of SW 480 cells (passage n+4).

FIG. 3 shows the neutral N-glycan profile of SW 480 cells in growth phase, and the sialylated glycan fraction is shown in FIG. 6. FIG. 4 shows the relative abundancies of sialylated and neutral glycans after desialylation of the sialylated glycan fraction. Cell condition dependent changes in neutral glycan profiles are depicted in FIG. 5. The present results indicate that starvated, confluent, and old cells resemble each other and are different from young cells with respect to relative abundancies of their glycan biosynthetic groups. It is indicated that high-mannose type N-glycans are significantly more abundant when compared to e.g. low-mannose type N-glycans or complex-type N-glycans including sialylated N-glycans, when the cells are both young and in growth phase. Also other changes, both in individual glycan signals and in the overall glycan profiles, are evident as presented in the Figures.

General Change in Cultured Human Cell Lines.

Similar phenomena were observed in also other human cell lines studied, including over 10 cancer cell lines as well as cell lines derived from normal human tissues. The major change occurring in the cells when they are cultured in vitro, is that high-mannose type N-glycans are significantly more abundant when compared to e.g. low-mannose type N-glycans or complex-type N-glycans including sialylated N-glycans.

Example 7

Analysis of Antibody Glycosylation and its Modification In Vitro

Experimentation and Results
Analysis of Antibody Glycosylation.

Monoclonal antibodies (mAbs) are typically produced as recombinant proteins in mammalian cell lines or in plants, and polyclonal antibodies can be purified from e.g. serum by methods known in the art. IgG is a glycoprotein with two N-glycosylation sites per molecule (one per heavy chain), but occasionally also two (or 2n) extra N-glycosylation sites per molecule (one per variable region, or n). The structures of the conserved N-glycans are highly conserved (REF1), but they can change due to e.g. disturbances in the recombinant protein production. The present method as described above allows for detection of these abnormalities, as demonstrated by model mAbs analyzed by the present method, as described below. The glycan profiles were analyzed from glycan pools isolated by N-glycosidase F, or N-glycosidase A (from almonds; Calbiochem, USA) in the case of plant glycoproteins, and analyzed as described in the preceding Examples.

In an example where antibody molecules contain abnormal N-glycans in the conserved site, glycan signals arising from the abnormal glycans are observed in increased amounts compared to the normal glycan signals that correspond to the monosaccharide compositions $Hex_{3-5}HexNAc_4dHex_1$. Easily detected abnormal structures include mannose type N-glycans corresponding to the monosaccharide compositions $Hex_{2-9}HexNAc_2$.

In an example where antibody molecules contain normal N-glycans in the conserved site, but in abnormal relative amounts compared to each other, the abnormality can be observed from the glycan profile according to the present invention. Normal glycan profiles of IgG molecules are described in the literature (e.g. Raju et al., 2000). An example of an abnormal profile of normal glycans is such that the relative amounts of the $Hex_3HexNAc_4dHex_1$ glycoforms are significantly increased compared to the $Hex_{4-5}HexNAc_4dHex_1$ glycoforms, which can give rise to side effects in the potential use of the antibody molecule, such as affinity towards receptors of the innate immunity and/or serum clearance systems. Observed examples (1. and 2.) of differential proportions of the glycoforms $Hex_3HexNAc_4dHex_1$: $Hex_3HexNAc_4dHex_1$:$Hex_3HexNAc_4dHex$, are presented below together with examples from the literature (3. and 4.). The present results suggest that the method of glycan analysis according to the present invention is useful in the characterization of recombinant antibodies.

| No. | Proportions | IgG source | Glycosylation state |
| --- | --- | --- | --- |
| 1. | 3:2:1 | Preparate of human serum IgG | Abnormal |
| 2. | 10:5:1 | Recombinant glycoprotein | Abnormal |
| 3. | 1:1, 8:1 | Human serum, Raju et al. (2000) | Normal |
| 4. | 1:2:1 | Recombinant glycoprotein, Sheeley et al. (1997) | Normal |

In an example where antibody molecules contain normal complex-type N-glycans in the conserved sites and abnormal glycan types in an extra N-glycosylation site, the abnormality can be observed in the glycan profile according to the present invention: in this case the abnormal variable region N-glycans and the normal conserved N-glycans occur in approximate molar proportions of 1:1. For example, high-mannose type N-glycans observed in an extra variable region N-glycosylation site can give rise to side effects in the potential use of the antibody molecule, such as affinity towards receptors of the innate immunity and/or serum clearance systems.

In an example where antibody molecules are produced in plants, the glycan profiles can differ significantly from animal-type glycan profiles. For evaluating suitability of glycosylation for antibodies, the relationship of $Hex_3HexNAc_4dHex_1$, less preferentially $Hex_3HexNAc_4$, even less preferentially $Hex_3HexNAc_2dHex_{0-1}$, monosaccharide compositions, to other glycan signals is calculated, with the proviso that the deoxyhexose-containing N-glycans can be liberated by N-glycosidase F as well as N-glycosidase A enzymes, indicating that they do not contain α1,3-linked fucose in the N-glycan core. Generally, glycan profiles generated by N-glycosidase F and N-glycosidase A enzymes should not differ at all, if the antibody is suited for human use. As another means of evaluating the suitability of glycosylation for antibodies, non-animal type glycans should not appear in the glycan profile. These include all glycan signals corresponding to monosaccharide compositions containing pentose or more than one deoxyhexose. For reasons listed above, also high-mannose or low-mannose type N-glycans are not preferred in recombinant antibodies. In conclusion, the present method allows for effective and rapid evaluation of recombinant protein glycosylation, when they are produced in plants or other non-animal systems.

In Vitro Modification of Native Preparations—Galactosylation.

It was observed that an antibody preparation had the relative amounts of the $Hex_3HexNAc_4dHex_{0-1}$ glycoforms significantly increased compared to the $Hex_{4-5}HexNAc_4dHex_{0-1}$ glycoforms, possibly causing side effects in the use of the antibody. A normal glycoform profile of the preparation was restored by in vitro incubation with β1,4-galactosyltransferase, uridine diphospho-galactose, divalent cations, and suitable buffer and temperature as known in the art, without denaturing the antibody.

In Vitro Modification of Native Preparations—Demannosylation.

It was observed that an antibody preparation had abnormal variable region N-glycans, since its N-glycan profile showed the normal conserved N-glycans and high-mannose type N-glycans occurring in approximate molar proportions of 1:1 in the profile. High-mannose glycoforms were removed from the glycan profile by in vitro incubation with either α-mannosidase from Jack beans (*C. ensiformis*; Sigma, USA) or Endoglycosidase H (Calbiochem, USA) in suitable reaction buffers and temperature as known in the art, without denaturing the antibody. In these reactions, the characterized reaction products were antibody preparations containing $Hex_{1-5}HexNAc_2$ ($Manα_{1-4}Manβ1-4GlcNAcβ1-4GlcNAc$) and GlcNAc variable region extra N-glycans, respectively.

Example 8

Novel Oligosaccharides of Human Milk and Methods for Production and Analysis

Experimentation and Results
Isolation and Fractionation of Human Milk Oligosaccharides.
Samples of human milk were defatted by centrifugation and deproteinized by precipitation with 68% (v/v) aqueous ethanol. The supernatant was dried and the residue was extracted with water. The water-soluble oligosaccharides were subjected to gel filtration chromatography in water. High-molecular weight neutral oligosaccharides were separated from sialylated oligosaccharides at the void volume by porous graphitized carbon chromatography as described above. The gel filtration chromatography phase resulted in enrichment of high-molecular weight neutral and sialylated oligosaccharides, as described below. Furthermore, from a sample of $Le^{a-b-}$ milk, neutral oligosaccharide fraction corresponding approximately to lacto-N-octaoses was further fractionated by normal-phase high-performance liquid chromatography (HPLC) on amino-bonded silica column and porous graphitized carbon HPLC (Hypercarb), with absorbance detection at 214 nm and either descending (normal-phase) or ascending (Hypercarb) acetonitrile gradient in aqueous mild ammonia solution. The enhanced separation capabilities resulted in isolation of a heptasaccharide not previously described in human milk, as described below.

Novel High-Molecular Weight Oligosaccharides in Human Milk.

By MALDI-TOF mass spectrometry, novel neutral and acidic oligosaccharides were detected in high-molecular weight fractions of the gel filtration chromatography step. The detected neutral and sialylated oligosaccharides had molecular masses up to nearly 3700 Da and nearly 2600 Da, respectively. Overall, the detected neutral oligosaccharides had apparent monosaccharide compositions $Hex_{m+2}HexNAc_mdHex_n$, corresponding to $(Gal_mGlcNAc_mFuc_n)Galβ1-4Glc$, where (n≤m) and (1≤m≤8), or even (m≤9) when (n=0). Overall, the detected sialylated oligosaccharides had apparent monosaccharide compositions $NeuAc_0Hex_{m+2}HexNAc_mdHex_n$, corresponding to $(Gal_mGlcNAc_mFuc_nNeuAc_o)Galβ1-4Glc$, where (n≤in) and (o≤in) and (1≤m≤4), or even (m≤5) when (n=0) and (o=1).

Novel Fucosylated Heptasaccharide in Human Milk.

From the $Le^{a-b-}$ milk sample, the following isomeric neutral heptasaccharides eluting into the same fraction in normal-phase HPLC, were isolated and characterized: (I) Galβ1-4(Fucα1-3)GlcNAcβ1-6(Galβ1-4GlcNAcβ1-3)Galβ1-4Glc, (U) Galβ1-4(Fucα1-3)GlcNAcβ1-6(Galβ1-3GlcNAcβ1-3)Galβ1-4Glc, (E) Galβ1-4(Fucα1-3)GlcNAcβ1-3(Galβ1-4GlcNAcβ1-6)Galβ1-4Glc, (IV) Fucα1-2Galβ1-3GlcNAcβ1-3(Galβ1-4GlcNAcβ1-6)Galβ1-4Glc, (V) Galβ1-4GlcNAcβ1-3Galβ1-4(Fucα1-3)GlcNAcβ1-3Galβ1-4Glc, and (VI) Galβ1-3GlcNAcβ1-3Galβ1-4(Fucα1-3)GlcNAcβ1-3Galβ1-4Glc. The structures were verified by sequential exoglycosidase digestions, mild acid hydrolysis, ID $^1$H-NMR against known standard molecules, chromatographic coelution with known standard molecules, and MALDI-TOF mass spectrometry. The oligosaccharide III has not been previously described in human milk.

Example 9

Figure 15:
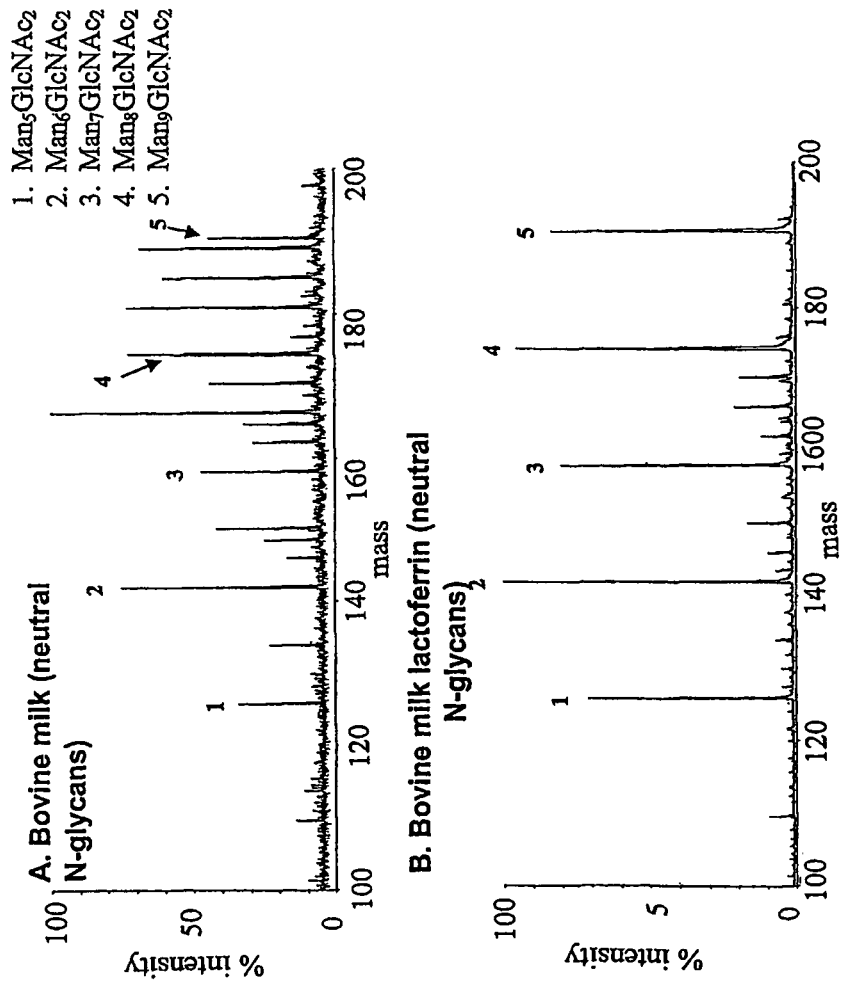
FIG. 15. Neutral protein-linked glycans of human tissues, A. stomach, and B. colon.

Oligosaccharide and Glycoprotein Compositions of Bovine Milk and Methods for Analysis Experimentation and Results
Analysis of Bovine Milk Glycoprotein Fractions.
Neutral N-glycans were analyzed from samples of dilapidated bovine milk and milk powder as described in the preceding Examples. Lactoferrin was also isolated from the same samples by cation exchange chromatography and the purified lactoferrin was analyzed similarly as the total milk sample. FIG. 15. shows the analysis results. It is evident from the glycan profiles that the glycosylation of total milk glycoproteins (FIG. 15A) and a single glycoprotein, lactoferrin (FIG. 15B), isolated among them can differ significantly. Similar glycans occur also in the total milk glycoprotein fraction, but some they are enriched in the lactoferrin fraction. Bovine lactoferrin has been determined to contain significant amounts of complex N-glycans previously, but it is evident that there is significant sample-to-sample variation in lactoferrin glycan structures.

Analysis of Human Digestive Tract Tissue Samples.

Figure 16:
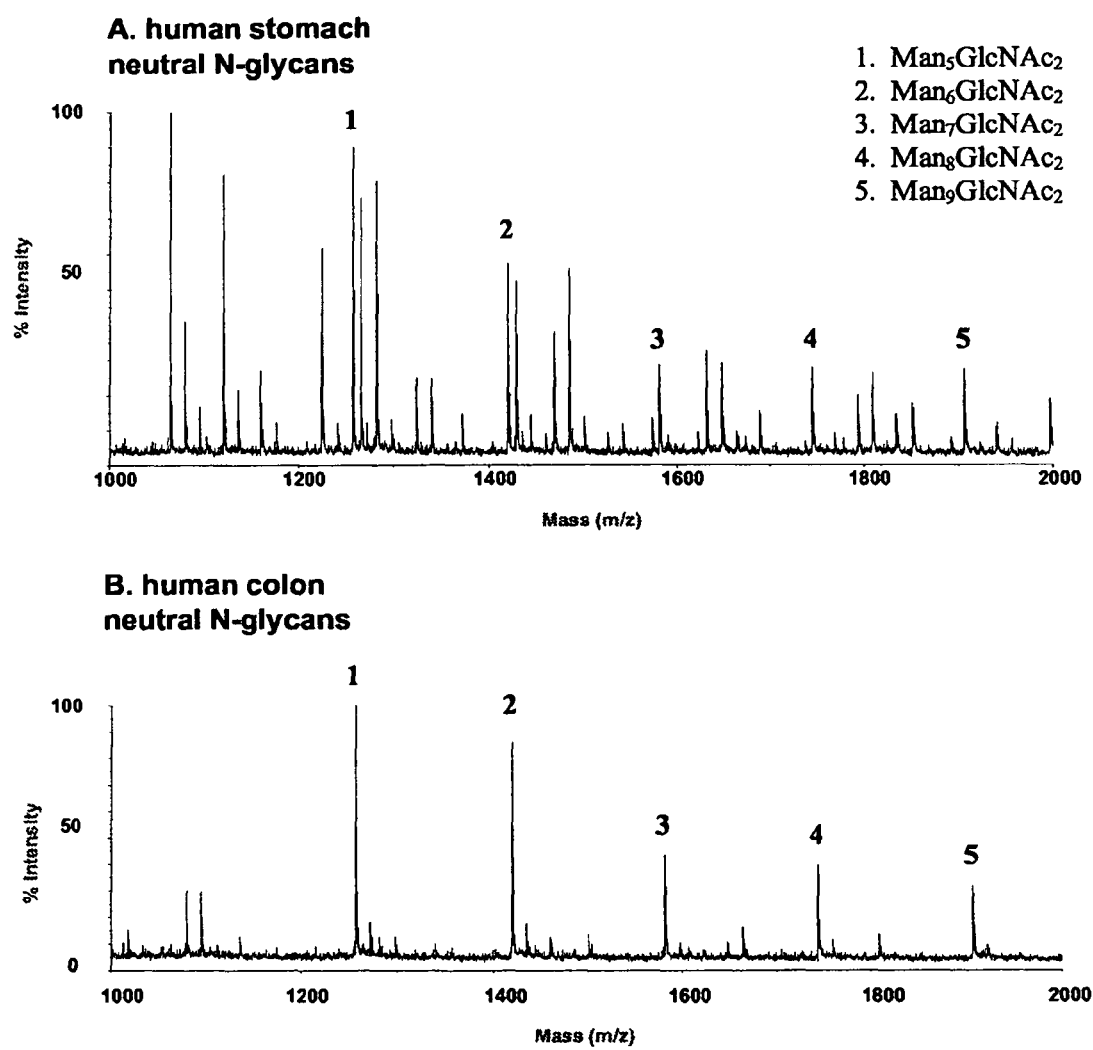
FIG. 16. Neutral protein-linked glycans of bovine milk glycoproteins from A. total milk, and B. lactoferrin isolated from total mile.

FIG. 16. shows the neutral protein-linked glycan analysis results obtained from human stomach (FIG. 16A) and colon (FIG. 16B). Both these tissues contain similar glycan structures than lactoferrin described above. It is concluded that there occurs in bovine milk neutral N-glycans that resemble human digestive tract N-glycans, and that a specific fraction of bovine milk can be selected to resemble more closely the human glycosylation in specific organs.

Example 10

Protein-Linked Glycan Profiling of Human Tissues

Experimental Procedures

Figure 7:
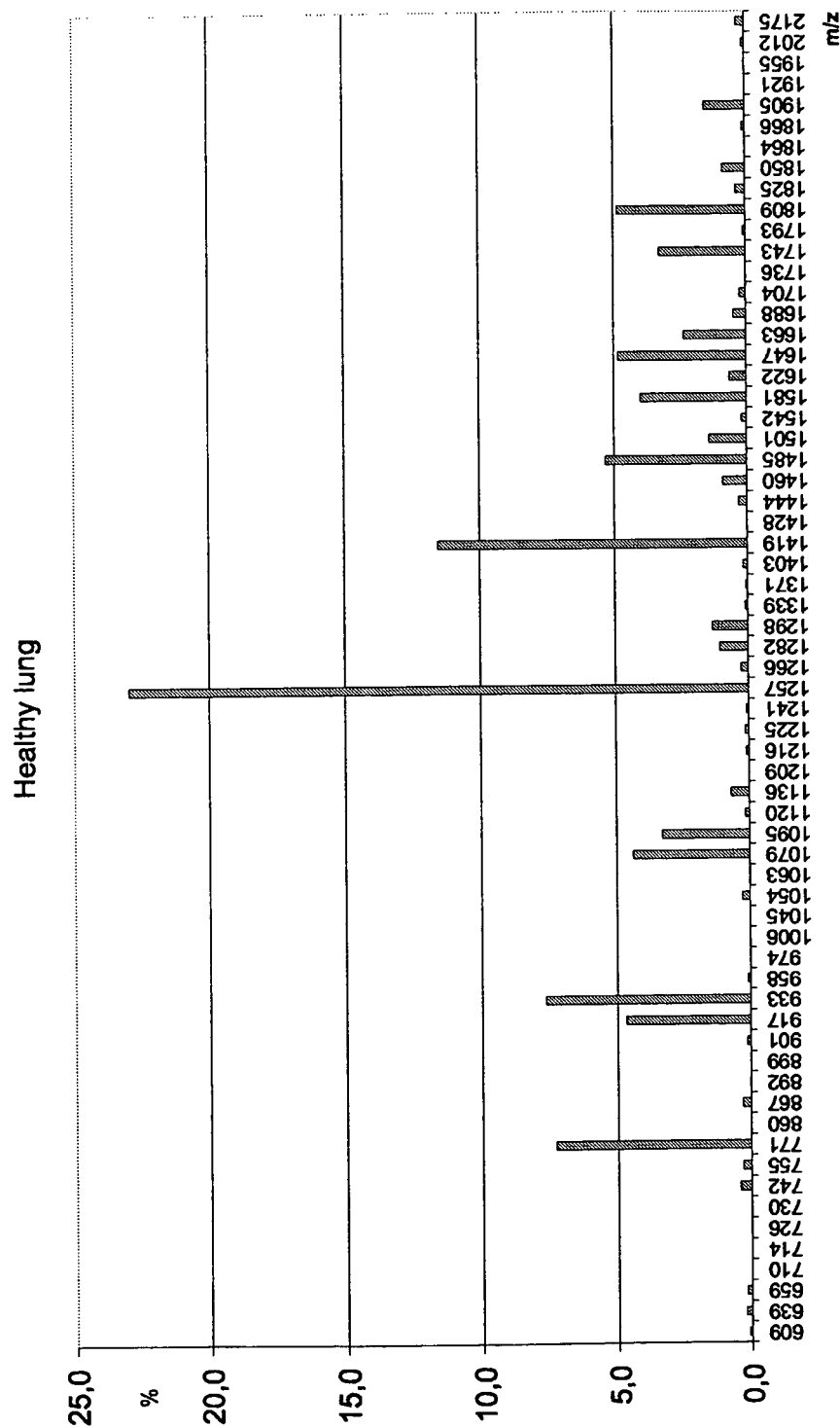
FIG. 7. Neutral protein-linked glycans of human lung tissue.
Figure 8:
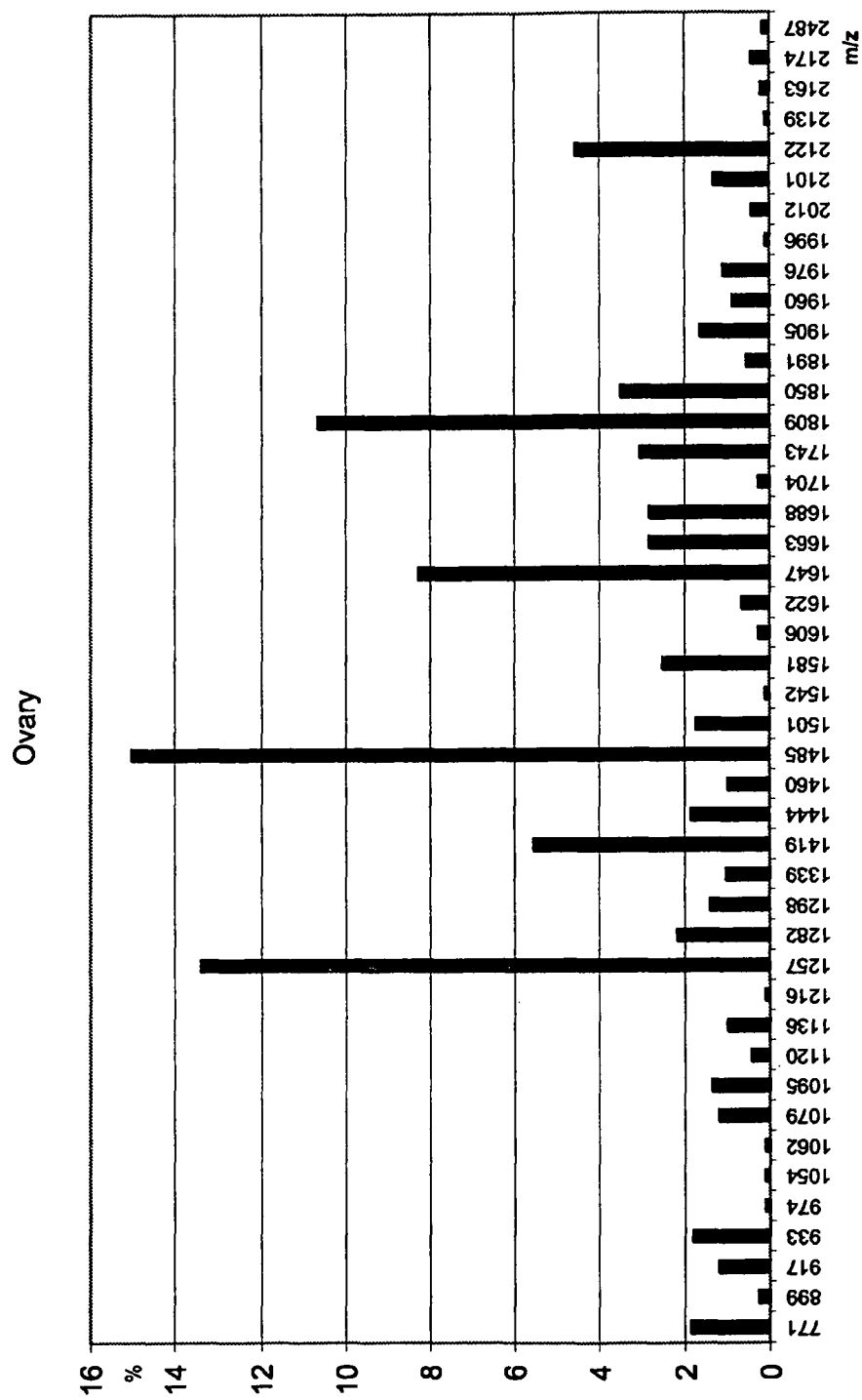
FIG. 8. Neutral protein-linked glycans of human ovary tissue.

FIGS. 7. through 14. show neutral protein-linked glycan analyses of protein-linked glycans, performed on paraffin-embedded and formalin-fixed archival human tissue samples, performed after deparaffinisation essentially as described above in the preceding Examples. The glycan isolation was however done by non-reductive alkaline elimination essentially as described by Huang et al. (2000). The m/z values in the Figures refer to the Tables in the present invention. Sialylated glycans were analyzed similarly Results and Discussion Tissue-Specific Glycosylation Information and it Use.

It is seen that each tissue depicted in the Figures differs from another by 1) differences in overall glycan profiles, 2) differences in individual glycan signals, and/or 3) relative abundancies of individual glycan signals or glycan signal groups according to the present invention. The tissues can be recognized based on the glycan profiles and individual glycan signals that correspond to tissue-specific expression of glycans. The sialylated glycan fractions also contain similar specific information that can be combinated with the neutral glycan fraction information to gain more specificity and resolving power.

Individual Differences in Tissue Glycosylation.

Figure 11:
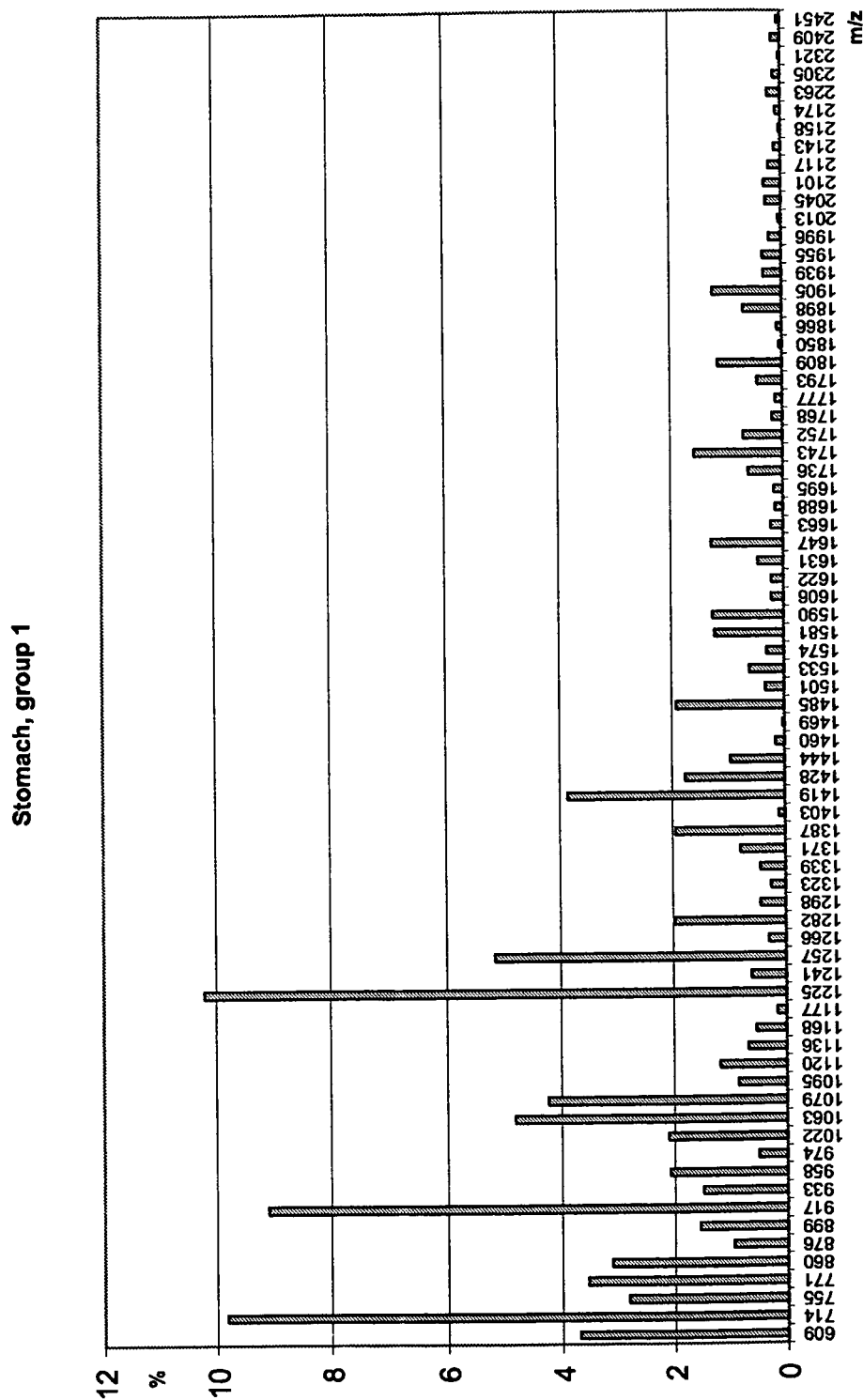
FIG. 11. Neutral protein-linked glycans of human stomach tissue from blood group specific donors.
Figure 12:
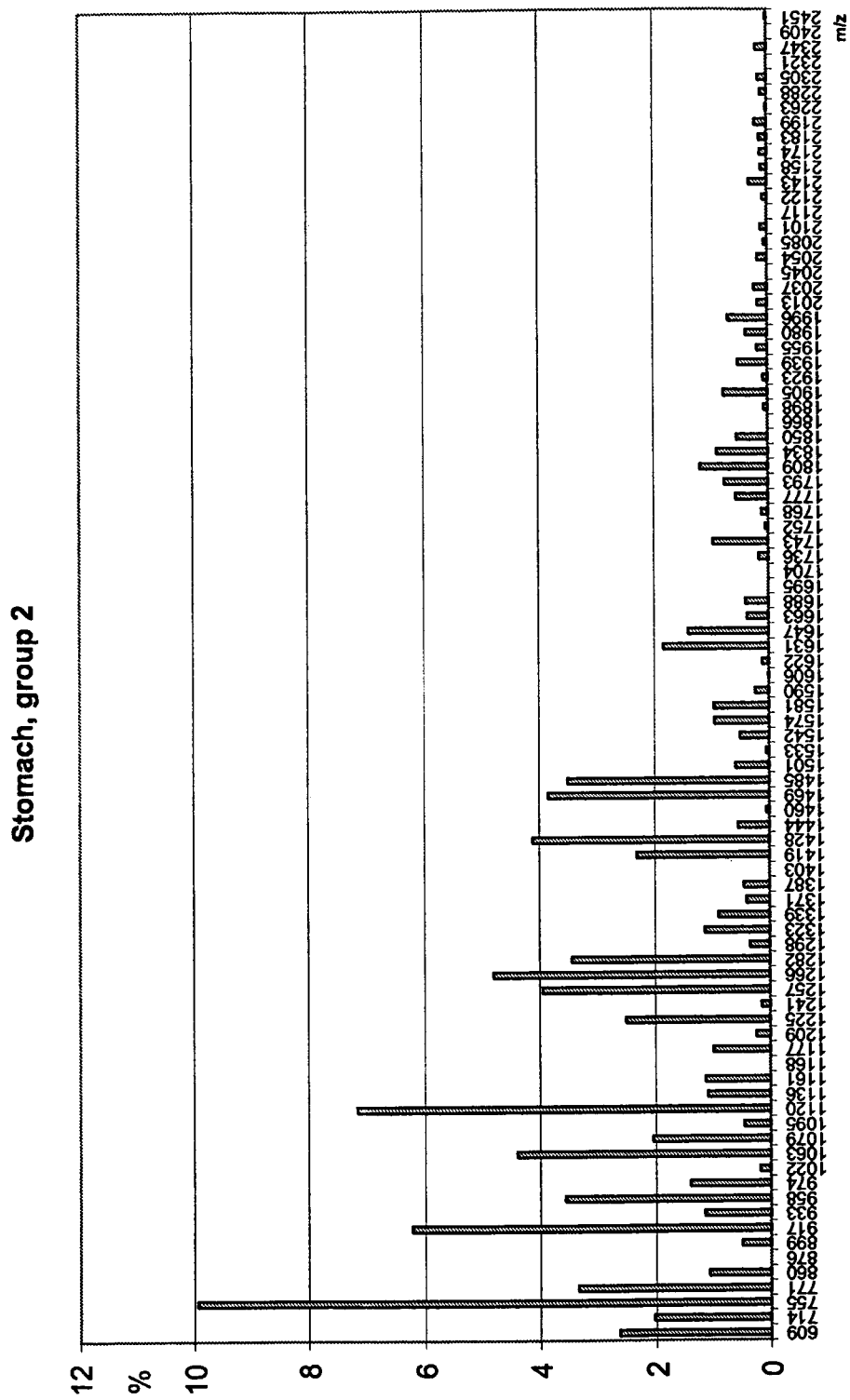
FIG. 12. Neutral protein-linked glycans of human stomach tissue from blood group specific donors.
Figure 13:
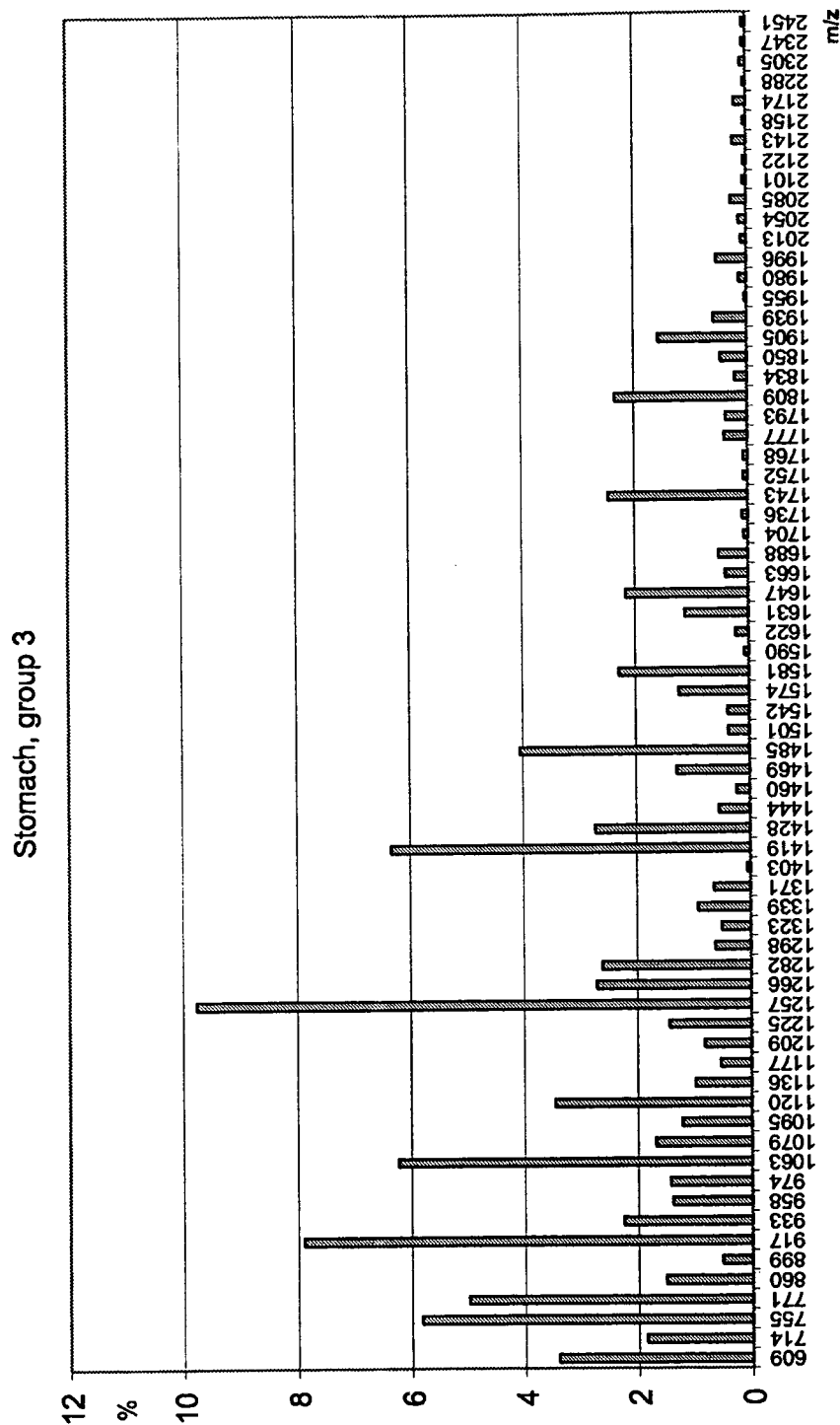
FIG. 13. Neutral protein-linked glycans of human stomach tissue from blood group specific donors.

FIGS. 11, 12, and 13 show neutral protein-linked glycan profiles of tissue samples from human stomach. The results are presented as groups 1-3 according to distinct blood-group-specific glycan structures that are present in each donor group. Any future stomach sample can be grouped accordingly in its blood-group specific group. Also other individual differences can be observed among tissues from different donors. It is therefore indicated that the present method can detect individual differences in tissue glycosylation.

Disease-Specific Differences in Glycosylation.

Figure 9:
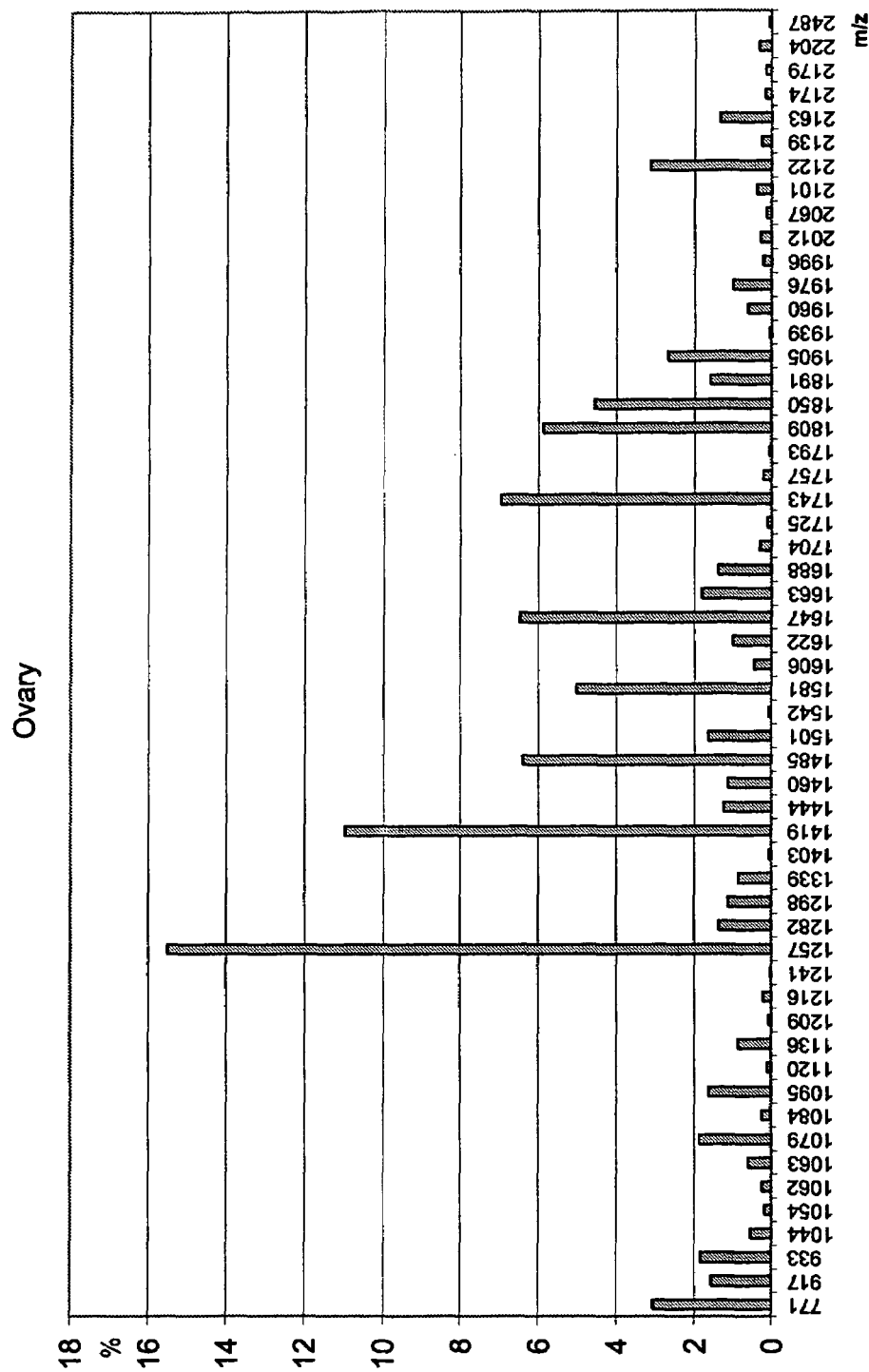
FIG. 9. Neutral protein-linked glycans of human ovary tissue with abnormal growth.
Figure 10:
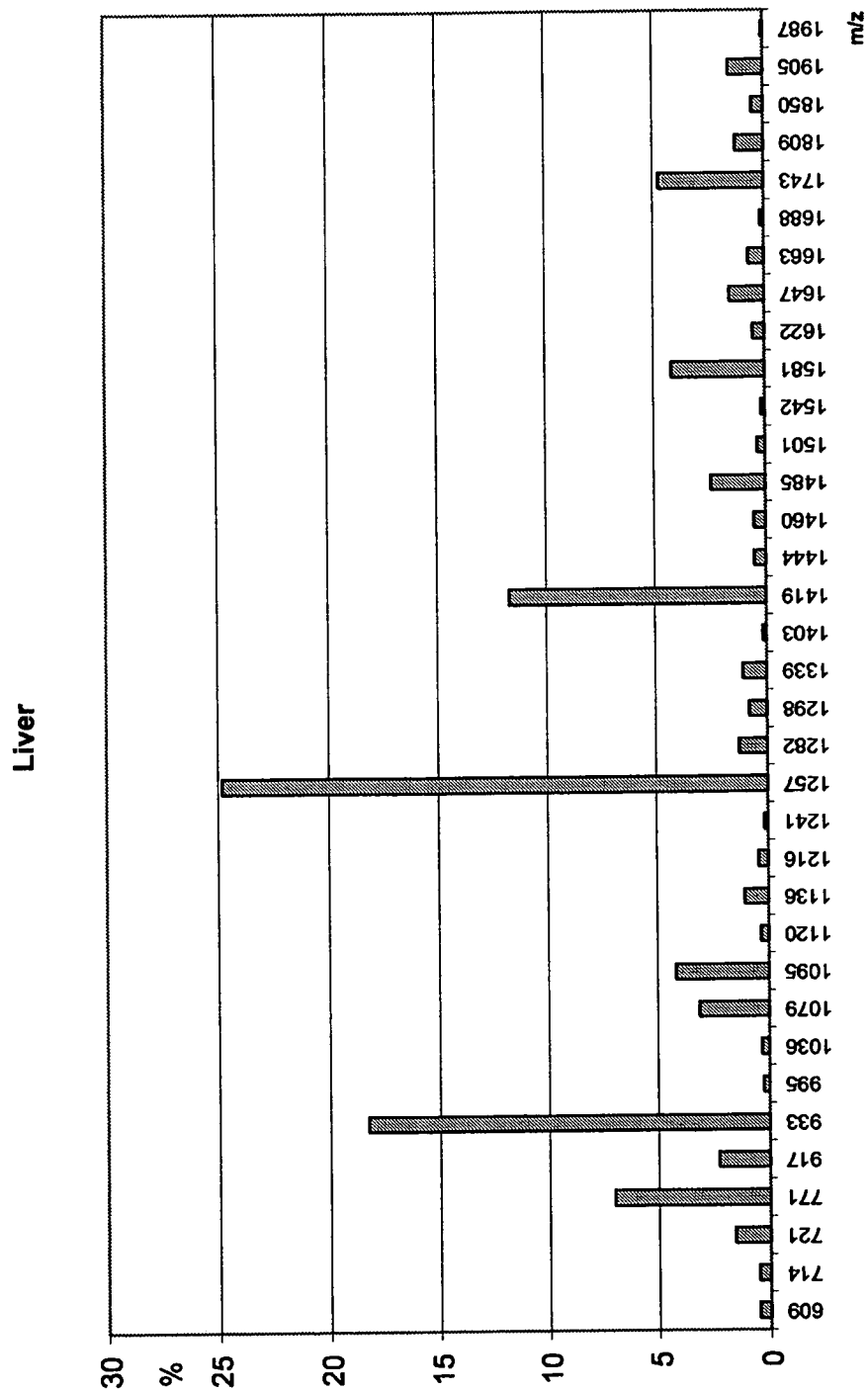
FIG. 10. Neutral protein-linked glycans of human liver tissue.
Figure 14:
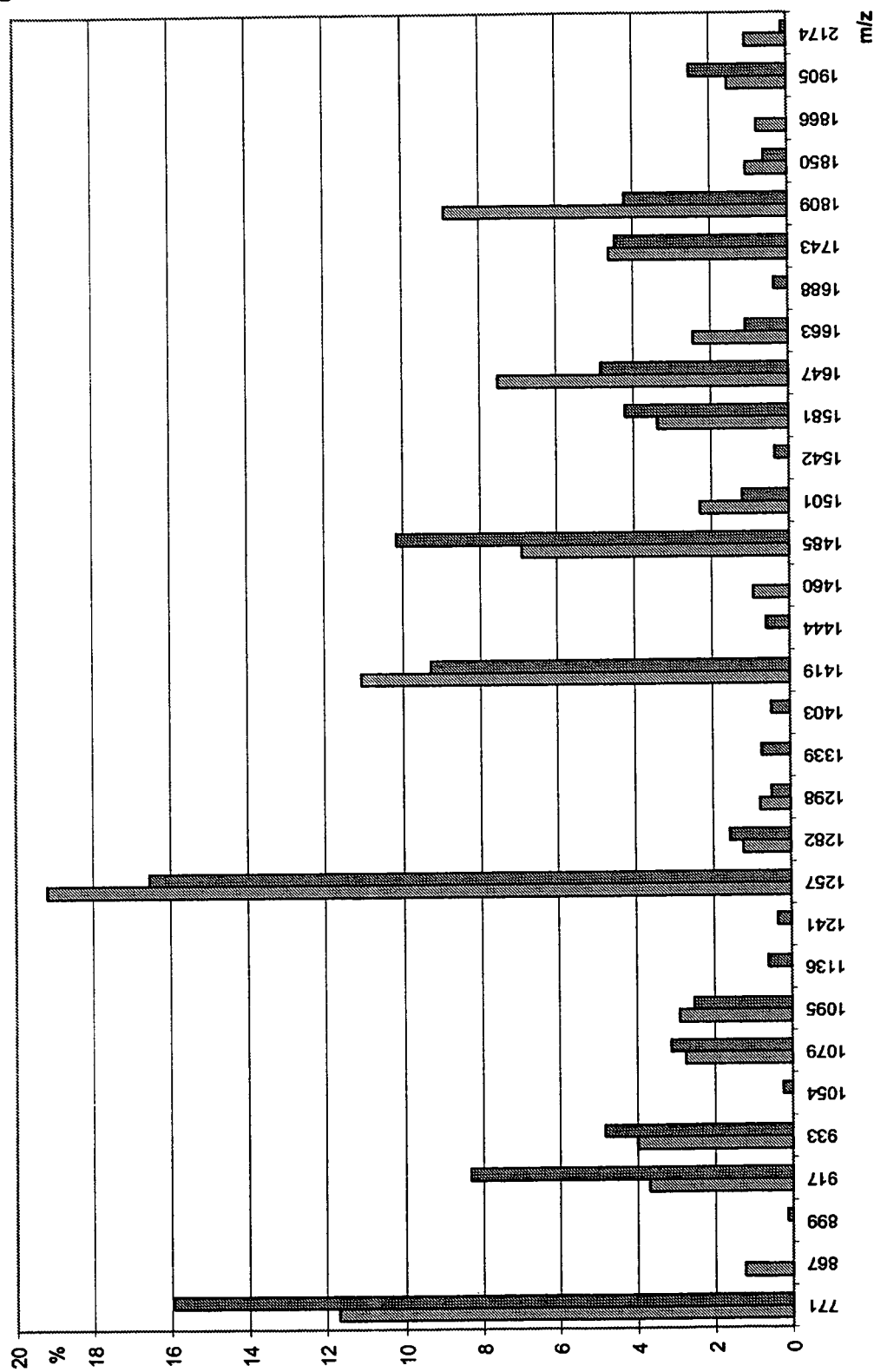
FIG. 14. Neutral protein-linked glycans of healthy lung tissue (light columns) and lung cancer tumor (dark columns).

FIG. 14. shows the comparison of neutral glycan profiles from healthy lung tissue and tumor tissue from a patient with non-small cell lung cancer. It is seen that the disease state can be differentiated from the healthy state according to the methods of the present invention. Numerous cancer-associated glycan signals in the present patient that are changed in cancer are indicative of cancer also in other patients. FIG. 9. shows a neutral protein-linked glycan profile of human ovary with abnormal growth. There are clear differences in the overall glycan profiles, Example 11

N-Glycan Profiling of Rat Liver

Results and Discussion

Total N-glycans were isolated and analyzed as described above from formalin-fixed rat liver. The major difference between the glycan profiles of rat and humans was in the sialylated glycan fraction, namely the occurrence of acetylated sialylated glycans at m/z 1972, 2263, and 2305, corresponding to $Ac_1NeuAc_1Hex_5HexNAc_4$, $Ac_1NeuAc_2Hex_5HexNAc_4$, and $Ac_2NeuAc_2Hex_5HexNAc_4$, respectively, as major sialylated N-glycans in rat liver. It is concluded that the present method is well suited to finding species-specific differences in glycosylation.

Example 12

MALDI-TOF Mass Spectrometric Glycolipid Glycan Profiling of Peripheral Blood Mononuclear Cells Experimental Procedures and Results Glycolipid and Glycan Isolation.

Glycolipids were isolated from peripheral blood mononuclear cells essentially as described in (Karlsson et al., 2000). Sphingoglycolipids were detached by digestion with endoglycoceramidase from *Macrobdella decora* (Calbiochem, USA). After the reaction, liberated glycans were purified, fractionated into sialylated and neutral glycan fractions, and analyzed by MALDI-TOF mass spectrometry as described in the preceding Examples.

Glycolipid Glycan Profiles.

Table 3 describes the detected glycan signals and their proposed monosaccharide compositions. The monosaccharide compositions correlate with known glycolipid core structures, such as gangliosides, lacto- and neolactoglycolipids, and globosides, and extensions of the core structures, such as poly-N-acetyllactosanine chains. Several glycans show fucosylation and/or sialylation of the core and extended structures.

Example 13

MALDI-TOF Mass Spectrometric Profiling of Cell Surface Glycans

Experimental Procedures and Results

Cells, Mononuclear cells were isolated from human peripheral blood by Ficoll-Hypaque density gradient (Amersham Biosciences, Piscataway, USA) essentially as described. The surface glycoprotein glycans were liberated by mild trypsin treatment (80 micrograms/ml in PBS) at +37 degrees Celsius for 2 hours. The intact cells were harvested by centrifugation, and the supernatant containing the liberated glycans (at this stage as cell surface glycoprotein glycopeptides) was taken for further analyses. The harvested cells and the supernatant were subjected to Glycan profiling by protein N-glycosidase as described in the preceding examples. The N-glycan profiles of the supernatant containing the cell surface glycoprotein glycopeptides, were compared against N-glycan profiles of the cells harvested from the trypsin treatment.

Results

N-Glycan analyses of HMC cell surface glycopeptide glycomes. HMC were isolated from peripheral blood, treated with trypsin to release the surface glycoprotein glycopeptides, followed by release of glycopeptide glycans, and subjected to glycome profiling as described under Experimental procedures. In MALDI-TOF mass spectrometry of the sialylated N-glycan fractions, several glycon signals were detected in these samples. When the resulting glycome profile was compared to a corresponding glycome isolated from the trypsin treated cells, it could be observed that many sialylated components were enriched in the surface glycoprotein glycopeptide fraction, whereas some structures appeared to have more intracellular localization. Examples or the former structures are (monosaccharide compositions in parenthesis): m/z [M−H]⁻ 1930 (SaHex5HexNAc4), 2221 (Sa2Hex5HexNAc4), 2222 (SaHex5HexNAc4dHex2), 2367 (Sa2Hex5HexNAc4dHex), 2368(SaHex5HexNAc4dHex3), 2587 (SaHex6HexNAc5dHex2), and 3024 (Sa3Hex6HexNAc5dHex). Examples of the latter are m/z 1873(SaHex5HexNAc3dHex), and 2035 (SaHexHexNAc3dHex).

Example 14

Analyses of Human Tissue Material and Cell Protein-Linked Glycan Structures

Experimental Procedures

Protein-linked glycans were isolated by non-reductive alkaline elimination essentially as described by Huang et al. (2000), or by N-glycosidase digestion to specifically retrieve N-glycans as described in the preceding Examples.

Results and Discussion

Tissue-Specific Glycosylation Analyses and Comparison of Glycan Profiles Between Tissues.

Human tissue protein-linked glycan profiles were analyzed from lung, breast, kidney, stomach, pancreas, lymph nodes, liver, colon, larynx, ovaries, and blood cells and serum. In addition, cultured human cells were analyzed similarly. Tables 6 and 7 show neutral and acidic protein-linked glycan signals, respectively, observed in these human tissues and cells together with their classification into glycan structure groups. However, the individual glycan signals in each structure group varied from sample type to sample type, reflecting tissue material and cell type specific glycosylation. Importantly, in analyses of multiple samples, such as 10 samples from an individual human tissue type, glycan group feature proportions remain relatively constant with respect to variation in the occurrence of individual glycan signals.

Furthermore, it was observed that each tissue demonstrated a specific glycan profile that could be distinguished from the other tissues, cells, or blood or serum samples by comparison of glycan profiles according to the methods described in the present invention. It was also found out that glycan profile difference could be quantitated by comparing the difference between two glycan profiles, for example according to the Equation (resulting in difference expressed in %):

$$\text{difference} = \frac{1}{2}\sum_{i=1}^{n}|p_{i,a} - p_{i,b}|,$$

wherein p is the relative abundance (%) of glycan signal i in profile a or b, and n is the total number of glycan signals. For example, the Equation reveals that human lung and ovary tissue protein-linked glycan profiles differ from each other significantly more than human lung and kidney tissue protein-linked glycan profiles differ from each other. Each tissue or cell type could be compared in this manner.

Comparison of Glycosylation Features Between Human Tissue Materials.

Table 8 shows how glycan signal structural classification according to the present invention was applied to the comparison of quantitative differences in glycan structural features in glycan profiles between human tissue materials. The results show that each sample type was different from each other with respect to the quantitative glycan grouping and classification. Specifically, normal human lung and lung cancer tissues were different from each other both in the neutral glycan and sialylated glycan fractions with respect to the quantitative glycan structure grouping. In particular, lung cancer showed increased amounts of glycan signals classified into terminal HexNAc containing glycans. In analysis of individual glycan signals by β-glucosaminidase digestion, it was found that lung cancer associated glycan signals, such as Hex₃HexNAc₄dHex₁, contained terminal β-linked GlcNAc residues, correlating with the classification of these glycan signals into the terminal HexNAc (N>H and/or N═H) glycan groups. Furthermore, the human serum protein-linked glycan profile showed significantly lower amounts of high-mannose and especially low-mannose type N-glycan signals. It is concluded that the glycan grouping profile of human serum is significantly different from the corresponding profiles of solid tissues, and the present methods are suitable for identification of normal and diseased human tissue materials and blood or serum typical glycan profiles from each other.

Disease- and Tissue-Specific Differences in Glycan Structure Groups.

FIG. 9 shows a neutral protein-linked glycan profile of human ovary with abnormal growth. As described above, there are clear differences in the overall glycan profiles of FIG. 9 and other human tissue samples. In analyses of multiple samples of ovarian tissues, it was found that benign abnormal growth of the ovary is especially characterized by increased amounts of glycan signals classified as terminal HexNAc (N>M). In structural analyses by fragmentation mass spectrometry and combined β-hexosaminidase and β-glucosaminidase digestions, the corresponding terminal HexNAc glycan signals were found to include structures with terminal and sialylated β-GalNAc, more specifically terminal and sialylated GalNAcβ4GlcNAcβ (LacdiNAc) structures. According to the glycan structure classification, the protein-linked glycan profiles of normal ovarian tissue also contain increased amounts of terminal HexNAc glycans compared to other human tissues studied in the present invention, and normal human ovary preferentially also contains higher amounts of terminal and/or sialylated LacdiNAc structures than other human tissues on average. However, in malignant transformation the proportion of LacdiNAc structures among the protein-linked glycans of the ovary are decreased, and this is also reflected in the glycan grouping classification of malignant ovarian glycan profiles.

The analysis of protein-linked glycan profiles of human tissues revealed also that tissues with abundant epithelial structures, such as stomach, colon, and pancreas, contain increased amounts of small glycan structures, preferentially mucin-type glycans, and fucosylated glycan structures compared to the other glycan structure groups in structure classification. Similarly as epithelial tissues, mucinous carcinomas were differentiated from other carcinoma types based on analysis of their protein-linked glycan profiles and structure groups according to the methods of the present invention.

Example 15

Proton-NMR Analysis of Glycan Fractions

Glycan material is liberated from biological material by enzymatic or chemical means. To obtain a less complex sample, glycans are fractionated into neutral and acidic glycan fractions by chromatography on a graphitized carbon as described above. A useful purification step prior to NMR analysis is gel filtration high-performance liquid chromatography (HPLC). For glycans of glycoprotein or glycolipid origin, a Superdex Peptide HR10/300 column (Amersham Pharmacia) may be used. For larger glycans, chromatography on a Superdex 75 HR10/300 column may yield superior results. Superdex columns are eluted at a flow rate of 1 ml per minute with water or with 50-200 mM ammonium bicarbonate for the neutral and acidic glycan fractions, respectively, and absorbance at 205-214 nm is recorded. Fractions are collected (typically 0.5-1 ml) and dried. Repeated dissolving in water and evaporation may be necessary to remove residual ammonium bicarbonate salts in the fractions. The fractions are subjected to MALDI-TOF mass spectrometry and all fractions containing glycans are pooled.

Prior to NMR analysis, the pooled fractions are dissolved in deuterium oxide and evaporated. With glycan preparations containing about 100 nmol or more material, the sample is finally dissolved in 600 microliters of high-quality deuterium oxide (99.9-99.996%) and transferred to a NMR analysis tube. A roughly equimolar amount of an internal standard, e.g. acetone, is commonly added to the solution. With glycan preparations derived from small tissue specimens or from a small number of cells (5-25 million cells), the sample is preferably evaporated from very high quality deuterium oxide (99.996%) twice or more to eliminate $H_2O$ as efficiently as possible, and then finally dissolved in 99.996% deuterium oxide. These low-material samples are preferably analyzed by more sensitive NMR techniques. For example, NMR analysis tubes of smaller volumes cap be used to obtain higher concentration of glycans. This kind of tubes include e.g. nanotubes (Varian) in which sample is typically dissolved in a volume of 37 microliters. Alternatively, higher sensitivity is achieved by analyzing the sample in a cryo-NMR instrument, which increases the analysis sensitivity through low electronic noise. The latter techniques allow gathering of good quality proton-NMR data from glycan samples containing about 1-5 nmol of glycan material.

It is realized that numerous studies have shown that proton-NMR data has the ability to indicate the presence of several structural features in the glycan sample. In addition, by careful integration of the spectra, the relative abundancies of these structural features in the glycan sample can be obtained.

For example, the proton bound to monosaccharide carbon-1, i.e. H-1, yields a distinctive signal at the lower field, well separated from the other protons of sugar residues. Most monosaccharide residues e.g. in N-glycans are identified by their H-1 signals (see Tables 4 and 5 for representative examples). In addition, the H-2 signals of mannose residues are indicative of their linkages.

Sialic acids do not possess a H-1, but their H-3 signals (H-3 axial and H-3 equatorial) reside well separated from other protons of sugar residues. Moreover, differently bound sialic acids may be identified by their H-3 signals. For example, the Neu5Ac H-3 signals of Neu5Acα2-3Gal structure are found at 1.797 ppm (axial) and 2.756 ppm (equatorial). On the other hand, the Neu5Ac H-3 signals of Neu5Acα2-6Gal structure are found at 1.719 ppm (axial) and 2.668 ppm (equatorial). By comparing the integrated areas of these signals, the molar ratio of these structural features is obtained.

Other structural reporter signals are commonly known and those familiar with the art use the extensive literature for reference in glycan NMR assignments.

NMR References

Fu D., Chen L. and O'Neill R. A. (1994) *Carbohydr. Res.* 261, 173-186 Hård K., Mekking A., Kamerling J. P., Dacremont G. A. A. and Vliegenthart J. F. G. (1991) *Glycoconjugate J.* 8, 17-28

Hård K., Van Zadelhoff G., Moonen P., Kamerling J. P. and Viegenthart J. F. G. (1992) *Eur. J. Biochem.* 209, 895-915

Helin J., Maaheimo H., Seppo A., Keane A. and Renkonen O. (1995) *Carbohydr. Res.* 266, 191-209

Example 16

Lysosomal Organelle-Specific N-Glycosylation

Experimental Procedures

Lysosomal protein sample including human myeloperoxidase was chosen to represent lysosomal organelle glycoproteins. The sample was digested with N-glycosidase F to isolate N-glycans, and they were purified for MALDI-TOF mass spectrometric analysis as described in the preceding Examples.

Alkaline phosphatase digestion was performed essentially according to manufacturer's instructions. After the digestion glycans were purified for MALDI-TOF mass spectrometric analysis as above.

Results and Discussion

Neutral N-Glycan Profiles.

Figure 19:
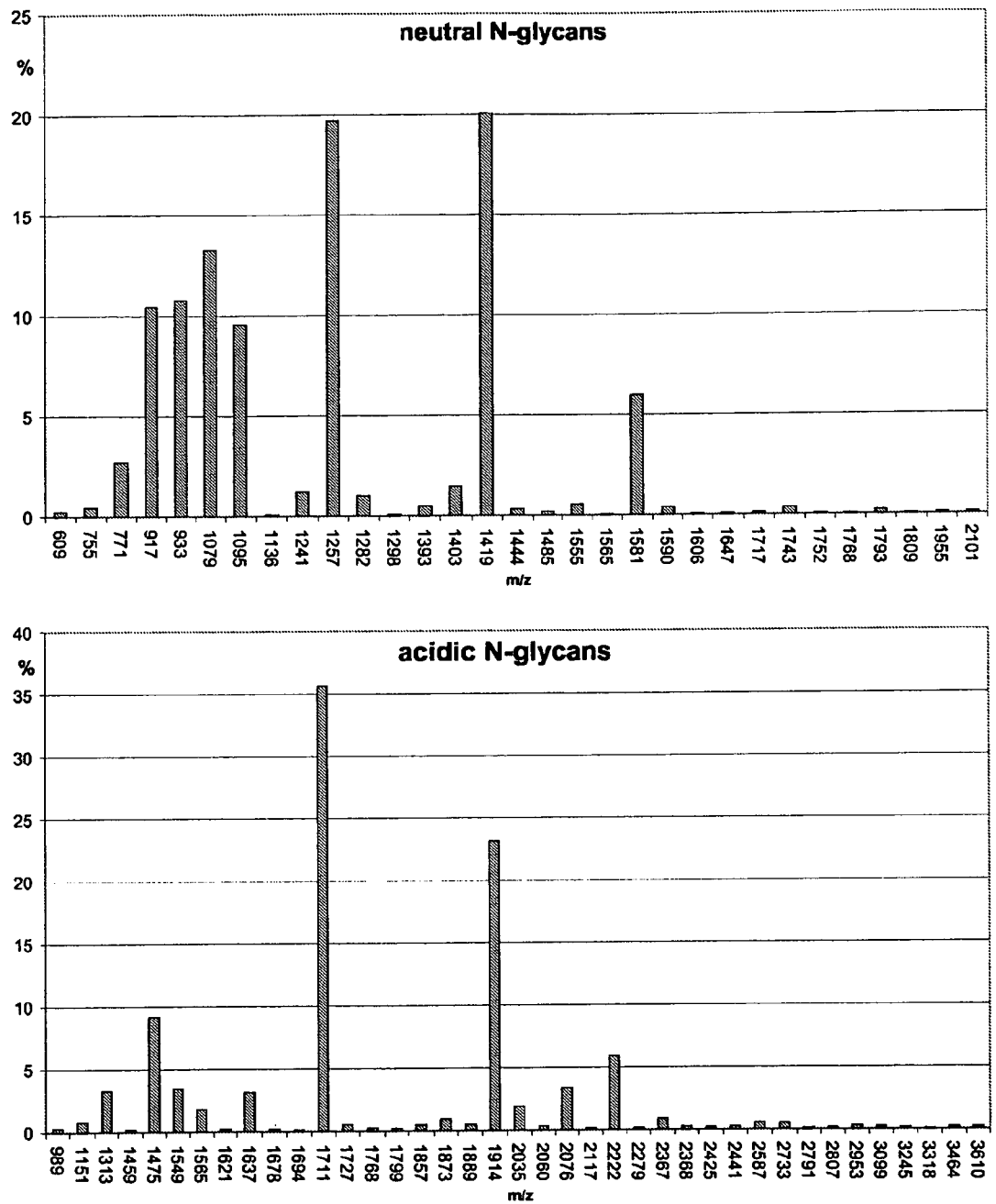
FIG. 19. Neutral and acidic N-glycan profiles of lysosomal protein sample.

The neutral N-glycan profile is presented in FIG. 19 (upper panel). The profile is dominated by low-mannose type and high-mannose-type N-glycan signals, comprising 49% and 46% of the total signal intensity, respectively. Especially the high proportion of low-mannose type N-glycans is characteristic to the sample (Table 9, upper panel).

Acidic N-Glycan Profiles.

The acidic N-glycan profile is presented in FIG. 19 (lower panel). The profile is dominated by three glycan signal groups: 1) sulphated or phosphorylated low-mannose type and high-mannose type N-glycans ($Hex_{3-8}HexNAc_2SP$), 2) fucosylated hybrid-type or monoantennary N-glycans ($NeuAc_1Hex_{3-4}HexNAc_3dHex_1$), and 3) fucosylated complex-type N-glycans ($NeuAc_1Hex_{4-5}HexNAc_4dHex_{1-2}$). Unusual features of the sample are the high proportion of hybrid-type or monoantennary N-glycans (Table 9, lower panel), high fucosylation rate of hybrid-type, monoantennary, and complex-type N-glycans, and the high proportion of the characteristic sulphated or phosphorylated low-mannose type and high-mannose type N-glycans.

Phosphorylated N-Glycans.

Major glycan signals with phosphate or sulphate ester (SP) in their monosaccharide compositions were $Hex_5HexNAc_2SP$ (1313), $Hex_6HexNAc_2SP$ (1475), and $Hex_7HexNAc_2SP$ (1637). When the acidic glycan fraction was subjected to alkaline phosphatase digestion, these major signals were specifically digested and disappeared from the acidic glycan spectrum as detected by MALDI-TOF mass spectrometry (data not shown). In contrast, the major glycan signals with sialic acids in their monosaccharide compositions were not digested, including NeuAc, $Hex_3HexNAc_3dHex$, (1549). This indicates that the three original glycan signals corresponded to phosphorylated N-glycans $(PO_3H)Hex_5HexNAc_2$, $(PO_3H)Hex6HexNAc_2$, and $(PO_3H)Hex_7HexNAc_2$, respectively, wherein $PO_3H$ denotes phosphate ester.

The data further indicated that the present organelle-specific N-glycan profile included phosphorylated low-mannose type and high-mannose type N-glycans ($PO_3H$)

Hex$_3$HexNAc$_2$ (989), (PO$_3$M)Hex4HexNAc$_2$ (1151), (PO$_3$H)Hex$_5$HexNAc$_2$ (1313), (PO$_3$H)Hex6HexNAc$_2$ (1475), (PO$_3$H)Hex$_7$HexNAc$_2$ (1637), and (PO$_3$H)Hex8HexNAc$_2$ (1799). In this glycan profile the phosphorylated glycan residues are preferentially mannose residues, more preferentially α-mannose residues, and most preferentially 6-phospho-α-mannose residues i.e. (PO$_3$H-6Manα).

Example 17

Identification of Specific Glycosylation Signatures from Glycan Profiles of Malignant and Normal Human Tissue Samples Based on Quantitative Glycomics Experimental Procedures Normal lung (Sample I) and malignant lung tumor samples (Sample II) were archival formalin-fixed and paraffin-embedded tissue sections from cancer patients with small cell lung cancer. Protein-linked glycans were isolated from the representative samples by non-reductive β-elimination, purified, and analyzed by MALDI-TOF mass spectrometry as described in the preceding Examples. In the present analysis, the total desialylated protein-linked glycomes from each sample were used.

To analyze the data and to find the major glycan signals associated with either the normal state or the disease, two variables were calculated for the comparison of glycan signals between the two samples:
1. absolute difference A=(SII−SI), and
2. relative difference R=A/SI,
wherein SI and SII are relative abundances of a given glycan signal in Sample I (normal human lung tissue) and Sample II (small cell lung cancer), respectively.

The glycan signals were further classified into structure classes by a one letter code:
a b c d,
wherein a is either N (neutral) or S (sialylated); b is either L (low-mannose type), M (high-mannose type), H (hybrid-type or monoantennary), C (complex-type), S (soluble), or O (other); c is either—(nothing), F (fucosylated), or E (multifucosylated); and d is either—(nothing), T (terminal HexNAc, N>H), or B (terminal HexNAc, N=H); as described in the present invention.

Results

To identify protein-linked glycan signals correlating with malignant tumors in total tissue glycomes from cancer patient, major signals specific to either normal lung tissue or malignant small cell lung cancer tumors were selected based on their relative abundances. When A and R were calculated for the glycan profile datasets of the two samples, and the glycan signals thereafter sorted according to the values of A and R, the most significant differing glycan signals between the two samples could be identified (Table 10). Among the most abundant protein-linked glycan signals in the data, the following three signals had emerged in II (new in Table x): 1955, 2685, and 2905, corresponding to fucosylated complex-type N-glycans. The absolute differences of these signals were among the ten most large in the data, indicating that they were significant. The signals that experienced the highest relative increase in R were: 771 (R=2.4, corresponding to 3.4-fold increase), 1905 (R=2.2, corresponding to 3.2 fold increase), and 1485 (R=1.3, corresponding to 2.3 fold increase). The latter signal corresponded to complex-type N-glycans with terminal HexNAc. Significantly, its +2Hex counterpart 1809 was the most drastically reduced glycan signal in II with A=−8.9 and R=−0.4 (corresponding to 40% decrease in II), indicating a large change in terminal HexNAc expression. Moreover, the data easily shows that the glycan signals 1704, 1866, 1136, and 755 were not present in II.

Further, the obtained results, especially the identified major glycan signals indicative of either Sample II (high A and R) or Sample I (low A and R) were used to compile two alternative algorithms to produce glycan score with which lung cancer sample could be identified from normal lung sample based on the glycan signal values of the quantitative glycome data:
1. glycan score=I(1485)−I(1809),
wherein I(1485) is the relative abundance of glycan signal 1485 and I(1809) is the relative abundance of glycan signal 1809;
and alternatively:
2. glycan score=I(1485)/I(1809)

These glycan score algorithms yield high numerical value when applied to lung cancer sample and low numerical value when applied to normal lung sample.

Discussion

The present identification analysis produced selected glycan signal groups, from where indifferent glycan signals have been removed and that have reduced noise or background and less observation points, but have the resolving power of the initially obtained glycan profiles. Such selected signal groups and their patterns in different sample types can serve as a signature for the identification of for example 1) normal human glycosylation, 2) tissue-specific glycosylation, 3) disease states affecting tissue glycosylation, 4) malignant cancer, 5) malignancy in comparison to benign tumors, and grade of malignancy, or 6) glycan signals that have individual variation. Moreover, glycan signals can be identified that do not change between samples, including major glycans that can be considered as invariant or housekeeping glycans.

The present data analysis identified potential glycan marker signals for future identification of either the normal lung of the lung tumor glycome profiles. Further, glycan classes that are associated with e.g. disease state in humans can be identified. Specifically, the analysis revealed that within the total complex-type N-glycan structure class in the tissue glycomes, terminal HexNAc (N>H) were typical to small cell lung cancer.

The method also allows identification of major glycans or major changes within glycan structure classes. For example, the proportion of multifucosylated glycans within the total tissue glycome profile was increased in II (1.1%) compared to I (0.3%). The data analysis identified this change predominantly to the appearance of glycan signals 1955 and 2685 in II.

Example 18

Glycosphingolipid Glycans of Human Cells

Experimental Procedures

Samples from human leukocytes were analyzed. Neutral and acidic glycosphingolipid fractions were isolated from the cells essentially as described (Miller-Podraza et al., 2000; Karlsson et al., 2000). Glycans were detached by *Macrobdella decora* endoglycoceramidase digestion (Calbiochem, USA) essentially according to manufacturer's instructions, yielding the total glycan oligosaccharide fractions from the samples. The oligosaccharides were purified and analyzed by MALDI-TOF mass spectrometry as described in the preceding Examples for the protein-linked oligosaccharide fractions. Proposed compositions for the oligosaccharides and signal nomenclature are presented in Tables 11 and 12 for the neutral and acidic glycan fractions, respectively.

Results and Discussion;

Leukocyte Neutral Lipid Glycans.

Figure 20:
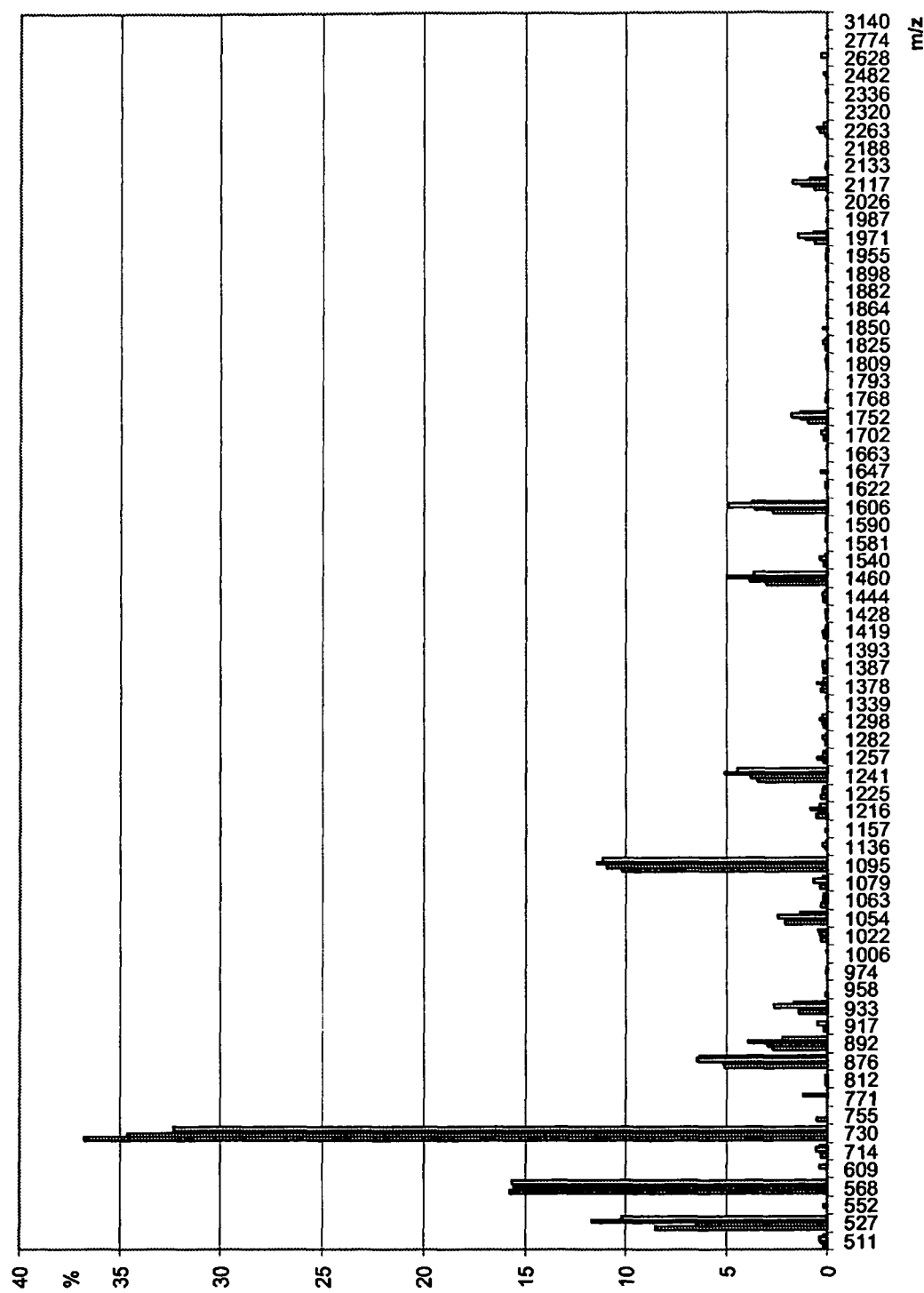
FIG. 20. Neutral glycosphingolipid glycan profile from human leukocytes.

The analyzed mass spectrometric profile of the glycosphingolipid neutral glycan fraction is shown in FIG. 20.

Structural Analysis of the Major Neutral Lipid Glycans.

The four major glycan signals, together comprising more than 75% of the total glycan signal intensity, corresponded to monosaccharide compositions $Hex_3HexNAc$, (730), $Hex_2HexNAc$, (568), $Hex_4HexNAc_2$ (1095), and $Hex_3HexNAc_1dHex_1$ (876).

Acidic Lipid Glycans.

Figure 21:
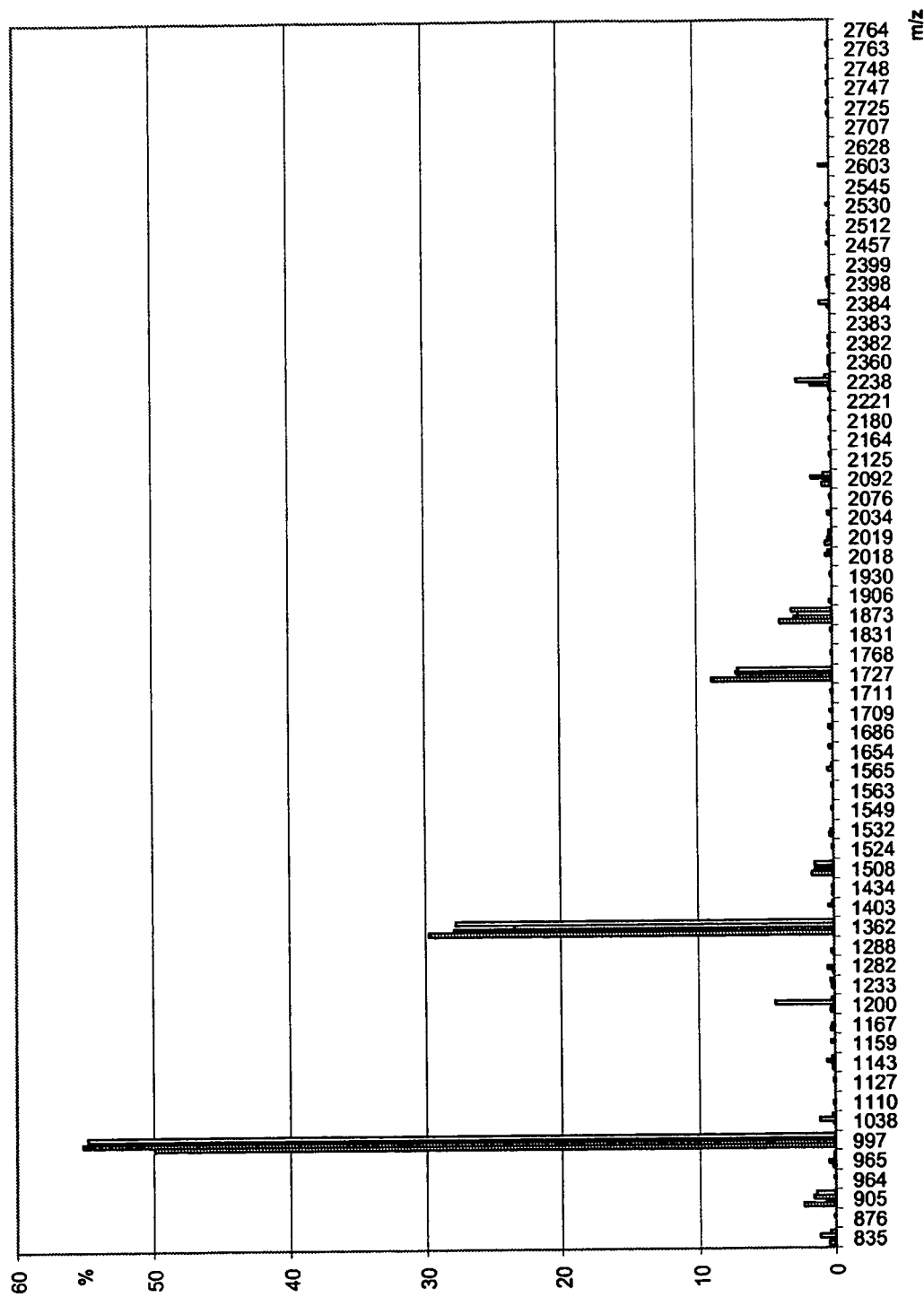
FIG. 21. Acidic glycosphingolipid glycan profile from human leukocytes.

The analyzed mass spectrometric profile of the hESC glycosphingolipid sialylated glycan fraction is shown in FIG. 21. The four major glycan signals, together comprising more than 90% of the total glycan signal intensity, corresponded to monosaccharide compositions $NeuAc_1Hex_3HexNAc$, (997), $NeuAc_1Hex4HexNAc_2$ (1362), $NeuAc_1Hex_5HexNAc_3$ (1727), and $NeuAc_3Hex_5HexNAc_3dHex$, (1873).

Terminal glycan epitopes that were demonstrated in the present experiments in leukocyte glycosphingolipid glycans include, as demonstrated by β1,4-galactosidase, α1,3/4-fucosidase, α1,2-fucosidase, and α2,3-sialidase digestions:

Gal
Galβ4Glc (Lac)
Galβ4GlcNAc (LacNAc type 2)
Non-reducing terminal HexNAc
Fuc
α1,3-Fuc
Neu5Ac
Neu5Acα2,3
Neu5Acα2,6

TABLE 1

Preferred neutral glycan compositions. Calculated mass-to-charge ratios (calc. m/z) refer to the first isotope signal of $[M + Na]^+$ ion.

| Proposed composition | calc. m/z |
|---|---|
| HexHexNAc | 406.13 |
| Hex3 | 527.16 |
| HexHexNAcdHex | 552.19 |
| Hex2HexNAc | 568.19 |
| HexHexNAc2 | 609.21 |
| Hex4 | 689.21 |
| Hex2HexNAcdHex | 714.24 |
| Hex3HexNAc | 730.24 |
| HexHexNAc2dHex | 755.27 |
| Hex2HexNAc2 | 771.26 |
| HexHexNAc3 | 812.29 |
| Hex5 | 851.26 |
| Hex2HexNAcdHex2 | 860.30 |
| Hex4HexNAc | 892.29 |
| HexHexNAc2dHex2 | 901.33 |
| Hex2HexNAc2dHex | 917.32 |
| Hex3HexNAc2 | 933.32 |
| HexHexNAc3dHex | 958.35 |
| Hex2HexNAc3 | 974.34 |
| Hex2HexNAcdHex3 | 1006.36 |
| Hex6 | 1013.32 |
| HexHexNAc4 | 1015.37 |
| Hex3HexNAcdHex2 | 1022.35 |
| Hex5HexNAc | 1054.34 |
| Hex2HexNAc2dHex2 | 1063.38 |
| Hex3HexNAc2dHex | 1079.38 |
| Hex4HexNAc2 | 1095.37 |
| HexHexNAc3dHex2 | 1104.41 |
| Hex2HexNAc3dHex | 1120.40 |
| Hex3HexNAc3 | 1136.40 |
| Hex2HexNAcdHex4 | 1152.42 |

TABLE 1-continued

Preferred neutral glycan compositions. Calculated mass-to-charge ratios (calc. m/z) refer to the first isotope signal of $[M + Na]^+$ ion.

| Proposed composition | calc. m/z |
|---|---|
| HexHexNAc4dHex | 1161.43 |
| Hex7 | 1175.37 |
| Hex2HexNAc4 | 1177.42 |
| Hex2HexNAc2dHex3 | 1209.44 |
| Hex6HexNAc | 1216.40 |
| HexHexNAc5 | 1218.45 |
| Hex3HexNAc2dHex2 | 1225.43 |
| Hex4HexNAc2dHex | 1241.43 |
| Hex5HexNAc2 | 1257.42 |
| Hex2HexNAc3dHex2 | 1266.46 |
| Hex3HexNAc3dHex | 1282.45 |
| Hex4HexNAc3 | 1298.45 |
| HexHexNAc4dHex2 | 1307.49 |
| Hex2HexNAc4dHex | 1323.48 |
| Hex8 | 1337.42 |
| Hex3HexNAc4 | 1339.48 |
| Hex2HexNAc2dHex4 | 1355.50 |
| HexHexNAc5dHex | 1364.51 |
| Hex3HexNAc2dHex3 | 1371.49 |
| Hex7HexNAc | 1378.45 |
| Hex4HexNAc2dHex2 | 1387.49 |
| Hex2HexNAc5 | 1380.50 |
| Hex5NexNAc2dHex | 1403.48 |
| Hex2HexNAc3dHex3 | 1412.52 |
| Hex6HexNAc2 | 1419.48 |
| HexHexNAc6 | 1421.53 |
| Hex3HexNAc3dHex2 | 1428.51 |
| Hex4HexNAc3dHex | 1444.51 |
| HexHexNAc4dHex3 | 1453.54 |
| Hex5HexNAc3 | 1460.50 |
| Hex2HexNAc4dHex2 | 1469.54 |
| Hex3HexNAc4dHex | 1485.53 |
| Hex9 | 1499.48 |
| Hex4HexNAc4 | 1501.53 |
| HexHexNAc5dHex2 | 1510.57 |
| Hex3HexNAc2dHex4 | 1517.55 |
| Hex2HexNAc5dHex | 1526.56 |
| Hex4HexNAc2dHex3 | 1533.54 |
| Hex8HexNAc | 1540.50 |
| Hex3HexNAc5 | 1542.56 |
| Hex5HexNAc2dHex2 | 1549.54 |
| Hex6HexNAc2dHex | 1565.53 |
| Hex3HexNAc3dHex3 | 1574.57 |
| Hex7HexNAc2 | 1581.53 |
| Hex2HexNAc6 | 1583.58 |
| Hex4HexNAc3dHex2 | 1590.57 |
| Hex5HexNAc3dHex | 1606.56 |
| Hex2HexNAc4dHex3 | 1615.60 |
| Hex6HexNAc3 | 1622.56 |
| Hex3HexNAc4dHex2 | 1631.59 |
| Hex4HexNAc4dHex | 1647.59 |
| Hex10 | 1661.53 |
| Hex5HexNAc4 | 1663.58 |
| Hex2HexNAc5dHex2 | 1672.62 |
| Hex3HexNAc5dHex | 1688.61 |
| Hex5HexNAc2dHex3 | 1695.60 |
| Hex9HexNAc | 1702.56 |
| Hex4HexNAx5 | 1704.61 |
| Hex6HexNAc2dHex2 | 1711.59 |
| Hex3HexNAc3dHex4 | 1720.63 |
| Hex7HexNAc2dHex | 1727.59 |
| Hex2HexNAc6dHex | 1729.64 |
| Hex4HexNAc3dHex3 | 1736.62 |
| Hex8HexNAc2 | 1743.58 |
| Hex3HexNAc6 | 1745.64 |
| Hex5HexNAc3dHex2 | 1752.62 |
| Hex6HexNAc3dHex | 1768.61 |
| Hex3HexNAc4dHex3 | 1777.65 |
| Hex7HexNAc3 | 1784.61 |
| Hex4HexNAc4dHex2 | 1793.64 |
| Hex5HexNAc4dHex | 1809.64 |
| Hex2HexNAc5dHex3 | 1818.68 |
| Hex11 | 1823.58 |
| Hex6HexNAc4 | 1825.63 |

TABLE 1-continued

Preferred neutral glycan compositions. Calculated mass-to-charge ratios (calc. m/z) refer to the first isotope signal of [M + Na]⁺ ion.

| Proposed composition | calc. m/z |
|---|---|
| Hex3HexNAc5dHex2 | 1834.67 |
| Hex4HexNAc5dHex | 1850.67 |
| Hex6HexNAc2dHex3 | 1857.65 |
| Hex10HexNAc | 1864.61 |
| Hex5HexNAc5 | 1866.66 |
| Hex7HexNAc2dHex2 | 1873.64 |
| Hex2HexNAc6dHex2 | 1875.70 |
| Hex4HexNAc3dHex4 | 1882.68 |
| Hex8HexNAc2dHex | 1889.64 |
| Hex3HexNAc6dHex | 1891.69 |
| Hex5HexNAc3dHex3 | 1898.68 |
| Hex9HexNAc2 | 1905.63 |
| Hex4HexNAc6 | 1907.69 |
| Hex6HexNAc3dHex2 | 1914.67 |
| Hex3HexNAc4dHex4 | 1923.71 |
| Hex7HexNAc3dHex | 1930.67 |
| Hex2HexNAc7dHex | 1932.72 |
| Hex4HexNAc4dHex3 | 1939.70 |
| Hex8HexNAc3 | 1946.66 |
| Hex5HexNAc4dHex2 | 1955.70 |
| Hex6HexNAc4dHex | 1971.69 |
| Hex3HexNAc5dHex3 | 1980.73 |
| Hex12 | 1985.63 |
| Hex7HexNAc4 | 1987.69 |
| Hex4HexNAc5dHex2 | 1996.72 |
| Hex5HexNAc5dHex | 2012.72 |
| Hex7HexNAc2dHex3 | 2019.70 |
| Hex2HexNAc6dHex3 | 2021.76 |
| Hex11HexNAc | 2026.66 |
| Hex6HexNAc5 | 2028.71 |
| Hex8HexNAc2dHex2 | 2035.70 |
| Hex3HexNAc6dHex2 | 2037.75 |
| Hex5HexNAc3dHex4 | 2044.73 |
| Hex4HexNAc6dHex | 2053.75 |
| Hex6HexNAc3dHex3 | 2060.73 |
| Hex10HexNAc2 | 2067.69 |
| Hex5HexNAc6 | 2069.74 |
| Hex7HexNAc3dHex2 | 2076.72 |
| Hex2HexNAc7dHex2 | 2078.78 |
| Hex4HexNAc4dHex4 | 2085.76 |
| Hex8HexNAc3dHex | 2092.72 |
| Hex3HexNAc7dHex | 2094.77 |
| Hex5HexNAc4dHex3 | 2101.76 |
| Hex9HexNAc3 | 2108.71 |
| Hex4HexNAc7 | 2110.77 |
| Hex6HexNAc4dHex2 | 2117.75 |
| Hex3HexNAc5dHex4 | 2126.79 |
| Hex7HexNAc4dHex | 2133.75 |
| Hex4HexNAc5dHex3 | 2142.78 |
| Hex13 | 2147.69 |
| Hex8HexNAc4 | 2149.74 |
| Hex5HexNAc5dHex2 | 2158.78 |
| Hex6HexNAc5dHex | 2174.77 |
| Hex8HexNAc2dHex3 | 2181.76 |
| Hex3HexNAc6dHex3 | 2183.81 |
| Hex12HexNac | 2188.71 |
| Hex7HexNAc5 | 2190.77 |
| Hex4HexNAc6dHex2 | 2199.80 |
| Hex5HexNAc6dHex | 2215.80 |
| Hex7HexNAc3dHex3 | 2222.78 |
| Hex2HexNAc7dHex3 | 2224.84 |
| Hex11HexNAc2 | 2229.74 |
| Hex6HexNAc6 | 2231.79 |
| Hex8HexNAc3dHex2 | 2238.78 |
| Hex3HexNAc7dHex2 | 2240.83 |
| Hex5HexNAc4dHex4 | 2247.81 |
| Hex4HexNAc7dHex | 2256.83 |
| Hex6HexNAc4dHex3 | 2263.81 |
| Hex5HexNAc7 | 2272.82 |
| Hex7HexNAc4dHex2 | 2279.80 |
| Hex4HexNAc5dHex4 | 2288.84 |
| Hex5HexNAc5dHex3 | 2304.84 |
| Hex14 | 2309.74 |
| Hex9HexNAc4 | 2311.79 |
| Hex6HexNAc5dHex2 | 2320.83 |
| Hex7HexNAc5dHex | 2336.82 |
| Hex4HexNAc6dHex3 | 2345.86 |
| Hex8HexNAc5 | 2352.82 |
| Hex5HexNAc6dHex2 | 2361.86 |
| Hex6HexNAc6dHex | 2377.85 |
| Hex8HexNAc3dHex3 | 2384.83 |
| Hex3HexNAc7dHex3 | 2386.89 |
| Hex12HexNac2 | 2391.79 |
| Hex7HexNAc6 | 2393.85 |
| Hex4HexNAc7dHex2 | 2402.88 |
| Hex6HexNAc4dHex4 | 2409.87 |
| Hex5HexNAc7dHex | 2418.88 |
| Hex7HexNAc4dHex3 | 2425.86 |
| Hex6HexNAc7 | 2434.87 |
| Hex5HexNAc5dHex4 | 2450.89 |
| Hex6HexNAc5dHex3 | 2466.89 |
| Hex15 | 2471.79 |
| Hex7HexNAc5dHex2 | 2482.88 |
| Hex8HexNAc5dHex | 2498.88 |
| Hex5HexNAc6dHex3 | 2507.91 |
| Hex6HexNAc6dHex2 | 2523.91 |
| Hex7HexNAc6dHex | 2539.90 |
| Hex4HexNAc7dHex3 | 2548.94 |
| Hex13HexNAc2 | 2553.85 |
| Hex8HexNAc6 | 2555.90 |
| Hex5HexNAc7dHex2 | 2564.94 |
| Hex6HexNAc7dHex | 2580.93 |
| Hex6HexNAc5dHex4 | 2612.95 |
| Hex7HexNAc5dHex3 | 2628.94 |
| Hex16 | 2633.85 |
| Hex8HexNAc5dHex2 | 2644.94 |
| Hex6HexNAc6dHex3 | 2669.97 |
| Hex7HexNAc6dHex2 | 2685.96 |
| Hex5HexNAc7dHex3 | 2710.99 |
| Hex14HexNAc2 | 2715.90 |
| Hex6HexNAc7dHex2 | 2726.99 |
| Hex7HexNAc7dHex | 2742.98 |
| Hex8HexNAc7 | 2758.98 |
| Hex7Hexnac5dHex4 | 2775.00 |
| Hex8HexNAc5dHex3 | 2790.99 |
| Hex17 | 2795.90 |
| Hex7HexNAc6dHex3 | 2832.02 |
| Hex16HexNAc | 2836.92 |
| Hex9HexNAc6dHex | 2864.01 |
| Hex6HexNAc7dHex3 | 2873.05 |
| Hex15HexNAc2 | 2877.95 |
| Hex8HexNAc7dHex | 2905.04 |
| Hex8Hexnac5dHex4 | 2937.05 |
| Hex18 | 2957.95 |
| Hex7HexNAc6dHex4 | 2978.08 |
| Hex17HexNAc | 2998.98 |
| Hex8HexNAc7dHex2 | 3051.09 |
| Hex9HexNAc8 | 3124.11 |
| Hex8HexNAc6dHex4 | 3140.13 |
| Hex8HexNAc7dHex3 | 3197.15 |
| Hex9HexNAc8dHex/ Hex7HexNAc6dHex6 | 3270.17 |
| Hex9HexNAc6dHex4 | 3302.18 |
| Hex8HexNAc7dHex4 | 3343.21 |
| Hex9HexNAc8dHex2 | 3416.23 |
| Hex10HexNAc6dHex4 | 3464.24 |
| Hex10HexNAc9 | 3489.24 |
| Hex9HexNAc8dHex3 | 3562.28 |
| Hex11HexNAc6dHex4 | 3626.29 |
| Hex10HexNAc9dHex | 3635.30 |
| Hex9HexNAc8dHex4 | 3708.34 |
| Hex10HexNAc9dHex2/ Hex8HexNAc7dHex7 | 3781.36 |
| Hex9HexNAc8dHex5/ Hex7HexNAc6dHex10 | 3854.40 |

TABLE 2

Preferred acidic glycan compositions. Calculated mass-to-charge ratios (calc. m/z) refer to the first isotope signal of [M − H]⁻ ion.

| Proposed composition | calc. m/z |
|---|---|
| NeuAcHexHexNAc | 673.23 |
| NeuAcHexHexNAcdHex | 819.29 |
| NeuAcHex2HexNAc | 835.28 |
| NeuAcHexHexNAc2 | 876.31 |
| NeuAc2HexHexNAc | 964.33 |
| NeuAcHexHexNAcdHex2 | 965.35 |
| NeuAcHex2HexNAcdHex | 981.34 |
| Hex3HexNAc2SP | 989.28 |
| NeuAcHex3HexNAc | 997.34 |
| NeuAcHexHexNAc2dHex | 1022.37 |
| NeuAcHex2HexNAc2 | 1038.36 |
| NeuAcHexHexNAc3 | 1079.39 |
| NeuAc2HexHexNAcdHex | 1110.38 |
| NeuAcHex2Hex2HexNAc | 1126.38 |
| NeuAcHexHexNAcdHex2 | 1127.40 |
| NeuAcHex3HexNAcdHex | 1143.39 |
| Hex4HexNAc2SP | 1151.33 |
| NeuAcHex4HexNAc | 1159.39 |
| NeuAcHex2HexNAc2 | 1167.41 |
| NeuAcHexHexNAc2dHex2 | 1168.43 |
| NeuAcHex2HexNAc2dHex | 1184.42 |
| Hex3HexNAc3SP | 1192.36 |
| NeuAcHex3HexNAc2/ NeuGcHex2HexNAc2dHex | 1200.42 |
| NeuGcHex3HexNAc2 | 1216.41 |
| NeuAcHexHexNAc3dHex | 1225.45 |
| NeuAcHex2HexNAc3 | 1241.44 |
| NeuAc2Hex2HexNAcdHex | 1272.44 |
| NeuAcHexHexNAc4 | 1282.47 |
| NeuAc2Hex3HexNAc | 1288.43 |
| NeuAcHex4HexNAcdHex | 1305.45 |
| NeuAc2HexHexNAc2dHex | 1313.46 |
| NeuAcHex5HexNAc/ NeuAcHex2HexNAc3SP | 1321.44/ 1321.40 |
| NeuAc2Hex2HexNAc2/ NeuGcNeuAcHexHexNAc2dHex | 1329.46 |
| NeuAcHex2HexNAc2dHex2 | 1330.48 |
| Hex3HexNAc3dHexSP | 1338.41 |
| NeuAcHex3HexNAc2dHex | 1346.47 |
| Hex4HexNAc3SP | 1354.41 |
| NeuAcHex4HexNAc2 | 1362.47 |
| NeuAc2HexHexNAc3 | 1370.48 |
| NeuAcHex2HexNAc3dHex | 1387.50 |
| NeuAcHex3HexNAc3 | 1403.49 |
| NeuGcHex3HexNAc3 | 1419.49 |
| NeuAcHexHexNAc4dHex | 1428.53 |
| NeuAc2Hex3HexNAcdHex | 1434.49 |
| NeuAcHex2HexNAc4 | 1444.52 |
| NeuAcHex3HexNAc3Ac | 1445.51 |
| NeuAc2Hex4HexNAc | 1450.48 |
| Hex5HexNAc2dHexSP | 1459.44 |
| NeuAc2Hex2HexNAc2dHex | 1475.52 |
| NeuAcHex6HexNAc/ NeuAcHex3HexNAc3SP | 1483.49/ 1483.45 |
| NeuAc2Hex3HexNAc2 | 1491.51 |
| NeuAcHex2HexNAc3dHex2 | 1492.53 |
| Hex4HexNAc3dHexSP | 1500.47 |
| NeuAcHex4HexNAc2dHex | 1508.53 |
| NeuAc2HexHexNAc3dHex/ Hex5HexNAc3SP | 1516.54/ 1516.46 |
| NeuAcHex5HexNAc2 | 1524.52 |
| NeuAc2Hex2HexNAc3 | 1532.54 |
| NeuAc2Hex2HexNAc3dHex2 | 1533.56 |
| NeuAcHex3HexNAc3dHex | 1549.55 |
| NeuAc2Hex2HexNAc2dHexSP | 1555.47 |
| Hex4HexNAc4SP | 1557.49 |
| NeuAcHex3HexNAc3(SP)2 | 1563.41 |
| NeuAcHex4HexNAc3 | 1565.55 |
| NeuAc2HexHexNAc4 | 1573.56 |
| NeuGcHex4HexNAc3 | 1581.54 |
| NeuAcHex2HexNac4dHex | 1590.58 |
| NeuAc2Hex4HexNAcdHex | 1596.54 |
| NeuAcHex3HexNAc4 | 1606.57 |
| NeuAc2Hex2HexNAc2dHex2/ | 1621.57/ |
| Hex6HexNAc2dHexSP | 1621.49 |
| NeuAc2Hex3HexNAc2dHex | 1637.57 |
| NeuAcHex4HexNAc3SP | 1645.50 |
| NeuAcHex2HexNAc5 | 1647.60 |
| NeuAcHex4HexNAc2dHex2 | 1654.58 |
| Hex5HexNAc3dHexSP | 1662.52 |
| NeuAcHex5HexNAc2dHex | 1670.58 |
| NeuAc2Hex2HexNAc3dHex | 1678.60 |
| NeuAcHex2HexNAc2dHex3 | 1679.62 |
| NeuAcHex6HexNAc2 | 1686.57 |
| NeuAc2Hex3HexNAc3 | 1694.59 |
| Hex4HexNAc4dHexSP | 1703.55 |
| NeuAcHex3HexNAc3dHex(SP)2 | 1709.47 |
| NeuGcNeuAcHex3HexNAc3 | 1710.59 |
| NeuAcHex4HexNAc3dHex | 1711.61 |
| Hex5HexNAc4SP | 1719.54 |
| NeuAcHex4HexNAc3(SP)2 | 1725.46 |
| Hex4HexNAc3dHex2(SP)2/ NeuGc2Hex3HexNAc3 | 1726.48/ 1726.58 |
| NeuAcHex5HexNAc3/ NeuGcHex4HexNAc3dHex | 1727.60 |
| NeuAc2Hex2HexNAc4 | 1735.62 |
| NeuAc2Hex2HexNAc4dHex2 | 1736.64 |
| NeuGcHex5HexNAc3 | 1743.60 |
| NeuAcHex3HexNAc4dHex | 1752.63 |
| NeuAc2Hex2HexNAc3dHexSP | 1758.55 |
| NeuAcHex3HexNAc4(SP)2/ NeuAcHex6HexNAc2SP | 1766.49/ 1766.53 |
| Hex6HexNAc2dHex2SP/ Hex3HexNAc4dHex2(SP)2/ NeuAc2Hex2HexNAc2dHex3 | 1767.55/ 1767.51 |
| NeuAcHex4HexNAc4 | 1768.63 |
| NeuAc2Hex6HexNAc/ NeuAc2Hex3HexNAc3SP | 1774.59/ 1774.55 |
| Hex7HexNAc2dHexSP | 1783.55 |
| NeuGcHex4HexNac4 | 1784.62 |
| NeuAcHex4HexNAc3dHexSP | 1791.56 |
| NeuAcHex2HexNAc5dHex | 1793.66 |
| NeuAc2Hex4HexNAc2dHex/ Hex5HexNAc4(SP)2 | 1799.62 |
| NeuAcHex3HexNac5 | 1809.65 |
| NeuAc2Hex5HexNAc2/ NeuAc2Hex2HexNAc4SP | 1815.62 |
| NeuAcHex5HexNAc2dHex2/ NeuAcHex2HexNAc4dHex2SP | 1816.64 |
| Hex6NexNAc3dHexSP | 1824.57 |
| NeuGcHex3HexNAc5 | 1825.65 |
| NeuAcHex6HexNAc2dHex | 1832.63 |
| NeuAc2Hex3HexNAc3dHex | 1840.65 |
| NeuAcHex3HexNAc3dHex3 | 1841.67 |
| NeuAc2Hex4HexNAc3 | 1856.64 |
| NeuAcHex4HexNAc3dHex2 | 1857.66 |
| Hex5HexNAc4dHexSP | 1865.60 |
| NeuAcHex4HexNAc3dHex(SP)2 | 1871.52 |
| NeuAcHex5HexNAc3dHex/ NeuGcHex4HexNAc3dHex2 | 1873.66 |
| Hex6HexNAc4SP | 1881.65 |
| NeuAcHex5HexNAC3(SP)2 | 1887.51 |
| NeuAcHex6HexNAc3 | 1889.65 |
| NeuAcHex3HexNAc4dHex2 | 1898.69 |
| Hex4HexNAc5dHexSP | 1906.63 |
| NeuAcHex6HexNAc2dHexSP/ NeuAcHex3HexNAc4dHex(SP)2 | 1912.59 |
| NeuAcHex4HexNAc4dHex | 1914.68 |
| NeuAc2Hex3HexNAc3dHexSP | 1920.60 |
| Hex5HexNAc5SP | 1922.62 |
| NeuAcHex4HexNAc4(SP)2 | 1928.54 |
| NeuAcHex5HexNAc4 | 1930.68 |
| NeuGcHex5HexNAc4 | 1946.67 |
| NeuAcHex5HexNAc4dHexSP | 1953.62 |
| NeuAcHex3HexNAc5dHex | 1955.71 |
| NeuAc2Hex5HexNAc2dHex/ Hex6HexNAc4(SP)2 | 1961.67/ 1961.55 |
| NeuAcHex4HexNAc5 | 1971.71 |

TABLE 2-continued

Preferred acidic glycan compositions. Calculated mass-to-charge ratios (calc. m/z) refer to the first isotope signal of [M − H]⁻ ion.

| Proposed composition | calc. m/z |
|---|---|
| NeuAcHex5HexNAc4Ac | 1972.69 |
| NeuAcHex6HexNAc2dHex2/ | 1978.69/ |
| NeuAcHex3HexNAc4dHex2SP | 1978.65 |
| NeuAc2Hex4HexNAc3dHex/ | 2002.70/ |
| Hex8HexNAc3SP | 2002.62 |
| NeuAcHex4HexNAc3dHex3 | 2003.72 |
| NeuAcHex5HexNAc4SP | 2010.64 |
| Hex5HexNAc4dHex2SP | 2011.66 |
| NeuAc2Hex5HexNAc3/ | 2018.70 |
| NeuGcNeuAcHex4HexNAc3dHex | |
| NeuAcHex5HexNAc3dHex2 | 2019.72 |
| NeuGcHex5HexNAc4SP | 2026.63 |
| Hex6HexNAc4dHexSP | 2027.65 |
| NeuAcHex6HexNAc3dHex | 2035.71 |
| NeuAc2Hex3HexNAc4dHex/ | 2043.73/ |
| Hex7HexNAc4SP | 2043.65 |
| NeuAcHex7HexNAc3 | 2051.71 |
| Hex4HexNAc5dHex2SP | 2052.68 |
| NeuAc2Hex4HexNAc4 | 2059.72 |
| NeuAcHex4HexNAc4dHex2 | 2060.74 |
| Hex5HexNAc5dHexSP | 2068.68 |
| NeuAcHex4HexNAc4dHex(SP)2 | 2074.60 |
| NeuAcHex5HexNAc4dHex | 2076.74 |
| NeuAc2Hex4HexNAc3dHexSP | 2082.66 |
| NeuGc2Hex4HexNAc4 | 2091.71 |
| NeuAcHex6HexNAc4/ | 2092.73 |
| NeuGcHex5HexNAc4dHex | |
| NeuAc2Hex5HexNAc3SP/ | 2098.65 |
| NeuGcNeuAcHex4HexNAc3dHexSP | |
| NeuAcHex5HexNAc3dHex2SP/ | 2099.67 |
| NeuGcHex5HexNAc3dHex3SP | |
| NeuAc2Hex3HexNAc5 | 2100.75 |
| NeuAcHex3HexNAc5dHex2/ | 2101.77/ |
| NeuAc2Hex4HexNAc4Ac | 2101.73 |
| NeuAcHex6HexNAc3dHexSP | 2115.67 |
| NeuAcHex4HexNAc5dHex | 2117.76 |
| Hex7HexNAc3dHex2SP/ | 2132.68/ |
| NeuAc2Hex3HexNAc3dHex3 | 2132.76 |
| NeuAcHex5HexNAc5 | 2133.76 |
| Hex8HexNAc4dHexSP/ | 2148.68 |
| NeuAc2Hex4HexNAc3dHex2 | |
| NeuAcHex8Hexnac2dHex/ | 2156.74/ |
| NeuAcHex5HexNAc4dHexSP | 2156.69 |
| Hex5HexNAC4dHex3SP | 2157.71 |
| NeuAc2Hex5HexNAc3dHex | 2164.75 |
| NeuAcHex5HexNAc3dHex3 | 2165.77 |
| NeuAcHex9HexNAc2/ | 2172.73/ |
| NeuAcHex6HexNAc4SP/ | 2172.69 |
| NeuGcHex5HexNAc4dHexSP | |
| NeuAcHex4Hexnac6 | 2174.79 |
| NeuAc2Hex6HexNAc3/ | 2180.75 |
| NeuGc2Hex4HexNAc3dHex2 | |
| NeuAcHex6HexNAc3dHex2 | 2181.77 |
| NeuAc3Hex3HexNAc4/ | 2188.76/ |
| NeuGcHex6HexNAc4SP/ | 2188.68 |
| NeuAc2NeuGcHex2HexNAc4dHex | |
| NeuAc2Hex3HexNAc4dHex2/ | 2189.79/ |
| Hex7HexNAc4dHexSP | 2189.70 |
| NeuAcHex3HexNAc4dHex4 | 2190.81 |
| NeuGcNeuAcHex6HexNAc3/ | 2196.74 |
| NeuGc2Hex5HexNAc3dHex | |
| Hex4HexNAc5dHex3SP | 2198.74 |
| NeuAc2Hex4HexNAc4dHex | 2205.78 |
| NeuAcHex4HexNAc4dHex3 | 2206.80 |
| NeuAc2Hex4HexNAc4(SP)2 | 2219.64 |
| NeuAc2Hex5HexNAc4 | 2221.78 |
| NeuAcHex5HexNAc4dHex2 | 2222.80 |
| Hex6HexNAc5dHexSP | 2230.73 |
| NeuGcNeuAcHex5HexNAc4 | 2237.77 |
| NeuAcHex6HexNAc4dHex/ | 2238.79 |
| NeuGcHex5HexNAc4dHex2 | |
| NeuAc2Hex3HexNAc5dHex | 2246.81 |
| NeuAcHex3HexNAc5dHex3 | 2247.83 |
| NeuGc2Hex5Hexnac4 | 2253.76 |
| NeuAcHex7HexNAc4/ | 2254.79 |
| NeuGcHex6HexNAc4dHex | |
| NeuAc2Hex4HexNAc5 | 2262.80 |
| NeuAcHex4HexNAc5dHex2/ | 2263.82/ |
| NeuAc2Hex5HexNAc4Ac | 2263.79 |
| NeuAcHex5HexNAc5dHex | 2279.82 |
| NeuAc2Hex4HexNAc4dHexSP | 2285.74 |
| NeuAcHex4HexNAc4dHex3SP | 2286.76 |
| NeuAcHex8HexNAc3SP/ | 2293.72/ |
| NeuAc3Hex4HexNAc3dHex | 2293.80 |
| NeuAc2Hex4HexNAc3dHex3 | 2294.82 |
| NeuAcHex6HexNAc5 | 2295.81 |
| NeuAc2Hex5HexNAc4SP | 2301.73 |
| NeuAcHex5HexNAc4dHex2SP | 2302.75 |
| NeuAc2Hex5HexNAc4Ac2 | 2305.80 |
| NeuAc2Hex5HexNAc3dHex2/ | 2310.81 |
| NeuGcNeuAcHex4HexNAc3dHex3 | |
| NeuAcHex5HexNAc3dHex4/ | 2311.83 |
| NeuGcHex6HexNAc5 | |
| NeuAcHex6HexNAc4dHexSP | 2318.75 |
| Hex6HexNAc4dHex3SP/ | 2319.77 |
| NeuGcNeuAcHex3HexNAc6 | |
| NeuAcHex4HexNAc6dHex | 2320.84 |
| NeuAcHex5HexNAc5dHexAc | 2321.83 |
| NeuAc2Hex6HexNAc3dHex | 2326.81 |
| NeuAcHex6HexNAc3dHex3 | 2327.83 |
| NeuAcHex7HexNAc4SP/ | 2334.74/ |
| NeuGcHex6HexNAc4dHexSP/ | 2334.79 |
| NeuAcHex10HexNAc2 | |
| NeuAcHex5HexNAc6 | 2336.84 |
| NeuAc3Hex4HexNac4 | 2350.82 |
| NeuAc2Hex4HexNAc4dHex2/ | 2351.84/ |
| Hex8HexNAc4dHexSP | 2351.76 |
| NeuGcNeuAc2Hex4HexNAc4 | 2366.81 |
| NeuAc2Hex5HexNAc4dHex | 2367.83 |
| NeuAcHex5HexNAc4dHex3 | 2368.85 |
| NeuAcHex5HexNAc4dHex2(SP)2 | 2382.71 |
| NeuAc2Hex6HexNAc4/ | 2383.83 |
| NeuGcNeuAcHex5HexNAc4dHex | |
| NeuAcHex6HexNAc4dHex2/ | 2384.85 |
| NeuGcHex5HexNAc4dHex3 | |
| NeuAc3Hex5HexNAc3SP/ | 2389.75/ |
| NeuAc2Hex5HexNAc4Ac4 | 2389.82 |
| NeuAc2Hex5HexNAc3dHex2SP | 2390.77 |
| NeuAcHex5HexNAc3dHex4SP/ | 2391.79/ |
| NeuAc3Hex3HexNAc5 | 2391.84 |
| NeuAc2Hex3HexNAc5dHex2 | 2392.86 |
| NeuAcHex3HexNAc5dHex4 | 2393.89 |
| NeuGc2Hex5HexNAc4dHex | 2399.82 |
| Hex4HexNAc6dHex3SP | 2401.82 |
| NeuAc2Hex6HexNAc3dHexSP | 2406.76 |
| NeuAc2Hex4HexNAc5dHex | 2408.86 |
| NeuAcHex4HexNAc5dHex3/ | 2409.88/ |
| NeuAc2Hex5HexNAc4dHexAc | 2409.84 |
| NeuAc2Hex5HexNAc5 | 2424.85 |
| NeuAcHex5HexNAc5dHex2 | 2425.87 |
| NeuAcHex8HexNAc2dHex5SP/ | 2439.77 |
| NeuAc3Hex4HexNAc3dHex2 | |
| NeuAcHex6HexNAc5dHex | 2441.87 |
| NeuAc2Hex8HexNAc2dHex/ | 2447.83/ |
| NeuAc2Hex5HexNAc4dHexSP | 2447.79 |
| NeuAcHex8HexNAc2dHex3/ | 2448.85/ |
| NeuAcHex5HexNAc4dHex3SP | 2448.81 |
| NeuAcHex3HexNAc6dHex3 | 2450.91 |
| NeuAc2Hex5HexNAc4dHexAc2 | 2451.85 |
| NeuAc2Hex5HexNAc3dHex3 | 2456.87 |
| NeuAcHex7HexNAc5 | 2457.86 |
| NeuAcHex5HexNAc5dHex2Ac | 2467.89 |
| NeuAc2Hex6HexNAc3dHex2 | 2472.86 |
| NeuAcHex6HexNAc3dHex4/ | 2473.88/ |
| NeuGcHex7HexNAc5 | |
| NeuAcHex5HexNAc6dHex | 2482.90 |
| NeuAcHex6HexNAc5Ac | 2483.88 |
| NeuAc2Hex7HexNAc3dHex | 2488.86 |

TABLE 2-continued

Preferred acidic glycan compositions. Calculated mass-to-charge ratios (calc. m/z) refer to the first isotope signal of [M − H]⁻ ion.

| Proposed composition | calc. m/z |
|---|---|
| NeuAcHex7HexNAc3dHex3 | 2489.88 |
| NeuAcHex6HexNAc6/ | 2498.89 |
| NeuGcHex5hexNAc6dHex | |
| NeuAc3Hex5HexNAc4 | 2512.87 |
| NeuAc2Hex5HexNAc4dHex2 | 2513.89 |
| NeuAcHex6HexNAc4dHex4 | 2514.91 |
| NeuAcHex6HexNAc5dHexSP/ | 2521.83/ |
| NeuAcHex9HexNAc3dHex/ | 2521.87 |
| NeuAc3Hex2HexNAc5dHex2 | |
| Hex6HexNAc5dHex3SP | 2522.85 |
| NeuGcNeuAc2Hex5HexNAc4 | 2528.87 |
| NeuAc2Hex6HexNAc4dHex/ | 2529.89 |
| NeuGcNeuAcHex5HexNAc4dHex2 | |
| NeuAcHex6HexNAc4dHex3 | 2530.91 |
| NeuAc3Hex3HexNAc5dHex/ | 2537.90/ |
| NeuGcHex6HexNAc5dHexSP/ | 2537.82 |
| NeuAcHex7HexNAc5SP | |
| NeuAc2Hex3HexNAc5dHex3 | 2538.92 |
| NeuGcHex5HexNAc7/ | 2539.92 |
| NeuAcHex3HexNAc5dHex5 | |
| NeuGc2NeuAcHex5HexNAc4 | 2544.86 |
| NeuGc2Hex5Hexnac4dHex2/ | 2545.88 |
| NeuGcNeuAcHex6HexNAc4dHex | |
| NeuAc3Hex4HexNAc5 | 2553.90 |
| NeuAc2Hex4HexNAc5dHex2 | 2554.92 |
| NeuAcHex4HexNAc5dHex4 | 2555.94 |
| NeuGc3Hex5HexNAc4 | 2560.86 |
| NeuAc2Hex5HexNAc5dHex | 2570.91 |
| NeuAcHex5HexNAc5dHex3 | 2571.93 |
| NeuAc2Hex6HexNAc5 | 2586.91 |
| NeuAcHex6HexNAc5dHex2 | 2587.93 |
| Hex7HexNAc6dHexSP | 2595.86 |
| NeuGcNeuAcHex6HexNAc5 | 2602.90 |
| NeuAcHex7HexNAc5dHex/ | 2603.92/ |
| NeuGcHex6HexNAc5dHex2 | 603.92 |
| NeuGc2Hex5HexNac5 | 2618.90 |
| NeuAcHex8HexNAc5/ | 2619.92 |
| NeuGcHex7HexNAc5dHex | |
| NeuAc2Hex5HexNAc6 | 2627.93 |
| NeuAc2Hex5HexNAc6dHex2 | 2628.95 |
| NeuGcHex8HexNAc5/ | 2635.91/ |
| NeuAcHex4HexNAc5dHex4SP | 2635.89 |
| NeuAcHex6HexNAc6dHex | 2644.95 |
| NeuAc2Hex6HexNAc5dHexSP | 2650.87 |
| NeuAc2Hex5HexNAc4dHex3 | 2659.95 |
| NeuAcHex7HexNAc6 | 2660.94 |
| NeuGcNeuAc2Hex5HexNAc4dHex | 2674.92 |
| NeuAc3Hex6HexNAc4 | |
| NeuGcHex6HexNAc5dHexSP/ | 2683.88 |
| NeuAcHex7HexNAc5dHexSP | |
| NeuAcHex5HexNAc7dHex | 2685.98 |
| NeuAc2Hex7HexNAc4dHex | 2691.94 |
| NeuAcHex7HexNAc4dHex3 | 2692.96 |
| NeuAc2Hex4HexNAc5dHex2(SP)2 | 2714.83 |
| NeuAcHex4HexNAc5dHex4(SP)2/ | 2715.85/ |
| NeuAc3Hex5HexNAc5 | 2715.95 |
| NeuAc2Hex5HexNAc5dHex2 | 2716.97 |
| NeuAcHex5HexNAc5dHex4 | 2717.99 |
| NeuAc2Hex6HexNAc5dHex | 2732.97 |
| NeuAcHex6HexNAc5dHex3 | 2733.99 |
| NeuAcHex6HexNAc5dHex2(SP)2 | 2747.84 |
| NeuGcNeuAcHex6HexNAc5dHex | 2748.96 |
| NeuAc3Hex4HexNAc6 | 2756.98 |
| NeuAc2Hex4HexNAc6dHex2 | 2758.00 |
| NeuAcHex4HexNAc6dHex4 | 2759.02 |
| NeuAc3Hex6HexNAc3dHex2 | 2763.96 |
| NeuAc2Hex6HexNAc3dHex4/ | 2764.98/ |
| NeuGc2Hex6HexNAc5dHex/ | 2764.96 |
| NeuGcHex7HexNAc5 | |
| NeuAcHex8HexNAc5dHex | 2765.98 |
| NeuAc2Hex5HexNAc6dHex | 2773.99 |
| NeuAcHex5HexNAc6dHex3 | 2775.01 |
| NeuGc2Hex7HexNAc5 | 2780.95 |
| NeuGcHex8HexNAc5dHex/ | 2781.97 |
| NeuAcHex9HexNAc5 | |
| NeuAc2Hex6HexNAc6 | 2789.99 |
| NeuAcHex6HexNAc6dHex2 | 2791.01 |
| NeuAc4Hex5HexNAc4 | 2803.97 |
| NeuAc3Hex5HexNAc4dHex2/ | 2804.99/ |
| NeuAcHex6HexNAc6dHex(SP)2 | 2804.86 |
| Hex6HexNAc6dHex3SP2 | 2805.88 |
| NeuAc2Hex5HexNAc4dHex4 | 2806.01 |
| NeuAcHex7Hexnac6dHex | 2807.00 |
| NeuAc2Hex6HexNAc5dHexSP | 2812.92 |
| NeuAcHex6HexNAc5dHex3SP | 2813.94 |
| NeuGcNeuAc3Hex5HexNAc4 | 2819.96 |
| NeuAc3Hex6HexNAc4dHex/ | 2820.98 |
| NeuGcNeuAc2Hex5HexNAc4dHex2 | |
| NeuAc2Hex6HexNAc4dHex3 | 2822.00 |
| NeuAcHex8HexNAc6 | 2823.00 |
| NeuGc2NeuAc2Hex5HexNAc4 | 2835.96 |
| NeuGc2NeuAcHex5HexNAc4dHex2 | 2836.98 |
| NeuAc3Hex6HexNAc5 | 2878.00 |
| NeuAc2Hex8HexNAc5dHex2 | 2879.02 |
| NeuAcHex6HexNAc5dHex4 | 288.04 |
| NeuAcHex7HexNAc6dHexSP/ | 2886.96/ |
| NeuAcHex10HexNAc4dHex | 2887.00 |
| NeuGcNeuAc2Hex6HexNAc5 | 2894.00 |
| NeuAc2Hex7HexNAc5dHex/ | 2895.02 |
| NeuGcNeuAcHex6HexNAc5dHex2 | |
| NeuAc3Hex6HexNAc4dHexSP/ | 2900.94 |
| NeuGcNeuAc2Hex5HexNAc4dHex2SP | |
| NeuGc2NeuAcHex6HexNAc5 | 2909.99 |
| NeuGc2Hex6HexNAc5dHex2 | 2911.01 |
| NeuAc3Hex5HexNAc6 | 2919.03 |
| NeuAc2Hex5HexNAc6dHex2 | 2920.05 |
| NeuAcHex5HexNAc6dHex4 | 2921.07 |
| NeuGc3Hex6HexNAc5 | 2925.99 |
| NeuGcNeuAc2Hex5HexNAc6 | 2935.02 |
| NeuAc2Hex6HexNAc6dHex/ | 2936.04 |
| NeuGcNeuAcHex5HexNAc6dHex2 | |
| NeuAcHex6HexNAc6dHex3 | 2937.07 |
| NeuGc2NeuAcHex5HexNAc6/ | 2951.02/ |
| NeuAc3Hex5HexNAc4dHex3 | 2951.04 |
| NeuAc2Hex7HexNAc6 | 2952.04 |
| NeuAcHex7HexNAc6dHex2 | 2953.06 |
| NeuAc2Hex6HexNAc5dHex2SP | 2958.98 |
| NeuAcHex6HexNAc5dHex4SP | 2960.00 |
| NeuAc2Hex4HexNAc7dHex2 | 2961.08 |
| NeuAcHex4HexNAc7dHex4 | 2962.10 |
| NeuAcHex6HexNAc6dHex2 | 2994.09 |
| NeuAcHex7HexNAc7dHex | 3010.08 |
| NeuAc3Hex6HexNAc5dHex | 3024.06 |
| NeuAc2Hex6HexNAc5dHex3 | 3025.08 |
| NeuAcHex8HexNAc7 | 3026.08 |
| NeuAc3Hex5HexNAc6dHex | 3065.09 |
| NeuAc2Hex5HexNAc6dHex3 | 3066.11 |
| NeuAcHex7HexNAc8 | 3067.10 |
| NeuAc3Hex6HexNAc6 | 3081.08 |
| NeuAc2Hex6HexNAc6dHex2 | 3082.10 |
| NeuAc2Hex7HexNAc6dHex | 3098.10 |
| NeuAcHex7HexNAc6dHex3 | 3099.12 |
| NeuAc3Hex6HexNAc5dHexSP | 3104.02 |
| NeuAc2Hex6HexNAc5dHex3SP | 3105.04 |
| NeuAcHex8HexNAc7SP/ | 3106.03/ |
| NeuAc3Hex4HexNAc7dHex | 3106.11 |
| Hex8HexNAc7dHex2SP/ | 3107.05/ |
| NeuAc2Hex4HexNAc7dHex3 | 3107.13 |
| NeuAcHex7HexNAc7dHex2 | 3156.14 |
| NeuAc3Hex6HexNAc5dHex2 | 3170.12 |
| NeuAc2Hex6HexNAc5dHex4 | 3171.14 |
| NeuAcHex8HexNAc7dHex | 3172.13 |
| NeuAc2Hex7HexNAc6dHexSP | 3178.05 |
| NeuAc3Hex6HexNAc6dHex | 3227.14 |
| NeuAc2Hex6HexNAc6dHex3 | 3228.16 |
| NeuAcHex8HexNAc8 | 3229.16 |
| NeuAc3Hex7HexNAc6 | 3243.13 |

TABLE 2-continued

Preferred acidic glycan compositions. Calculated mass-to-charge ratios (calc. m/z) refer to the first isotope signal of [M − H]⁻ ion.

| Proposed composition | calc. m/z |
|---|---|
| NeuAc2Hex7HexNAc6dHex2 | 3244.16 |
| NeuAcHex7HexNAc6dHex4 | 3245.18 |
| NeuAc2Hex8HexNAc6dHex/ NeuGcNeuAcHex7HexNAc6dHex2 | 3260.15 |
| NeuAcHex8HexNAc6dHex3/ NeuGcHex7HexNAc6dHex4 | 3261.17 |
| NeuAc3Hex7HexNAc5dHexSP/ NeuGcNeuAc2Hex6HexNAc5dHex2SP | 3266.07 |
| NeuAc3Hex5HexNAc7dHex/ NeuGcHex8HexNAc7dHexSP | 3268.17/ 3268.09 |
| NeuAc2Hex5HexNAc7dHex3 | 3269.19 |
| NeuAcHex7HexNAc9 | 3270.18 |
| NeuGc2Hex7HexNAc6dHex2 | 3276.15 |
| NeuAc4Hex4HexNAc5dHex2(SP)2 | 3297.02 |
| NeuAc3Hex4HexNAc5dHex4(SP)2 | 3298.04 |
| NeuAc2Hex7HexNAc7dHex | 3301.18 |
| NeuAcHex7HexNAc7dHex3 | 3302.20 |
| NeuAc3Hex6HexNAc5dHex3 | 3316.18 |
| NeuAc2Hex8HexNAc7 | 3317.17 |
| NeuAcHex8HexNAc7dHex2 | 3318.19 |
| NeuAc3Hex7HexNAc6dHex | 3389.19 |
| NeuAc2Hex7HexNAc6dHex3 | 3390.21 |
| NeuAcHex7HexNAc6dHex5/ NeuAcHex9HexNAc8 | 3391.23 |
| NeuAc3Hex5HexNAc7dHex2 | 3414.22 |
| NeuAc2Hex5HexNAc7dHex4 | 3415.24 |
| NeuAcHex7HexNAc9dHex | 3416.24 |
| NeuAc3Hex6HexNAc7dHex | 3430.22 |
| NeuAc2Hex6HexNAc7dHex3 | 3431.24 |
| NeuAcHex8HexNAc9 | 3432.24 |
| NeuAc2Hex8Hexnac7dHex | 3463.23 |
| NeuAcHex8HexNAc7dHex3 | 3464.25 |
| NeuAc3Hex7HexNAc6dHexSP | 3469.15 |
| NeuAc2Hex7HexNAc6dHex3SP | 3470.17 |
| NeuAc3Hex5HexNAc8dHex | 3471.25 |
| NeuAc2Hex5HexNAc8dHex3 | 3472.27 |
| NeuAcHex7HexNAc10 | 3473.26 |
| NeuAc4Hex7HexNAc6 | 3534.23 |
| NeuAc3Hex7HexNAc6dHex2 | 3535.25 |
| NeuAc2Hex7HexNAc6dHex4 | 3536.27 |
| NeuAcHex9HexNAc8dHex | 3537.27 |
| NeuAc4Hex5HexNAc7dHex | 3559.26 |
| NeuAc3Hex5HexNAc7dHex3 | 3560.28 |
| NeuAc2Hex7HexNAc9 | 3561.28 |
| NeuAcHex7HexNAc9dHex2 | 3562.30 |
| NeuAc3Hex7HexNAc7dHex | 3592.27 |
| NeuAc2Hex7HexNAc7dHex3 | 3593.29 |
| NeuAcHex9HexNAc9 | 3594.29 |
| NeuAc3Hex8HexNAc7 | 3608.27 |
| NeuAc2Hex8HexNAc7dHex2 | 3609.29 |
| NeuAcHex8HexNAc7dHex4 | 3610.31 |
| NeuAc3Hex5HexNAc8dHex2 | 3617.30 |
| NeuAc2Hex5HexNAc8dHex4 | 3618.32 |
| NeuAcHex7HexNAc10dHex | 3619.32 |
| NeuAc3Hex6HexNAc8dHex | 3633.30 |
| NeuAc4Hex7HexNAc6dHex | 3680.29 |
| NeuAc3Hex7HexNAc6dHex3 | 3681.31 |
| NeuAc2Hex9HexNAc8 | 3682.30 |
| NeuAcHex9HexNAc8dHex2 | 3683.32 |
| NeuAc4Hex6HexNAc7dHex | 3721.31 |
| NeuAc3Hex6HexNAc7dHex3 | 3722.34 |
| NeuAc2Hex8HexNAc9 | 3723.33 |
| NeuAcHex8HexNAc9dHex2 | 3724.35 |
| NeuAc3Hex7HexNAc7dHex2 | 3738.33 |
| NeuAc2Hex7HexNAc7dHex4 | 3739.35 |
| NeuAcHex9HexNAc9dHex | 3740.35 |
| NeuAc3Hex8HexNAc7dHex | 3754.33 |
| NeuAc2Hex8HexNAc7dHex3 | 3755.35 |
| NeuAcHex10HexNAc9/ NeuAcHex8HexNAc7dHex5 | 3756.34 |
| NeuAc4Hex6HexNAc8 | 3778.34 |
| NeuAc3Hex6HexNAc8dHex2 | 3779.36 |
| NeuAc2Hex6HexNAc8dHex4 | 3780.38 |
| NeuAcHex8HexNAc10dHex | 3781.37 |
| NeuAc4Hex7HexNAc6dHex2 | 3826.35 |
| NeuAc3Hex7Hexnac6dHex4 | 3827.37 |
| NeuAc2Hex9HexNAc8dHex | 3828.36 |
| NeuAcHex9HexNAc8dHex3 | 3829.38 |
| NeuAc4Hex8HexNAc7 | 3899.36 |
| NeuAc3Hex8HexNAc7dHex2 | 3900.38 |
| NeuAc2Hex8HexNAc7dHex4 | 3901.40 |
| NeuAcHex10HexNAc9dHex | 3902.40 |
| NeuAc4Hex6HexNAc8dHex | 3924.39 |
| NeuAc3Hex6HexNAc8dHex3 | 3925.41 |
| NeuAc2Hex8HexNAc10 | 3926.41 |
| NeuAcHex8HexNAc10dHex2 | 3927.43 |
| NeuAc3Hex9HexNAc8 | 3973.40 |
| NeuAc2Hex9HexNAc8dHex2 | 3974.42 |
| NeuAcHex9HexNAc8dHex4 | 3975.44 |
| NeuAc4Hex8HexNAc7dHex | 4045.42 |
| NeuAc3Hex8HexNAc7dHex3 | 4046.44 |
| NeuAc2Hex10HexNAc9/ NeuAc2Hex8HexNAc7dHex5 | 4047.44 |
| NeuAcHex10HexNAc9dHex2 | 4048.46 |
| NeuAc3Hex9HexNAc8dHex | 4119.46 |
| NeuAc2Hex9HexNAc8dHex3 | 4120.48 |
| NeuAcHex11HexNAc10/ NeuAcHex9HexNAc8dHex5 | 4121.47 |
| NeuAc2Hex10HexNAc9dHex2 | 4339.55 |
| NeuAcHex10HexNAc9dHex4 | 4340.57 |
| NeuAc2Hex10HexNAc9dHex3 | 4485.61 |

TABLE 3

MALDI-TOF mass spectrometric analysis of endoglycoceramidase-released peripheral blood mononuclear cell glycolipid glycans.

| Proposed composition | calc. m/z | exp. m/z |
|---|---|---|
| A. Neutral oligosaccharides detected from glycolipids of peripheral blood mononuclear cells. Five major peaks are bolded. | | |
| Hex2HexNAc | 568.18 | 568.09 |
| Hex3HexNAc | 730.24 | 730.18 |
| Hex3HexNAcdHex | 876.30 | 876.27 |
| Hex4HexNAc | 892.29 | 892.27 |
| Hex3HexNAc2 | 933.31 | 933.30 |
| Hex5HexNAc | 1054.34 | 1054.33 |
| Hex4HexNAc2 | 1095.37 | 1095.36 |
| Hex4HexNAc2dHex | 1241.43 | 1241.42 |
| Hex4HexNAc2dHex2 | 1387.49 | 1387.48 |
| Hex6HexNAc2 | 1419.48 | 1419.47 |
| Hex5HexNAc3 | 1460.50 | 1460.49 |
| Hex5HexNAc4dHex | 1606.56 | 1606.55 |
| Hex5HexNAc3dHex2 | 1752.62 | 752.60 |
| Hex6HexNAc4dHex2 | 2117.75 | 2117.71 |
| Hex6HexNAc4dHex3 | 2263.81 | 2263.76 |
| B. Acidic oligosaccharides detected from glycolipids of peripheral blood mononuclear cells. Five major peaks are bolded. | | |
| NeuAcHexHexNAc | 673.23 | 673.95 |
| NeuAcHex2HexNAc | 835.28 | 835.31 |
| NeuAcHex3HexNAc | 997.34 | 997.52 |
| NeuAcHex3HexNAc2 | 1200.42 | 1200.62 |
| NeuAcHex4HexNAc2 | 1362.47 | 1362.80 |
| NeuAcHex4HexNAc2dHex | 1508.53 | 1508.89 |
| NeuAcHex2HexNAc3dHex2 | 1533.56 | 1533.66 |
| NeuAc2Hex2HexNAc2dHexSP | 1555.47 | 1555.66 |
| NeuAcHex5HexNAc3 | 1727.60 | 1728.01 |
| NeuAcHex5HexNAc3dHex | 1873.66 | 1874.07 |
| NeuAc2Hex3HexNAc3dHexSP | 1920.60 | 1920.87 |
| NeuAcHex3HexNAc5dHex3 | 2247.83 | 2247.99 |

TABLE 4

| Glycan residue | linkage | proton | A[1] ppm | B ppm | C ppm | D ppm |
|---|---|---|---|---|---|---|
| D-GlcNAc | | H-1α | 5.191 | 5.187 | 5.187 | 5.188 |
| | | H-1β | 4.690 | 4.693 | 4.693 | 4.695 |
| | | NAc | 2.042 | 2.037 | 2.037 | 2.038 |
| β-D-GlcNAc | 4 | H-1 | 4.596 | 4.586 | 4.586 | 4.600 |
| | | NAc | 2.072 | 2.063 | 2.063 | 2.064 |
| β-D-Man | 4,4 | H-1 | 4.775 | 4.771 | 4.771 | 4.780 |
| | | H-2 | 4.238 | 4.234 | 4.234 | 4.240 |
| α-D-Man | 6,4,4 | H-1 | 4.869 | 4.870 | 4.870 | 4.870 |
| | | H-2 | 4.149 | 4.149 | 4.149 | 4.150 |
| α-D-Man | 6,6,4,4 | H-1 | 5.153 | 5.151 | 5.151 | 5.143 |
| | | H-2 | 4.025 | 4.021 | 4.021 | 4.020 |
| α-D-Man | 2,6,6,4,4 | H-1 | 5.047 | 5.042 | 5.042 | 5.041 |
| | | H-2 | 4.074 | 4.069 | 4.069 | 4.070 |
| α-D-Man | 3,6,4,4 | H-1 | 5.414 | 5.085 | 5.415 | 5.092 |
| | | H-2 | 4.108 | 4.069 | 4.099 | 4.070 |
| α-D-Man | 2,3,6,4,4 | H-1 | 5.047 | — | 5.042 | — |
| | | H-2 | 4.074 | — | 4.069 | — |
| α-D-Man | 3,4,4 | H-1 | 5.343 | 5.341 | 5.341 | 5.345 |
| | | H-2 | 4.108 | 4.099 | 4.099 | 4.120 |
| α-D-Man | 2,3,4,4 | H-1 | 5.317 | 5.309 | 5.050 | 5.055 |
| | | H-2 | 4.108 | 4.099 | 4.069 | 4.070 |
| α-D-Man | 2,2,3,4,4 | H-1 | 5.047 | 5.042 | — | — |
| | | H-2 | 4.074 | 4.069 | — | — |

Figure 17:
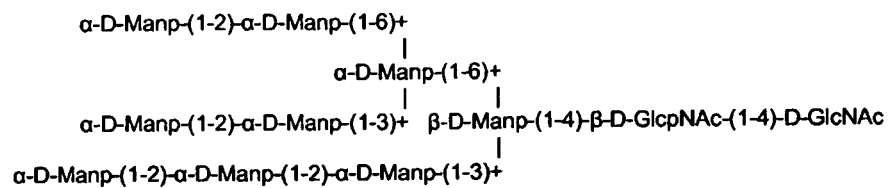
FIG. 17. Reference neutral N-glycan structures for NMR analysis (A-D).
Figure 17:
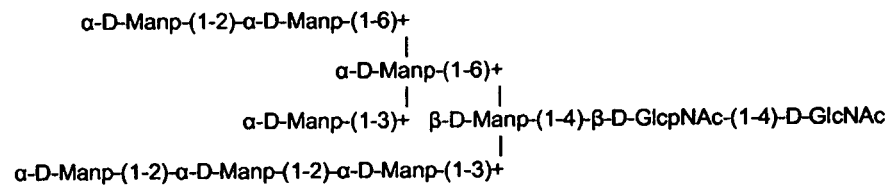
Figure 17:
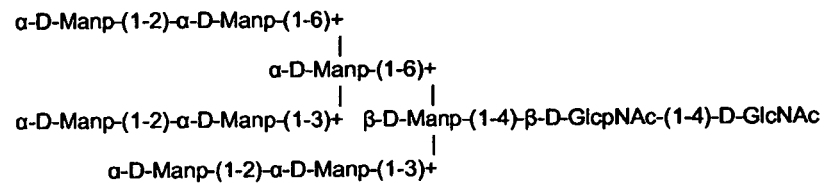
Figure 17:
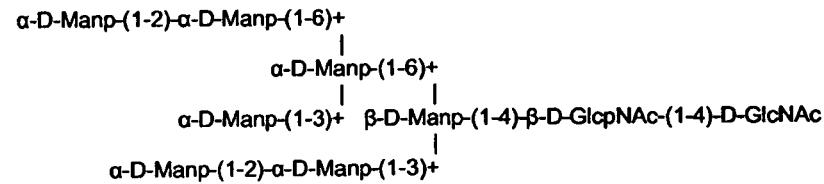

[1] See FIG. 17 for structures.
Chemical shift values obtained from Fu et al., 1994 and Hard et al., 1991.

TABLE 5

| Glycan residue | linkage | proton | A[1] ppm | B ppm | C ppm | D ppm | E ppm |
|---|---|---|---|---|---|---|---|
| D-GlcNAc | | H-1α | 5.180 | 5.188 | 5.189 | 5.181 | 5.189 |
| | | H-1β | 4.692 | n.a.[2] | 4.695 | n.a. | 4.694 |
| | | NAc | 2.038 | 2.038 | 2.038 | 2.039 | 2.038 |
| α-L-Fuc | 6 | H-1α | 4.890 | —[3] | — | 4.892 | — |
| | | H-1β | 4.897 | — | — | 4.900 | — |
| | | H-5α | 4.098 | — | — | 4.10 | — |
| | | H-5β | 4.134 | — | — | n.a. | — |
| | | CH3α | 1.209 | — | — | 1.211 | — |
| | | CH3β | 1.220 | — | — | 1.223 | — |
| β-D-GlcNAc | 4 | H-1α | 4.664 | 4.612 | 4.614 | 4.663 | 4.613 |
| | | H-1β | 4.669 | 4.604 | 4.606 | n.a. | 4.604 |
| | | NAc (α/β) | 2.097 | 2.081 | 2.081 | 2.096/ 2.093 | 2.084 |
| β-D-Man | 4,4 | H-1 | 4.772 | n.a. | n.a. | n.a. | n.a. |
| | | H-2 | 4.257 | 4.246 | 4.253 | 4.248 | 4.258 |
| α-D-Man | 6,4,4 | H-1 | 4.929 | 4.928 | 4.930 | 4.922 | 4.948 |
| | | H-2 | 4.111 | 4.11 | 4.112 | 4.11 | 4.117 |
| β-D-GlcpNAc | 2,6,4,4 | H-1 | 4.583 | 4.581 | 4.582 | 4.573 | 4.604 |
| | | NAc | 2.048 | 2.047 | 2.047 | 2.043 | 2.066 |
| β-D-Gal | 4,2,6,4,4 | H-1 | 4.544 | 4.473 | 4.473 | 4.550 | 4.447 |
| | | H-3 | n.a. | n.a. | n.a. | 4.119 | n.a. |
| | | H-4 | 4.185 | n.a. | n.a. | n.a. | n.a. |
| α-D-Galp | 3,4,2,6,4,4 | H-1 | 5.149 | — | — | — | — |
| α-D-Neup5Ac | 3,4,2,6,4,4 | H-3a | — | — | — | 1.800 | — |
| | | H-3e | — | — | — | 2.758 | — |
| | | NAc | — | — | — | 2.031 | — |
| α-D-Neup5Ac | 6,4,2,6,4,4 | H-3a | — | — | — | — | 1.719 |
| | | H-3e | — | — | — | — | 2.673 |
| | | NAc | — | — | — | — | 2.029 |
| α-D-Man | 3,4,4 | H-1 | 5.135 | 5.118 | 5.135 | 5.116 | 5.133 |
| | | H-2 | 4.195 | 4.190 | 4.196 | 4.189 | 4.197 |
| β-D-GlcpNAc | 2,3,4,4 | H-1 | 4.605 | 4.573 | 4.606 | 4.573 | 4.604 |
| | | NAc | 2.069 | 2.047 | 2.069 | 2.048 | 2.070 |
| β-D-Galp | 4,2,3,4,4 | H-1 | 4.445 | 4.545 | 4.445 | 4.544 | 4.443 |
| | | H-3 | n.a. | 4.113 | n.a. | 4.113 | n.a. |
| α-D-Neup5Ac | 6,4,2,3,4,4 | H-3a | 1.722 | — | 1.719 | — | 1.719 |
| | | H-3e | 2.666 | — | 2.668 | — | 2.667 |
| | | NAc | 2.029 | — | 2.030 | — | 2.029 |
| α-D- | 3,4,2,3,4,4 | H-3a | — | 1.797 | — | 1.797 | — |
| Neup5Ac | | H-3e | — | 2.756 | — | 2.758 | — |
| | | NAc | — | 2.030 | — | 2.031 | — |

Figure 18:
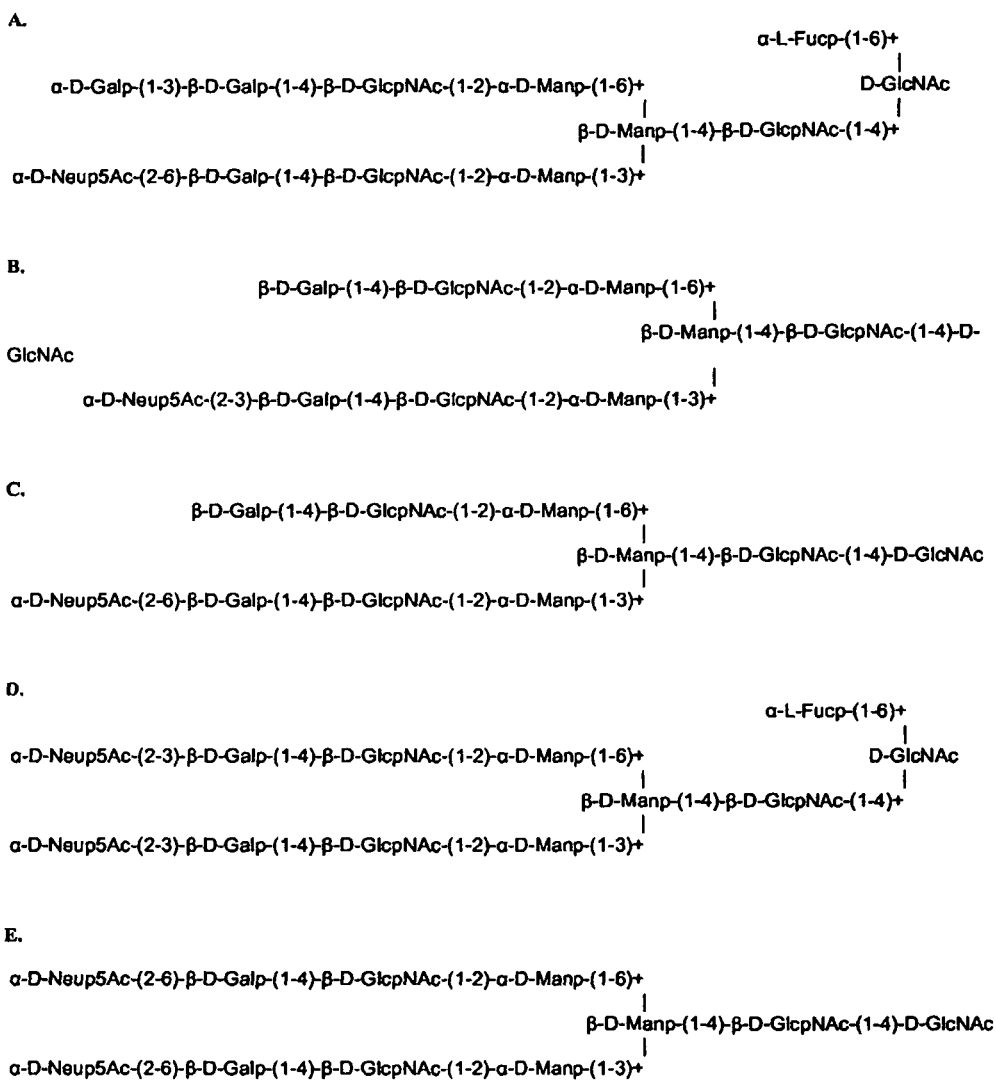
FIG. 18. Reference acidic N-glycan structures for NMR analysis (A-E).

[1] See FIG. 18 for structures
[2] n.a., not assigned.
[3] —, not present.
Chemical shift values obtained from Hard et al., 1992 and Helin et al., 1995.

TABLE 6

| $Hex_{5-9}HexNAc_2$ (including high-mannose type N-glycans) | | | |
|---|---|---|---|
| Proposed composition | m/z | Human tissue | Human cell line |
| Hex5HexNAc2 | 1257 | + | + |
| Hex6HexNAc2 | 1419 | + | + |
| Hex7HexNAc2 | 1581 | + | + |
| Hex8HexNAc2 | 1743 | + | + |
| Hex9HexNAc2 | 1905 | + | + |

| $Hex_{1-4}HexNAc_2dHex_{0-1}$ (including low-mannose type N-glycans) | | | |
|---|---|---|---|
| Proposed composition | m/z | Human tissue | Human cell line |
| HexHexNAc2 | 609 | + | |
| HexHexNAc2dHex | 755 | + | |
| Hex2HexNAc2 | 771 | + | + |
| Hex2HexNAc2dHex | 917 | + | + |
| Hex3HexNAc2 | 933 | + | + |
| Hex3HexNAc2dHex | 1079 | + | + |
| Hex4HexNAc2 | 1095 | + | + |
| Hex4HexNAc2dHex | 1241 | + | + |

| $Hex_{10-12}HexNAc_2$ (including glucosylated high-mannose type N-glycans) | | | |
|---|---|---|---|
| Proposed composition | m/z | Human cells | Human cell line |
| Hex10HexNAc2 | 2067 | + | + |
| Hex11HexNAc2 | 2229 | + | |
| Hex12HexNAc2 | 2391 | + | |

| $Hex_{5-9}HexNAc_2dHex_1$ (including fucosylated high-mannose type N-glycans) | | | |
|---|---|---|---|
| Proposed composition | m/z | Human tissue | Human cell line |
| Hex5HexNAc2dHex | 1403 | + | + |
| Hex6HexNAc2dHex | 1565 | + | + |

| HexNAc = 3 and Hex ≥ 2 (including hybrid-type and monoantennary N-glycans) | | | |
|---|---|---|---|
| Proposed composition | m/z | Human cells | Human cell line |
| Hex2HexNAc3 | 974 | + | |
| Hex2HexNAc3dHex | 1120 | + | |
| Hex3HexNAc3 | 1136 | + | + |
| Hex3HexNAc3dHex2 | 1266 | + | |
| Hex3HexNAc3dHex | 1282 | + | + |
| Hex4HexNAc3 | 1298 | + | + |
| Hex3HexNAc3dHex2 | 1428 | + | |
| Hex4HexNAc3dHex | 1444 | + | + |

TABLE 6-continued

| Proposed composition | m/z | Human cells | Human cell line |
|---|---|---|---|
| Hex5HexNAc3 | 1460 | + | + |
| Hex4HexNAc3dHex2 | 1590 | + | + |
| Hex5HexNAc3dHex | 1606 | + | + |
| Hex6HexNAc3 | 1622 | + | + |
| Hex5HexNAc3dHex2 | 1752 | + | + |
| Hex6HexNAc3dHex | 1768 | + | + |
| Hex7HexNAc3 | 1784 | + | + |
| Hex7HexNAc3dHex | 1930 | + | + |
| Hex8HexNAc3 | 1946 | + | |

HexNAc ≥ 4 and Hex ≥ 3
(including complex-type N-glycans)

| Proposed composition | m/z | Human cells | Human cell line |
|---|---|---|---|
| Hex3HexNAc4 | 1339 | + | + |
| Hex3HexNAc4dHex | 1485 | + | + |
| Hex4HexNAc4 | 1501 | + | + |
| Hex3HexNAc5 | 1542 | + | + |
| Hex4HexNAc4dHex | 1647 | + | + |
| Hex5HexNAc4 | 1663 | + | + |
| Hex3HexNAc5dHex | 1688 | + | + |
| Hex4HexNAx5 | 1704 | + | + |
| Hex4HexNAc4dHex2 | 1793 | + | + |
| Hex5HexNAc4dHex | 1809 | + | + |
| Hex6HexNAc4 | 1825 | + | + |
| Hex4HexNAc5dHex | 1850 | + | + |
| Hex5HexNAc5 | 1866 | + | |
| Hex3HexNAc6dHex | 1891 | + | + |
| Hex5HexNAc4dHex2 | 1955 | + | |
| Hex6HexNAc4dHex | 1971 | + | + |
| Hex7HexNAc4 | 1987 | + | + |
| Hex4HexNAc5dHex2 | 1996 | + | + |
| Hex5HexNAc5dHex | 2012 | + | |
| Hex6HexNAc5 | 2028 | + | + |
| Hex5HexNAc4dHex3 | 2101 | + | + |
| Hex6HexNAc4dHex2 | 2117 | + | |
| Hex7HexNAc4dHex | 2133 | + | + |
| Hex4HexNAc5dHex3 | 2142 | + | |
| Hex8HexNAc4 | 2149 | + | + |
| Hex5HexNAc5dHex2 | 2158 | + | |
| Hex6HexNAc5dHex | 2174 | + | + |
| Hex7HexNAc5 | 2190 | + | + |
| Hex5HexNAc6dHex | 2215 | + | + |
| Hex6HexNAc6 | 2231 | + | |
| Hex6HexNAc4dHex4 | 2247 | + | + |
| Hex7HexNAc4dHex2 | 2279 | + | |
| Hex5HexNAc5dHex3 | 2304 | + | + |
| Hex6HexNAc5dHex2 | 2320 | + | + |
| Hex7HexNAc5dHex | 2336 | + | |
| Hex8HexNAc5 | 2352 | + | + |
| Hex7HexNAc6 | 2393 | + | + |
| Hex7HexNAc4dHex3 | 2425 | + | |
| Hex6HexNAc5dHex3 | 2466 | + | |
| Hex8HexNAc5dHex | 2498 | + | |
| Hex7HexNAc6dHex | 2539 | + | + |
| Hex6HexNAc5dHex4 | 2612 | + | + |
| Hex8HexNAc7 | 2758 | + | |
| Hex7Hexnac5dHex4 | 2775 | + | + |
| Hex8HexNAc5dHex4 | 2937 | + | + |
| Hex8HexNAc6dHex4 | 3140 | + | + |
| Hex9HexNAc6dHex4 | 3302 | + | + |
| Hex10HexNAc6dHex4 | 3464 | + | + |
| Hex11HexNAc6dHex4 | 3626 | + | + |

Hex$_{1-9}$HexNAc$_1$
(including soluble glycans)

| Proposed composition | m/z | Human cells | Human cell line |
|---|---|---|---|
| Hex2HexNAc | 568 | + | |
| Hex3HexNAc | 730 | + | + |
| Hex4HexNAc | 892 | + | |
| Hex5HexNAc | 1054 | + | |
| Hex6HexNAc | 1216 | + | |
| Hex7HexNAc | 1378 | + | + |
| Hex8HexNAc | 1540 | + | + |
| Hex9HexNAc | 1702 | + | |

HexNAc ≥ 3 and dHex ≥ 1
(including fucosylated hybrid/monoant. N-glycans)

| Proposed composition | m/z | Human cells | Human cell line |
|---|---|---|---|
| Hex2HexNAc3dHex | 1120 | + | |
| Hex2HexNAc3dHex2 | 1266 | + | |
| Hex3HexNAc3dHex | 1282 | + | + |
| Hex3HexNAc3dHex2 | 1428 | + | |
| Hex4HexNAc3dHex | 1444 | + | + |
| Hex4HexNAc3dHex2 | 1590 | + | + |
| Hex5HexNAc3dHex | 1606 | + | + |
| Hex5HexNAc3dHex2 | 1752 | + | + |
| Hex6HexNAc3dHex | 1768 | + | + |
| Hex7HexNAc3dHex | 1930 | + | + |
| Hex3HexNAc4dHex | 1485 | + | + |
| Hex4HexNAc4dHex | 1647 | + | + |
| Hex3HexNAc5dHex | 1688 | + | + |
| Hex4HexNAc4dHex2 | 1793 | + | + |
| Hex5HexNAc4dHex | 1809 | + | + |
| Hex4HexNAc5dHex | 1850 | + | + |
| Hex3HexNAc6dHex | 1891 | + | + |
| Hex5HexNAc4dHex2 | 1955 | + | + |
| Hex6HexNAc4dHex | 1971 | + | + |
| Hex4HexNAc5dHex2 | 1996 | + | + |
| Hex5HexNAc5dHex | 2012 | + | |
| Hex5HexNAc4dHex3 | 2101 | + | + |
| Hex6HexNAc4dHex2 | 2117 | + | |
| Hex7HexNAc4dHex | 2133 | + | + |
| Hex4HexNAc5dHex3 | 2142 | + | |
| Hex5HexNAc5dHex2 | 2158 | + | |
| Hex6HexNAc5dHex | 2174 | + | + |
| Hex5HexNAc6dHex | 2215 | + | + |
| Hex5HexNAc4dHex4 | 2247 | + | + |
| Hex7HexNAc4dHex2 | 2279 | + | |
| Hex5HexNAc5dHex3 | 2304 | + | + |
| Hex6HexNAc5dHex2 | 2320 | + | + |
| Hex7HexNAc5dHex | 2336 | + | |
| Hex7HexNAc4dHex3 | 2425 | + | |
| Hex6HexNAc5dHex3 | 2466 | + | |
| Hex8HexNAc5dHex | 2498 | + | |
| Hex7HexNAc6dHex | 2539 | + | + |
| Hex6HexNAc5dHex4 | 2612 | + | + |
| Hex7Hexnac5dHex4 | 2775 | + | + |
| Hex8HexNAc5dHex4 | 2937 | + | + |
| Hex8HexNAc6dHex4 | 3140 | + | + |
| Hex9HexNAc6dHex4 | 3302 | + | + |
| Hex10HexNAc6dHex4 | 3464 | + | + |
| Hex11HexNAc6dHex4 | 3626 | + | + |

HexNAc = Hex ≥ 5
(terminal HexNAc, N = H)

| Proposed composition | m/z | Human cells | Human cell line |
|---|---|---|---|
| Hex5HexNAc5 | 1866 | + | |
| Hex5HexNAc5dHex | 2012 | + | |
| Hex5HexNAc5dHex2 | 2158 | + | |
| Hex6HexNAc6 | 2231 | + | |

HexNAc ≥ 3 and dHex ≥ 2
(including multifucosylated hybrid/monoant. N-glycans)

| Proposed composition | m/z | Human cells | Human cell line |
|---|---|---|---|
| Hex2HexNAc3dHex2 | 1266 | + | |
| Hex3HexNAc3dHex2 | 1428 | + | |
| Hex4HexNAc3dHex2 | 1590 | + | + |
| Hex5HexNAc3dHex2 | 1752 | + | + |
| Hex4HexNAc4dHex2 | 1793 | + | + |
| Hex5HexNAc4dHex2 | 1955 | + | + |
| Hex4HexNAc5dHex2 | 1996 | + | + |

TABLE 6-continued

| Proposed composition | m/z | Human cells | Human cell line |
|---|---|---|---|
| Hex5HexNAc4dHex3 | 2101 | + | + |
| Hex6HexNAc4dHex2 | 2117 | + | |
| Hex4HexNAc5dHex3 | 2142 | + | |
| Hex5HexNAc5dHex2 | 2158 | + | |
| Hex5HexNAc4dHex4 | 2247 | + | + |
| Hex7HexNAc4dHex2 | 2279 | + | |
| Hex5HexNAc5dHex3 | 2304 | + | + |
| Hex6HexNAc5dHex2 | 2320 | + | + |
| Hex7HexNAc4dHex3 | 2425 | + | |
| Hex6HexNAc5dHex3 | 2466 | + | |
| Hex6HexNAc5dHex4 | 2612 | + | + |
| Hex7Hexnac5dHex4 | 2775 | + | + |
| Hex8HexNAc5dHex4 | 2937 | + | + |
| Hex8HexNAc6dHex4 | 3140 | + | + |
| Hex9HexNAc6dHex4 | 3302 | + | + |
| Hex10HexNAc6dHex4 | 3464 | + | + |
| Hex11HexNAc6dHex4 | 3626 | + | + |

HexNAc > Hex ≥ 2
(terminal HexNAc, N > H)

| Proposed composition | m/z | Human cells | Human cell line |
|---|---|---|---|
| Hex2HexNAc3 | 974 | + | |
| Hex2HexNAc3dHex | 1120 | + | |
| Hex2HexNAc3dHex2 | 1266 | + | |
| Hex3HexNAc4 | 1339 | + | + |
| Hex3HexNAc4dHex | 1485 | + | + |
| Hex3HexNAc5 | 1542 | + | + |
| Hex3HexNAc5dHex | 1688 | + | + |
| Hex4HexNAx5 | 1704 | + | + |
| Hex4HexNAc5dHex | 1850 | + | + |
| Hex3HexNAc6dHex | 1891 | + | + |
| Hex4HexNAc5dHex2 | 1996 | + | + |
| Hex4HexNAc5dHex3 | 2142 | + | |
| Hex5HexNAc6dHex | 2215 | + | |

TABLE 7

HexNAc = 3 and Hex ≥ 2
(including hybrid-type and monoantennary N-glycans)

| Proposed composition | m/z | Human cells | Human cell line |
|---|---|---|---|
| Hex3HexNAc3SP | 1192 | + | + |
| Hex3HexNAc3dHexSP | 1338 | + | + |
| Hex4HexNAC3SP | 1354 | + | + |
| NeuAcHex3HexNAc3 | 1403 | + | + |
| NeuGcHex3HexNAc3 | 1419 | + | |
| Hex4HexNAc3dHexSP | 1500 | + | + |
| Hex5HexNAc3SP | 1516 | + | + |
| NeuAcHex3HexNAc3dHex | 1549 | + | + |
| NeuAcHex3HexNAc3SP2 | 1563 | + | |
| NeuAcHex4HexNAc3 | 1565 | + | + |
| NeuGcHex4HexNAc3 | 1581 | + | + |
| Hex4HexNAc3dHex2SP | 1646 | + | |
| Hex5HexNAc3dHexSP | 1662 | + | + |
| Hex6HexNAc3SP and/or NeuAc2Hex2HexNAc3dHex | 1678 | + | + |
| NeuAc2Hex3HexNAc3 | 1694 | + | + |
| NeuAcHex3HexNAc3dHexSP2 | 1709 | + | |
| NeuAcHex4HexNAc3dHex | 1711 | + | + |
| NeuAcHex5HexNAc3 and/or NeuGcHex4HexNAc3dHex | 1727 | + | + |
| NeuGcHex5HexNAc3 | 1743 | + | + |
| NeuAcHex4HexNAc3dHexSP | 1791 | + | |
| Hex5HexNAc3dHex2SP | 1808 | + | |
| Hex6HexNAc3dHexSP | 1824 | + | + |
| NeuAc2Hex3HexNAc3dHex | 1840 | + | |
| NeuAc2Hex4HexNAc3 | 1856 | + | |
| NeuAcHex4HexNAc3dHex2 | 1857 | + | |
| NeuAcHex5HexNAc3dHex and/or NeuGcHex4HexNAc3dHex2 | 1873 | + | + |
| NeuAcHex5HexNAc3SP2 | 1887 | + | |

TABLE 7-continued

| Proposed composition | m/z | Human cells | Human cell line |
|---|---|---|---|
| NeuAcHex6HexNAc3 | 1889 | + | + |
| Hex8HexNAc3SP and/or NeuAc2Hex4HexNAc3dHex | 2002 | + | + |
| NeuAcHex5HexNAc3dHex3 | 2003 | + | |
| NeuAc2Hex5HexNAc3 and/or NeuGcNeuAcHex4HexNAc3dHex | 2018 | + | + |
| NeuAcHex5HexNAc3dHex2 | 2019 | + | + |
| NeuGcNeuAcHex5HexNAc3 and/or NeuGc2Hex4HexNAc3dHex | 2034 | + | |
| NeuAcHex6HexNAc3dHex | 2035 | + | + |
| NeuGc2Hex5HexNAc3 | 2050 | + | |
| NeuAcHex7HexNAc3 | 2051 | + | + |
| NeuAc2Hex4HexNAc3dHexSP and/or Hex8HexNAc3SP2 | 2082 | + | |
| NeuAcHex6HexNAc3dHexSP | 2115 | + | |
| Hex8HexNAc3dHexSP and/or NeuAc2Hex4HexNAc3dHex2 | 2148 | + | |
| NeuAc2Hex5HexNAc3dHex and/or Hex6HexNAc5SP2 | 2164 | + | + |
| NeuAcHex5HexNAc3dHex3 | 2165 | + | + |
| NeuAcHex8HexNAc3SP and/or NeuAc3Hex4HexNAc3dHex | 2293 | + | |
| NeuAc2Hex5HexNAc3dHex2 and/or NeuGcNeuAcHex4HexNAc3dHex3 | 2310 | + | |
| NeuAc3Hex5HexNAc3SP | 2389 | + | |
| NeuAc2Hex5HexNAc3dHex2SP | 2390 | + | + |
| NeuAc2Hex6HexNAc3dHexSP | 2406 | + | |
| NeuAcHex8HexNAc3dHexSP and/or NeuAc3Hex4HexNAc3dHex2 | 2439 | + | |
| NeuAcHex9HexNAc3dHex | 2521 | + | |

HexNAc ≥ 4 and Hex ≥ 3
(including complex-type N-glycans)

| Proposed composition | m/z | Human cells | Human cell line |
|---|---|---|---|
| Hex4HexNAc4SP | 1557 | + | + |
| NeuAcHex3HexNAc4 | 1606 | + | |
| Hex4HexNAc4SP2 | 1637 | + | |
| Hex4HexNAc4dHexSP | 1703 | + | + |
| Hex4HexNAc4SP3 and/or Hex7HexNAc2SP2 | 1717 | + | |
| Hex5HexNAc4SP | 1719 | + | + |
| NeuAcHex4HexNAc4 | 1768 | + | + |
| NeuGcHex4HexNac4 | 1784 | + | |
| Hex5HexNAc4SP2 and/or Hex8HexNAc2SP | 1799 | + | |
| NeuAcHex3HexNac5 | 1809 | + | |
| NeuGcHex3HexNAc5 | 1825 | + | + |
| Hex5HexNAc4dHexSP | 1865 | + | + |
| Hex6HexNAc4SP | 1881 | + | + |
| Hex4HexNAc5dHexSP | 1906 | + | |
| NeuAcHex4HexNAc4dHex | 1914 | + | |
| NeuAcHex4HexNAc4SP2 | 1928 | + | |
| NeuAcHex5HexNAc4 | 1930 | + | + |
| NeuGcHex5HexNAc4 | 1946 | + | + |
| NeuAcHex4HexNAc5 | 1971 | + | |
| NeuAcHex5HexNAc4Ac | 1972 | + | |
| Hex5HexNAc5SP2 | 2002 | + | |
| NeuAcHex5HexNAc4SP | 2010 | + | + |
| Hex5HexNAc4dHex2SP | 2011 | + | |
| NeuGcHex5HexNAc4SP | 2026 | + | |
| Hex6HexNAc4dHexSP | 2027 | + | + |
| Hex7HexNAc4SP and/or Hex4HexNAc6SP2 and/or NeuAc2Hex3HexNAc4dHex | 2043 | + | |
| NeuAcHex4HexNAc5SP | 2051 | + | |
| Hex4HexNAc5dHex2SP | 2052 | + | |
| NeuAc2Hex4HexNAc4 | 2059 | + | |
| NeuAcHex4HexNAc4dHex2 | 2060 | + | + |
| NeuAcHex4HexNAc4dHexSP2 | 2074 | + | |
| NeuAcHex5HexNAc4dHex | 2076 | + | + |
| NeuAcHex6HexNAc4 and/or NeuGcHex5HexNAc4dHex | 2092 | + | |
| NeuAcHex3HexNAc5dHex2 and/or NeuAc2Hex4HexNAc4Ac | 2101 | + | |
| NeuGcHex6HexNAc4 | 2108 | + | |
| NeuAcHex4HexNAc5dHex | 2117 | + | |

TABLE 7-continued

| Composition | Mass | | |
|---|---|---|---|
| Hex4HexNAc5dHex2SP2 | 2132 | + | |
| NeuAcHex5HexNAc5 | 2133 | + | + |
| NeuAc2Hex4HexNAc4SP | 2139 | + | |
| NeuAcHex5HexNAc4dHexSP | 2156 | + | + |
| Hex5HexNAc4dHex3SP | 2157 | + | |
| Hex6HexNAc5SP2 | 2164 | + | |
| NeuAcHex6HexNAc4SP and/or NeuGcHex5HexNAc4dHexSP | 2172 | + | + |
| Hex6HexNAc4dHex2SP and/or Hex3HexNAc6dHex2SP2 | 2173 | + | |
| NeuAcHex4HexNAc6 | 2174 | + | |
| NeuAc3Hex3HexNAc4 and/or NeuGcHex6HexNAc4SP and/or NeuAc2NeuGcHex2HexNAc4dHex | 2188 | + | |
| NeuAc2Hex3HexNAc4dHex2 and/or Hex7HexNAc4dHexSP and/or Hex4HexNAc6dHexSP2 | 2189 | + | + |
| NeuAcHex3HexNAc4dHex4 | 2190 | + | + |
| Hex4HexNAc5dHex3SP | 2198 | + | + |
| NeuAc2Hex4HexNAc4dHex | 2205 | + | |
| NeuAc2Hex4HexNAc4SP2 | 2219 | + | |
| NeuAc2Hex5HexNAc4 | 2221 | + | + |
| NeuAcHex5HexNAc4dHex2 | 2222 | + | + |
| Hex6HexNAc5dHexSP | 2230 | + | |
| NeuGcNeuAcHex5HexNAc4 | 2237 | + | |
| NeuAcHex6HexNAc4dHex and/or NeuGcHex5HexNAc4dHex2 | 2238 | + | + |
| NeuAc2Hex3HexNAc5dHex and/or Hex7HexNAc5SP | 2246 | + | |
| NeuGc2Hex5HexNAc4 | 2253 | + | |
| NeuAcHex7HexNAc4 and/or NeuGcHex6HexNAc4dHex | 2254 | + | + |
| NeuAcHex4HexNAc5 | 2262 | + | |
| NeuAcHex4HexNAc5dHex2 and/or NeuAc2Hex5HexNAc4Ac | 2263 | + | |
| Hex5HexNAc6dHexSP | 2271 | + | |
| NeuAcHex5HexNAc5dHex | 2279 | + | + |
| NeuAc2Hex4HexNAc4dHexSP and/or Hex11HexNAc2SP | 2285 | + | |
| NeuAcHex6HexNAc5 | 2295 | + | + |
| NeuAcHex5HexNAc4SP | 2301 | + | |
| NeuAcHex5HexNAc4dHex2SP | 2302 | + | |
| NeuAc2Hex5HexNAc4Ac2 | 2305 | + | |
| NeuAcHex6HexNAc4dHexSP | 2318 | + | + |
| Hex6HexNAc4dHex3SP and/or NeuGcNeuAcHex3HexNAc6 | 2319 | + | |
| NeuAcHex4HexNAc6dHex | 2320 | + | |
| NeuAcHex5HexNAc5dHexAc | 2321 | + | |
| Hex7HexNAc4dHex2SP and/or Hex4HexNAc6dHex2SP2 | 2335 | + | |
| NeuAcHex5HexNAc6 | 2336 | + | + |
| NeuAc3Hex4HexNac4 | 2350 | + | |
| NeuAc2Hex4HexNAc4dHexSP | 2365 | + | |
| NeuAc2Hex6HexNAc5 | 2367 | + | + |
| NeuAcHex5HexNAc4dHex3 | 2368 | + | + |
| NeuAc2Hex6HexNAc4 and/or NeuGcNeuAcHex5HexNAc4dHex | 2383 | + | + |
| NeuAcHex6HexNAc4dHex2 and/or NeuGcHex5HexNAc4dHex3 | 2384 | + | + |
| NeuAc2Hex3HexNAc5dHex2 and/or Hex7HexNAc5dHexSP | 2392 | + | + |
| NeuAcHex3HexNAc5dHex4 | 2393 | + | |
| NeuGc2Hex5HexNAc4dHex | 2399 | + | |
| NeuAcHex4HexNAc6dHexSP and/or NeuGcHex6HexNAc4dHex2 and/or NeuAcHex7HexNAc4dHex Hex4HexNAc6dHex3SP | 2400 | + | |
| | 2401 | + | |
| NeuAc2Hex4HexNAc5dHex | 2408 | + | |
| NeuAcHex4HexNAc5dHex3 and/or NeuAc2Hex5HexNAc4dHexAc | 2409 | + | |
| NeuAcHex5HexNAc5 | 2424 | + | |
| NeuAcHex5HexNAc5dHex2 | 2425 | + | + |
| NeuAcHex6HexNAc5dHex | 2441 | + | + |
| NeuAc2Hex5HexNAc4dHexSP | 2447 | + | + |
| NeuAcHex5HexNAc4dHex3SP | 2448 | + | |
| NeuAcHex7HexNAc5 and/or NeuGcHex6HexNAc5dHex | 2457 | + | + |
| NeuGcHex7HexNAc5 | 2473 | + | |
| NeuAcHex5HexNAc6dHex | 2482 | + | |
| NeuAcHex4HexNAc5dHex3SP | 2489 | + | |
| Hex6HexNAc7SP | 2490 | + | |
| NeuAc3Hex5HexNAc4 | 2512 | + | |
| NeuAc2Hex5HexNAc4dHex2 | 2513 | + | + |
| NeuAcHex5HexNAc4dHex4 | 2514 | + | |
| NeuAcHex6HexNAc5dHexSP and/or NeuAc3Hex2HexNAc5dHex2 | 2521 | + | |
| Hex6HexNAc5dHex3SP | 2522 | + | |
| NeuGcNeuAc2Hex5HexNAc4 | 2528 | + | |
| NeuAc2Hex6HexNAc4dHex and/or NeuGcNeuAcHex5HexNAc4dHex2 | 2529 | + | |
| NeuGc2NeuAcHex5HexNAc4 | 2544 | + | |
| NeuGc2Hex5HexNAc4dHex2 and/or NeuGcNeuAcHex6HexNAc4dHex | 2545 | + | |
| NeuGc3Hex5HexNAc4 | 2560 | + | |
| NeuGc2Hex6HexNAc4dHex | 2561 | + | |
| NeuAc2Hex5HexNAc5dHex | 2570 | + | + |
| NeuAcHex5HexNAc5dHex3 | 2571 | + | |
| NeuAc2Hex6HexNAc5 | 2586 | + | + |
| NeuAcHex6HexNAc5dHex2 | 2587 | + | + |
| Hex7HexNAc6dHexSP | 2595 | + | |
| NeuGcNeuAcHex6HexNAc5 | 2602 | + | |
| NeuAcHex7HexNAc5dHex and/or NeuGcHex6HexNAc5dHex2 | 2603 | + | + |
| NeuAcHex8HexNAc5 and/or NeuGcHex7HexNAc5dHex | 2619 | + | |
| NeuAc2Hex5HexNAc6 | 2627 | + | |
| NeuGcHex8HexNAc5 and/or NeuAcHex4HexNAc5dHex4SP | 2635 | + | |
| NeuAcHex6HexNAc6dHex | 2644 | + | |
| NeuAc2Hex5HexNAc4dHex3 | 2659 | + | |
| NeuAcHex7HexNAc6 | 2660 | + | + |
| NeuGcNeuAc2Hex5HexNAc4dHex and/or NeuAc3Hex6HexNAc4 | 2674 | + | |
| NeuAc2Hex4HexNAc5dHex2SP2 | 2714 | + | |
| NeuAcHex4HexNAc5dHex4SP2 and/or NeuAc3Hex5HexNAc5 | 2715 | + | + |
| NeuAc2Hex5HexNAc5dHex2 | 2716 | + | |
| NeuAcHex6HexNAc5dHex | 2732 | + | + |
| NeuAcHex6HexNAc5dHex3 | 2733 | + | + |
| NeuGcNeuAcHex6HexNAc5dHex | 2748 | + | |
| NeuAcHex8HexNAc5dHex | 2765 | + | + |
| NeuGcHex8HexNAc5dHex and/or NeuAcHex9HexNAc5 | 2781 | + | |
| NeuAcHex6HexNAc6dHex2 | 2791 | + | |
| NeuAc3Hex5HexNAc4dHex2 and/or NeuAcHex6HexNAc6dHexSP2 | 2804 | + | |
| Hex6HexNAc6dHex3SP2 | 2805 | + | |
| NeuAcHex7HexNAc6dHex | 2807 | + | + |
| NeuAc2Hex6HexNAc5dHexSP | 2812 | + | |
| NeuAcHex6HexNAc5dHex3SP | 2813 | + | |
| NeuGcNeuAc3Hex5HexNAc4 | 2819 | + | |
| NeuAc3Hex6HexNAc4dHex and/or NeuGcNeuAc2Hex5HexNAc4dHex2 | 2820 | + | |
| NeuAc3Hex6HexNAc5 | 2878 | + | + |
| NeuAc2Hex6HexNAc5dHex2 | 2879 | + | + |
| NeuAcHex6HexNAc5dHex4 | 2880 | + | + |
| NeuGcNeuAc2Hex6HexNAc5 | 2894 | + | |
| NeuAc2Hex7HexNAc5dHex and/or NeuGcNeuAcHex6HexNAc5dHex2 | 2895 | + | + |
| NeuAc3Hex6HexNAc4dHexSP and/or NeuGcNeuAc2Hex5HexNAc4dHex2SP | 2900 | + | |
| NeuGc2Hex6HexNAc5dHex2 | 2911 | + | |
| NeuAc2Hex5HexNAc6dHex2 | 2920 | + | |
| NeuGc3Hex6HexNAc5 | 2925 | + | |
| NeuGcNeuAc2Hex5HexNAc6 | 2935 | + | |
| NeuAc2Hex6HexNAc6dHex and/or NeuGcNeuAcHex5HexNAc6dHex2 | 2936 | + | |
| NeuAcHex6HexNAc6dHex3 | 2937 | + | |
| NeuGc2NeuAcHex5HexNAc6 and/or NeuAc3Hex5HexNAc4dHex3 | 2951 | + | |
| NeuAcHex7HexNAc6 | 2952 | + | |
| NeuAcHex7HexNAc6dHex2 | 2953 | + | + |
| Hex8HexNAc7dHexSP | 2961 | + | |
| NeuAc2Hex4HexNAc7dHex2 | 2961 | + | |
| NeuAcHex7HexNAc7dHex | 3010 | + | |
| NeuAc3Hex6HexNAc5dHex | 3024 | + | + |
| NeuAc2Hex6HexNAc5dHex3 | 3025 | + | + |
| NeuAcHex8HexNAc7 | 3026 | + | |
| NeuGc3Hex6HexNAc5dHex and/or NeuGc2NeuAcHex7HexNAc5 | 3072 | + | |

TABLE 7-continued

| Proposed composition | m/z | Human cells | Human cell line |
|---|---|---|---|
| NeuAc3Hex6HexNAc6 | 3081 | + | + |
| NeuAc2Hex6HexNAc6dHex2 | 3082 | + | |
| NeuAc2Hex7HexNAc6dHex | 3098 | + | + |
| NeuAcHex7HexNAc6dHex3 | 3099 | + | + |
| NeuAc3Hex6HexNAc5dHexSP | 3104 | + | |
| NeuAc2Hex6HexNAc5dHex3SP | 3105 | + | |
| NeuAc3Hex6HexNAc5dHex2 | 3170 | + | |
| NeuAc2Hex6HexNAc5dHex4 | 3171 | + | |
| NeuAcHex8HexNAc7dHex | 3172 | + | |
| NeuAc3Hex6HexNAc6dHex | 3227 | + | |
| NeuAc2Hex6HexNAc6dHex3 | 3228 | + | |
| NeuAc3Hex7HexNAc6 | 3243 | + | |
| NeuAc2Hex7HexNAc6dHex2 | 3244 | + | + |
| NeuAcHex7HexNAc6dHex4 | 3245 | + | + |
| NeuAc2Hex7HexNAc7dHex | 3301 | + | |
| NeuAcHex7HexNAc7dHex3 | 3302 | + | |
| NeuAc2Hex8HexNAc7 | 3317 | + | |
| NeuAcHex8HexNAc7dHex2 | 3318 | + | |
| NeuAc3Hex7HexNAc6dHex | 3389 | + | + |
| NeuAc2Hex7HexNAc6dHex3 | 3390 | + | + |
| NeuAcHex7HexNAc6dHex5 and/or NeuAcHex9HexNAc8 | 3391 | + | |
| NeuAc2Hex8HexNAc7dHex | 3463 | + | |
| NeuAcHex8HexNAc7dHex3 | 3464 | + | |
| NeuAc2Hex7HexNAc6dHex4 | 3536 | + | |
| NeuAcHex9HexNAc8dHex | 3537 | + | |
| NeuAc3Hex8HexNAc7 | 3608 | + | |
| NeuAc2Hex8HexNac7dHex2 | 3609 | + | |
| NeuAcHex8HexNac7dHex4 | 3610 | + | |
| NeuAc4Hex7HexNAc6dHex | 3680 | + | |
| NeuAc3Hex7HexNAc6dHex3 | 3681 | + | |
| NeuAc2Hex9HexNAc8 | 3682 | + | |
| NeuAcHex9HexNAc8dHex2 | 3683 | + | |
| NeuAc3Hex8HexNAc7dHex | 3754 | + | |
| NeuAc2Hex8HexNAc7dHex3 | 3755 | + | |
| NeuAcHex10HexNAc9 and/or NeuAcHex8HexNAc7dHex5 | 3756 | + | |
| NeuAc4Hex6HexNAc8 | 3778 | + | |
| NeuAc3Hex7HexNAc6dHex4 | 3827 | + | |
| NeuAc2Hex9HexNAc8dHex | 3828 | + | |
| NeuAcHex9HexNAc8dHex3 | 3829 | + | |
| NeuAc2Hex8HexNAc7dHex4 | 3901 | + | |
| NeuAc2Hex9HexNAc8dHex2 | 3974 | + | |
| NeuAcHex9HexNAc8dHex4 | 3975 | + | |
| NeuAc4Hex8HexNAc7dHex | 4045 | + | |
| NeuAc3Hex8HexNAc7dHex3 | 4046 | + | |
| NeuAc2Hex10HexNAc9 and/or NeuAc2Hex8HexNAc7dHex5 | 4047 | + | |
| NeuAc3Hex9HexNAc8dHex | 4119 | + | |
| NeuAc2Hex9HexNAc8dHex3 | 4120 | + | |

HexNAc ≥ 3 and dHex ≥ 1 (including fucosylated N-glycans)

| Proposed composition | m/z | Human cells | Human cell line |
|---|---|---|---|
| Hex3HexNAc3dHexSP | 1338 | + | + |
| Hex3HexNAc3dHexSP | 1500 | + | + |
| NeuAcHex3HexNAc3dHex | 1549 | + | + |
| Hex4HexNAc3dHex2SP | 1646 | + | |
| Hex5HexNAc3dHexSP | 1662 | + | + |
| Hex6HexNAc3SP and/or NeuAc2Hex2HexNAc3dHex | 1678 | + | + |
| NeuAcHex3HexNAc3dHexSP2 | 1709 | + | |
| NeuAcHex4HexNAc3dHex | 1711 | + | + |
| NeuAcHex5HexNAc3 and/or NeuGcHex4HexNAc3dHex | 1727 | + | + |
| NeuAcHex4HexNAc3dHexSP | 1791 | + | |
| Hex5HexNAc3dHex2SP | 1808 | + | |
| Hex6NexNAc3dHexSP | 1824 | + | + |
| NeuAc2Hex3HexNAc3dHex | 1840 | + | + |
| NeuAcHex4HexNAc3dHex2 | 1857 | + | |
| NeuAcHex5HexNAc3dHex and/or NeuGcHex4HexNAc3dHex2 | 1873 | + | + |
| Hex8HexNAc3SP and/or NeuAc2Hex4HexNAc3dHex | 2002 | + | + |
| NeuAcHex4HexNAc3dHex3 | 2003 | + | |
| NeuAc2Hex5HexNAc3 and/or NeuGcNeuAcHex4HexNAc3dHex | 2018 | + | + |
| NeuAcHex5HexNAc3dHex2 | 2019 | + | + |
| NeuGcNeuAcHex5HexNAc3 and/or NeuGc2Hex4HexNAc3dHex | 2034 | + | |
| NeuAcHex6HexNAc3dHex | 2035 | + | + |
| NeuAc2Hex4HexNAc3dHexSP and/or Hex8HexNAc3SP2 | 2082 | + | |
| NeuAcHex6HexNAc3dHexSP | 2115 | + | |
| Hex8HexNAc3dHexSP and/or NeuAc2Hex4HexNAc3dHex2 | 2148 | + | |
| NeuAc2Hex5HexNAc3dHex and/or Hex6HexNAc5SP2 | 2164 | + | + |
| NeuAcHex5HexNAc3dHex3 | 2165 | + | + |
| NeuAcHex8HexNAc3SP and/or NeuAc3Hex4HexNAc3dHex | 2293 | + | |
| NeuAc2Hex5HexNAc3dHex2 and/or NeuGcNeuAcHex4HexNAc3dHex3 | 2310 | + | |
| NeuAc2Hex5HexNAc3dHex2SP | 2390 | + | + |
| NeuAc2Hex6HexNAc3dHexSP | 2406 | + | |
| NeuAcHex8HexNAc3dHexSP and/or NeuAc3Hex4HexNAc3dHex2 | 2439 | + | |
| NeuAcHex9HexNAc3dHex | 2521 | + | |
| Hex4HexNAc4dHexSP | 1703 | + | + |
| Hex5HexNAc4dHexSP | 1865 | + | + |
| Hex6HexNAc5dHexSP | 1906 | + | |
| NeuAcHex4HexNAc4dHex | 1914 | + | + |
| Hex5HexNAc4dHex2SP | 2011 | + | |
| NeuAcHex4HexNAc4dHexSP | 2027 | + | |
| Hex7HexNAc4SP and/or Hex4HexNAc6SP2 and/or NeuAc2Hex3HexNAc4dHex | 2043 | + | |
| Hex4HexNAc5dHex2SP | 2052 | + | |
| NeuAcHex4HexNAc4dHex2 | 2060 | + | + |
| NeuAcHex4HexNAc4dHexSP2 | 2074 | + | |
| NeuAcHex5HexNAc4dHex | 2076 | + | + |
| NeuAcHex6HexNAc4 and/or NeuGcHex5HexNAc4dHex | 2092 | + | + |
| NeuAcHex3HexNAc5dHex2 and/or NeuAc2Hex4HexNAc4Ac | 2101 | + | |
| NeuAcHex4HexNAc5dHex | 2117 | + | |
| NeuAcHex5HexNAc5dHex2SP2 | 2132 | + | |
| NeuAcHex5HexNAc4dHexSP | 2156 | + | + |
| Hex5HexNAc4dHex3SP | 2157 | + | |
| NeuAcHex6HexNAc4SP and/or NeuGcHex5HexNAc4dHexSP | 2172 | + | + |
| Hex6HexNAc4dHex2SP and/or Hex3HexNAc6dHex2SP2 | 2173 | + | |
| NeuAc3Hex3HexNAc4 and/or NeuGcHex6HexNAc4SP and/or NeuAc2NeuGcHex2HexNAc4dHex | 2188 | + | |
| NeuAc2Hex3HexNAc4dHex2 and/or Hex7HexNAc4dHexSP and/or Hex4HexNAc6dHexSP2 | 2189 | + | + |
| NeuAcHex3HexNAc4dHex4 | 2190 | + | + |
| Hex4HexNAc5dHex3SP | 2198 | + | + |
| NeuAc2Hex4HexNAc4dHex | 2205 | + | |
| NeuAcHex5HexNAc4dHex2 | 2222 | + | |
| Hex6HexNAc5dHexSP | 2230 | + | |
| NeuAcHex6HexNAc4dHex and/or NeuGcHex5HexNAc4dHex | 2238 | + | + |
| NeuAc2Hex3HexNAc5dHex and/or Hex7HexNAc5SP | 2246 | + | |
| NeuAcHex7HexNAc4 and/or NeuGcHex6HexNAc4dHex | 2254 | + | + |
| NeuAcHex4HexNAc5dHex2 and/or NeuAc2Hex5HexNAc4Ac | 2263 | + | |
| Hex5HexNAc6dHexSP | 2271 | + | |
| NeuAcHex5HexNAc5dHex | 2279 | + | + |
| NeuAc2Hex4HexNAc4dHexSP and/or Hex11HexNAc2SP | 2285 | + | |
| NeuAcHex5HexNAc4dHex2SP | 2302 | + | |
| NeuAcHex6HexNAc4dHexSP | 2318 | + | + |
| Hex6HexNAc4dHex3SP and/or NeuGcNeuAcHex3HexNAc6 | 2319 | + | |
| NeuAcHex4HexNAc6dHex | 2320 | + | |
| NeuAcHex5HexNAc5dHexAc | 2321 | + | |
| Hex7HexNAc4dHex2SP and/or Hex4HexNAc6dHex2SP2 | 2335 | + | |
| NeuAc2Hex4HexNAc4dHexSP | 2365 | + | |

TABLE 7-continued

| Proposed composition | m/z | Human cells | Human cell line |
|---|---|---|---|
| NeuAc2Hex5HexNAc4dHex | 2367 | + | + |
| NeuAcHex5HexNAc4dHex3 | 2368 | + | + |
| NeuAc2Hex6HexNAc4 and/or NeuGcNeuAcHex5HexNAc4dHex | 2383 | + | + |
| NeuAcHex6HexNAc4dHex2 and/or NeuGcHex5HexNAc4dHex3 | 2384 | + | |
| NeuAc2Hex3HexNAc5dHex2 and/or Hex7HexNAc5dHexSP | 2392 | + | + |
| NeuAcHex3HexNAc5dHex4 | 2393 | + | |
| NeuGc2Hex5HexNAc4dHex | 2399 | + | |
| NeuAcHex4HexNAc6dHexSP and/or NeuGcHex5HexNAc4dHex2 and/or NeuAcHex7HexNAc4dHex Hex4HexNAc6dHex3SP | 2400 2401 | + + | |
| NeuAc2Hex4HexNAc5dHex | 2408 | + | |
| NeuAcHex4HexNAc5dHex3 and/or NeuAcHex5HexNAc4dHexAc | 2409 | + | |
| NeuAcHex5HexNAc5dHex2 | 2425 | + | + |
| NeuAcHex6HexNAc5dHex | 2441 | + | + |
| NeuAc2Hex5HexNAc4dHexSP | 2447 | + | + |
| NeuAcHex5HexNAc4dHex3SP | 2448 | + | + |
| NeuAcHex7HexNAc5 and/or NeuGcHex6HexNAc5dHex | 2457 | + | + |
| NeuAcHex5HexNAc6dHex | 2482 | + | |
| NeuAcHex5HexNAc5dHex3SP | 2489 | + | |
| NeuAc2Hex5HexNAc4dHex2 | 2513 | + | + |
| NeuAcHex5HexNAc4dHex4 | 2514 | + | |
| NeuAcHex6HexNAc5dHexSP and/or NeuAc3Hex2HexNAc5dHex2 Hex6HexNAc5dHex3SP | 2521 2522 | + + | |
| NeuAc2Hex6HexNAc4dHex and/or NeuGcNeuAcHex5HexNAc4dHex2 | 2529 | + | |
| NeuGc2Hex5HexNAc4dHex2 and/or NeuGcNeuAcHex6HexNAc4dHex | 2545 | + | |
| NeuGc2Hex6HexNAc4dHex | 2561 | + | |
| NeuAc2Hex5HexNAc5dHex | 2570 | + | + |
| NeuAcHex5HexNAc5dHex3 | 2571 | + | |
| NeuAcHex6HexNAc5dHex2 | 2587 | + | + |
| Hex7HexNAc6dHexSP | 2595 | + | |
| NeuAcHex7HexNAc5dHex and/or NeuGcHex6NexNAc5dHex2 | 2603 | + | + |
| NeuAcHex8HexNAc5 and/or NeuGcHex7NexNAc5dHex | 2619 | + | |
| NeuGcHex8HexNAc5 and/or NeuAcHex4HexNAc5dHex4SP | 2635 | + | |
| NeuAcHex6HexNAc6dHex | 2644 | + | + |
| NeuAc2Hex5HexNAc4dHex3 | 2659 | + | |
| NeuGcNeuAc2Hex5HexNAc4dHex and/or NeuAc3Hex6HexNAc4 | 2674 | + | |
| NeuAc2HexNAc5dHex2SP2 | 2714 | + | |
| NeuAcHex4HexNAc5dHex4SP2 and/or NeuAc3Hex5HexNAc5 | 2715 | + | + |
| NeuAc2Hex5HexNAc5dHex2 | 2716 | + | |
| NeuAc2Hex6HexNAc5dHex | 2732 | + | + |
| NeuAcHex6HexNAc5dHex3 | 2733 | + | + |
| NeuGcNeuAcHex6HexNAc5dHex | 2748 | + | |
| NeuAcHex8HexNAc5dHex | 2765 | + | + |
| NeuGcHex8HexNAc5dHex and/or NeuAcHex9HexNAc5 | 2781 | + | |
| NeuAcHex6HexNAc6dHex2 | 2791 | + | |
| NeuAc3Hex5HexNAc4dHex2 and/or NeuAcHex6HexNAc6dHexSP2 Hex6HexNAc6dHex3SP2 | 2804 2805 | + + | |
| NeuAcHex7HexNAc6dHex | 2807 | + | + |
| NeuAc2Hex6HexNAc5dHexSP | 2812 | + | |
| NeuAc2Hex6HexNAc5dHex3SP | 2813 | + | |
| NeuAc3Hex6HexNAc4dHex and/or NeuGcNeuAc2Hex5HexNAc4dHex2 | 2820 | + | |
| NeuAc2Hex6HexNAc5dHex2 | 2879 | + | + |
| NeuAcHex6HexNAc5dHex4 | 2880 | + | + |
| NeuAc2Hex7HexNAc5dHex and/or NeuGcNeuAcHex6HexNAc5dHex2 | 2895 | + | + |
| NeuAc3Hex6HexNAc4dHexSP and/or NeuGcNeuAc2Hex5HexNAc4dHex2SP | 2900 | + | |
| NeuGc2Hex6HexNAc5dHex2 | 2911 | + | |
| NeuAc2Hex5HexNAc6dHex2 | 2920 | + | |
| NeuAc2Hex6HexNAc6dHex and/or NeuGcNeuAcHex5HexNAc6dHex2 | 2936 | + | |
| NeuAcHex6HexNAc6dHex3 | 2937 | + | |
| NeuGc2NeuAcHex5HexNAc6 and/or NeuAc3Hex5HexNAc4dHex3 | 2951 | + | |
| NeuAcHex7HexNAc6dHex2 | 2953 | + | + |
| Hex8HexNAc7dHexSP | 2961 | + | |
| NeuAc2Hex4HexNAc7dHex2 | 2961 | + | |
| NeuAcHex7HexNAc7dHex | 3010 | + | |
| NeuAc3Hex6HexNAc5dHex | 3024 | + | + |
| NeuAc2Hex6HexNAc5dHex3 | 3025 | + | + |
| NeuGc3Hex6HexNAc5dHex and/or NeuGc2NeuAcHex7HexNAc5 | 3072 | + | |
| NeuAc2Hex6HexNAc6dHex2 | 3082 | + | |
| NeuAc2Hex7HexNAc6dHex | 3098 | + | + |
| NeuAcHex7HexNAc6dHex3 | 3099 | + | + |
| NeuAc3Hex6HexNAc5dHexSP | 3104 | + | |
| NeuAc2Hex6HexNAc5dHex3SP | 3105 | + | |
| NeuAc3Hex6HexNAc5dHex2 | 3170 | + | |
| NeuAc2Hex6HexNAc5dHex4 | 3171 | + | |
| NeuAcHex8HexNAc7dHex | 3172 | + | |
| NeuAc3Hex6HexNAc6dHex | 3227 | + | |
| NeuAc2Hex6HexNAc6dHex3 | 3228 | + | |
| NeuAc2Hex7HexNAc6dHex2 | 3244 | + | + |
| NeuAcHex7HexNAc6dHex4 | 3245 | + | + |
| NeuAc2Hex7HexNAc7dHex | 3301 | + | |
| NeuAcHex7HexNAc7dHex3 | 3302 | + | |
| NeuAcHex8HexNAc7dHex2 | 3318 | + | |
| NeuAc3Hex7HexNAc6dHex | 3389 | + | + |
| NeuAc2Hex7HexNAc6dHex3 | 3390 | + | + |
| NeuAcHex7HexNAc6dHex5 and/or NeuAcHex9HexNAc8 | 3391 | + | |
| NeuAc2Hex8HexNAc7dHex | 3463 | + | |
| NeuAcHex8HexNAc7dHex3 | 3464 | + | |
| NeuAc2Hex7HexNAc6dHex4 | 3536 | + | |
| NeuAcHex9HexNAc8dHex | 3537 | + | |
| NeuAc2Hex8HexNac7dHex2 | 3609 | + | |
| NeuAcHex8HexNac7dHex4 | 3610 | + | |
| NeuAc4Hex7HexNAc6dHex | 3680 | + | |
| NeuAc3Hex7HexNAc6dHex3 | 3681 | + | |
| NeuAcHex9HexNAc8dHex2 | 3683 | + | |
| NeuAc3Hex8HexNAc7dHex | 3754 | + | |
| NeuAc2Hex8HexNAc7dHex3 | 3755 | + | |
| NeuAcHex10HexNAc9 and/or NeuAcHex8HexNAc7dHex5 | 3756 | + | |
| NeuAc3Hex7HexNAc6dHex4 | 3827 | + | |
| NeuAc2Hex9HexNAc8dHex | 3828 | + | |
| NeuAcHex9HexNAc8dHex3 | 3829 | + | |
| NeuAc3Hex8HexNAc7dHex4 | 3901 | + | |
| NeuAc2Hex9HexNAc8dHex2 | 3974 | + | |
| NeuAcHex9HexNAc8dHex4 | 3975 | + | |
| NeuAc4Hex8HexNAc7dHex | 4045 | + | |
| NeuAc3Hex8HexNAc7dHex3 | 4046 | + | |
| NeuAc2Hex10HexNAc9 and/or NeuAc2Hex8HexNAc7dHex5 | 4047 | + | |
| NeuAc3Hex9HexNAc8dHex | 4119 | + | |
| NeuAc2Hex9HexNAc8dHex3 | 4120 | + | |

| HexNAc ≥ 3 and dHex ≥ 2 (including multifucosytated N-glycans) | | | |
|---|---|---|---|
| Proposed composition | m/z | Human cells | Human cell line |
| Hex4HexNAc3dHex2SP | 1646 | + | |
| NeuAcHex3HexNAc3dHexSP2 | 1709 | + | |
| Hex5HexNAc3dHex2SP | 1808 | + | |
| NeuAcHex4HexNAc3dHex2 | 1857 | + | |
| NeuAcHex5HexNAc3dHex and/or NeuGcHex4HexNAc3dHex2 | 1873 | + | + |
| NeuAcHex4HexNAc3dHex3 | 2003 | + | |
| NeuAcHex5HexNAc3dHex2 | 2019 | + | + |
| Hex8HexNAc3dHexSP and/or NeuAc2Hex4HexNAc3dHex2 | 2148 | + | |
| NeuAcHex5HexNAc3dHex3 | 2165 | + | + |
| NeuAc2Hex5HexNAc3dHex2 and/or NeuGcNeuAcHex4HexNAc3dHex3 | 2310 | + | |
| NeuAc2Hex5HexNAc3dHex2SP | 2390 | + | + |
| NeuAcHex8HexNAc3dHexSP and/or NeuAc3Hex4HexNAc3dHex2 | 2439 | + | |
| Hex5HexNAc4dHex2SP | 2011 | + | |
| Hex4HexNAc5dHex2SP | 2052 | + | |

TABLE 7-continued

| Proposed composition | m/z | Human cells | Human cell line |
|---|---|---|---|
| NeuAcHex4HexNAc4dHex2 | 2060 | + | + |
| NeuAcHex3HexNAc5dHex2 and/or NeuAc2Hex4HexNAc4Ac | 2101 | + | |
| Hex4HexNAc5dHex2SP2 | 2132 | + | |
| Hex5HexNAc4dHex3SP | 2157 | + | |
| NeuAcHex6HexNAc4SP and/or NeuGcHex5HexNAc4dHexSP | 2172 | + | + |
| Hex6HexNAc4dHex2SP and/or Hex3HexNAc6dHex2SP2 | 2173 | + | |
| NeuAc2Hex3HexNAc4dHex2 and/or Hex7HexNAc4dHexSP and/or Hex4HexNAc6dHexSP2 | 2189 | + | + |
| NeuAcHex3HexNAc4dHex4 | 2190 | + | + |
| Hex4HexNAc5dHex3SP | 2198 | + | + |
| NeuAcHex5HexNAc4dHex2 | 2222 | + | + |
| NeuAcHex6HexNAc4dHex and/or NeuGcHex5HexNAc4dHex2 | 2238 | + | + |
| NeuAcHex4HexNAc5dHex2 and/or NeuAc2Hex5HexNAc4Ac | 2263 | + | |
| NeuAc2Hex4HexNAc4dHexSP and/or Hex11HexNAc2SP | 2285 | + | |
| NeuAcHex5HexNAc4dHex2SP | 2302 | + | |
| Hex6HexNAc4dHex3SP and/or NeuGcNeuAcHex3HexNAc6 | 2319 | + | |
| Hex7HexNAc4dHex2SP and/or Hex4HexNAc6dHex2SP2 | 2335 | + | |
| NeuAc2Hex4HexNAc4dHexSP | 2365 | + | |
| NeuAcHex5HexNAc4dHex3 | 2368 | + | + |
| NeuAcHex6HexNAc4dHex2 and/or NeuGcHex5HexNAc4dHex3 | 2384 | + | + |
| NeuAc2Hex3HexNAc5dHex2 and/or Hex7HexNAc5dHexSP | 2392 | + | + |
| NeuAcHex3HexNAc5dHex4 | 2393 | + | |
| NeuAcHex4HexNAc6dHexSP and/or NeuGcHex6HexNAc4dHex2 and/or NeuAcHex7HexNAc4dHex | 2400 | + | |
| Hex4HexNAc6dHex3SP | 2401 | + | |
| NeuAcHex4HexNAc5dHex3 and/or NeuAc2Hex5HexNAc4dHexAc | 2409 | + | |
| NeuAcHex5HexNAc5dHex2 | 2425 | + | + |
| NeuAcHex5HexNAc4dHex3SP | 2448 | + | |
| NeuAcHex4HexNAc5dHex3SP | 2489 | + | |
| NeuAc2Hex5HexNAc4dHex2 | 2513 | + | + |
| NeuAcHex5HexNAc4dHex4 | 2514 | + | |
| NeuAcHex6HexNAc5dHexSP and/or NeuAc3Hex2HexNAc5dHex2 | 2521 | + | |
| Hex6HexNAc5dHex3SP | 2522 | + | |
| NeuAc2Hex6HexNAc4dHex and/or NeuGcNeuAcHex5HexNAc4dHex2 | 2529 | + | |
| NeuGc2Hex5HexNAc4dHex2 and/or NeuGcNeuAcHex6HexNAc4dHex | 2545 | + | |
| NeuAcHex5HexNAc5dHex3 | 2571 | + | |
| NeuAcHex6HexNAc5dHex2 | 2587 | + | + |
| NeuAcHex7HexNAc5dHex and/or NeuGCHex7HexNAc5dHex2 | 2603 | + | + |
| NeuGcHex8HexNAc5 and/or NeuAcHex4HexNAc5dHex4SP | 2635 | + | |
| NeuAc2Hex5HexNAc4dHex3 | 2659 | + | |
| NeuAc2Hex4HexNAc5dHex2SP2 | 2714 | + | |
| NeuAcHex4HexNAc5dHex4SP2 and/or NeuAc3Hex5HexNAc5 | 2715 | + | + |
| NeuAc2Hex5HexNAc5dHex2 | 2716 | + | |
| NeuAcHex5HexNAc5dHex3 | 2733 | + | + |
| NeuAcHex6HexNAc6dHex2 | 2791 | + | |
| NeuAc3Hex5HexNAc4dHex2 and/or NeuAcHex6HexNAc6dHexSP2 | 2804 | + | |
| Hex6HexNAc6dHex3SP2 | 2805 | + | |
| NeuAcHex6HexNAc5dHex3SP | 2813 | + | |
| NeuAc3Hex6HexNAc4dHex and/or NeuGcNeuAc2Hex5HexNAc4dHex2 | 2820 | + | |
| NeuAc2Hex6HexNAc5dHex2 | 2879 | + | + |
| NeuAcHex6HexNAc5dHex4 | 2880 | + | + |
| NeuAc2Hex7HexNAc5dHex and/or NeuGcNeuAcHex6HexNAc5dHex2 | 2895 | + | + |
| NeuAc3Hex6HexNAc4dHexSP and/or NeuGcNeuAc2Hex5HexNAc4dHex2SP | 2900 | + | |
| NeuGc2Hex6HexNAc5dHex2 | 2911 | + | |
| NeuAc2Hex5HexNAc6dHex2 | 2920 | + | |
| NeuAc2Hex6HexNAc6dHex and/or NeuGcNeuAcHex5HexNAc6dHex2 | 2936 | + | |
| NeuAcHex6HexNAc6dHex3 | 2937 | + | |
| NeuGc2NeuAcHex5HexNAc6 and/or NeuAc3Hex5HexNAc4dHex3 | 2951 | + | |
| NeuAcHex7HexNAc6dHex2 | 2953 | + | + |
| NeuAc2Hex4HexNAc7dHex2 | 2961 | + | |
| NeuAc2Hex6HexNAc5dHex3 | 3025 | + | + |
| NeuAc2Hex6HexNAc6dHex2 | 3082 | + | |
| NeuAcHex7HexNAc6dHex3 | 3099 | + | + |
| NeuAc3Hex6HexNAc5dHexSP | 3104 | + | |
| NeuAc2Hex6HexNAc5dHex3SP | 3105 | + | |
| NeuAc3Hex6HexNAc5dHex2 | 3170 | + | |
| NeuAc2Hex6HexNAc5dHex4 | 3171 | + | |
| NeuAc2Hex6HexNAc6dHex3 | 3228 | + | |
| NeuAc2Hex7HexNAc6dHex2 | 3244 | + | + |
| NeuAcHex7HexNAc6dHex4 | 3245 | + | + |
| NeuAcHex7HexNAc7dHex3 | 3302 | + | |
| NeuAcHex8HexNAc7dHex2 | 3318 | + | |
| NeuAcHex7HexNAc6dHex3 | 3390 | + | + |
| NeuAcHex7HexNAc6dHex5 and/or NeuAcHex9HexNAc8 | 3391 | + | |
| NeuAcHex8HexNAc7dHex3 | 3464 | + | |
| NeuAc2Hex7HexNAc6dHex4 | 3536 | + | |
| NeuAc2Hex8HexNac7dHex2 | 3609 | + | |
| NeuAcHex8HexNac7dHex4 | 3610 | + | |
| NeuAc3Hex7HexNAc6dHex3 | 3681 | + | |
| NeuAcHex9HexNAc8dHex2 | 3683 | + | |
| NeuAc2Hex8HexNAc7dHex3 | 3755 | + | |
| NeuAcHex10HexNAc9 and/or NeuAcHex8HexNAc7dHex5 | 3756 | + | |
| NeuAc3Hex7HexNAc6dHex4 | 3827 | + | |
| NeuAcHex9HexNAc8dHex3 | 3829 | + | |
| NeuAc2Hex8HexNAc7dHex4 | 3901 | + | |
| NeuAc2Hex9HexNAc8dHex2 | 3974 | + | |
| NeuAcHex9HexNAc8dHex4 | 3975 | + | |
| NeuAc3Hex8HexNAc7dHex3 | 4046 | + | |
| NeuAc2Hex10HexNAc9 and/or NeuAc2Hex8HexNAc7dHex5 | 4047 | + | |
| NeuAc2Hex9HexNAc8dHex3 | 4120 | + | |

HexNAc > Hex ≥ 3
(terminal HexNAc, N > H)

| Proposed composition | m/z | Human cells | Human cell line |
|---|---|---|---|
| Hex6HexNAc3SP and/or NeuAc2Hex2HexNAc3dHex | 1678 | + | + |
| NeuAcHex3HexNAc4 | 1606 | + | |
| NeuAcHex3HexNac5 | 1809 | + | |
| NeuGc2Hex2HexNAc5 | 1825 | + | + |
| Hex4HexNAc5dHexSP | 1906 | + | |
| NeuAcHex4HexNAc5 | 1971 | + | |
| Hex7HexNAc4SP and/or Hex4HexNAc6SP2 and/or NeuAc2Hex3HexNAc4dHex | 2043 | + | |
| NeuAcHex4HexNAc5SP | 2051 | + | |
| Hex4HexNAc5dHex2SP | 2052 | + | |
| NeuAcHex3HexNAc5dHex2 and/or NeuAc2Hex4HexNAc4Ac | 2101 | + | |
| NeuAcHex4HexNAc5dHex | 2117 | + | |
| Hex4HexNAc5dHex2SP2 | 2132 | + | |
| Hex6HexNAc4dHex2SP and/or Hex3HexNAc6dHex2SP2 | 2173 | + | |
| NeuAcHex4HexNAc6 | 2174 | + | |
| NeuAc3Hex3HexNAc4 and/or NeuGcHex6HexNAc4SP and/or NeuAc2NeuGcHex2HexNAc4dHex | 2188 | + | |
| NeuAc2Hex3HexNAc4dHex2 and/or Hex7HexNAc4dHexSP and/or Hex4HexNAc6dHexSP2 | 2189 | + | + |
| NeuAcHex3HexNAc4dHex4 | 2190 | + | + |
| Hex4HexNAc5dHex3SP | 2198 | + | + |
| NeuAc2Hex4HexNAc5 | 2262 | + | |
| NeuAcHex4HexNAc5dHex2 and/or NeuAc2Hex5HexNAc4Ac | 2263 | + | |
| Hex5HexNAc6dHexSP | 2271 | + | |
| NeuAcHex4HexNAc6dHex | 2320 | + | |
| Hex7HexNAc4dHex2SP and/or Hex4HexNAc6dHex2SP2 | 2335 | + | |
| NeuAcHex5HexNAc6 | 2336 | + | + |

TABLE 7-continued

| Proposed composition | m/z | Human cells | Human cell line |
|---|---|---|---|
| NeuAc2Hex3HexNAc5dHex2 and/or Hex7HexNAc5dHexSP | 2392 | + | + |
| NeuAcHex3HexNAc5dHex4 | 2393 | + | |
| NeuAcHex4HexNAc6dHexSP and/or NeuGcHex6HexNAc4dHex2 and/or NeuAcHex7HexNAc4dHex | 2400 | + | |
| Hex4HexNAc6dHex3SP | 2401 | + | |
| NeuAc2Hex4HexNAc5dHex | 2408 | + | |
| NeuAcHex4HexNAc5dHex3 and/or NeuAc2Hex5HexNAc4dHexAc | 2409 | + | |
| NeuAcHex5HexNAc6dHex | 2482 | + | |
| NeuAcHex4HexNAc5dHex3SP | 2489 | + | |
| Hex6HexNAc7SP | 2490 | + | |
| NeuGc3Hex5HexNAc4 | 2560 | + | |
| NeuAc2Hex5HexNAc6 | 2627 | + | |
| NeuAc2Hex4HexNAc5dHex2SP2 | 2714 | + | |
| NeuAcHex4HexNAc5dHex4SP2 and/or NeuAc3Hex5HexNAc5 | 2715 | + | + |
| NeuAc2Hex5HexNAc6dHex2 | 2920 | + | |
| NeuGcNeuAc2Hex5HexNAc6 | 2935 | + | |
| NeuAc2Hex4HexNAc7dHex2 | 2961 | + | |
| NeuAc4Hex6HexNAc8 | 3778 | + | |

HexNAc = Hex ≥ 5
(terminal HexNAc, N = H)

| Proposed composition | m/z | Human cells | Human cell line |
|---|---|---|---|
| Hex5HexNAc5SP2 | 2002 | + | |
| NeuAcHex5HexNAc5 | 2133 | + | + |
| NeuAcHex5HexNAc5dHex | 2279 | + | + |
| NeuAcHex5HexNAc5dHexAc | 2321 | + | |
| NeuAc2Hex5HexNAc5 | 2424 | + | |
| NeuAcHex5HexNAc5dHex2 | 2425 | + | + |
| NeuAc2Hex5HexNAc5dNex | 2570 | + | + |
| NeuAcHex5HexNAc5dHex3 | 2571 | + | |
| NeuAcHex5HexNAc6dHex | 2644 | + | + |
| NeuAcHex4HexNAc5dHex4SP2 and/or NeuAc3Hex5HexNAc5 | 2715 | + | + |
| NeuAc2Hex5HexNAc5dHex2 | 2716 | + | |
| NeuAcHex5HexNAc6dHex2 | 2791 | + | |
| Hex6HexNAc6dHex3SP2 | 2805 | + | |
| NeuAc2Hex6HexNAc6dHex and/or NeuGcNeuAcHex5HexNAc6dHex2 | 2936 | + | |
| NeuAcHex6HexNAc6dHex3 | 2937 | + | |
| NeuAcHex7HexNAc7dHex | 3010 | + | |
| NeuAc3Hex6HexNAc6 | 3081 | + | + |
| NeuAc2Hex6HexNAc6dHex2 | 3082 | + | |
| NeuAc3Hex6HexNAc6dHex | 3227 | + | |
| NeuAc2Hex6HexNAc6dHex3 | 3228 | + | |
| NeuAc2Hex7HexNAc7dHex | 3301 | + | |
| NeuAcHex7HexNAc7dHex3 | 3302 | + | |

SP ≥ 1
(including sulphated and/or phosphorylated glycans)

| Proposed composition | m/z | Human cells | Human cell line |
|---|---|---|---|
| Hex3HexNAc2SP | 989 | + | |
| Hex3HexNAc2dHexSP | 1135 | + | |
| Hex4HexNAc2SP | 1151 | + | |
| Hex3HexNAc3SP | 1192 | + | + |
| Hex5HexNAc2SP | 1313 | + | |
| Hex3HexNAc3dHexSP | 1338 | + | + |
| Hex4HexNAc3SP | 1354 | + | + |
| Hex5HexNAc2dHexSP | 1459 | + | + |
| Hex6HexNAc2SP | 1475 | + | |
| Hex4HexNAc3dHexSP | 1500 | + | + |
| Hex5HexNAc3SP | 1516 | + | |
| Hex6HexNAc2SP2 | 1555 | + | |
| Hex4HexNAc4SP | 1557 | + | + |
| NeuAcHex3HexNAc3SP2 | 1563 | + | |
| Hex6HexNAc2dHexSP | 1621 | + | + |
| Hex4HexNAc4SP2 and/or Hex7HexNAc2SP | 1637 | + | |
| Hex4HexNAc3dHex2SP | 1646 | + | |
| Hex5HexNAc3dHexSP | 1662 | + | + |
| Hex6HexNAc3SP | 1678 | + | |
| Hex4HexNAc4dHexSP | 1703 | + | + |
| NeuAcHex3HexNAc3dHexSP2 | 1709 | + | |
| Hex4HexNAc4SP3 and/or Hex7HexNAc2SP2 | 1717 | + | |
| Hex5HexNAc4SP | 1719 | + | + |
| Hex7HexNAc2dHexSP | 1783 | + | |
| NeuAcHex4HexNAc3dHexSP | 1791 | + | |
| Hex5HexNAc4SP2 and/or Hex8HexNAc2SP | 1799 | + | |
| Hex5HexNAc3dHex2SP | 1808 | + | |
| NeuAc2Hex5HexNAc2 and/or NeuAc2Hex2HexNAc4SP | 1815 | + | |
| Hex6NexNAc3dHexSP | 1824 | + | + |
| Hex5HexNAc4dHexSP | 1865 | + | + |
| Hex6HexNAc4SP | 1881 | + | + |
| Hex4HexNAc5dHexSP | 1906 | + | |
| NeuAcHex6HexNAc2dHexSP and/or NeuAcHex3HexNAc4dHexSP2 | 1912 | + | |
| NeuAcHex4HexNAc4SP2 | 1928 | + | |
| Hex8HexNAc3SP and/or Hex5HexNAc5SP2 and/or NeuAc2Hex4HexNAc3dHex | 2002 | + | + |
| NeuAcHex5HexNAc4SP | 2010 | + | + |
| Hex5HexNAc4dHex2SP | 2011 | + | |
| NeuGcHex5HexNAc4SP | 2026 | + | |
| Hex6HexNAc4dHexSP | 2027 | + | + |
| Hex7HexNAc4SP and/or Hex4HexNAc6SP2 and/or NeuAc2Hex3HexNAc4dHex | 2043 | + | |
| NeuAcHex7HexNAc3 and/or NeuAcHex4HexNAc5SP | 2051 | + | + |
| Hex4HexNAc5dHex2SP | 2052 | + | |
| NeuAc2Hex4HexNAc4dHexSP2 | 2074 | + | |
| NeuAc2Hex4HexNAc3dHexSP2 and/or Hex8HexNAc3SP2 and/or Hex5HexNAc5SP3 | 2082 | + | |
| NeuAcHex6HexNAc3dHexSP | 2115 | + | |
| Hex8HexNAc3dHexSP and/or NeuAc2Hex4HexNAc3dHex2 | 2148 | + | |
| NeuAcHex5HexNAc4dHexSP and/or Hex8HexNAc2dHex | 2156 | + | + |
| Hex5HexNAc4dHex3SP | 2157 | + | |
| NeuAc2Hex5HexNAc3dHex and/or Hex6HexNAc5SP2 | 2164 | + | + |
| NeuAcHex6HexNAc4SP and/or NeuGcHex5HexNAc4dHexSP and/or NeuAcHex9HexNAc2 | 2172 | + | + |
| Hex6HexNAc4dHex2SP and/or Hex3HexNAc6dHex2SP2 | 2173 | + | |
| NeuAc3Hex3HexNAc4 and/or NeuGcHex6HexNAc4SP and/or NeuAc2NeuGcHex2HexNAc4dHex | 2188 | + | |
| NeuAc2Hex3HexNAc4dHex2 and/or Hex7HexNAc4dHexSP and/or Hex4HexNAc6dHexSP2 | 2189 | + | + |
| Hex4HexNAc5dHex3SP | 2198 | + | + |
| NeuAc2Hex4HexNAc4SP2 | 2219 | + | |
| Hex6HexNAc5dHexSP | 2230 | + | |
| NeuAc2Hex3HexNAc5dHex and/or Hex7HexNAc5SP | 2246 | + | |
| NeuAc2Hex4HexNAc4dHexSP and/or Hex11HexNAc2SP | 2285 | + | |
| NeuAcNex8HexNAc3SP and/or NeuAc3Hex4HexNAc3dHex | 2293 | + | |
| NeuAc2Hex5HexNAc4SP | 2301 | + | |
| NeuAcHex5HexNAc4dHex2SP | 2302 | + | |
| NeuAcHex6HexNAc4dHexSP | 2318 | + | + |
| Hex6HexNAc4dHex3SP | 2319 | + | |
| Hex7HexNAc4dHex2SP and/or Hex4HexNAc6dHex2SP2 | 2335 | + | |
| NeuAc2Hex4HexNAc4dHexSP | 2365 | + | |
| NeuAc3Hex5HexNAc3SP and/or NeuAc2Hex5HexNAc4Ac4 | 2389 | + | |
| NeuAc2Hex5HexNAc4dHex2SP | 2390 | + | + |
| NeuAc2Hex3HexNAc5dHex2 and/or Hex7HexNAc5dHexSP | 2392 | + | + |
| NeuAcHex4HexNAc6dHexSP and/or NeuGcHex6HexNAc4dHex2 and/or NeuAcHex7HexNAc4dHex | 2400 | + | |

TABLE 7-continued

| | | |
|---|---|---|
| NeuAc2Hex6HexNAc3dHexSP | 2406 | + |
| NeuAcHex8HexNAc3dHexSP and/or | 2439 | + |
| NeuAc3Hex4HexNAc3dHex2 | | |
| NeuAc2Hex5HexNAc4dHexSP and/or | 2447 | + + |
| NeuAc2Hex8HexNAc2dHex and/or | | |
| Hex12HexNAc2SP | | |
| NeuAcHex5HexNAc4dHex3SP and/or | 2448 | + |
| NeuAcHex8HexNAc2dHex3 | | |
| NeuAcHex7HexNAc3dHex3 and/or | 2489 | + |
| NeuAcHex4HexNAc5dHex3SP | | |
| Hex6HexNAc7SP | 2490 | + |
| NeuAcHex6HexNAc5dHexSP and/or | 2521 | + |
| NeuAcHex9HexNAc3dHex and/or | | |
| NeuAc3Hex2HexNAc5dHex2 | | |
| Hex6HexNAc5dHex3SP | 2522 | + |
| Hex7HexNAc6dHexSP | 2595 | + |
| NeuGcHex6HexNAc5 and/or | 2635 | + |
| NeuAcHex4HexNAc5dHex4SP | | |
| NeuAc2Hex5HexNAc5dHexSP | 2650 | + |
| Hex7HexNAc7SP | 2652 | + |
| Hex6HexNAc7dHex4SP | 2668 | + |
| NeuGcHex6HexNAc5dHexSP and/or | 2683 | + |
| NeuAcHex7HexNAc5dHexSP | | |
| NeuAc2Hex4HexNAc5dHex2SP2 | 2714 | + |

TABLE 7-continued

| | | |
|---|---|---|
| Hex7HexNAc7dHex2SP | 2945 | + |
| NeuAc2Hex6HexNAc5dHex2SP | 2958 | + |
| NeuAcHex6HexNAc5dHex4SP | 2960 | + |
| Hex8HexNAc7dHexSP | 2961 | + |
| Hex8HexNAc8SP | 3018 | + |
| Hex7HexNAc6dHex4SP | 3034 | + |
| Hex7HexNAc7dHex3SP | 3091 | + |
| NeuAc3Hex6HexNAc5dHexSP | 3104 | + |
| NeuAc2Hex6HexNAc5dHex3SP | 3105 | + |
| NeuAcHex8HexNAc7SP and/or | 3106 | + |
| NeuAc3Hex4HexNAc7dHex | | |
| Hex8HexNAc7dHex2SP and/or | 3107 | + |
| NeuAc2Hex4HexNAc7dHex3 | | |
| NeuAc2Hex7HexNAc6dHexSP | 3178 | + |
| Hex7HexNAc7dHex4SP | 3237 | + |
| NeuAc3Hex7HexNAc5dHexSP and/or | 3266 | + |
| NeuGcNeuAc2Hex6HexNAc5dHex2SP | | |
| NeuAc3Hex5HexNAc7dHex and/or | 3268 | + |
| NeuGcHex8HexNAc7dHexSP | | |
| NeuAc4Hex4HexNAc5dHex2SP2 | 3297 | + |
| NeuAc3Hex4HexNAc5dHex4SP2 | 3298 | + |
| Hex8HexNAc8dHex3SP and/or | 3456 | + |
| NeuAc2Hex4HexNAc8dHex4 | | |
| NeuAc3Hex7HexNAc6dHexSP | 3469 | + |
| NeuAc2Hex7HexNAc6dHex3SP | 3470 | + |

TABLE 8

Structural classification of neutral glycan fraction glycan signals isolated from normal human lung tissue (1. column), human lung cancer tissue (2. column), normal human serum (5. column), and a cultured human cell line (6. column). Acidic glycan fraction glycans analyzed as neutral desialylated glycan signals together with the corresponding neutral glycan fraction are similarly classified from the same human tissue samples (3. and 4. column, total normal and total cancer).

| Structural features of Neutral N-glycans | | % | | | | | |
|---|---|---|---|---|---|---|---|
| structural feature | proposed composition | normal lung | lung cancer | total normal | total cancer | human serum | human cell line |
| $Hex_{5-9}HexNAc_2$ | high-mannose | 47.0 | 46.0 | 17.8 | 22.3 | 25.7 | 53.7 |
| $Hex_{1-4}HexNAc_2dHex_{0-1}$ | low-mannose | 28.0 | 19.5 | 15.5 | 24.4 | 0.7 | 8.5 |
| $Hex_{10-12}HexNAc_2$ | high-mannose/Glc | 0.0 | 0.0 | 0.0 | 0.0 | 0.0 | 1.9 |
| $Hex_{5-6}HexNAc_2dHex_1$ | low-mannose + Fuc | 0.7 | 0.0 | 0.3 | 0.2 | 0.0 | 1.0 |
| $n_{HexNAc} = 3$ ja $n_{Hex} \geq 2$ | hybrid/monoantennary | 7.9 | 8.7 | 8.4 | 7.1 | 6.6 | 7.3 |
| $n_{HexNAc} \geq 4$ ja $n_{Hex} \geq 2$ | complex type | 15.8 | 24.4 | 57.8 | 46.0 | 66.2 | 9.3 |
| $Hex_{1-9}HexNAc$ | soluble | 0.7 | 0.5 | 0.0 | 0.0 | 0.8 | 11.3 |
| other | — | 0.0 | 0.9 | 0.2 | 0.0 | 0.0 | 6.9 |
| $n_{dHex} \geq 1$ | fucosylation | 19.4 | 33.6 | 42.8 | 34.6 | 50.5 | 13.9 |
| $n_{dHex} \geq 2$ | α2/3/4-Fuc | 0.0 | 0.8 | 0.3 | 1.1 | 0.0 | 1.3 |
| $n_{HexNAc} > n_{Hex} \geq 2$ | terminal HexNAc | 3.9 | 17.8 | 3.8 | 7.1 | 21.8 | 4.2 |
| $n_{HexNAc} = n_{Hex} \geq 3$ | terminal HexNAc | 6.9 | 8.2 | 8.2 | 5.0 | 31.4 | 1.9 |

TABLE 7-continued

| | | |
|---|---|---|
| NeuAcHex4HexNAc5dHex4SP2 and/or | 2715 | + |
| NeuAc3Hex5HexNAc5 | | |
| Hex6HexNAc6dHex3SP | 2725 | + |
| Hex7HexNAc6dHex2SP | 2741 | + |
| NeuAcHex6HexNAc5dHex2SP2 | 2747 | + |
| NeuAc2Hex4HexNAc6dHex2 and/or | 2757 | + |
| Hex8HexNAc6dHexSP | | |
| Hex7HexNAc7dHexSP | 2798 | + |
| NeuAc3Hex5HexNAc4dHex2 and/or | 2804 | + |
| NeuAcHex6HexNAc6dHexSP2 | | |
| Hex6HexNAc6dHex3SP2 | 2805 | + |
| NeuAc2Hex6HexNAc5dHexSP | 2812 | + |
| NeuAcHex6HexNAc5dHex3SP | 2813 | + |
| Hex8HexNAc7SP | 2814 | + |
| Hex6HexNAc6dHex4SP | 2871 | + |
| NeuAcHex7HexNAc6dHexSP and/or | 2887 | + |
| NeuAcHex10HexNAc4dHex | | |
| Hex7HexNAc6dHex3SP | 2887 | + |
| NeuAc3Hex6HexNAc4dHexSP and/or | 2900 | + |
| NeuGcNeuAc2Hex5HexNAc4dHex2SP | | |
| NeuAc3Hex4HexNAc6dHex and/or | 2903 | + |
| NeuAcHex8HexNAc6SP | | |

TABLE 9

N-glycan structural classification of lysosomal protein sample.

| Glycan feature | Proposed structure | Proportion, % |
|---|---|---|
| Neutral N-glycan structural features: | | |
| $Hex_{5-10}HexNAc_2$ | High-mannose type/$Glc_1$ | 46 |
| $Hex_{1-4}HexNAc_2dHex_{0-1}$ | Low-mannose type | 49 |
| $n_{HexNAc} = 3$ ja $n_{Hex} \geq 2$ | Hybrid-type/Monoantennary | 2 |
| $n_{HexNAc} \geq 4$ ja $n_{Hex} \geq 2$ | Complex-type | 0.6 |
| Other | — | <3 |
| $n_{dHex} \geq 1$ | Fucosylation | 29 |
| $n_{dHex} \geq 2$ | α2/3/4-linked Fuc | 0.8 |
| $n_{HexNAc} > n_{Hex} \geq 2$ | Terminal HexNAc (N > H) | 0.2 |
| $n_{HexNAc} = n_{Hex} \geq 5$ | Terminal HexNAc (N = H) | — |
| Acidic N-glycan structural features: | | |
| $n_{HexNAc} = 3$ ja $n_{Hex} \geq 3$ | Hybrid-type/Monoantennary | 46 |
| $n_{HexNAc} \geq 4$ ja $n_{Hex} \geq 3$ | Complex-type | 37 |
| muut | — | 17 |
| $n_{dHex} \geq 1$ | Fucosylation | 80 |
| $n_{dHex} \geq 2$ | α2/3/4-linked Fuc | 10 |

TABLE 9-continued

N-glycan structural classification of lysosomal protein sample.

| Glycan feature | Proposed structure | Proportion, % |
|---|---|---|
| $n_{HexNAc} > n_{Hex} \geq 2$ | Terminal HexNAc (N > H) | 0.1 |
| $n_{HexNAc} = n_{Hex} \geq 5$ | Terminal HexNAc (N = H) | 0.4 |
| +80 Da | Sulphate or phosphate ester | 17 |

TABLE 10

Identification of disease-specific glycosylation by quantitative glycome analysis.

| Composition | m/z | Class | I | II | m/z | Class | Abs. differ. | m/z | Class | Rel. differ. |
|---|---|---|---|---|---|---|---|---|---|---|
| Hex1HexNAc2 | 609 | NL | 0.00 | 0.00 | 771 | NL | 12.8 | 1955 | NCE | new |
| Hex2HexNAc1dHex1 | 714 | NOF | 0.00 | 0.00 | 1485 | NCFT | 3.5 | 2685 | NCE | new |
| Hex3HexNAc1 | 730 | NS | 0.00 | 0.00 | 1743 | NM | 2.1 | 2905 | NCF | new |
| Hex1HexNAc2dHex1 | 755 | NLF | 2.47 | 0.00 | 1905 | NM | 1.8 | 771 | NL | 2.4 |
| Hex2HexNAc2 | 771 | NL | 5.44 | 18.25 | 1419 | NM | 1.4 | 1905 | NM | 2.2 |
| Hex2HexNAc2dHex1 | 917 | NLF | 1.81 | 2.61 | 917 | NLF | 0.8 | 1485 | NCFT | 1.3 |
| Hex3HexNAc2 | 933 | NL | 2.47 | 1.12 | 1581 | NM | 0.5 | 2394 | NC | 1.3 |
| Hex2HexNAc3 | 974 | NH-T | 0.00 | 0.00 | 1955 | NCE | 0.4 | 1743 | NM | 1.2 |
| Hex2HexNAc2dHex2 | 1063 | NOE | 0.00 | 0.00 | 2685 | NCE | 0.4 | 917 | NLF | 0.4 |
| Hex3HexNAc2dHex1 | 1079 | NLF | 1.81 | 1.12 | 2905 | NCF | 0.4 | 1419 | NM | 0.4 |
| Hex4HexNAc2 | 1095 | NL | 1.48 | 1.30 | 2539 | NCF | 0.3 | 2539 | NCF | 0.4 |
| Hex2HexNAc3dHex1 | 1120 | NHFT | 0.00 | 0.00 | 2394 | NC | 0.2 | 1581 | NM | 0.2 |
| Hex3HexNAc3 | 1136 | NH | 0.82 | 0.00 | 2175 | NCF | 0.2 | 1282 | NHF | 0.1 |
| Hex2HexNAc2dHex3 | 1209 | NOE | 0.00 | 0.00 | 1622 | NH | 0.2 | 2012 | NCFB | 0.1 |
| Hex3HexNAc2dHex2 | 1225 | NOE | 0.00 | 0.00 | 1282 | NHF | 0.1 | 1622 | NH | 0.1 |
| Hex4HexNAc2dHex1 | 1241 | NLF | 0.00 | 0.00 | 2012 | NCFB | 0.1 | 1339 | NH-T | 0.1 |
| Hex5HexNAc2 | 1257 | NM | 8.90 | 7.64 | 1339 | NH-T | 0.0 | 2320 | NCE | 0.1 |
| Hex2HexNAc3dHex2 | 1266 | NHET | 0.00 | 0.00 | 2320 | NCE | 0.0 | 2175 | NCF | 0.0 |
| Hex3HexNAc3dHex1 | 1282 | NHF | 0.82 | 0.93 | 609 | NL | 0.0 | 609 | NL | 0.0 |
| Hex4HexNAc3 | 1298 | NH | 1.48 | 1.12 | 714 | NOF | 0.0 | 714 | NOF | 0.0 |
| Hex3HexNAc4 | 1339 | NH-T | 0.33 | 0.37 | 730 | NS | 0.0 | 730 | NS | 0.0 |
| Hex5HexNAc2dHex1 | 1403 | NMF | 0.33 | 0.19 | 974 | NH-T | 0.0 | 974 | NH-T | 0.0 |
| Hex6HexNAc2 | 1419 | NM | 3.95 | 5.40 | 1063 | NOE | 0.0 | 1063 | NOE | 0.0 |
| Hex3HexNAc3dHex2 | 1428 | NHE | 0.00 | 0.00 | 1120 | NHFT | 0.0 | 1120 | NHFT | 0.0 |
| Hex4HexNAc3dHex1 | 1444 | NHF | 1.65 | 1.30 | 1209 | NOE | 0.0 | 1209 | NOE | 0.0 |
| Hex5HexNAc3 | 1460 | NH | 2.47 | 2.42 | 1225 | NOE | 0.0 | 1225 | NOE | 0.0 |
| Hex3HexNAc4dHex1 | 1485 | NCFT | 2.64 | 6.15 | 1241 | NLF | 0.0 | 1241 | NLF | 0.0 |
| Hex4HexNAc4 | 1501 | NC | 1.32 | 0.93 | 1266 | NHET | 0.0 | 1266 | NHET | 0.0 |
| Hex3HexNAc5 | 1542 | NC-T | 0.00 | 0.00 | 1428 | NHE | 0.0 | 1428 | NHE | 0.0 |
| Hex7HexNAc2 | 1581 | NM | 2.31 | 2.79 | 1542 | NC-T | 0.0 | 1542 | NC-T | 0.0 |
| Hex6HexNAc3 | 1622 | NH | 1.15 | 1.30 | 1688 | NCFT | 0.0 | 1688 | NCFT | 0.0 |
| Hex4HexNAc4dHex1 | 1647 | NCF | 3.95 | 2.23 | 2028 | NC | 0.0 | 2028 | NC | 0.0 |
| Hex5HexNAc4 | 1663 | NC | 17.63 | 13.97 | 1460 | NH | −0.1 | 1460 | NH | 0.0 |
| Hex3HexNAc5dHex1 | 1688 | NCFT | 0.00 | 0.00 | 1850 | NCFT | −0.1 | 1095 | NL | −0.1 |
| Hex4HexNAc5 | 1704 | NC-T | 0.16 | 0.00 | 1403 | NMF | −0.1 | 1257 | NM | −0.1 |
| Hex8HexNAc2 | 1743 | NM | 1.81 | 3.91 | 1704 | NC-T | −0.2 | 1850 | NCFT | −0.2 |
| Hex5HexNAc4dHex1 | 1809 | NCF | 20.59 | 11.73 | 1095 | NL | −0.2 | 1663 | NC | −0.2 |
| Hex6HexNAc4 | 1825 | NC | 2.47 | 0.56 | 1444 | NHF | −0.3 | 1444 | NHF | −0.2 |
| Hex4HexNAc5dHex1 | 1850 | NCFT | 0.66 | 0.56 | 1298 | NH | −0.4 | 1298 | NH | −0.2 |
| Hex5HexNAc5 | 1866 | NC-B | 0.49 | 0.00 | 1501 | NC | −0.4 | 1501 | NC | −0.3 |
| Hex9HexNAc2 | 1905 | NM | 0.82 | 2.61 | 1866 | NC-B | −0.5 | 1079 | NLF | −0.4 |
| Hex5HexNAc4dHex2 | 1955 | NCE | 0.00 | 0.37 | 1079 | NLF | −0.7 | 1809 | NCF | −0.4 |
| Hex6HexNAc5dHex1 | 2012 | NCFB | 0.82 | 0.93 | 1136 | NH | −0.8 | 1647 | NCF | −0.4 |
| Hex6HexNAc5 | 2028 | NC | 1.32 | 1.30 | 1257 | NM | −1.3 | 1403 | NMF | −0.4 |
| Hex6HexNAc5dHex1 | 2175 | NCF | 4.12 | 4.28 | 933 | NL | −1.4 | 933 | NL | −0.5 |
| Hex6HexNAc5dHex2 | 2320 | NCE | 0.33 | 0.37 | 1647 | NCF | −1.7 | 1825 | NC | −0.8 |
| Hex7HexNAc6 | 2394 | NC | 0.16 | 0.37 | 1825 | NC | −1.9 | 1704 | NC-T | gone |
| Hex7HexNAc6dHex1 | 2539 | NCF | 0.82 | 1.12 | 755 | NLF | −2.5 | 1866 | NC-B | gone |
| Hex7HexNAc6dHex2 | 2685 | NCE | 0.00 | 0.37 | 1663 | NC | −3.7 | 1136 | NH | gone |
| Hex8HexNAc7dHex1 | 2905 | NCF | 0.00 | 0.37 | 1809 | NCF | −8.9 | 755 | NLF | gone |

TABLE 11

Neutral glycan signal nomenclature for glycosphingolipid glycans.

| Proposed composition | m/z | |
|---|---|---|
| Hex2dHex | 511.24 | 511 |
| Hex3 | 527.15 | 527 |
| Hex2HexNAc | 568.19 | 568 |
| Hex2HexNAcdHex | 714.24 | 714 |
| Hex3HexNAc | 730.24 | 730 |
| Hex2HexNAc2 | 771.26 | 771 |
| HexHexNAc3 | 812.29 | 812 |
| Hex3HexNAcdHex | 876.30 | 876 |
| Hex4HexNAc | 892.29 | 892 |
| HexHexNAc2dHex2 | 901.33 | 901 |

TABLE 11-continued

Neutral glycan signal nomenclature for glycosphingolipid glycans.

| Proposed composition | m/z | |
|---|---|---|
| Hex2HexNAc2dHex | 917.32 | 917 |
| Hex3HexNAc2 | 933.31 | 933 |
| Hex2HexNAc3 | 974.34 | 974 |
| Hex2HexNAcdHex3 | 1006.36 | 1006 |
| Hex3HexNAcdHex2 | 1022.35 | 1022 |
| Hex5HexNAc | 1054.34 | 1054 |
| Hex2HexNAc2dHex2 | 1063.38 | 1063 |
| Hex2HexNAc2dHex | 1079.38 | 1079 |
| Hex4HexNAc2 | 1095.37 | 1095 |
| Hex3HexNAc3 | 1136.40 | 1136 |
| Hex6HexNAc | 1216.40 | 1216 |
| Hex3HexNAc2dHex2 | 1225.43 | 1225 |
| Hex4HexNAc2dHex | 1241.43 | 1241 |
| Hex5HexNAc2 | 1257.42 | 1257 |
| Hex3HexNAc3dHex | 1282.45 | 1282 |
| Hex4HexNAc3 | 1298.45 | 1298 |
| Hex2HexNAc4dHex | 1323.48 | 1323 |
| Hex3HexNAc2dHex3 | 1371.49 | 1371 |
| Hex7HexNAc | 1378.45 | 1378 |
| Hex4HexNAc2dHex2 | 1387.49 | 1387 |
| Hex5HexNAc2dHex | 1403.48 | 1403 |
| Hex6HexNAc2 | 1419.48 | 1419 |
| Hex3HexNAc3dHex2 | 1428.51 | 1428 |
| Hex4HexNAc3dHex | 1444.51 | 1444 |
| Hex5HexNAc3 | 1460.50 | 1460 |
| Hex4HexNAc2dHex3 | 1533.54 | 1533 |
| Hex8HexNAc | 1540.5 | 1540 |
| Hex6HexNAc2dHex | 1565.53 | 1565 |
| Hex4HexNAc3dHex2 | 1590.57 | 1590 |
| Hex5HexNAc3dHex | 1606.56 | 1606 |
| Hex6HexNAc3 | 1622.56 | 1622 |
| Hex9HexNAc | 1702.56 | 1702 |
| Hex4HexNAc3dHex3 | 1736.62 | 1736 |
| Hex5HexNAc3dHex2 | 1752.62 | 1752 |
| Hex4HexNAc5dHex | 1850.67 | 1850 |
| Hex10HexNAc | 1864.61 | 1864 |
| Hex7HexNAc2dHex2 | 1873.64 | 1873 |
| Hex4HexNAc3dHex4 | 1882.68 | 1882 |
| Hex5HexNAc5dHex3 | 1898.68 | 1898 |
| Hex5HexNAc4dHex2 | 1955.70 | 1955 |
| Hex11HexNAc | 2026.66 | 2026 |
| Hex5HexNAc4dHex3 | 2101.76 | 2101 |
| Hex6HexNAc4dHex2 | 2117.75 | 2117 |
| Hex4HexNAc5dHex3 | 2142.78 | 2142 |
| Hex12HexNAc | 2188.71 | 2188 |

TABLE 12

Acidic glycan signal nomenclature for glycosphingolipid glycans.

| Proposed composition | m/z | |
|---|---|---|
| NeuAcHexHexNAcdHex | 819.29 | 819 |
| NeuAcHex2HexNAc | 835.28 | 835 |
| NeuAc2Hex2 | 905.30 | 905 |
| NeuAcHexHexNAcdHex2 | 965.35 | 965 |
| NeuAcHex3HexNAc | 997.34 | 997 |
| NeuAc2Hex2HexNAc | 1126.38 | 1126 |
| NeuAcHex3HexNAcdHex | 1143.39 | 1143 |
| Hex4HexNAc2SP | 1151.33 | 1151 |
| NeuAcHex4HexNAc | 1159.39 | 1159 |
| NeuAcHexHexNAc2dHex2 | 1168.43 | 1168 |
| NeuAcHex3HexNAc2 | 1200.42 | 1200 |
| NeuGcHex3HexNAc2 | 1216.41 | 1216 |
| Hex2HexNAc4SP | 1233.38 | 1233 |
| NeuAc2Hex3HexNAc | 1288.43 | 1288 |
| NeuAc2HexHexNAc2dHex | 1313.46 | 1313 |
| NeuAcHex2HexNAc2dHex | 1330.48 | 1330 |
| NeuAcHex4HexNAc2 | 1362.47 | 1362 |
| NeuAc2Hex4HexNAc/ NeuAc2HexHexNAc3SP | 1450.48 | 1450 |
| NeuAcHex4HexNAc2dHex | 1508.53 | 1508 |
| NeuAc2Hex2HexNAc3dHex2 | 1533.56 | 1533 |

TABLE 12-continued

Acidic glycan signal nomenclature for glycosphingolipid glycans.

| Proposed composition | m/z | |
|---|---|---|
| Hex6HexNAc2SP2/ NeuAc2Hex2HexNac2dHexSP | 1555.47/1555.39 | 1555 |
| NeuAcHex4HexNAc3 | 1565.55 | 1565 |
| NeuAcHex5HexNAc3 | 1727.60 | 1727 |
| NeuGcHex5HexNAc3 | 1743.60 | 1743 |
| NeuAcHex5HexNAc3dHex | 1873.66 | 1873 |
| NeuAcHex6HexNAc3 | 1889.65 | 1889 |
| NeuAcHex3HexNAc4dHex2 | 1898.69 | 1898 |
| NeuAc2Hex3HexNac3dHexSP | 1920.60 | 1920 |
| NeuAc2Hex5HexNAc3 | 2018.70 | 2018 |
| NeuAcHex6HexNAc3dHex | 2035.71 | 2035 |
| NeuAcHex6HexNAc4 | 2092.73 | 2092 |
| NeuGcHex6HexNAc4 | 2108.73 | 2108 |
| NeuAcHex4HexNAc4dHex3SP | 2286.76 | 2286 |
| NeuAc2Hex5HexNAc4SP | 2301.73 | 2301 |
| NeuGc3Hex4HexNAc4 | 2398.80 | 2398 |
| NeuAcHex5HexNAc4dHex3SP/ NeuAcHex8HexNAc2dHex3 Hex7HexNAc6SP | 2448.81 2449.81 | 2448 2449 |
| NeuGc2Hex7HexNAc5 | 2780.95 | 2780 |
| NeuGcHex8HexNAc5dHex/ NeuAcHex9HexNAc5 | 2781.97 | 2781 |

TABLE 13

Detected tissue material N-linked and soluble glycome compositions.

Neutral N-glycan structural features:

| Glycan feature | Proposed structure | Proportion, % |
|---|---|---|
| $Hex_{5-10}HexNAc_2$ | High-mannose type/$Glc_1$ | 10-60 |
| $Hex_{1-4}HexNAc_2dHex_{0-1}$ | Low-mannose type | 0-50 |
| $n_{HexNAc} = 3$ ja $n_{Hex} \geq 2$ | Hybrid-type/Monoantennary | 5-20 |
| $n_{HexNAc} \geq 4$ ja $n_{Hex} \geq 2$ | Complex-type | 5-75 |
| $Hex_{1-9}HexNAc_1$ | Soluble | 0-10 |
| $n_{dHex} \geq 1$ | Fucosylation | 10-80 |
| $n_{dHex} \geq 2$ | α2/3/4-linked Fuc | 0-40 |
| $n_{HexNAc} > n_{Hex} \geq 2$ | Terminal HexNAc (N > H) | 1-30 |
| $n_{HexNAc} = n_{Hex} \geq 5$ | Terminal HexNAc (N = H) | 1-40 |

Acidic N-glycan structural features:

| Glycan feature | Proposed structure | all Proportion, % |
|---|---|---|
| $n_{HexNAc} = 3$ ja $n_{Hex} \geq 3$ | Hybrid-type/Monoantennary | 5-60 |
| $n_{HexNAc} \geq 4$ ja $n_{Hex} \geq 3$ | Complex-type | 40-95 |
| $n_{dHex} \geq 1$ | Fucosylation | 20-90 |
| $n_{dHex} \geq 2$ | α2/3/4-linked Fuc | 0-50 |
| $n_{HexNAc} > n_{Hex} \geq 2$ | Terminal HexNAc (N > H) | 0-40 |
| $n_{HexNAc} = n_{Hex} \geq 5$ | Terminal HexNAc (N = H) | 0-40 |
| +80 Da | Sulphate or phosphate ester | 0-25 |

REFERENCES

Davies, et al. (1992) *J. Chromatogr.* 609(1-2): 125-31
Harvey, D. J., et al. (1993) *Rapid Commun. Mass Spectrom.* 7(7):614-9
Hemmerich et al. (1995) *J. Biol. Chem.* 270(20): 12035-47
Huang, et al. (2000) *Anal. Chem.* 73(24): 6063-9
Karlsson, H., et al. (2000) *Glycobiology* 10(12): 1291-309
Miller-Podraza, H., et al. (2000) *Glycobiology.* 10: 975-982.
Naven, T. J. & Harvey, D. J. (1996) *Rapid Commun. Mass Spectrom.* 10(11): 1361-6
Nyman, T. A., et al. (1998) *Eur. J. Biochem.* 253(2): 485-93
Papac, D., et al. (1996) *Anal. Chem.* 68(18): 3215-23
Raju, et al. (2000) *Glycobiology* 10: 477-86
Saarinen, J., et al. (1999) *Eur. J. Biochem.* 259(3): 82940

Sheeley, et al. (1997) *Anal. Biochem.* 247: 102-10
Verostek et al., (2000) *Anal. Biochem.* 278(2): 111-22

The invention claimed is:

1. A method of evaluating the status of a human tissue material preparation comprising the step of detecting the presence of a glycan structure in said preparation, wherein the detection is performed by mass spectrometry or by an antibody, lectin, or enzyme specifically binding to said glycan structure, wherein the amount of the glycan structure is determined in comparison to the same glycan structure from control tissue, which is healthy tissue or tissue altered by disease or another cell line or cell sample derived from the same tissue and wherein said glycan structure consists of a terminal non-reducing end structure according to

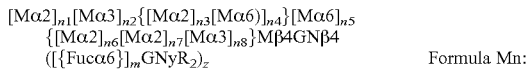  Formula Mn:

wherein n1, n2, n3, n4, n5, n6, n7, n8, and m, and z are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0;

y is anomeric linkage structure α and/or β or linkage from derivatized anomeric carbon, and $R_2$ is reducing end hydroxyl, chemical reducing end derivative or natural asparagine N-glycoside derivative and/or peptides derived from protein;

[ ] and ( ) indicates determinant either being present or absent depending on the value of n1, n2, n3, n4, n5, n6, n7, n8, and m; and { } indicates a branch in the structure, M is mannose residue (Man) and GN is N-acetylglucosaminyl residue (GlcNAc) with the provisions that
i) z is 0 indicating soluble mannose-GlcNAc1-glycome, or
ii) the structure comprises 5 or less mannose residues or
iii) m is 1 and there are 6 or less mannose units.

2. The method according to claim 1, with the provision that when m is 0, and z is 1, then the glycan structure comprises 4 or less mannose residues and the glycan structure consists of low mannose glycans according to Formula
1) non-fucosylated, with composition $Man_nGlcNAc_2$, where $1 \leq n \leq 4$, and/or
2) core-fucosylated, with composition $Man_nGlcNAc_2Fuc_1$, where $1 \leq n \leq 5$ and/or
a soluble mannose-GlcNAc1-glycome according to

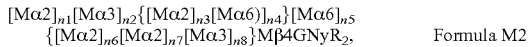  Formula M2 wherein the variables are as described for Formula Mn.

3. The method according to claim 2, wherein the human tissue material preparation is human solid tissue or cells.

4. The method according to claim 3, wherein both low mannose glycan(s) with z is 1, and soluble glycan(s) with z is 0 are analyzed, and the total N-glycome further comprising 1) high-mannose type, 2) hybrid-type or monoantennary, and 3) complex-type N-glycans, is determined.

5. The method according to claim 2, wherein the detection is performed by releasing glycans, or by extracting free glycans from said preparation, or by analyzing the amount or presence of at least one glycan structure in said preparation by an antibody, lectin or enzyme specifically binding to said glycan structure.

6. The method according to claim 2, wherein the detection is performed by mass spectrometry.

7. The method according to claim 2, wherein the detection is performed by a specific antibody.

8. The method according to claim 1, wherein said glycan structure is selected from the group of structures consisting of:
Mβ4GNβ4GN,
Mα6Mβ4GNβ4GN,
Mα3Mβ4GNβ4GN, and
Mα6{Mα3}Mβ4GNβ4GN.

9. The method according to claim 1, wherein said glycan structure is selected from the group of structures consisting of:
Mβ4GNβ4GN,
Mα6Mβ4GNβ4GN,
Mα3Mβ4GNβ4GN,
Mα6{Mα3}Mβ4GNβ4GN,
Mα3Mα6{Mα3}Mβ4GNβ4GN, and
Mα6Mα6{Mα3}Mβ4GNβ4GN.

10. The method according to claim 1, wherein m is 1 and there is 6 or less mannose units.

11. The method as described in claim 1, wherein the detection comprises one or more of the following methods:
a) preparation of substrate cell materials for analysis by the use of a chemical buffer solution, or by the use of detergents, chemical reagents and/or enzymes;
b) release or extraction of glycome(s) from the cells, including various subglycome types;
c) purification of glycomes and various subglycomes from complex mixtures;
d) glycome analysis, including profiling by mass spectrometry; and
e) data processing and analysis between different sample types and quantitative analysis of glycome data obtained.

12. The method according to claim 11, wherein the glycome is non-derivatized or singly derivatized, and Mass spectrometry is MALDI mass spectrometry.

13. The method according to claim 11, wherein the glycome is purified by at least one prepurification step selected from the group:
1) precipitation and/or extraction,
2) cation exchange of contaminants,
3) hydrophobic adsorption of contaminants, and
4) hydrophilic purification, and/or carbohydrate affinity purification and by at least one purification step including one or both chromatography methods selected from the group:
a) Hydrophilic interactions and b) Ion exchange.

14. The method according to claim 11, wherein the glycome comprises oligosaccharides with molecular weight from about 400 to about 4000.

15. The method according to claim 11, wherein the amount of cells to be analysed by mass spectrometry is between $10^3$ and 5 000 000 cells, which yield between 0.1-100 μmol of glycome composition or 2 to 100 million cells for NMR.

16. The method according to claim 2, wherein the glycan structure is released from the surface of the cells.

17. The method according to claim 2, wherein the human tissue material preparation comprises human tissue or cultivated cells derived thereof, a cultivated cell population, human tissue cells, healthy tissue cells, or malignant or tumor tissue cells.

18. The method according to claim 2, wherein the human tissue material preparation is obtained from a tissue secretion preferably serum, urine, saliva or milk.

19. The method according to claim 2, wherein the human tissue material preparation is obtained from human serum.

20. The method according to claim 2 for the control of cell status and/or potential contaminations by glycosylation analysis using mass spectrometric analysis of glycans in said cell preparation.

21. The method according to claim 2, wherein one specific low mannose glycan is detected.

22. The method according to claim 20, wherein the cell status is controlled during cell culture or during cell or tissue purification, in context with cell storage or handling at lower temperatures, or in context with cryopreservation of tissues.

23. The method according to claim 20, wherein time dependent changes of cell status are detected.

24. The method according to claim 23, wherein time dependent changes of cell status depend on the nutritional status of the cells, confluency of the cell culture, density of the cells, changes in genetic stability of the cells, integrity of the cell structures or cell age, or chemical, physical, or biochemical factors affecting the cells.

25. The method according to claim 1, wherein said method comprises the steps of:
i) preparing a tissue or cell sample containing glycans for the analysis;
ii) releasing total glycans from the sample, or extracting free glycans from the sample;
iii) optionally modifying glycans;
iv) purifying the glycan fraction/fractions from biological material of the sample;
v) optionally modifying glycans;
vi) analysing the composition of the released glycans by mass spectrometry;
vii) optionally presenting the data about released glycans quantitatively and comparing the quantitative data set with another data set from another sample; and
viii) comparing data about the released glycans quantitatively or qualitatively with data produced from another sample.

26. The method according to claim 1, wherein the method further comprises modification of cell surface glycans according to Formula Mn of an isolated human tissue or cell population, the method comprising the steps of:
a) contacting said tissue or cell population with a glycosidase or glycosyl transferring enzyme capable of modifying surface glycans of said tissue or cell population according to the Formula Mn, wherein Formula Mn is

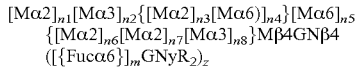

wherein n1, n2, n3, n4, n5, n6, n7, n8, and m, and z are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0;

y is anomeric linkage structure α and/or β or linkage from derivatized anomeric carbon, and $R_2$ is reducing end hydroxyl, chemical reducing end derivative or natural asparagine N-glycoside derivative such as asparagine N-glycosides including asparagines N-glycoside amino acid and/or peptides derived from protein;

[ ] and ( ) indicates determinant either being present or absent depending on the value of n1, n2, n3, n4, n5, n6, n7, n8, and m; and { } indicates a branch in the structure, M is mannose residue (Man) and GN is N-acetylglucosaminyl residue (GlcNAc) with the provisions that i) z is 0 indicating soluble mannose-GlcNAc1-glycome or
ii) the structure comprises 5 or less mannose residues or
iii) m is 1 and there are 6 or less mannose units; and
b) optionally isolating a modified cell population obtained from step a).

27. The method according to claim 2, wherein the detection is performed by a binder being a recombinant protein selected from the group: monoclonal antibody, glycosidase, glycosyl transferring enzyme, plant lectin, animal lectin and a peptide mimetic thereof.

28. The method according to claim 27, wherein the recombinant protein is a high specificity binder recognizing at least partially two monosaccharide structures and bond structure between the monosaccharide residues.

29. The method according to claim 27, wherein the binder protein is labelled by a detectable marker structure.

30. The method according to claim 27, wherein the binder is used for sorting or selecting cells from biological materials or samples including cell materials comprising other cell types.

31. The method according to claim 28, wherein the binder is used for sorting or selecting between different human cell types.

32. The method according to claim 1, wherein the analysis includes:
1) detection of the glycomes according to Formula Mn:
by an antibody, lectin or enzyme specifically binding to said glycan structure or
by mass spectrometry,
and optionally
2) quantitative and/or comparative data-analysis methods for the glycomes, wherein the Formula Mn is

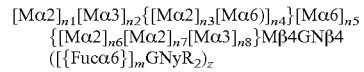

wherein n1, n2, n3, n4, n5, n6, n7, n8, and m, and z are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0;

y is anomeric linkage structure α and/or β or linkage from derivatized anomeric carbon, and $R_2$ is reducing end hydroxyl, chemical reducing end derivative or natural asparagine N-glycoside derivative such as asparagine N-glycosides including asparagines N-glycoside amino acid and/or peptides derived from protein;

[ ] and ( ) indicates determinant either being present or absent depending on the value of n1, n2, n3, n4, n5, n6, n7, n8, and m; and { } indicates a branch in the structure, M is mannose residue (Man) and GN is N-acetylglucosaminyl residue (GlcNAc) with the provisions that i) z is 0 indicating soluble mannose-GlcNAc1-glycome or
ii) the structure comprises 5 or less mannose residues or
iii) m is 1 and there are 6 or less mannose units.

33. The method according to claim 1, wherein said glycan structure is a low mannose structure comprising ManβG1cNAc.

34. The method according to claim 26, wherein said reagent or enzyme capable of modifying surface glycans is selected from the group consisting of a) glycosidase-type enzymes capable of releasing monosaccharide units from glycans, b) glycosyltransferring enzymes, and c) glycan modifying enzymes.

35. The method according to claim 26, wherein said enzyme capable of modifying surface glycans is selected from the group consisting of α-mannosidase, β-mannosidase, transglycosylating enzymes, gylcosyltransferases, sulphate modifying enzymes and phosphate modifying enzymes.

36. A method of evaluating the status of a human tissue material preparation comprising the step of detecting the presence of a glycan structure in said preparation, wherein said human tissue material preparation is from solid tissue, serum, saliva or milk, wherein the amount of the glycan structure is determined in comparison to the same glycan structure from control tissue, which is healthy tissue or tissue altered by disease or another cell line or cell sample derived from the same tissue and wherein said glycan structure consists of a terminal non-reducing end structure according to $[M\alpha2]_{n1}[M\alpha3]_{n2}\{[M\alpha2]_{n3}[M\alpha6]_{n4}\}[M\alpha6]_{n5}$
$\{[M\alpha2]_{n6}[M\alpha2]_{n7}[M\alpha3]_{n8}\}M\beta4GN\beta4$
$([\{Fuc\alpha6\}]_{m}GNyR_{2})_{z}$  Formula Mn:

wherein n1, n2, n3, n4, n5, n6, n7, n8, and m, and z are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0;

y is anomeric linkage structure α and/or β or linkage from derivatized anomeric carbon, and $R_2$ is reducing end hydroxyl, chemical reducing end derivative or natural asparagine N-glycoside derivative and/or peptides derived from protein;

[ ] and ( ) indicates determinant either being present or absent depending on the value of n1, n2, n3, n4, n5, n6, n7, n8, and m; and { } indicates a branch in the structure, M is mannose residue (Man) and GN is N-acetylglucosaminyl residue (GlcNAc) with the provisions that i) z is 0 indicating soluble mannose-GlcNAc1-glycome, or ii) the structure comprises 5 or less mannose residues or iii) m is 1 and there are 6 or less mannose units.

* * * * *